US005824791A

United States Patent [19]

Progulske-Fox et al.

[11] Patent Number: 5,824,791

[45] Date of Patent: Oct. 20, 1998

[54] **CLONED *PORPHYROMONAS GINGIVALIS* GENES AND PROBES FOR THE DETECTION OF PERIODONTAL DISEASE**

[75] Inventors: Ann Progulske-Fox, Gainesville, Fla.; Somying Tumwasorn, Bangkok, Thailand; Guylaine Lepine, Fort Erie, Canada; Naiming Han, Gainesville, Fla.; Marilyn Lantz, Indianapolis, Ind.; Joseph M. Patti, Missouri City, Tex.

[73] Assignees: University of Florida, Gainesville, Fla.; UAB Research Foundation, Birmingham, Ala.

[21] Appl. No.: 570,311

[22] Filed: Dec. 11, 1995

Related U.S. Application Data

[63] Continuation-in-part of Ser. No. 353,485, Dec. 9, 1994, which is a continuation-in-part of Ser. No. 647,119, Jan. 25, 1991, abandoned, which is a continuation-in-part of Ser. No. 241,640, Sep. 8, 1988, abandoned.

[51] Int. Cl.[6] .......................... C07H 21/04; C07H 19/00; C12N 1/20

[52] U.S. Cl. ...................... 536/237; 536/22.1; 435/252.3

[58] Field of Search ................................. 536/22.1, 23.7; 435/256.1, 252.3

[56] References Cited

U.S. PATENT DOCUMENTS

| | | | |
|---|---|---|---|
| 4,358,535 | 11/1982 | Falkow et al. | 435/5 |
| 4,661,350 | 4/1987 | Tsurumizu et al. | 424/92 |
| 4,866,167 | 9/1989 | Chen et al. | 537/27 |
| 5,475,097 | 12/1995 | Travis et al. . | |
| 5,523,390 | 6/1996 | Travis et al. . | |

FOREIGN PATENT DOCUMENTS

| | | | |
|---|---|---|---|
| 9507286 | 3/1995 | WIPO | C07H 17/00 |
| WO 95/26404 | 1/1997 | WIPO . | |

OTHER PUBLICATIONS

Houghten et al. Vaccine 86, Cold Spring Harbor Laboratory, pp. 21–25, 1986.

Data base Search for Kirszhoun et al.

Progulske–Fox et al J. Periodontal Res 28:473–4, 1993.

Progulske–Fox Oral Microbiol Immunol 10:311–318, 1995.

Benas et al. Nucleic Acids Research 19:4189–4192, 1991.

Data base search for Banas.

Lepine Dissertation, pp. 73–80, 118–148, 170, 204–213 Apr., 1994.

White, D., D. Mayrand (1981) "Association of oral Bacteriodes with gingivitis and adult periodontitis" Journal of Periodontal Research 16:259–265.

Takazoe, I. et al. (1984) "Colonization of the Subgingival Area by *Bacteriodes gingivalis*" J. Dent. Res. 63(3):422–426.

Slots, J., E. Hausmann (1979) "Longitudinal Study of Experimentally Induced Periodontal Disease in Macaca arctoides: Relationship Between Microflora and Alveolar Bone Loss" Infection and Immunity 23(2):260–269.

Boyd, J., B. C. McBride (1984) "Fractionation of Hemagglutinating and Bacterial Binding Adhesins of *Bacteriodes gingivalis*" Infection and Immunity 45(2):403–409.

Inoshita, E. et al. (1986) "Isolation and Some Properties of Exohemagglutinin from the Cuture Medium of *Bacteriodes gingivalis*381" Infection and Immunity 52(2):421–427.

Okuda, K. et al. (1986) "Purification and Properties of Hemaggluitnin from Culture Supernatant of *Bacteriodes gingivalis*" Infection and Immunity 54(3):659–665.

Naito, Y. et al. (1987) "Detection of Specific Antibody in Adult Human Periodontis Sera to Surface Antigens of *Bacteriodes gingivalis*" Infection and Immunity 55(3):832–834.

Naito, Y. et al. (1985) "Monoclonal Antibodies against Surface Antigens of *Bacteriodes gingivalis*" Infection and Immunity 50(1);231–235.

Okuda, K. et al. (1986) "Antigenic Characteristics and Serological Identification of 10 Black–Pigmented Bacteroides Species" Journal of Clinical Microbiology 24(1):89–95.

Abiko, Y. et al. (1988) "Gene Cloning and Expression of a *Bacteroides gingivalis*–Specific Protein Antigen in *Escherichia coli*" Adv. Dent. Res. 2(2):310–314.

Dickinson, D.P. et al. (1988) "Molecular Cloning and Sequencing of the Gene Encoding the Fimbrial Subunit Protein of *Bacteroides gingivalis*" Journal of Bacteriology 170(4):1658–1665.

Okuda, K. et al. (1988) "Protective Efficiacy of Active and Passive Immunizations against Experimental Infection with *Bacteroides gingivalis* in Ligated Hamsters" J. Dent. Res. 67(5):807–811.

Mouton, C. et al. (1989) "Immunochemical Identification and Preliminary Characterization of a Nonfimbrial Hemagglutinating Adhesion of *Bacteroides gingivalis*" Infection and Immunity 57(2):566–573.

Progulske–Fox, A. et al. (1989) "The expression and function of a *Bacteroides gingivalis* hemagglutinin gene in *Escherichia coli*" Oral Microbial. Immunol. 4:121–131.

Roberts, M.C. et al. (1987) "Chromosomal DNA Probes for the Identification of Bacteroides Species" Journal of General Microbiology 133:1423–1430.

Dickinson, D.P. et al. (1986) "Molecular Cloning of *B. gingivalis* Fimbrial Protein Subunit Gene" J. Dental. Res. 65:737, abstract No. 105.

Abiko, Y. (1986) "Cloning and Expression of *Bacteroides gingivalis* Antigen Gene into *Escherichia coli*" J. Dental Res. 65:737, abstract No. 106.

Kawamoti, Y. et al. (1991) "Purification and Immunochemical Characterization of a Recombinant Outer Membrane Protein from *Bacteroides gingivalis*" Int. J. Biochem. 23(10):1053–1061.

(List continued on next page.)

*Primary Examiner*—Susan A. Loring

*Attorney, Agent, or Firm*—Gerard H. Bencen, Esq.; Gerard H. Bencen, P.A.

[57] ABSTRACT

DNA fragments from *Porphyromonas gingivalis* which express proteins that elicit anti-*P. gingivalis* immunologic responses are described. Microorganisms, genetically modified to express *P. gingivalis* antigens, are provided. Also disclosed are probes, vaccines, and monoclonal antibodies for the detection and prevention of periodontal disease.

5 Claims, 4 Drawing Sheets

OTHER PUBLICATIONS

Roberts, M.C. et al. (1987) "Chromosomal DNA Probes for the Identification of Bacteroides Species" Journal of General Microbiology 133:1423–1430.

Lerner, R.A. et al. (1983) "The Development of Synthetic Vaccines" in The Biology of Immunologic Disease, Chapter 31, pp. 331–338.

Helfman, D.M., S.H. Hughes (1987) "Use of Antibodies to Screen cDNA Expression Libraries Prepared in Plasmid Vectors" Methods in Enzymology 152:451–457.

Helfman, D.M. et al. (1983) "Identification of clones that encode chicken tropomnyosin by direct Immunological screening of a cDNA expression library" Proc. Natl. Acad. Sci. USA 80:31–35.

Young, R.A., R.W. Davis (1983) "Efficient isolation of genes by using antibody probes" Proc. Natl. Acad. Sci. USA 80:1194–1198.

Hoiseth, S.K., B.A.D. Stocker (1981) "Aromatic–dependent *Salmonella typhimurium* are non–virulent and effective as live vaccines" Nature 291:238–239.

Brown, A. et al. (1987) "An Attenuated aroA *Salmonell typhimurium* vaccine Elicits Humoral and Cellular Immunity to Cloned β–Galactosidase in Mice" The Journal of Infectious Diseases 155(1):86–92.

Sadoff, J.C. et al. (1988) "Oral *Salmonella typhimurium* Vaccine Expressing Circumsporozoite Protein Protects Against Malaria" Science 24:336–338.

French, C.K. et al. (1987) "DNA Probe–Based Technology Compared to Standard Culture Methodology for the Detection of Periodontal Pathogens" 33(6):963.

Lepine, G. et al. (1994) "Cloning and Characterization of a Fourth Putative Hemagglutinin Gene from *Porphyromonas gingivalis*" 94th Meeting of the American Society for Microbiology, Las Vegas, NV, May 23–27, *abstract No. D–117.

Fletcher, H.M. et al. (1994) "Cloning and Characterization of a Protease Gene (prtH) from *Porphyromonas ginivalis*" Infection and Immunity 62(10):4279–4286.

Kirszbaum, L. et al. (1985) "Complete Nucleotide Sequence of a Gene prtR of *Porphymonas gingivalis* W50 Encoding a 132 kDa Protein that Contains an Arginine–Specific Thiol Endopeptidase Domain and a Haemagglutinin Domain" Biochemical and Biophysical Research Communications 207(1):424–431.

Pavloff, N. et al. (1995) "Moklecular Cloning and STructural Characterization of the ArgGingipain Proteinase of *Porphyromonas gingivalis*" The Journal of Biological Chemistry 270(3):1007–1010.

Hunt, J.M., D.H. Persing (1993) "acterial Detection" DNA Probes, pp. 525–564.

Dusek, D.M. et al. (1994) "Systemic and Mucsal Immune Responses in Mice Orally Immunzed with Avirulent *Salmonella typhinurium* Expressing a Cloned *Porphyromonas gingivalis* Hemagglutinin" Infectin and Immunity 62(5):1652–1657.

CLONED *PORPHYROMONAS GINGIVALIS* GENES AND PROBES FOR THE DETECTION OF PERIODONTAL DISEASE

CROSS-REFERENCE TO A RELATED APPLICATION

This is a continuation-in-part of co-pending application Ser. No. 08/353,485, filed Dec. 9, 1994, which is a continuation-in-part of application Ser. No. 07/647,119, filed Jan. 25, 1991; which is a continuation-in-part of application Ser. No. 07/241,640, filed Sep. 8, 1988, now abandoned.

The subject invention was made with government support under a research project supported by the National Institutes of Health Grant Nos. DE 07496 and DE 00336. The government has certain rights in this invention.

BACKGROUND OF THE INVENTION

Periodontal disease (PD) is a chronic inflammatory disease which results in the destruction of the supporting tissues of teeth. Although the specific microbial etiology of PD is not known, it is widely accepted that bacteria are the contributing agents of the disease.

The presence of a complex micro flora in the subgingival crevice has complicated the identification of the specific etiologic agents of PD. However, it appears that a few genera, primarily gram-negative anaerobes, are associated with disease progression. Several lines of evidence strongly implicate the gram-negative anaerobic bacterium *Porphyromonas gingivalis*, previously known to those skilled in the art as *Bacteronides gingivalis*, as an etiological agent of adult periodontal disease (White, D., D. Mayrand [1981] "Association of Oral Bacteroides with Gingivitis and Adult Periodontitis," *J. Periodont. Res.* 1:1–18; Takazoe, L., T. Nakamura, K. Okuda [1984] "Colonization of the Subgingival Area by *Bacteroides gingivalis," J. Dent. Res.* 63:422–426. For example, relatively high proportions of *P. gingivalis* have been isolated from adult periodontitis lesions, patients with adult periodontitis have been found to have higher levels of IgG antibodies to *P. gingivalis* than do normal adults, and local immunity to *P. gingivalis* is greater in the more advanced cases than in the early forms of periodontal disease. *P. gingivalis* also appears to be a causative agent of experimental periodontitis in animals (Slots, J., E. Hausmann [1979] "Longitudinal Study of Experimentally Induced Periodontal Disease in *Macaca arctoides*: Relationship Between Microflora and Alveolar Bone Loss," *Infect. Immun.* 23:260–269). In addition, *P. gingivalis* possesses a variety of suspected virulence factors such as proteases, collagenases, immunoglobulin degrading enzymes, and adhesins.

In order to exert their pathogenic effects, periodontopathic bacteria such as *P. gingivalis* must possess characteristics which enable them to colonize the host, survive in the periodontal pocket, possibly invade the gingival tissues, and to destroy the collagenous periodontal ligament, the alveolar bone, and other tissue components surrounding the tooth. Components of bacteria which mediate attachment to host tissues include surface structures such as fimbriae, capsular materials, lipopolysaccharides, and membrane-associated extracellular vesicles.

The hemagglutinating activity of *P. gingivalis* has been studied as a parameter that affects the adherence of this organism in the periodontal pocket. Sera from patients with adult periodontitis possess high antibody levels to the *P. gingivalis* hemagglutinin. It is thus suggested that the adhesive surface structures such as hemagglutinin participate in *P. gingivalis* colonization and antigenic stimulation of the host.

Investigations have reported the isolation of hemagglutinin activity from *P. gingivalis*. Boyd and McBride (Boyd, J., B. C. McBride [1984] "Fractionation of Hemagglutinating and Bacterial Binding Adhesins of *Bacteroides gingivalis," Infect. Immun.* 45:403–409) prepared an outer membrane component containing hemagglutinating activity from *P. gingivalis* W12. This preparation contained three major proteins with molecular weights of 69,000, 41,500, and 22,000. Inoshita et al. (Inoshita, E., A. Amano, T. Hanioka, H. Tamagawa, S. Shizukushi, A. Tsunemitsu [1986] "Isolation and Some Properties of Exohemagglutinin from the Culture Medium of *Bacteroides gingivalis* 381, *"Infect. Immun.* 52:421–427) isolated hemagglutinating activity from culture supernatants of *P. gingivalis* 381. The isolated hemagglutinin component contains three major proteins with molecular weights of 24,000, 37,000, and 44,000. Okuda et aL (Okuda, K., A. Yamanoto, Y. Naito, I. Takazoe, J. Slots, R. J. Genco [1986] "Purification and Properties of Hemagglutinin from Culture Supernatant of *Bacteroides gingivalis," Infect. Immun.* 55:659–665) also purified a hemagglutinin of *P. gingivalis* 381 from culture supernatant which appears to have vesicle or tubelike structures and is comprised mainly of a 40,000 molecular-weight protein. Their recent report indicated that sera from most patients with adult periodontitis reacts to the hemagglutinin antigen at 43,000 and 57,000 molecular weights (Naito, Y., K. Okuda, I. Takazoe [1987] "Detection of Specific Antibody in Adult Human Periodontitis Sera to Surface Antigens of *Bacteroides gingivals," Infect. Immun.* 55(3):832–834).

Recombinant DNA techniques have proven to be powerful tools for the study of pathogenesis. However, recombinant DNA techniques have been applied only sparingly to the study of gram-negative anaerobic pathogens and even less to the study of the molecular mechanisms of periodontopathogenesis. The recombinant DNA methodologies offer advantages over previous methods used in the study of oral pathogens. For example, the cloning of *P. gingivalis* antigens allows for a genetic and molecular analysis of the gene(s) which presently is difficult due to the lack of knowledge about the genetic system in *P. gingivalis.*

BRIEF SUMMARY OF THE INVENTION

Genes have been cloned and the proteins encoded thereby have been isolated from organisms associated with periodontal disease (PD). In particular, genes from *Porphyromonas gingivalis*, which is an etiological agent of adult PD have been identified, characterized, and sequenced. These genes have also been ligated to an appropriate vector and used to transform an appropriate host cell. The recombinant cells express antigens which elicit immunological responses. Antigens expressed by the *P. gingivalis* clones are also identified and described here.

The invention provides, inter alia, a means of detecting the presence of disease-causing *P. gingivalis*. The detection method involves the use of DNA probes and antibody probes which selectively identify the presence of these bacteria or can be used to identify other organisms, including other prokaryotes or eukaryotes, which have similar nucleic acid or amino acid sequences. Also provided are polypeptides which can be used for the production of antibodies to the organisms associated with PD. The antibodies selectively and specifically bind to the subject proteins and can be utilized in purification and identification procedures. These genes and polypeptides can be used as a vaccine against PD. Further, a means of producing monoclonal antibodies for the antigens associated with periodontal disease is also provided.

BRIEF DESCRIPTION OF THE SEQUENCES

Figure 1:
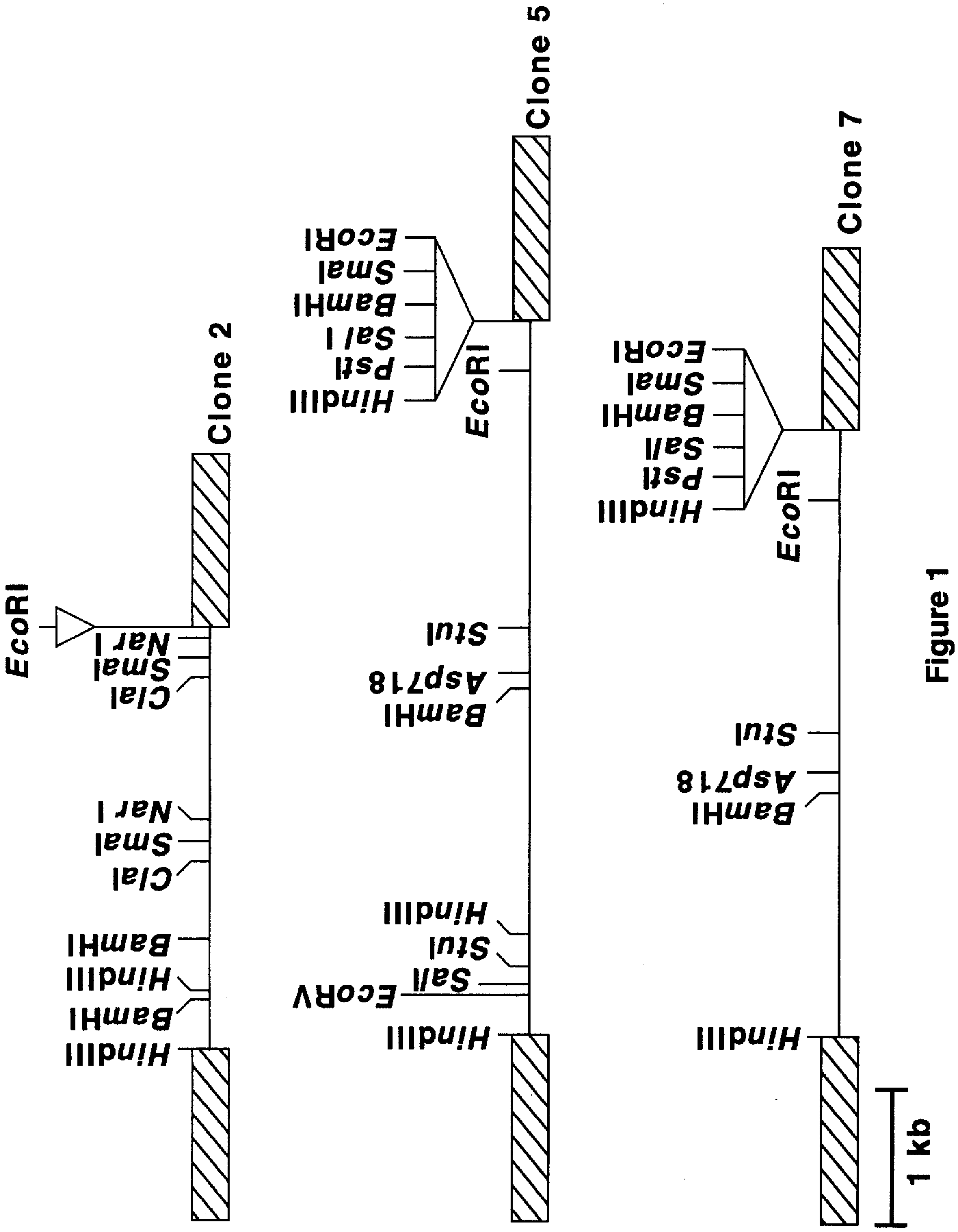
FIG. 1 shows a schematic diagram of restriction enzyme recognition sites of recombinant plasmids from clones 2, 5, and 7. The solid lines represent *P. gingivalis* DNA inserts. The hatched boxes represent pUC9 regions.
Figure 2:
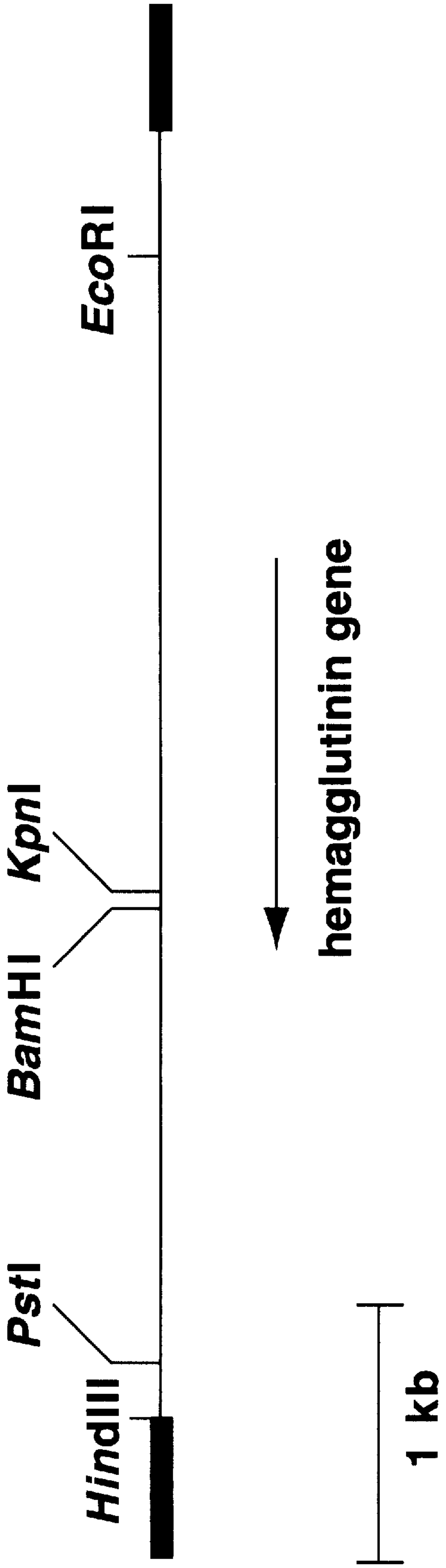
FIG. 2 shows a restriction map of a hemagglutinin gene, hagB. The hemagglutinin gene is contained on a HindIII fragment in pUC9.
Figure 3:
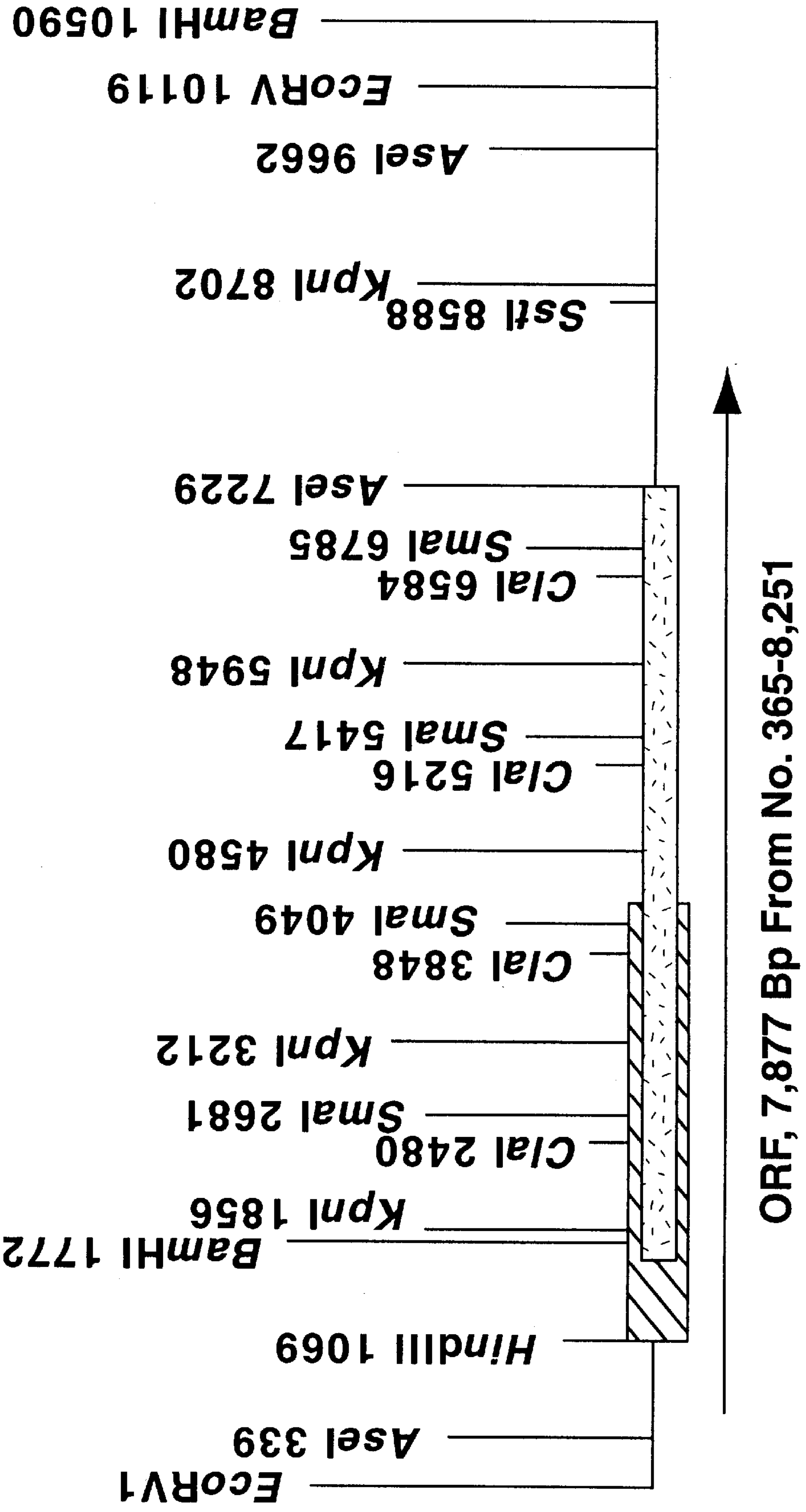
FIG. 3 shows a restriction enzyme map of cloned EcoRV fragments of *P. gingivalis* 381. The heavy shaded area designates the originally cloned ST2 fragment; the thin shaded area designates the amplified IPCR fragment.
Figure 4:
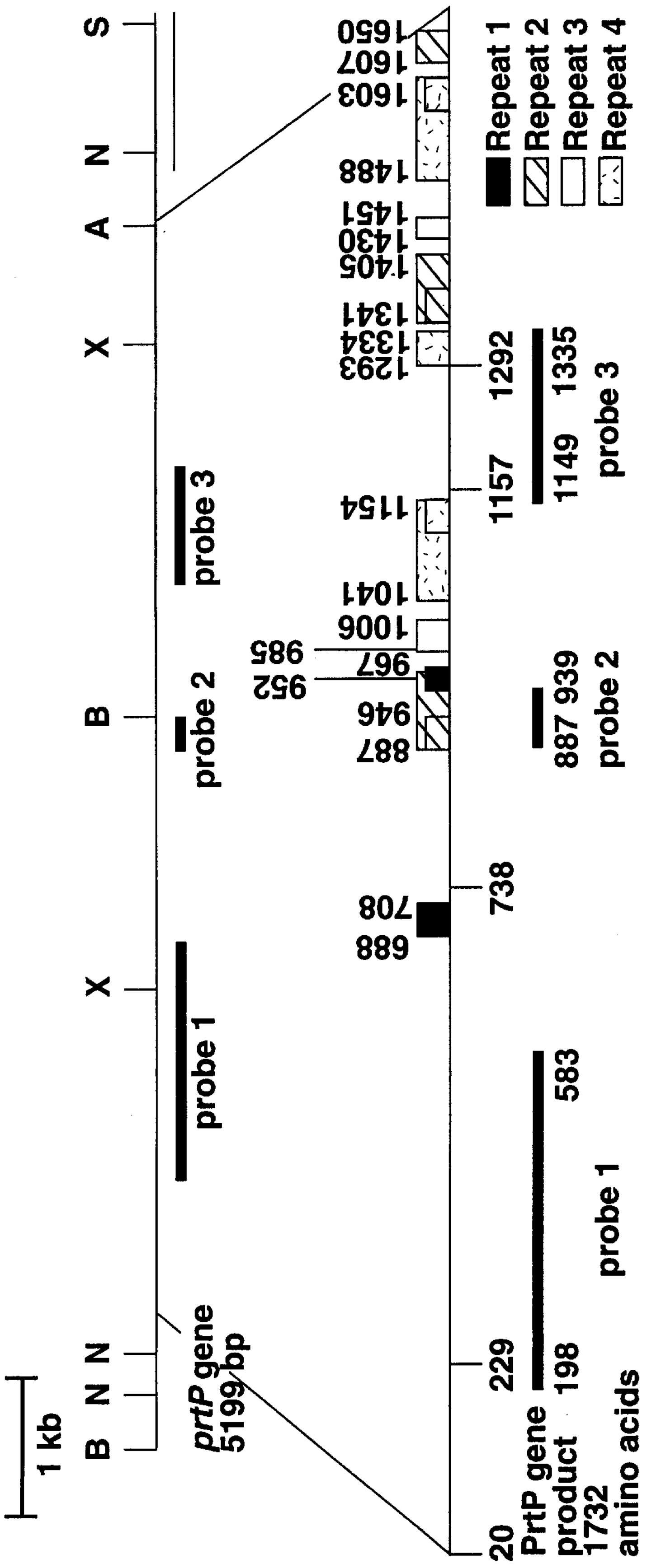
FIG. 4 shows the restriction enzyme map of the prtP gene. The top line represents the prtP gene sequence; the bottom line represents the gene product. Restriction sites shown are: B, BamHI; N, NspI; A, AspEI; S, SacI; X, XcmI. Fragments used as probes for Southern blot analyses are shown as heavy bars below the DNA sequence and in the comparable position below the protein sequence. The DNA region homologous to IS1126 is underlined. Regions repeated within the protein are shown as identical boxes, and the Pro-Asn repeat region is indicated by an asterisk. Putative autodegradation cleavage sites and the signal peptide cleavage site are indicated below the gene product.

SEQ ID NO. 1 is the nucleotide sequence of the hemagglutinin gene designated hagA.

SEQ ID NO.2 is the derived amino acid sequence of the polypeptide encoded by the hagA, gene.

SEQ ID NO. 3 is the nucleotide sequence of the hemagglutinin gene designated hagB.

SEQ ID NO.4 is the derived amino acid sequence of the polypeptide encoded by the hagB gene.

SEQ ID NO. 5 is the nucleotide sequence of the hemagglutinin gene designated hagC.

SEQ ID NO.6 is the derived amino acid sequence of the polypeptide encoded by the hagC gene.

SEQ ID NO. 7 is the nucleotide sequence of the hemagglutinin gene designated hagD.

SEQ ID NO.8 is the derived amino acid sequence of the polypeptide encoded by the hagD gene.

SEQ ID NO.9 is the nucleotide sequence of the gene designated prtP.

SEQ ID NO. 10 is the derived amino acid sequence of the polypeptide encoded by the prtP gene.

SEQ ID NO. 11 is primer APF 147 used according to the subject invention.

SEQ ID NO. 12 is primer APF 148 used according to the subject invention.

SEQ ID NO. 13 is the nucleotide sequence for the entire hagA gene obtained from the EcoRV fragment of the *P. gingivalis* strain, according to the subject invention.

SEQ ID NO. 14 is the deduced amino acid sequence of the polypeptide encoded by the entire hagA gene.

SEQ ID NO. 15 is the nucleotide sequence of the first approximately 1.3 kb repeat sequence from hagA, designated HArep1.

SEQ ID NO. 16 is the deduced amino acid sequence of the polypeptide encoded by HArep1.

SEQ ID NO. 17 is the nucleotide sequence of the second approximately 1.3 kb repeat sequence from hagA, designated HArep2.

SEQ ID NO. 18 is the deduced amino acid sequence of the polypeptide encoded by HArep2.

SEQ ID NO. 19 is the nucleotide sequence of the third approximately 1.3 kb repeat sequence from hagA, designated HArep3.

SEQ ID NO. 20 is the deduced amino acid sequence of the polypeptide encoded by HArep3.

SEQ ID NO. 21 is the nucleotide sequence of the fourth approximately 1.3 kb repeat sequence from hagA, designated HArep4.

SEQ ID NO. 22 is the deduced amino acid sequence of the polypeptide encoded by HArep4.

SEQ ID NO. 23 is a negative primer at 405 nucleotide (t) upstream of the 5' end of the ST 2 fragment used according to the subject invention.

SEQ ID NO. 24 is a positive primer at 529 nt 3' of the ST 2 fragment used according to the subject invention.

SEQ ID NO. 25 is the nucleotide sequence of the entire hagD gene.

SEQ ID NO. 26 is the deduced amino acid sequence of a polypeptide encoded by a first open reading frame of the entire hagD gene.

SEQ ID NO.27 is the deduced amino acid sequence of a polypeptide encoded by a second open reading frame of the entire hagD gene.

SEQ ID NO. 28 is the nucleotide sequence of the hemagglutinin gene designated hagE.

SEQ ID NO. 29 is the deduced amino acid sequence of the polypeptide encoded by an open reading frame of the hagE gene.

DETAILED DESCRIPTION OF THE INVENTION

The DNA sequences of the present invention comprise structural genes encoding proteins which can be involved in the pathogenesis of bacteria responsible for periodontal disease. The genes of the subject invention can be isolated from the DNA of *Porphyromonas gingivalis*. The genes of the subject invention are further characterized by determination of their nucleotide sequences. After obtaining the DNA, a gene library can be developed and the resulting DNA fragments inserted into suitable cloning vectors which are introduced into a compatible host. Depending on the particular host used, the vector can include various regulatory and other regions, usually including an origin of replication, and one or more promoter regions and markers for the selection of transformants. In general, the vectors will provide regulatory signals for expression, amplification, and for a regulated response to a variety of conditions and reagents.

Various markers can be employed for the selection of transformants, including biocide resistance, particularly to antibiotics such as ampicillin, tetracycline, trimethoprim, chloramphenicol, and penicillin; toxins, such as colicin; and heavy metals, such as mercuric salts. Alternatively, complementation providing an essential nutrient to an auxotrophic host can be employed.

Hosts which may be employed for the production of the polypeptides of the present invention include unicellular microorganisms, such as prokaryotes, i.e., bacteria; and eukaryotes, such as fungi, including yeasts, algae, protozoa, molds, and the like. Specific bacteria which are susceptible to transformation include members of the Enterobacteriaceae, such as strains of *Escherichia coli*;

Salmonella; Bacillaceae, such as *Bacillus subtilis*; Pneumococcus; Streptococcus; *Haemophilus influenzae*, and yeasts such as Saccharomyces, among others.

The DNA sequences can be introduced directly into the genome of the host or can first be incorporated into a vector which is then introduced into the host. Exemplary methods of direct incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

Genomic libraries of *P. gingivalis* DNA were constructed in known plasmid expression vectors. For example, the plasmid expression vector, pUC9, contains the pBR 322 origin of replication, the pBR 322 ampicillin resistance gene, and a portion of the lac Z gene of *E. coli* which codes for the α-peptide of β-galactosidase. The amino terminus of the lac Z gene contains a polylinker region which has multiple unique cloning sites. Transformation of *E. coli* JM109, which is defective in β-galactosidase, with pUC9 complements the bacterial β-galactosidase activity, resulting in the ability of the bacterial cell to metabolize the lactose analog X-GAL to a blue color. Cloned DNA inserted in the polylinker region interrupts the lac Z gene of the plasmid. Therefore *E. coli* transformants resulting from recombinant plasmids are unable to metabolize X-GAL and appear as white colonies on X-GAL containing plates.

*E. coli* clones were isolated which stably exhibited *P. gingivalis* antigen expression. These antigens were detected in intact cells both by filter-binding enzyme immunoassay and ELISA. One of these clones, clone 2, was found to encode a polypeptide with an average molecular weight of greater than 125 kD, seen in polyacrylamide gels and detected by Western blot analysis. This polypeptide was later determined to be greater than 144 kD. The entire hagA gene which was originally identified from clone 2 is now determined to encode a 283.3 kD protein. Expression of the *P. gingivalis* antigen in clone 2 occurs either in the presence or absence of IPTG but is enhanced by IPTG stimulation. The expression of the clone 3 antigen was also found to be stimulated by IPTG in the same manner as clone 2.

When antigen-expressing clones were surveyed for functional activities, clones 2, 5, and 7 were able to agglutinate erythrocytes whereas *E. coli* JM109 (pUC9) was not. The restriction maps and Southern blot hybridization of these clones indicated that clone 2 cells contain a Porphyromonas DNA insert different from clones 5 and 7. Clone 5, which is also able to autoagglutinate, has a 760 bp DNA fragment in addition to a 4,800 bp fragment in common with the clone 7 insert. Subcloning of these two fragments in different orientations revealed that the 4,800 bp DNA encoded for the hemagglutinating activity and the 760 bp DNA for the autoagglutinating activity. Both fragments must contain a Porphyromonas promoter since the subclones with opposite orientations of the inserts still express functional proteins, indicating that antigen expression of clones 5 and 7 is not stimulated by IPTG.

Western blot analysis of clones 5 and 7 and minicell analysis of the subclones further revealed that the *P. gingivalis* DNA fragment encoded polypeptides of approximately 16 kD and approximately 49–50 kD. These polypeptides were sized using SDS-PAGE, under denaturing conditions. A native 49–50 kD protein was also purified by immurtoaffinity chromatography. No other purified 49–50 kD protein associated with hemagglutination has been reported. Therefore, the 49–50 kD protein is a previously undetected surface antigen involved in hemagglutination.

*E. coli* adsorbed rabbit-polyclonal antibody against clone 2 was found to react with several bands in the *P. gingivalis* cell lysate preparation separated by SDS-PAGE. The most rapidly Developing and strongest reaction appeared at two bands of 43 kD and 38 kD. Two bands of 32 kD and 30 kD appeared later and three faint bands of 110 kD, 90 kD and 75 kD sometimes were visible still later. This strongly suggests that the *P. gingivalis* hemagglutinin is expressed in clone 2.

*E. coli* adsorbed rabbit-polyclonal antibody against clones 5 and 7 also reacted with two bands of 43 kD and 38 kD, but barely reacted with the higher bands of 110 kD, 90 kD, and 75 kD, and did not react with the bands of 32 kD and 30 kD. Thus, clones 5 and 7 contain DNA inserts which are nonhomologous with clone 2 and express different antigenic epitopes, but all function as hemagglutinin. The clone 7 insert contains a Porphyromonas promoter but the clone 2 insert does not.

An *E. coli* host (clone 2) has been designated *E. coli* pST 2 and deposited with the American Type Culture Collection (ATCC), 12301 Parklawn Drive, Rockville, Md. 20852. Also, an *E. coli* host (clone 5) has been designated *E. coli* pST 5 and it, too, has been deposited with the ATCC. These deposits were assigned the following accession numbers:

| Culture | Accession number | Deposit date |
|---|---|---|
| *E. coli* pST 2 | ATCC 67733 | June 24, 1988 |
| *E. coli* pST 5 | ATCC 67734 | June 24, 1988 |

The subject cultures have been deposited under conditions that assure access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace a deposit should the depository be unable to furnish a sample when requested. All restrictions on the availability to the public of the subject culture deposits will be irrevocably removed upon the granting of a patent disclosing them.

The novel genes disclosed and claimed herein can be probed out of the *E. coli* strains which have been deposited with the ATCC. The isolation of these genes can be performed using techniques which are well-known in the molecular biology art. The isolated genes can be inserted into appropriate vehicles which can then be used to transform another microbe.

It is well understood in the field of biotechnology that the subject genes and gene products have many valuable uses.

For example, the genes themselves, and fragments thereof, which comprise particular nucleic acid sequences can be used to specifically and selectively hybridize to, or probe, other nucleic acid sequences to determine the presence of homologous sequences therein. This use of the subject nucleotide sequences, or fragments thereof, as probes can have advantageous applications in their use as a diagnostic tool, identifying organisms or other transformants that have nucleic acid sequences which are sufficiently homologous such that, using standard procedures and conditions, hybridization can occur between the test sequences and the probe. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designated to improve the function of the sequence or otherwise provide a methodological advantage.

In addition, the subject nucleotide and fragments thereof can be sequences useful as primers in the preparation and manufacture of sequences by polymerase chain reaction (PCR), inverse polymerase chain reaction (IPCR), or other nucleic acid synthesis methods. Obviously, the subject genes and fragments can be useful for the production of the gene product, i.e., the antigen or polypeptides encoded thereby.

Mutations, insertions, and deletions can be produced in a given polynucleotide sequence in many ways, and these methods are known to the ordinary skilled artisan. Other methods may be come known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention. Thus, mutational, insertional, and deletional variants of the disclosed sequences can be readily prepared by methods which are well known to those skilled in the art. These variants can be used in the same manner as the instant probes so long as the variants have substantial sequence homology with the probes.

The gene products can also have a variety of uses. For example, the antigens so produced by a gene in a transformed host can be useful in the production of antibodies to the antigen. Those antibodies can be used as probes, when labeled, or can be used in affinity separation techniques. These polypeptides can also be useful as molecular weight markers in chromatographic or electrophoretic procedures, or the like, where molecular weights are used to characterize an unknown polypeptide or identify or confirm the existence of a known polypeptide.

Following are examples which illustrate materials, methods and procedures, including the best mode, for practicing the invention. These examples are illustrative and should not be construed as limiting.

EXAMPLE 1

Preparation of chromosomal DNA

*Porphyromorias gingivalis* 381 obtained from a stock culture was grown on plates containing Trypticase soy agar (MBL Microbiology Systems, Cockeysville, Md.) supplemented with sheep blood (5%), hemin (5 μg/ml), and menadione (5 μg/ml). The organism was also grown in 10 ml of Todd-Hewitt broth (BBL) supplemented with hemin (5 μg/ml), menadione (5 μg/ml) and glucose (2 mg/ml). Cultures were incubated in an anaerobic chamber in a $N_2$—$H_2$—$CO_2$ (85:10:5) atmosphere at 37° C. until the log phase of growth was obtained. The 10 ml broth culture was transferred into 25 ml of the same medium and subsequently transferred to 500 ml of medium. Incubation was at 37° C. anaerobically until a late log phase culture was obtained. *E. coli* JM109 [rec A1, end A1, gyr A96, thi, hsd R17 sup E44, rel A1, (lac-pro AN), (F;tra D36, proAB, lac IZ M15)] and the plasmid expression vector pUC9 have been described previously (Viera, J., J. Messing [1982] "The pUC Plasmids, an M13 mp 7-Derived System for Insertion Mutagenesis and Sequencing with Synthetic Universal Primers," *Gene* 19:259–268). *E. coli* JM109 was cultured in Luria-Bertani (LB) medium consisting of Bacto-tryptone (10 g/l), Bacto-yeast extract (5 g/l), and NaCl (5 g/l). For solid media, Bacto-agar was added at a final concentration of 15 g/l. *E. coli* JM109 transformants were selected and maintained on LB plates containing 50 μg of ampicillin/ml.

Next, chromosomal DNA from *P. gingivalis* 381 was prepared as follows: One to three liters of cells were pelleted by centrifugation and washed once with 1× SSC buffer (0.87% NaCl, 0.04% sodium citrate) containing 27% sucrose and 10 mM ethylenediaminetetraacetic acid (EDTA). The cells were pelleted and resuspended in 1/50 of the original volume of the same buffer at 4° C. Lysozyme (5 mg/ml) in SSC was added to 0.5 mg/ml; the mixture was mixed thoroughly and incubated at 37° C. for 10 minutes. Nine volumes of 1% SSC containing 27% sucrose 10 mM EDTA and 1.11% SDS (prewarmed to 39° C.) were added and the cell suspension was incubated at 37° C. for 10 to 30(minutes until cell lysis was complete. In order to denature any contaminating proteins, proteinase K was added to a final concentration of 1 mg/ml and the lysate was incubated at 37° C. for 4 hours. DNA was extracted twice with phenol, twice with phenol-chloroform (1:1 by volume), and four times with chloroform. Two volumes of absolute alcohol were added and the precipitated DNA was spooled onto a glass rod. The purified DNA was rinsed with 70% ethanol and suspended in TE buffer, pH 8.0 (10 mM Tris-HCl pH 8.0, 1 mM EDTA).

Alternatively chromosomal DNA was isolated from *P. gingivalis* 381 by a method of CTAB (hexadecyltrimethyl ammonium bromide)/CsCl ultra centrifugation. Briefly, 0.4–0.5 g wet cells was resuspended in 9.5 ml TE buffer (10 mM Tris/Cl, pH 8.0, 1 mM EDTA, pH 8.0), and then 0.5 ml of 10% SDS, and 50 μl of 20 mg/ml proteinase K were added and incubated for 1 hour at 37° C. Then 1.8 ml of 5M NaCl and 1.5 ml CTAB/NaCl were added and incubated 20 minutes at 65° C. The mixture was extracted with Chloroform/isoamyl alcohol and precipitated with 0.6 volume isopropanol. DNA pellet was dissolved in 20 ml TE buffer and 20 g CsCl and 500 μl of 10 mg/ml ethidium bromide were added and centrifuged 30 minutes at 12,000 rpm using a Beckman GA-20 rotor. The supernatant was then centrifuged in a Beckman VTi50 rotor for 18 hours at 45,000 rpm. DNA band was collected under long wave UV lamp and ethidium bromide was removed by water saturated butanol extraction and dialyzed against TE buffer thoroughly to remove CsCl.

Chromosomal DNA from the *P. gingivalis* strain W12 can be obtained by similar methods.

EXAMPLE 2

Isolation of Plasmid DNA and Construction of Genomic Libraries

Plasmid DNA was isolated by the method of Ish-Horowicz and Burke (Ish-Horowicz, D., J. F. Burke [1981] "Rapid and Efficient Cosmid Cloning," *NucleicAcids Res.* 9:2989–2998) in which cells were lysed with SDS-EDTA in the presence of NaOH. Potassium acetate, pH 4.8, was added at 4° C. and cell debris, protein, RNA, and chromosomal DNA were removed by centrifugation. The plasmid was precipitated with two volumes of ethanol, washed with 70% ethanol, dried, and resuspended in TE buffer at pH 7.5. The plasmid was separated from contaminating RNA and any remaining chromosomal DNA by cesium chloride density centrifugation in the presence of ethidium bromide. Ethidium bromide and cesium chloride were removed by butanol extraction and dialysis, respectively. The dialyzed plasmid was then phenol-chlorcform extracted, ethanol precipitated, and resuspended in TE buffer.

Purified *P. gingivalis* DNA was then partially digested with Sau3A restriction endonuclease to create fragments of 2–10 kilobases which were ligated to the dephosphorylated BamHI site of vector pUC9 with $T_4$ DNA ligase by standard methods (Maniatis, T., E. F. Fritsch, J. Sambrook [1982] *Molecular Cloning: A Laboratory Manual*, Cold Spring Harbor Laboratory, Cold Spring Harbor, N.Y.; Sambrook, J., E. F. Fritsch, T. Maniatis [1989] *Molecular Cloning: A Laboratory Manual*, Cold Spring Harbor Laboratory, Cold Spring Harbor, N.Y.; and Wizard Mini-Prep Kit, Promega Co., Madison, Wis.). Genomic fragments were also obtained by partial digestion of the chromosomal DNA with HindIII restriction endonuclease and ligated to the dephosphorylated HindIII site of pUC9. The recombinant plasmids were used to transform *E. coli* JM109. *E. coli* JM109 was grown to an early log phase ($OD_{550}$=0.2) in LB broth. Ten ml of the culture were centrifuged at 5,000 rpm, for 5 minutes at 4° C. and resuspended in 2 ml of transformation buffer 1 (TFM 1, 10 mM Tris-HCl, pH 7.5, 0.15M NaCl). The cells were then pelleted and resuspended in 2 ml of TFM 2 (50 mM $CaCl_2$) and incubated on ice for 45 minutes. The cells were again pelleted and gently resuspended in 3 ml of TFM 2, and dispensed into 0.2 ml aliquots. One-tenth ml of TFM 3 (10 mM Tris-HCl, pH 7.5, 50 mM $CaCl_2$, 10 mM $MgSO_4$) was added to each aliquot followed by varying amounts of DNA. The cells were then allowed to incubate on ice for 45 minutes, and heat shocked at 37° C. for 2 minutes. LB broth (0.5 ml) was added and the cell suspension was incubated at 37° C. for 1 hour. Finally, the cells were plated on LB agar containing ampicillin (50 $\mu$g/ml) and 5-bromo-4-chloro-3-indolyl-β-D-galactopyranoside (X-GAL) (200 $\mu$g/ml) and incubated for 24 to 48 hours at 37° C. All transformants were stored at −70° C. in LB broth with ampicillin (50 $\mu$g/ml) and 20% glycerol.

EXAMPLE 3

Preparation of Antisera and Assay of Antibody Titer

Late exponential phase cells of *P. gingivalis* strain 381 were pelleted, washed with 0.01M phosphate-buffered saline (PBS) pH 7.2, and resuspended in PBS and 0.01 sodium azide at 4° C. for at least 1 hour. The cells were again washed with PBS, resuspended to a concentration of $1\times10^9$ cells/ml and emulsified in an equal volume of Freund's incomplete adjuvant. The cell emulsion was injected in 3 doses at two week intervals for 4. weeks subcutaneously in the back of adult New Zealand rabbits. Each rabbit was given a booster dose 50 to 60 days later. Antisera were collected from the marginal ear veins just prior to immunization and beginning one week after the booster dose. All sera were stored at −20° C.

Rabbit anti-*P. gingivalis* antiserum was adsorbed 4 times with *E. coli* JM109 harboring pUC9 plasmid [*E. coli* JM109 (pUC9)]. For each adsorption, *E. coli* cells from 1 liter of a stationary phase culture were washed and mixed with 3 ml of serum at 4° C. for 1 hour. The serum was recovered by pelleting the cells at 5,000×g for 20 minutes. For sonicate adsorption, *E. coli* cells from 500 ml of stationary phase growth suspended in 5 ml PBS were disrupted by sonication and mixed with *E. coli* cell-adsorbed serum for 1 hour at 4° C. The mixture was centrifuged at 100,000×g for 1 hour and the resulting clear serum was stored at −20° C.

Sera were Then tested for anti-*P. gingivalis* and anti-*E. coli* activities by an enzyme-linked immunosorbent assay (ELISA). *P. gingivalis* cells suspended in carbonate-bicarbonate buffer, pH 9.6 ($10^8$ cells per well) were fixed to microtiter plates at 4° C. overnight. After the wells were washed with 0.5% "TWEEN-20" in PBS, 1% bovine serum albumin (BSA) in PBS was added to each well, and the plates were incubated for 2 hours at room temperature in order to saturate the binding sites. After washing the plates, serially diluted antiserum was added and plates were incubated for 1 hour at room temperature followed by a second wash with 0.5% "TWEEN-20" in PBS. Peroxidase conjugated goat anti-rabbit IgG, diluted 1:1000 in 1% BSA, was added and the plates were again incubated at room temperature for 1 hour. After a final washing, a color-forming substrate solution (0-phenylenediamine, 0.5 g/100 ml in 0.1M citrate buffer, pH 4.5, and 1.8% hydrogen peroxide) was added, and the plates were incubated for 30 minutes at room temperature. The absorbance at 492 nm was measured with a Titertek Multiscan reader. An absorbance of 0.05 or more over background was considered positive. Background readings were obtained from the wells in which all reagents except anti-*P. gingivalis* antiserum was added. Normal rabbit serum was also tested against *P. gingivalis* antigen. To test the effectiveness of adsorption, the titers of treated sera were assayed as described above except that *E. coli* JM109 (pUC9) whole cells were used as the antigen.

It was found that rabbit anti-*P. gingivalis* antiserum had an antibody titer of 1:64,000 to *P. gingivalis* and 1:160 to *E. coli* (pUC9), whereas normal rabbit serum had an antibody titer of 1:10 to *P. gingivalis* and 1:80 to *E. coli* (pUC9). Adsorption of anti-*P. gingivalis* antiserum with *E. coli* (pUC9) resulted in a slight reduction of antibody titer to *P. gingivalis* and reduced the anti-*E. coli* titer to zero or 1:10.

EXAMPLE 4

Filter-Binding Enzyme Immunoassay

Ampicillin-resistant transformants which formed white colonies in the presence of X-GAL were spotted onto LB3 agar plates with ampicillin, grown overnight, and blotted onto nitrocellulose filter disks. *P. gingivalis* and *E. coli* JM109 (pUC9) were also spotted onto each filter as a positive and negative control, respectively. Duplicate prints of the colonies on nitrocellulose filters were made and colonies on one of each duplicate print were lysed by a 15-minute exposure to chloroform vapor. Filters were then air dried for 30 minutes and soaked for 2 hours in PBS containing 3% BSA. After the filters were washed, adsorbed rabbit anti-*P. gingivalis* antiserum was added and the filters were incubated in a solution of peroxidase conjugated goat anti-rabbit immunoglobulin for 1 hour. After washing, the filters were developed in a color-forming substrate solution consisting of 0.06% 4-chloro-1-naphthol and 3% hydrogen peroxide in a 1:4 solution of methanol-TBS (50 mM Tris hydrochloride, 200 mM NaCl, pH 7.4). Clones which developed a blue color were picked and rescreened by the same procedure.

A total of 1,700 colonies of transformants resulting from HindIII restricted chromosomal DNA. were tested for the expression of *P. gingivalis* antigens. Seven clones gave positive signals.

EXAMPLE 5

Restriction and Southern Blot Analysis of Recombinant Plasmids

To further confirm the positive results of the filter-binding enzyme immunoassay, plasmid DNA was isolated from each positive clone. Electrophoresis of these unrestricted plasmids showed that each clone contained only one recombinant plasmid.

Southern blot analysis was also performed to confirm that the DNA inserts were derived from the *P. gingivalis* DNA. Plasmids were isolated from all the clones that were positive in the filter-binding enzyme immunoassay. Restriction endonuclease digestions were performed under conditions described by the manufacturer to produce complete digestion. Agarose gel electrophoresis was performed as described by Maniatis et al. (1982, supra).

Recombinant plasmid and pUC9 vector DNAs were digested to completion with the appropriate restriction enzymes and run on a 1.2% agarose gel. *P. gingivalis* DNA partially digested with Sau3A, and HindIII-digested *Eikenella corrodens* clone 18 DNA were also loaded in the gel. The DNA was transferred to "BIODYNE" nylon membrane by Southern transfer (Southern, E. M. [1975] " Detection of Specific Sequences Among DNA Fragments Separated by Gel Electrophoresis," *J. Mol. Biol.* 98:503–517). *P. gingivalis* DNA partially digested with HindIII was nick translated cloned DNAs were digested with various restriction enzymes and analyzed by agarose gel electrophoresis. The size of inserts of clones 1,2, and 4 were found to be 3.2, 3.2, and 3.3 kb, respectively (Table 1). Clones 1 and 2 also contained plasmids of the same size and identical restriction fragments.

TABLE 1

Characterization of *E. coli* transformants which express *P. gigivalis* antigens

| | Colonies reacted with antiserum | | Size of *B. gingivalis* |
|---|---|---|---|
| Clone No. | unlysed | lysed | DNA cloned (Kb) |
| 1 and 2 | +[a] | + | 3.2 |
| 3 | + | + | 1.1 |
| 4 | + | + | 3.3 |
| 5 and 6 | + | + | 5.5 |
| 7 | + | + | 4.8 |
| 8 | –[b] | + | 3.5 |

[a]= Positive reaction
[b]= Negative, not reactive

EXAMPLE 6

Assay of the Titer of Anti-*P. gingivalis* Antiserum to *E. coli* Transformants Which Express *P. gingivalis* Antigens Cultures of each representative clone were prepared by 100-fold dilution of overnight cultures and grown for 2 hours at 37° C. Isopropyl-β-D-thiogalactopyranoside (IPTG) was added to specific cultures at a final concentration of 1 mM and the cells were pelleted by centrifugation 4 hours later. The cells were washed, resuspended in 1/10 volume of PBS, and the optical density of each suspension was determined at 550 nm. Cell lysate antigen was prepared by breaking the cells with a sonicator. The protein concentration of each lysate was determined by the Bio-Rad protein assay (Bio-Rad Laboratories, Richmond, Calif.). Determination of the titer of anti-*P. gingivalis* 381 against these antigens was performed with the with ($\alpha$-$^{32}$P dCTP) (400 Ci/mmol, Amersham Corp., Arlington Heights, Ill.) as described by Maniatis et al. (1982, supra). The membrane-bound DNA was hybridized to the nick-translated probe at 42° C. in 50% formamide for 16 hours by the method recommended by the manufacturer (Pall Ultrafine Filtration Corp., Glen Cove, N.Y.) which was adapted from Wahl et al. (Wahl, G. M., M. Stern, G. R. Stark [1979] "Efficient Transfer of Large DNA Fragments from Agarose Gels to Diazobenzyloxy-Methyl-Paper and Rapid Hybridization by Using Dextran Sulfate," *Proc. Natl. Acad. Sci. USA* 76:3683–3687). The membrane was washed at room temperature in wash buffer (2×SSC and 0.1% SDS) four times each for 5 minutes and twice at 50° C. each for 15 minutes in 0.1×SSC, 0.1% SDS. An autoradiogram was obtained with Kodak XAR-5 film (Eastman Kodak Co., Rochester, N.Y.) and Cronex Quanta II intensifying screen (DuPont Co., Wilmington, Del.).

Clones 1, 2, 4, 5, 7, and 8 were generated from HindIII-restricted chromosomal DNA. After digestion with HindIII, only clones 5, 6, 7, and 8 revealed fragments of the linear pUC9 vector and fragments of *P. gingivalis* DNA inserts. Plasmid DNAs of these clones were restricted with various enzymes and analyzed by gel electrophoresis. The estimated size of inserts of clones 5, 6, 7, and 8 are 5.5, 5.5, 4.8, and 3.5 kb, respectively (Table 1). Thus clones 5 and 6 were found to contain plasmids of the same size and identical restriction fragments.

Clone 3, which was constructed by ligation of Sau3A partially digested *P. gingivalis* DNA with BamHI cut pUC9, was restricted with SmaI and SalI. Restriction analysis revealed a fragment of linear 9 bp-deleted pUC9 and 2 fragments of insert. Restriction analysis with different enzymes showed that the size of the insert of clone 3 was approximately 1.1 kb.

Although clones 1, 2, and 4 were generated from HindIII restricted DNA, they did not result in fragments of linear pUC9 after HindIII digestion. These cloned DNAs were then restricted with PvuII, which generates a 307 bp fragment containing the polylinker-cloning sites from pUC9. Clones 1, 2 and 4 revealed fragments of linear 307 bp-deleted pUC9 and inserts associated with the deleted fragment. These ELISA as described above ($10^8$ cells or 1 $\mu$g protein per well). Normal rabbit serum exhaustively adsorbed with *E. coli* JM109 (pUC9) was also tested in the same manner.

Anti-*P. gingivalis* antiserum was able to detect antigen expression in all positive clones except clone 8 in an enzyme-linked immunosorbent assay (ELISA). The antiserum reacted with both whole cell and cell lysate antigens. Isopropyl-β-D-thiogalactopyranoside (IPTG) was not necessary to induce antigen expression. However, in the presence of IPTG, clones 2 and 3 showed higher antigen expression, especially when the cell lysate preparations were tested. These results are shown in Table 2.

TABLE 2

Titer of anti-*P. gingivalis* antiserum against *E. coli* transformants which express *P. gingivalis* antigens

| | Antibody titers[a] against test antigens[b] | | | |
|---|---|---|---|---|
| | Whole cell | | Cell Lysate | |
| Organism | IPTG⁻ | IPTG⁺ | IPTG⁻ | IPTG⁺ |
| Clone 1 | 320 | NTC | 320–640 | NT |
| Clone 2 | 320 | 640 | 320–640 | 1280–2560 |
| Clone 3 | 20 | 160 | 40–160 | 1280 |
| Clone 4 | 20–100 | 20–40 | 20–40 | 20–40 |
| Clone 5 | 40–80 | 40–80 | 40–80 | 40–80 |
| Clone 6 | 40 | NT | 40 | NT |
| Clone 7 | 40 | 40 | 40 | 40 |
| Clone 8 | 0 | 0 | 0 | NT |
| *E. coli* JM109 (pUC9) | 0–10 | 0–10 | 0–10 | 0–10 |
| *P. gingivalis* | 40,960–64,000 | NT | NT | NT |
| Control NRS[d] | | | | |

[a]Number designates the reciprocal dilution of the sera which gave $OD_{492}$ reading of 0.05 or more over the background. Antiserum was exhaustively adsorbed with *E. coli* JM109 (pUC9).
[b]Antigens were prepared from cultures grown without IPTG (IPTG⁻) or in the presence of IPTG (IPTG⁺).
[c]Not tested.
[d]Normal rabbit serum exhaustively adsorbed with *E. coli* JM109 (pUC9) did not react to test antigens.

EXAMPLE 7

Sodium Dodecyl Sulfate—Polyacrylamide Gel Electrophoresis (SDS-PAGE)

Five stable representative clones were analyzed for antigen expression by SDS-PAGE. Each of the representative antigen-producing clones was grown to mid-log phase in 3.0 ml of LB broth with 50 μg of ampicillin/ml. The cells were pelleted, washed with PBS, resuspended in 0.3 ml of sample buffer (62.5 mM Tris-hydrochloride, 5% 2-mercaptoethanol, 2% SDS, 10% glycerol, 0.002% bromphenol blue, pH 6.8), and boiled for three minutes. The *P. gingivalis* cell lysate was mixed with an equal volume of sample buffer and treated in the same manner.

SDS-PAGE was performed using a 12% polyacrylamide gel in a vertical slab gel electrophoresis tank (Hoefer Scientific Instruments, San Francisco, Calif.) as described by Laemmli (Laemmli, U. K. [1970] "Cleavage of Structural Proteins During the Assembly of the Head of Bacteriophage T4," *Nature* (London) 227:680–685). A whole cell preparation from clone 2 was separated in a 5% SDS polyacrylamide gel and the expressed protein was initially estimated to have a molecular weight of more than 125 kD and later determined to be greater than 144 kD.

EXAMPLE 8

Assay for Removal of SHA Adherence Inhibition by Anti-*P. gingivalis* Antiserum The expression of components detected by in vitro methods was subjected to further examination. The antigen-expressing clones described in the previous examples were tested for the expression of adhesins for saliva-treated hydroxyapatite (SHA adhesin). Anti-*P. gingivalis* 381 antiserum which inhibits the adherence of *P. gingivalis* 381 to SHA was adsorbed with each antigen-expressing clone until the titer of the antiserum to each clone was reduced to zero. Each adsorbed antiserum was tested for inhibition of *P. gingivalis* adherence to SHA.

*Porphyromonas gingivalis* 381 was cultured in Todd-Hewitt broth. *E. coli* transformants were cultured in LB medium containing 50 μg of ampicillin/ml by preparing 100-fold dilutions of overnight cultures followed by incubation for 2 hours at 37° C. IPTG was added to the cultures, when used at a final concentration of 1 mM, and the cultures were incubated for an additional 4 hours.

An assay for the removal of SHA adherence inhibition using anti-*P. gingivalis* antiserum was used to test for SHA adherence. In order to do this, aliquots of anti-*P. gingivalis* antiserum were adsorbed with each antigen-expressing clone as well as *E. coli* JM109 (pUC9). The titer of each adsorbed antiserum was tested against each clone and *P. gingivalis* whole cell antigen by ELISA as described above.

Whole paraffin-stimulated human saliva was collected and heated at 56° C. for 30 minutes to inactivate degradative enzymes. Extraneous debris and cells were removed by centrifugation at 12,000 rpm for 10 minutes and sodium azide was added to a final concentration of 0.04%.

Hydroxyapatite (HA) beads (BDH Biochemical, Lt., Poole, England) were treated as previously described (Clark, W. B., L. L. Bammann, R. J. Gibbons [1978] "Comparative Estimates of Bacterial Affinities and Adsorption Sites on Hydroxyapatite Surfaces," *Infect. Immun.* 19:846–853). Briefly, 10 mg of beads were washed and hydrated in distilled water in 250 μl plastic microfuge tubes followed by equilibrium overnight with adsorption buffer (0.05M KCl, 1 mM $K_2HPO_4$, pH 7.3, 1 mM $CaCl_2$ and 0.1 mM $MgCl_2$). The beads were incubated with 200 μl of saliva for 24 hours at 4° C. and then washed with sterile adsorption buffer to remove nonadsorbing material. Control tubes without HA were treated identically.

*P. gingivalis* 381 cells were labeled by growth to late log phase in medium supplemented with ($^3H$) thymidine (10 mCi/ml). The cells were pelleted, washed twice in adsorption buffer, and dispersed with three 10-second pulses (medium power) with a micro ultrasonic cell disrupter.

The dispersed cells were mixed with each antiserum (1:100 dilution) and normal rabbit serum to a final concentration of $4\times10^6$ cell/ml. The cell-antiserum suspensions (200 μl) were then added to the SHA beads in microfuge tubes and the tubes were rotated in an anaerobic chamber for 1 hour. Labeled cells alone (no antisera) were treated in the same manner to determine the number of cells adhering to the SHA surface. A control tube containing cells but no SHA was tested to quantitate the amount of cells bound to the tubes rather than to the SHA. One hundred microliters of adsorption buffer containing unadhered cells was removed and placed in minivials containing 3 ml of aqueous scintillation cocktail (Amersham/Searle, Arlington Heights, Ill.), and counted with a scintillation counter (Model 455 Parkard Tricarb). Determination of the number of cells adhering to the SHA was done by subtracting the number of cells (no. of counts) in solution from the total number of cells (no. of counts) which did not adhere to the tube.

The results in Table 3 summarize the SHA inhibition data and indicate that the antiserum adsorbed with each antigen-expressing clone still inhibited the adherence of *P. gingivalis*.

TABLE 3

Inhibition of adherence to SHA by adsorbed anti-*P. gingivalis*

| Inhibitor and dilution | | % adherence[a] | % inhibition[b] |
|---|---|---|---|
| None | | 83.85 | — |
| Normal rabbit serum | 1:100 | 80.08 | 0.05 |
| Antiserum unadsorbed | 1:100 | 22.70 | 72.15 |
| Antiserum adsorbed with: | | | |
| *E. Coli* JM109 (pUC9) | 1:100 | 21.57 | 73.07 |
| Clone 2 | 1:100 | 10.73 | 86.59 |
| Clone 3 | 1:100 | 22.60 | 71.78 |
| Clone 4 | 1:100 | 16.24 | 79.71 |
| Clone 5 | 1:100 | 27.37 | 65.82 |
| Clone 7 | 1:100 | 19.90 | 75.15 |

[a]Percent adherence was calculated from the following formula: % adherence = [(cpm from tube without SHA-cpm from tube with SHA)/(cpm from tube without SHA)] × 100.
[b]Percent inhibition was calculated from the following formula: % inhibition = [1 − (% adherence in the presence of antibody/% adherence in the absence of antibody)] × 100.

EXAMPLE 9

Direct Hemagglutination Assay

The rationale to identify the clones which express hemagglutinin were analogous to those described for the SHA adhesin. The anti-*P. gingivalis* antiserum adsorbed with each antigen-expressing clone and *E. coli* JM109 (pUC9), as described for the SHA assay, were tested for removal of hemagglutination inhibition activity of anti-*P. gingivalis* antiserum. Since it is necessary to determine the minimum number of *P. gingivalis* cells which produce hemagglutinin before performing the hemagglutination inhibition assay, a direct hemagglutination assay of antigen-expressing clones together with *P. gingivalis* was first performed.

A direct hemagglutination assay was used to test for adhesion to erythrocytes. The hemagglutination assays were carried out in V-bottom microtiter plates (Dynatech Laboratories, Inc., Alexandria, Va.). Erythrocytes (sheep or human group O) were washed three times with PBS (0.02M phosphate buffered saline), pH 7.2, and resuspended to a final concentration of 0.2% (v/v). Cells of *P. gingivalis* and antigen-expressing clones were washed twice in PBS and resuspended to an optical density of 0.5 and 2.0, respectively, at 660 nm. The cell suspensions were diluted in a twofold series with PBS and 0.05 ml of the suspensions were added to the wells. *E. coli* JM109 (pUC9), which was prepared in the same manner as the antigen-expressing clones, was included as a control. An equal volume (0.05 ml) of washed erythrocytes was added and mixed with the bacterial cells. The plates were stored for 16 hours at 4° C. and then examined for evidence of hemagglutination as follows. Agglutinated erythrocytes will settle as clumps which will be dispersed throughout the bottom of the wells, resulting in a pinkish-red coating of each well. In the absence of hemagglutination, the erythrocytes will settle on the bottom of the well as a central, smooth, bright red round disk. The titer was expressed as the reciprocal of the highest dilution showing positive agglutination.

The hemagglutination inhibition assay was also carried out in V-bottom microtiter plates. *P. gingivalis* cell suspensions in PBS were adjusted to the optical density of 0.5 at 660 nm. Each antiserum examined for hemagglutination inhibition activity was diluted twofold in a series of wells. Fifty microliters of the bacterial suspension containing twice the minimum number of cells which produced hemagglutination was then added to each well. After incubation with gentle shaking at room temperature for 1 hour, 0.05 ml of the washed erythrocytes were added to each well and mixed. The plates are left for 16 hours at 4° C. and read for hemagglutination as described above for the hemagglutination assay. The titer was expressed as the reciprocal of the highest dilution showing hemagglutination inhibition.

*E. coli* transformants which were able to agglutinate erythrocytes were grown in LB broth containing ampicillin as described above. Two rabbits were injected with each clone as previously described. Sera were exhaustively adsorbed with *E. coli* JM109 (pUC9) and tested for anti-*P. gingivalis* activity by ELISA.

Anti-clone 2 antiserum diluted 1:10 was separately adsorbed with *P. gingivalis, E. coli* JM109 (pUC9), and clones 2, 5, and 7. Washed stationary phase cells of each bacterial culture were prepared as described above. For each adsorption, $10^7$, $10^8$, $10^9$ and $10^{10}$ bacterial cells were mixed with 200 $\mu$l of serum and the suspensions were stored at 4° C. overnight. The sera were recovered by centrifugation at 12,000×g for 10 minutes. Each adsorbed antiserum was assayed by ELISA to determine the titer to *P. gingivalis.*

The direct hemagglutination assay of these clones demonstrated that clones 2, 5, and 7 did agglutinate sheep erythrocytes, whereas *E. coli* JM109 (pUC9) did not. The hemagglutination titer of clone 2 was 2 and that of clones 5 and 7 agglutinated erythrocytes at the undiluted suspension. In addition, clone 5 was found to auto-agglutinate when resuspended in PBS, pH 7.2.

EXAMPLE 10

DNA Restriction Mapping and Characterization Procedures

Restriction endonuclease digestions of the recombinant plasmids from clones 2, 5, and 7 were performed according to manufacturer's directions. Clone 5 DNA was digested with HindIII and two fragments of *P. gingivalis* inserts were isolated from agarose gels by the method of Zhu et al (Zhu, J. W. Kempenaers, D. Van der Straeten, R. Contreras, W. Fiers [1985] "A Method for Fast and Pure DNA Elution from Agarose Gels by Centrifugal Filtration," *Biotech.* 3:1014–1016) employing centrifugal filtration of DNA fragments through a Millipore membrane inside a conical tip. The DNA preparations were extracted with phenol-chloroform, precipitated with ethanol and resuspended in TE, pH 8.0. Each DNA fragment was ligated to HindIII-digested pUC9 and the resulting recombinant plasmids were transformed into competent *E. coli* JM109 cells as described previously. Recombinant plasmids from these transformants were isolated by rapid plasmid DNA isolation (Silhavy, T. J., M. L. Berman, L. W. Enquist [1984] *Experiments with Gene Fusions*, Cold Spring Harbor Laboratory, Cold Spring Harbor, N.Y.), digested with appropriate restriction endonucleases, and analyzed by agarose gel electrophoresis.

The recombinant plasmids of clones, 2, 5, and 7 were restricted with several restriction endonucleases and analyzed in 1.2% agarose gels. A schematic diagram of restriction enzyme recognition sites of these three clones is detailed in FIG. 1. These data show that the clone 2 insert is different from that of clones 5 and 7, whereas clones 5 and 7 have one insert fragment in common. The restriction map of clone 2 revealed that the HindIII site of the DNA insert at the amino terminal end of the β-galactosidase gene was still intact, but a deletion occurred at the other end of the insert and included most of the linker. The linker region with recognition sites of PstI, SalI, BamHI and SmaI was deleted but the EcoRI site was still intact as well as other sites upstream such as PvuII and NarI.

To further confirm the results of the restriction maps, $^{32}P$-labeled clone 7 recombinant DNA was used as a probe for hybridization of restricted recombinant plasmids by Southern blot analysis. Clone 2 DNA restricted with HindIII, EcoRI, and SmaI resulted in DNA fragments of pUC9 and four pieces of insert of approximately 1,400, 1,300, 420, and 150 bp. Clone 5 DNA restricted with HindIII resulted in fragments of pUC9 and two pieces of insert approximately 4,800 and 760 bp. Fragment bands of pUC9 and inserts of approximately 2,800, 2,000, and 760 bp were generated from digestion of clone 5 DNA with HindIII and BamHI. Clone 7 DNA restricted with HindIII alone and HindIII together with BamHI resulted in pUC9 and an insert of 4,800 bp, and pUC9, insert of 2,800 and 2,000 bp, respectively.

Hybridization of these transferred restricted DNAs demonstrated that the clone 7 probe hybridized to pUC9 and the common insert of clones 5 and 7 but not to the insert of clone 2.

Clone 5 was found to agglutinate erythrocytes and autoagglutinate, while clone 7 was only able to agglutinate erythrocytes. Clone 5 has an insert of 760 bp in addition to the common insert of 4,800 bp of clone 7. This data suggested that the 760 bp insert might encode for the autoagglutinating activity and the 4,800 bp fragment for the hemagglutinating activity of clone 5. The recombinant plasmid of clone 5 was thus digested with HindIII to generate pUC9 and inserts of 4,800 and 760 bp. Each insert band was isolated from these transformants and digested with restriction endonucleases. Subclones with different orientations of the insert were obtained. Subclones of 760 bp inserts were designated clone 5.1 and 5.2 and the subclones of 4,800 bp inserts, clone 5.3 and 5.4. Recombinant plasmids of clones 5.1 and 5.2 digested with HindIII did result in pUC9 and the 760 bp inserts, and different patterns of restricted DNAs were seen when digested with SalI. HindIII-restricted recombinant plasmids of clones 5.3 and 5.4 revealed pUC9 and inserts of 4,800 bp, while EcoRI-restricted recombinant plasmids showed different patterns. Both clones 5.1 and 5.2 were able to autoagglutinate when resuspended in PBS, pH 7.2, but could not agglutinate erythrocytes. Clones 5.3 and 5.4 were both able to agglutinate erythrocytes but did not autoagglutinate.

EXAMPLE 11

Identification and Characterization of Gene Products by Sodium Dodecyl Sulfate-Polyacrylamide Gel Electrophoresis (SDS-PAGE), Western Blot, Minicell Analysis, and Immunoaffinity Chromatography

*P. gingivalis* cell lysate and cells of *E. coli* transformants were prepared and analyzed by SDS-PAGE as described above and Western blot as described by Burnette (Burnette, W. N. [1981] "Western Blotting: Electrophoretic transfer of proteins from sodium dodecyl sulfate-polyacrylamide gels to radiographic detection with antibody and radioiodinated protein A," *Anal. Biochem.* 112:195–203). Antisera to clones 2, 5, and 7 exhaustively adsorbed with *E. coli* JM109 (pUC9) were used as probes in the Western blot. Control antisera included anti-clone 2 antiserum also adsorbed with *P. gingivalis* at the ratio of $10^{10}$ cells per 100 $\mu$l of antiserum, and antiserum to *E. coli* JM109 harboring pUC9 with *Eikenella corrodens* DNA insert.

Upon Western blot analysis of clone 2, a protein antigen of approximately 125 kD and a smear of lower molecular weight were detected using *E. coli* adsorbed anti-*P. gingivalis* antiserum but no corresponding antigens expressed in clones 5 and 7 were detected by Western blot analysis. Clones 5 and 7 did, however, express a protein detected as a major band of approximate M. W. 49–50 kD by Western blot analysis and revealed an additional minor band of 27 kD upon minicell autoradiography.

For the identification of clones 5 and 7 gene products, the minicell procedure was used as described by Clark-Curtiss et al and Dougan et al. (Clark-Curtiss, J. E., R. Curtiss III [1983] "Analysis of Recombinant DNA Using *Escherichia coli* Minicells," *Methods Enzymol.* 101:347–362; Dougan, G., M. Kehoe [1984] "The minicell system as a method for studying expression from plasmid DNA," *Methods Microbiol.* 17:233–258). Recombinant plasmids were transformed into *E. coli* as previously described. Transformants were selected on LB plates containing 50 $\mu$g/ml ampicillin and 10 mM isopropyl-β-D-thiogalactopyranoside (IPTG). Colonies were streaked for isolation and grown overnight at 37° C. in BSG (phosphate-buffered saline +0.01% gelatin) containing 50 $\mu$g/ml ampicillin. Minicells were then isolated by sequential low speed centrifugation, high speed centrifugation of the low speed supernatant fluid, and centrifugation through a 5–30% (w/v) sucrose gradient. The sucrose gradient centrifugation was repeated at least once. The minicells were collected and diluted twofold in BSG, pelleted by centrifugation at 10,000 rpm for 10 minutes, and the resulting pellet was resuspended in minicell labeling medium containing no methionine. After incubation of the minicell suspension for 10 minutes at 37° C., 10 $\mu$Ci of $^{35}S$-methionine were added. Following a 15 minute incubation, the cells were chilled for 10 minutes on ice and pelleted by a two minute centrifugation in a microfuge. The cell pellets were then processed for SDS-PAGE. Autoradiography was performed on $^{35}S$-methionine labeled minicell preparations which were electrophoresed on a 12% SDS-PAGE.

In order to determine the native *P. gingivalis* antigens which clone 2 expressed, antisera against clone 2 were made in rabbits for use as a probe in Western blot analysis. Pooled anti-clone 2 antiserum had a titer of 1:16,000 against *P. gingivalis* whole cell antigen. This antiserum was adsorbed exhaustively with *E. coli* JM109 (pUC9) until the anti-*E. coli* titer was reduced from 1:50,000 to 1:10 in the *E. coli* whole cell ELISA. The adsorbed antiserum, diluted to 1:200, was used as a probe to detect antigens separated in a 12.5% SDS polyacrylamide gel and transferred to a nitrocellulose sheet. This antiserum reacted with two major bands of approximately MWs 43,000 and 38,000 and two bands of MWs 32,000 and 30,000 in *P. gingivalis* cell lysate antigen and the 125 kD protein band of expressed antigen in clone 2. Normal rabbit serum reacted to a common 40,000 molecular weight band of all the clones and *E. coli* JM109 (pUC9).

In order to prove that the *P. gingivalis* reactive polypeptides are exclusively *P. gingivalis* proteins, the native *P. gingivalis* antigens were reacted to *E. coli* adsorbed anti-clone 2 antiserum, *P. gingivalis* cell lysate antigen and clone 2 whole cell antigen were again separated in 12.5% SDS-polyacrylamide gel. Upon transfer to a nitrocellulose sheet, each was reacted with (1) *E. coli* adsorbed anti-clone 2 antiserum, (2) *P. gingivalis* adsorbed anti-clone 2 antiserum, and (3) antisera to *E. coli* JM109 harboring pUC9 with an *Eikenella corrodens* DNA insert. *E. coli* adsorbed anti-clone 2 reacted to *P. gingivalis* cell lysate at two major bands of MWs 43,000 and 33,000, two bands of MWs 32,000 and 30,000 and three faint bands of higher molecular weight of approximately 110,000, 90,000 and 75,000 daltons. This adsorbed antiserum also reacted to a band of expressed antigen having a molecular weight greater than 125 kD in clone 2.

To define the native *P. gingivalis* antigens which clones 5 and 7 expressed, antisera against clones 5 and 7 were also made in rabbits and had titers of 1:800 and 1:1,600 to *P. gingivalis* antigens. These antisera exhaustively adsorbed with *E. coli* were used to identify the reactive native *P. gingivalis* antigens. Antisera against clones 5 and 7 at the dilution of 1:5 and 1:10 were found to react with two bands of approximately 43,000 and 38,000 daltons in *P. gingivalis* cell lysate antigen preparation but did not react to the expressed clone 2 antigen. This antiserum also reacted to a common band of approximately 36,000 daltons of *E. coli* antigen in each clone and *E. coli* JM109 (pUC9). Normal rabbit serum did not react to any *P. gingivalis* antigens.

Immunoaffinity chromatography was used to identify and purify the native *P. gingivalis* gene product and to verify that inserts of clones 5 and 7 contained the entire gene. Immune rabbit IgG was purified via DEAE cellulose. Following the precipitation of IgG by the addition of saturated ammonium sulfate to the sera, the IgG was coupled to "AFFI-GEL" (Bio-Rad Laboratories, Richmond, Calif.) by incubation for two hours at room temperature and overnight at 4° C. The coupled material was then used to prepare a 3 $cm^3$ column. After the column was washed extensively with 0.02M phosphate buffer, pH 8.0, 1–2 ml of *P. gingivalis* 381 sonicate containing 18 mg/ml protein were added and run through the column using a peristaltic pump generating a flow rate of 20 ml/hr. The column eluate was monitored for absorbance at 280 nm. The column retentate was eluted from the column by addition of 0.1M glycine, pH 2.5. The recovered retentates were concentrated by centrifugation through a molecular weight cut-off filter, pressure concentration in an Amicon filter (Amicon, Danvers, Mass.), lyophilization, or a combination of the above. When a *P. gingivalis* 381 cell lysate was applied to an affinity column containing anti-clone 7 rabbit IgG, and the retained antigenic peptides were eluted and analyzed by SDS-PAGE, a major band at 49–50 kD was evident.

EXAMPLE 12

Determination of the Relationship Between the Expressed Antigens of Clones 2, 5 and 7

Although antisera against clones 2, 5, and 7 reacted to *P. gingivalis* cell lysate at two major bands of 43,000 and 38,000 MWs, *E. coli* adsorbed anti-clone 2 antiserum also reacted to the greater than 125 kD protein band synthesized in clone 2. However, *E. coli* adsorbed anti-clone 5 and anti-clone 7 antisera did not react to this expressed antigen band of clone 2.

To further define the relationship of the epitopes of the expressed antigen in clone 2 from that of clones 5 and 7, adsorption of anti-clone 2 antiserum with several antigens was performed and each adsorbed anti-clone 2 antiserum was tested for its titer to *P. gingivalis* whole cell antigen by ELISA. The antibody titer to *P. gingivalis* of anti-clone 2 antiserum was removed in a dose response manner by adsorption with *P. gingivalis* and clone 2 cells. Adsorption with *E. coli* JM109 (pUC9), clone 5 or clone 7 did not reduce the antibody titer to *P. gingivalis* of anti-clone 2 antiserum.

The ability of antisera to *P. gingivalis* and hemagglutinable *E. coli* to inhibit the hemagglutinating activity of *P. gingivalis* was determined and is summarized in Table 4. All antisera inhibited *P. gingivalis* hemagglutination at titers four to eight times that of normal rabbit sera.

TABLE 4

Inhibition of hemagglutinating activity of *P. gingivalis* by anti-hemagglutinating *E. coli* antisera.

| Antiserum | Hemagglutination inhibition titer |
|---|---|
| Anti-*P. gingivalis* | |
| unadsorbed | 640 |
| adsorbed with *E. coli* JM109 (pUC9) | 640 |
| Normal rabbit serum[a] | 160 |
| Anti-clone 2 | 320–640 |
| Preimmune | 80 |
| Anti-clone 5 | 160 |
| Preimmune | 40 |
| Anti-clone 7 | 160 |
| Preimmune | 40 |

[a]Normal rabbit serum and preimmune sera titers are from each particular group of rabbits.

EXAMPLE 13

DNA Sequencing of *P. gingivalis* Hemagglutinin Genes

The *P. gingivalis* 381 chromosome contains at least five genes which encode hemagglutinin. The *P. gingivalis* genes encoding hemagglutinin proteins have been designated hagA, hagB, hagC, hagD, and hagE. Genes encoding hemagglutinins were cloned using standard procedures as described above or with minor modifications as readily recognized and understood in the art. Plasmid DNA was isolated from the transformed hosts by a rapid method wherein DNA samples for sequencing were prepared by alkaline-lysis/PEG precipitation method. Briefly, transformed *E. coli* JM 109 cells growing in 50 ml Terrific broth with ampicillin were collected (ca. 0.5 g wet weight) and resuspended in 2 ml of 50 mM glucose, 25 mM Tris/Cl (pH 8.0), and 10 mM EDTA (pH 8.0). A freshly prepared 4 ml solution of 0.2N NaOH, 1% SDS was added and left on ice for 10 minutes. Then 3 ml of ice-cooled potassium acetate solution was added and left on ice for 10 minutes. The mixture was centrifuged 30 minutes at 9,000 rpm at 4° C. and RNase A was added to a final concentration of 20 $\mu$g/ml to the supernatant and incubated for 20 minutes at 37° C. The mixture was extracted thoroughly with chloroform/isoamyl alcohol. An equal volume of isopropanol was added to precipitate DNA, left for 10 minutes at room temperature, and centrifuged for 30 minutes at 9,000 rpm at room temperature. The DNA pellet was dissolved in 3.36 ml of $H_2O$. Then 0.64 ml of 5M NaCl and 4 ml of 13% PEG 8000 (polyethylene glycol, Sigma) were added and left on ice for more than 1 hour. After centrifugation for 15 minutes at 9,000 rpm at 4° C., the DNA pellet was dissolved in sterilized water. By this method, 200 to 400 $\mu$g of highly purified plasmid DNA can be obtained in one day.

A. Characterization of the hagA gene and gene product. The hemagglutinin gene designated hagA was obtained from the *P. gingivalis* 381-derived clone ST 2, and was determined to be more than 4500 bp in length. The sequence of the ST2-derived DNA sequence is shown in SEQ ID NO. 1. The open reading frame (ORF) of the hagA gene from clone 2 was determined to encode a polypeptide of at least 1339 amino acids, and >1.44 kD. The derived amino acid sequence encoded by the hagA gene from clone 2 is shown in SEQ ID NO. 2. A 10,119 bp EcoRV fragment was cloned that included an additional 338 bp of upstream sequence. The complete open reading frame (ORF) of hagA was found to be 7,887 bp in length (bases 365 to 8251 of the EcoRV fragment), encoding a protein of 2,628 amino acids with a molecular weight of 283.3 kD. The nucleotide and deduced amino acid sequences of the entire hagA gene are shown as SEQ ID NO. 13 and SEQ ID NO. 14, respectively. It was initially found that the hagA sequence has an approximately 1.1 kb repeating unit which repeats at least four times and may repeat as many as six times, with only minor differences in the repeat unit. Further analysis confirmed that the hagA gene has four large contiguous direct repeats totalling 5,404 bp in length, each ranging from 1,318 to 1,368 bp in length. Specifically, these approximately 1.3 kb repeat fragments, collectively referred to hereinafter as HArep, are (referring to bp number of EcoRV fragment): HArep3, bp 1862–3211 (SEQ ID NO. 15); HArep2, bp 3212–4579 (SEQ ID NO. 17); HArep3, bp 4580–5947 (SEQ ID NO. 19); and HArep4, bp 5948–7265 (SEQ ID NO. 21). The deduced amino acid sequences for the nucleotide repeat fragments HArep1, HArep2,HArep3, and HArep4are shown as SEQ ID NOS. 16, 18, 20, and 22, respectively. This repeat unit has been shown to have hemagglutinin activity. The results of the hemagglutinin assay for strains having varying numbers of HArep repeat units are shown in Table 5, below.

TABLE 5

| | Hemagglutinin titer | | |
|---|---|---|---|
| Strain | No. of HArep | $A_{660}$ | HA titer |
| 381 (wild-type strain) | >4 | 0.13 | 1/128 |
| pNH9 | 1 | 3 | 1/8 |
| pNH1 | 2 | 0.85 | 1/64 |
| *E. coli* | 0 | | |

When compared with that of hagA, several reported protease genes were found to contain at least one copy of the HArep sequence. For example, prtH, a gene encoding a C3 protease cloned from strain W83, shares a region of 271 amino acids with 95.6% homology to hagA. Rgp-1, the arginine-specific cysteine protease/hemagglutinin gene cloned from strain H66, contains a 522-amino acid region with 93.1% homology, as well as prtR cloned from strain W50. Agp, cloned from strain 381 by Okamoto et al., and prpR, cloned by Curtis et al., which are identical genes to rgp-1 isolated from different strains, each contain one HArep sequence of hagA. An additional gene, agp, which is missing a 713-amino acid internal portion of rgp-1, also contains one HArep sequence. In addition, prtP, a cysteine protease/hemagglutinin gene cloned from strain W12 and described herein, has an 849-amino acid C-terminal region which shares 92.2% homology to hagA, with the last 253 amino acids (almost half of the length of the prtP gene) absolutely identical. Tla, another protease gene cloned from strain W50 by Curtis et al., has a 789-amino acid C-terminal region with 95.2% homology to hagA, with the last 171 amino acids completely identical. This 171-amino acid region constitutes almost three-fourths of the length of the TLA gene. In addition, hagD, a fourth hemagglutinin gene cloned from strain 381, described hereinbelow, has a 523-amino acid region with 92.7% homology, as well as the 3'72-amino acid with 98.6% identity to hagA. HagE, an additional hemagglutinin gene cloned from strain 381, also described hereinbelow, contains a 518-amino acid region with 92.3% homology to hagA. Without exception, these high homology regions of each of these genes are within or extend from the repeat region of hagA. The hagA is a central member of a multigene family which share the HArep sequence.

In addition, each of these genes contains a common 72-amino acid C-terminus with hagA (81.9 to 100% homology), except for prtH, in which this region is located in the middle of the gene.

A search through the National Center for Biotechnology Information Database using the GENINFO Experimental Blast Network Service revealed no significant homology of hagA to any other sequences in the databases except for the *Mycoplasma gallisepticum* hemagglutinin genes (pMGA) and the circumsporozoite protein genes of *Plasmodium falciparum*. These genes were found to have homology to hagA in very short regions (9 of 13 amino acids for the circumsporozoite protein of *P. falciparum* and 11 of 14 amino acids for pMGA of *M. gallisepticum*).

To ensure that the complete hagA gene sequence was isolated from clone 2, chromosome DNA samples were digested by restriction enzymes which did not cut the original cloned fragment clone 2, including AccI, AseI, (Biolabs) VspI (the isoschizomer from Promega), BclI, BglII, BstXI, DraI (BRL), EcoRV, NruI (Stratagene), PstI, PvuII, SalI, SphI, SspI, SstI (Sigma), StuI, and XhoI. The digested fragments were transferred to positive-charged nylon membranes (Boehringer Mannheim Biochemicals, Indianapolis, Ind.) by capillary transfer method. The whole ST2 fragment was labeled and detected by non radioactive Genius Kit (Boehringer Mannheim Biochemicals). Alternatively, a region of the first 394 bp of clone 2, which is distant from the repeat sequence region, was labeled using the non radioactive DIG DNA Labeling and Detection Kit (Boehringer Mannheim) and used as a probe to detect the bound DNA fragments on the nylon membrane. The results were made visible on X-Ray films by Lumi-phos 530 system (Boehringer Mannheim Biochemicals).

Inverse polymerase chain reaction (IPCR) was employed to determine the complete sequence of a gene, and was used to obtain the flanking 5' and 3' sequences and thus the entire nucleotide sequence of the hagA gene. To carry out the IPCR procedure, two 18-mer oligo primers, negative primer at position nt 224 and positive primer at position nt 2032, were chosen and synthesized at University of Florida DNA Synthesis Core Lab. In addition, a negative primer at 405 nucleotide (t) upstream of the 5' end of the ST 2 fragment (GGC AAA CCA AAA AGA TTC, SEQ ID NO. 23) and a positive primer at 529 nt 3' of the ST 2 fragment (TTC TTC CAA CGA CTA CAC, SEQ ID NO. 24) were selected and synthesized at the University of Florida DNA Synthesis Core Facility.

The total AseI (VspI) digested fragments and the 3–7 kb fragments extracted from agarose gel were self-ligated at a DNA concentration of 1–10 ng/μl with 1 U of T4DNA ligase (Promega) per 50 μl reaction mixture for 16 hours at 16° C., respectively. Then, the ligation mixture was heated for 15 minutes at 65° and extracted with phenol/chloroform, chloroform, precipitated with ethanol and resuspended in sterilized distilled water. IPCR reactions were performed in 2 steps: first, the self-ligated DNA sample in buffer was heated for 30 minutes at 94° C.; then, Taq polymerase (Promega) was added and cycled using a PTC-100 Programmable Thermal Controller (MJ Research, Inc., Watertown, Mass.). We used 35 cycles of denaturation at 94° C. for 1 minute, primer annealing at 52° C. for 1 minute, and extension at 72° C. for about 5 minutes.

The amplified mixture was extracted with phenol/chloroform, chloroform and electrophoresed at 1% low melting agarose gel. The excised fragment was then treated with agarase (Boehringer Mannheim Biochemicals). The DNA samples treated with agarase are purified enough for direct sequencing. After analysis of direct sequencing data, the amplified IPCR fragment was cut by HindIII and KpnI and cloned into pBluescript II SK and transformed in *E. coli* JM 109. Several subclones were constructed and one oligo primer was also synthesized to complete the sequencing.

Sequencing of the hagA gene was carried out at the University of Florida DNA Sequencing Core lab using the Taq Dye Primer and Taq Dyedeoxy Terminator Cycle Sequencing Protocol developed by ABI (Applied Biosystems, Inc., Foster City, Calif.) with fluorescent labeled primer(s) and labeled dideoxy nucleotides, respectively. The labeled extension were analyzed on an ABI 373 DNA Sequencer. Sequence data were analyzed by the Sequence Analysis Software Package of the University of Wisconsin.

Southern blot analysis results indicated that AseI restriction of genomic DNA produced a single 6.9 kb fragment which hybridized to the probe used. Under the conditions used, as described, a 5,963 bp fragment was successfully amplified via IPCR which, when sequenced, was found to include an additional 2,997 bp sequence 3' to the ST 2 fragment. The start codon was found to be located 720 bp upstream of the 5' end of the ST 2 fragment. In order to obtain the 3' end of this gene, a BamHI gene bank was constructed from which an 8,818 bp cloned fragment containing an additional 3,362 bp downstream DNA was obtained. Sequencing this downstream region revealed that the stop codon was located 1,017 bp downstream of the 3' end of the 6.9 kb AseI fragment.

The complete ORF of hagA beginning at base No. 365 and ending at base No. 8251 is calculated to encode a 2628-amino acid protein with a molecular weight of 283.3 kD. Analysis of the sequence revealed potential −10, −35 consensus sequences located at bases 168 and 143, respectively. However, no *E. coli*-like ribosome binding site was found upstream of the start codon except for AGG at the −4 to −2 position. Two potential stem loop structures, forming 14 and 9 bp-long inverted repeats were identified 51 and 101 bp downstream of the stop codon, respectively.

Residues No. 5–21 are consistent with a typical, hydrophobic leader or signal sequence according to the Chou-Fasman Prediction. In addition, Chou-Fasman rules predict the beginning amino acids of HArep to be very antigenic and hydrophilic. The amino acid sequence which begins each of the HAreps, is very similar to a region of *M. gallisepticum* hemagglutinin genes. The common repeating amino acid sequence (Pro-Asn) among *P. gingivalis* and *M. gallisepticum* hemagglutinin genes listed above indicates that this region is involved in erythrocyte binding.

The repeat region was found to begin immediately after the first KpnI site at base No. 1862 and to end at base No. 7265, making the entire repeat region 5,404 bp in length without a single gap. The first repeat unit (HArep 1) is 1,350 bp and has 99.5% identity to the second repeat unit. The repeat units HArep 2 and HArep 3 are 1,368 bp in length and are 99.9% identical to each other. The fourth repeat unit (HArep 4) is 1,318 bp in length and has 98.6% identity to HArep 2 and HArep 3, respectively. As shown in SEQ ID NO. 16, the beginning amino acid sequence of the HArep 1 is "Pro Asn Pro Asn Pro Gly Thr Thr Thr . . . " while that of the other three is "Gly Thr Pro Asn Pro Asn Pro Asn Pro Asn Pro Gly Thr Thr Thr . . . " (see SEQ ID NOS. 18, 20, and 22). Thus, HAreps 2–4 at the very beginning contain six amino acids more than HArep 1. This difference is due to HArep 1 containing two fewer repeats of the Pro-Asn sequence since the Gly-Thr is present before the sequence of "Pro Asn Pro Asn Pro Gly Thr Thr Thr . . . " in HArep 1.

Another distinguishing characteristic of the hagA multigene family is the presence of a 72-amino acid sequence normally at the extreme carboxy terminus of the proteins. This region is hydrophobic according to the Chou-Fasman Prediction and can serve to anchor the proteins in the outer membrane or serve in some other common recognition function.

The hemagglutinin (HA) encoded by the hagA gene can have the characteristics of a cysteine protease, a trypsin-like protease, and a hemagglutinin. Hemagglutinins of *Porphyromonas gingivalis* can be involved in virulence. The HAs of *P. gingivalis* are nonfimbral adhesins, since biochemical studies have shown that the purified fimbrillin subunit of *P. gingivalis* failed to agglutinate red blood cells or to inhibit hemagglutination by *P. gingivalis*, and immunological studies have shown that monospecific antibody against the hemagglutinin did not bind strongly to the fibrillar structures of *P. gingivalis*.

It has been previously suggested that protease and hemagglutination activities of *P. gingivalis* are related. One study reported that mutant strains of *P. gingivalis* deficient in trypsin-like protease activity had markedly reduced hemagglutination activity. Others have reported that a 44 kD purified outer membrane hemagglutinin has been further characterized as a cysteine protease. The DNA sequence of hagA was compared with the DNA sequence of an approximately 4.5 kb fragment of genomic DNA from the λFBP1 clone made from the of *P. gingivalis* W12 strain. The gene from the λFBP1 clone was isolated and named prtP (see section F of this Example, below). The prtP gene encodes protein(s) reactive with antibody that inhibits a cysteine protease of *P. gingivalis* W12, and that binds a fibrinogen. The nucleotide sequences of hagA and prtP were compared, and were found to contain internal regions approximately 2 kb in size that share a high degree of sequence similarity. The hagA gene contains three regions that share greater than 90% sequence identity with prtP. These regions include a 217 bp sequence in which there is 90% identity, and a 884 bp sequence in which there is 94% identity and a 500 bp sequence in which there is 97% identity. These findings raise the possibility of relatedness between fibrinogen binding protein and a hemagglutinin of *P. gingivalis*.

B. Characterization of hagB gene and gene product. The gene encoding a hemagglutinin hagB was obtained for sequencing from *P. gingivalis* on a 2.0 kb HindIII BamHI fragment and 2.4 kb BamHI-EcoRI fragment cloned into pUC9 and transformed into *E. coli* JM109. These fragments were subcloned into the M13 bacteriophage vectors for sequencing (Yannish-Peron, C., J. Viera, J. Messing [1985] "Improved M13 phage cloning vectors and host strains: Nucleotide sequences of M13mp18 and pUC9 vectors," *Gene* 33:103–119). The entire lengths of these fragments were sequenced utilizing the universal priming site of M13 and by synthesizing oligonucleotide primers for the remaining regions of the fragments. The sequencing of the 1.7 kb KpnI-PstI fragment and the DNA adjacent to the BamHI site ensured that the 2.0 kb and 2.4 kb fragments were contiguous. *E. coli* JM109 was used as the host strain for transfection with M13 and grown in 2×YT broth. Recombinant phages were detected by using soft agar (0.75%) overlays of 2×YT broth base supplemented with 0.33 mM isopropyl-beta-D-thiogalactopyranoside (IPTG) and 0.02% 5-bromo-4-chloro-3-indolyl-3-galactoside (X-GAL).

Restriction enzymes, T4 DNA ligase, and M13 17-mer primer were purchased from either Bethesda Research Laboratories (Gaithersburg, Md.) or Fischer Scientific Co., St. Louis, Mo.) and were used in accordance with the specifications of the manufacturers. Other oligonucleotide primers were synthesized by the Molecular Biology Resource Facility (Oklahoma City, Okla.). Sequencing reagents were from the T7 Sequencing Kit of Pharmacia (Piscataway, N.J.) or the Sequenase DNA sequencing kit of U.S. Biochemical Corp. (Cleveland, Ohio). The [$\alpha$-$^{35}$S]dATP was purchased from DuPont, NEN Research Products (Boston, Mass.). IPTG and X-GAL were purchased from Sigma Chemical Co. (St. Louis, Mo.).

DNA sequencing was performed by using the dideoxy chain-termination method (Sanger, F., S. Nicklen, A. R. Coulson [1977] "DNA sequencing with chain terminating inhibitors," *Proc. Natl. Acad. Sci. USA* 74:5463–5467). Different portions of each fragment were sequenced from synthesized oligonucleotide primers. The DNA sequence of the gene was determined for both strands and was analyzed by the James M. Pustell DNA and protein sequencing program (International Biotechnologies, Inc., New Haven, Conn.). The nucleotide sequence of the hagB hemagglutinin gene is 1053 nucleotides in length as shown in SEQ ID NO. 3. The mol. % G+C content is 59.9%. The reading frame of the hemagglutinin gene was defined by a putative ribosome binding site and promoters upstream of the ATG start codon and potential stem-loop structures downstream of the stop codon. Beginning 181 to 239 bases upstream of the two potential promoters was a region of direct repeats. A sequence of 41 nucleotides was repeated four times contiguously with only minor differences. Open reading frames were also identified on the opposite strands both upstream and downstream of the hemagglutinin gene.

The amino acid sequence of the hemagglutinin was derived from the nucleotide sequence and determined to be 350 residues in length. The derived protein of $M_r$=39,375 was basic with an isoelectric point of 8.98 and hydrophilic. A potential signal peptide is evident. Cleavage is most probable after amino acids 32–36, though none of these sites conforms ideally to the −3,−1 rules of von Heijne. The derived amino acid sequence encoded by the hagB gene is shown in SEQ ID NO. 4.

Comparison of the nucleotide and derived amino acid sequences with the gene and protein bank libraries did not uncover any significant homology between the hemagglutinin and previously determined sequences.

Upstream from the hemagglutinin reading frame were two potential promoters which in turn were preceded by a series of direct repeats. The function of the direct repeats is not known but it would be reasonable to hypothesize that they have a role in gene expression.

The codon usage for the hemagglutinin was examined and found to follow the pattern for a gene with low level expression, though this pattern was broken in a few instances. In general, the pattern for low expression consists of a low U/C ratio in the third base position of the codon for some amino acids, but a high U/C ratio in the third position for other amino acids. Perhaps due to the high % G+C content of the hemagglutinin gene a low U/C ratio existed for most amino acids. Overall, however, the codon usage followed the pattern for low expression more often than that for high expression. The usage of some codons which specify rate tRNA species in *E. coli* may also be evidence of a lower level of expression of the hemagglutinin gene. Alternatively, the same tRNA species may not be rate limiting in *P. gingivalis* but could explain the difficulty in expressing the cloned product in *E. coli.*

C. Characterization of the hagC gene and gene product. A third hemagglutinin gene, designated hagc was isolated from *Porphyromonas gingivalis* 381. The nucleotide sequence of the hagc gene is shown in SEQ ID NO. 5 and has a 1050 bp coding region. The derived amino acid sequence is shown in SEQ ID NO. 6.

The hagc gene was isolated in a similar manner as the hagB gene. Briefly, isolated *P. gingivalis* 381 chromosomal DNA was digested with HindIII and electrophoresed through a 0.8% agarose gel in Tris-acetate buffer. A band of agarose containing the fragments ranging from 4 to 20 kb was cut out of the gel and the DNA extracted using a phenol freeze/thaw procedure. The DNA was ligated to the dephosphorylated HindIII restricted pUC18 plasmid (Pharmacia LKB Biotechnology, Piscataway, N.J.) using the T4 DNA ligase (Promega Corp.) overnight at 16° C. The recombinant plasmids were transformed into *E. coli* DH5$\alpha$ (BRL) and plated on LB plates supplemented with ampicillin, IPTG and X-GAL. Colonies were picked on duplicate plates and grown aerobically at 37° C. overnight. The clones from one of the duplicated plants were transferred to positively charged nylon membranes (BM Corp.) and lysed according to the procedure described by Sambrook et al. The membranes were then left to dry for 30 minutes and baked at 120° C. for 30 minutes. The hybridization was carried out as described above; however, a 960 bp BamHI-PstI DNA fragment from hagB gene was used as a probe.

Recombinant plasmid DNA was prepared using the alkaline lysis method, modified as described. The cells were grown in LB broth supplemented with 50 $\mu$g/ml ampicillin. The closed circular DNA was purified by equilibrium centrifugation in a continuous CsCl-ethidium bromide gradient. DNA further destined for sequence was additionally submitted to precipitation with polyethylene glycol.

Double stranded DNA sequencing was performed by the University of Florida Interdisciplinary Center for Biotechnology Research DNA Sequencing Core laboratory. Sequencing was accomplished by employing the Taq Dye Primer and Taq Dye Terminator cycle sequencing protocols (Applied Biosystems, Inc., Foster City, Calif.) using the fluorescent primers and dideoxynucleotides, respectively. The labeled extension products were analyzed on an ABI373a DNA sequencer (Applied Biosystems, Inc.). The sequence was obtained for both strands of DNA using the appropriate subclones or synthetic oligonucleotides synthesized by the University of Florida DNA Synthesis Core Facility. the sequencing strategy was designed to sequence overlapping sites used in DNA subcloning. The sequence was analyzed with the Genetic Computer Group Sequence analysis software.

The 1851 bp HindIII-SstII DNA fragment comprising the hagC gene revealed an open reading frame (ORF) of 350 amino acids corresponding to a 39.3 kD protein with an isoelectric point of 8.36. The ATG start site, located at position 374 of the DNA, is preceded by putative −10 ($^{339}$TATTAT$^{344}$) and −35 ($^{314}$TTGCTG sequences which differ from the *E. coli* consensus promoter sequences TATAAT and TTGACA, by one and three nucleotides respectively. However, no match to consensus Shine-Dalgarno sequence could be found upstream the ATG codon. A nearly perfect dyad symmetry of 18 nucleotides can be noticed at the end of the hagC ORF and may represent a potential stem-loop structure used in transcription-termination.

A comparison between the hagB and hagC nucleotide sequences revealed that their ORFs are 99% homologous, but their upstream and downstream regions are only 39.5 and 34.6% homologous, respectively. It is worth noting that both genes encode a 350-amino acid protein which are 98.6% homologous. The Hag B protein exhibits a deduced MW of 39.4 kD and pI of 8.98. The hagB gene possesses two sets of −10 and −35 sequences which are similar to the consensus sequences found in *E. coli*. Contrary to hagC however, a ribosome-binding site can be noted upstream the ATG initiation codon in position 363. Furthermore, four repeats of 42 bp each that are found in the promoter region of hagB are missing from the hagC gene. A potential transcription-termination stem-loop made by a nearly perfect 17 nucleotide long dyad symmetry can also be noted at the end of the hagB gene. No nucleotide sequence or protein exhibiting significant homology to the hagC gene or protein was found using the data bases GenBank, EMBL, or NBRF.

D. Characterization of the hagD gene and gene product. A fourth hemagglutinin gene, designated as hagD, was isolated from *P. gingivalis* 381 using standard procedures as described. The original nucleotide sequence comprising the hagD gene is shown in SEQ ID NO. 7. The hagD ORF as originally determined codes for a 1087 amino acid, 117 kD protein with a pI of 4.5. The derived amino acid sequence encoded by the original hagD gene is shown in SEQ ID NO. 8. The nucleotide sequence for the entire hagD gene is shown as SEQ ID NO. 25. Two open reading frames were identified within the hagD nucleotide sequence. The first open reading frame, bases 696–1790, encodes a polypeptide shown as SEQ ID NO. 26. This polypeptide can have activity as a protease. The second open reading frame, bases 1790–5866, encodes a polypeptide shown as SEQ ID NO. 27. The second encoded polypeptide has activity as a hemagglutinin.

The *P. gingivalis* 381 cells were grown at 37° C. in Todd-Hewitt broth (THB) supplemented with 5 μg/ml hemin and 1 μg/ml menadione in an atmosphere of 10% $H_2$-5% $CO_2$-85% $N_2$. HindIII-restricted genomic DNA was then electrophoresed through TAE agarose gel (9%). The DNA was transferred to a nylon membrane by the capillary alkaline transfer method using 0.4M NaOH-0.6M NaC and labeled using the non radioactive DNA labeling and detection kit (Genius, Boehringer Mannheim). The membrane was prehybridized for 2 hours at 42° C. in 5×SSC (0.75M NaCl, 0.085M sodium citrate (pH 7.0); blocking agent 0.5% (w/v); N-lauroylsarcosine (Na-salt), 0.1% (w/v); sodium dodecyl sulfate (SDS), 0.02% (w/v); formamide 50% (v/v)).

The EcoRI-PvuII DNA fragment from hagA was randomly primed by incorporation of digoxigenin-labeled dUTP. Hybridization was carried out overnight at 42° C. The membrane was washed twice with each of the following solutions: 2×SSC-0.1% (w/v) SDS at room temperature for 5 minutes, and 0.1×SSC-0.1% (w/v) SDS at 68° C. for 15 minutes. Detection was carried out using "LUMI-PHOS" 530 (Boehringer Mannheim), the enhancer for chemiluminescent detection of alkaline phosphatase, according to the manufacturer, and autoradiographed.

A genomic bank was created using HindIII-digested chromosomal DNA from *P. gingivalis* 381, as described above for hagc. Fragments ranging from 4.8 to 6.4 kb were cut out and the DNA was recovered using the phenol freeze/thaw procedure. The DNA was then ligated to the dephosphorylated HindIII restricted pUC18 (Pharmacia) using T4 DNA ligase overnight at 16° C.

Recombinant plasmids were transformed into *E. coli* DH5α (BRL) and plated on Luria-Bertani (LB)(10 g/l Bacto®Tryptone, 5 g/l yeast extract, 5 g/l NaCl, 15 g/l agar) plates supplemented with 50 μg/ml ampicillin. Colonies were picked, transferred to nylon membranes, and subjected to lysis in 10% (w/v) SDS, 3 minutes; 0.5N NaOH-1.5M NaCl, 5 minutes; 1.5M NaCl-0.5M Tris-Cl (pH 7.4), 5 minutes; and 2×SSC, 5 minutes. The membranes were then left to dry for 30 minutes and baked at 120° C. for 30 minutes. Prior to hybridization the membranes were washed in: 5×SSC, 0.5% SDS, 1 mM EDTA (pH 8.0) for 30 minutes at 50° C. Hybridization was then carried out as described above using a 1,228 bp HindIII-SmaI hagA DNA fragment as a probe.

Plasmid DNA was isolated and restriction mapping, was carried out according to procedures described.

Double-stranded DNA sequencing was performed by the University of Florida ICBR DNA Sequencing Core Laboratory. Sequencing was accomplished by employing the Taq Dye Primer and Taq Dye Terminator cycle sequencing protocols using the fluorescent primers and dideoxy nucleotides, respectively. The entire sequence was obtained for both strands of DNA using the appropriate subclones or synthetic oligonucleotides synthesized by the University of Florida DNA Synthesis Core Facility. The sequencing strategy was designed to sequence overlapping sites used in DNA subcloning.

The complete sequence was determined using the Genetic Computer Group Sequence analysis software and the inverse polymerase chain reaction (IPCR) method. For the IPCR procedure, 50–500 ng of *P. gingivalis* genomic DNA restricted with BamHI was circularized and self-ligated with T4 DNA ligase overnight at 16° C. The circularized genomic DNA was amplified by IPCR in a mixture containing: 160 mM each dNTPs, 1.5 mM $MgCl_2$, 1×Buffer [1×=50 mM KCl, 10 mM Tris-HCl (pH 8.3)], 4×$10^{-4}$ mM of the primers APF 147 (5'-GGAATGGGAGATGGAACT-3') (SEQ ID NO. 11) and APF 148 (5'-GTAACCCGTATTGTCTCC-3') (SEQ ID NO. 12) and 5 U Taq I. The IPCR amplification was accomplished with the "PTC-100" Programmable The;rmal Controller (MJ Research, Inc.) for 5 linked files as follows: (1) 30 minutes at 94° C. for 1 cycle after which the Taq I was added; (2) 1 minute at 94° C.; (3) 1 minute at 52° C.; (4) 5 minutes at 72° C., repeat steps 2,3, and 4, 34 more times; (5) 10 minutes at 72° C. The amplicon was gel purified and the DNA was extracted using agarase. The purified amplicon was sent to be sequenced using APF 147 (SEQ ID NO. 11) as the primer.

The recombinant plasmid comprising the hagD gene in *E. coli* expressed four proteins which were subjected to SDS-PAGE electrophoresis under denaturing conditions a doublet corresponding to proteins with Mr of 90 and 85.8 kD, as well as an 80 kD and a 20 kD protein. Based on the intensity of the bands, the 80 kD protein appeared to be the most strongly expressed. A comparison between hagD and hagA amino acid sequences revealed that they possess an overall homology of 73.8% composed of a central region with 90% homology flanked by regions sharing less than 60% homology. Hag D was also found to possess high homology (89.5%) to the prtP gene product isolated from the strain *P. gingivalis* W12. The N-terminus region of these two proteins was found to be more homologous (90%) than the C-terminus (72%). It is therefore possible that hagD and prtP gene products represent different alleles of the same gene which evolved, from a common ancestral strain and diverged. Both hagA and hagD transcripts, as determined by reverse PCR analysis, were detectable only in hemin-replete conditions as previously reported for hagC. These results show that hagA, hagC, and hagD might be coordinately regulated by hemin while hagB is differentially expressed.

E. Characterization of the hagE gene and gene product. Using a repeated sequence of hagA as a probe, an additional fragment approximately 2.6 bp in length was detected in *P. gingivalis* 381 genomic DNA by Southern analysis. In order to clone this fragment, a genebank was constructed from *P. gingivalis* strain 381 genomic DNA and screened by in situ hybridization with the probe. A total of 59 positive colonies were identified. Restriction enzyme digestion of mini-preparations of plasmid DNA from 8 positive colonies revealed that 7 of them contained the expected fragment. Hemagglutination assay demonstrated that the cloned fragment in one orientation conferred a high level of hemagglutination activity on the *E. coli* host strain but no activity when the fragment was in the opposite orientation. Sequencing data confirmed that the 5' sequence of the clone is unrelated to that of hagA while the 3' sequence of 600 bp has high homology to hagA. This homology occurs in the area of the 1.3 kb repeat in hagA. This discovery of yet another gene, designated hagE, with areas of homology to hagA, may indicate that these genes represent a multi-gene family with similar functions and perhaps identical active sites. It is likely that such duplication indicates an essential or important function to the bacterial species and its interaction with the host.

By constructing a gene library, an 8.64 kb fragment was obtained which, when sequenced, was found to contain the complete open reading frame (ORF) of hagE. This ORF is 5,064 bp in length and encodes a 1,687 amino acid, 183.7 kD protein. The nucleotide and amino acid sequences for hagE are shown as SEQ ID NOS. 28 and 29, respectively. Two other ORFs were found in hagE between nucleotides 6580–7551 and 7716–8641), respectively. When comparing the sequence of hagE with that of prth, which encodes a C3 protease from strain W83, it was found that the whole 3,658 bp cloned fragment of prtH was within the clone comprising hagE. The hagE fragment contains an additional 3,761 bp 5' and 1,327 bp 3' of the prtH fragment. The homology of the common sequence is 98%. However, there are also 16 gaps in comparing the two sequences, including one base deletion, 13 one-base, and 2 two-base additions in prtH. This is likely due to strain differences. However, a sequence of an additional protease gene (rpg-I) reported from another strain (HG66) showed only 2 gaps in this region and maintained the ORF in relation to hagE. Most interestingly, translation analysis of our cloned fragment showed there is no prtH-like ORF present. Therefore, prtH is likely not present in *P. gingivalis* strain 381. In addition, two additional ORFs directly downstream of hagE were identified within the cloned fragment. The sequencing of hagE has revealed it to be a member of the HagA multi-gene family.

F. Characterization of the prtP gene and gene product. A gene and polypeptide having homologous regions to those of the hagA, hagB, hagC, hagD, and hagE genes and gene products were isolated from *Porphyromonas gingivalis* W12. The *P. gingivalis* DNA insert in λFBP1 was 4.5 kb (pHW2) and was subcloned for sequencing. It contained a large open reading frame, which encodes approximately the carboxy-terminal two-thirds of the cysteine proteinase, porphypain. The complete gene encoding porphypain was obtained using PCR and IPCR technology. The gene, which has a nucleotide sequence as shown in SEQ ID NO. 9, is designated prtP. The deduced amino acid sequence of the prtP gene is shown in SEQ ID NO. 10.

Four repeated amino acid sequences and more than five Pro-Asn tandem repeats were identified in the carboxy-terminal three-fifths of the gene. Repeat 1 includes amino acid segments 688–708 and 946–967; repeat 2 includes three amino acid segments 887–952, 1341–1405, and 1607–1650; repeat three includes amino acids 985–1006 and 1430–1451; and repeat 4 includes amino acids 1041–(1100) and 1488–(1547). These repeats can br functionally or structurally important. For example, a Pro-X motif in the TonB protein has been implicated in crossing the periplasmic space. Based on Southern blot analyses, Repeat 2 was present in at least 20 copies in each of the seven *P. gingivalis* genomes examined. The pattern of bands observed in these analyses was very similar for strains W50 and W83, but not identical; these strains have been previously indistinguishable when analyzed by multilocus enzyme electrophoresis, DNA fingerprinting, and arbitrarily primed PCR. Therefore, the repeats can be useful for distinguishing *P. gingivalis* strains. Strains ATCC 33277 and 381 showed an identical banding pattern in our analysis, which supports previous analyses characterizing the relatedness of the strains and the suggestion that strain ATCC 33277 is actually a derivative of strain 381.

Several other *P. gingivalis* genes with homology to prtP have been described. Most of hagA, which encodes a hemagglutinin identified originally in strain 381 was highly homologous to the C-terminal portion of prtP, including four-and-a-half copies of a large DNA segment encompassing the prtP Repeat 2 sequence. Our data were consistent with the presence of hagA in the seven strains examined. Certain evidence suggests that an extracellular form of PrtP participates in hemagglutination, indicative of the function of the large region the proteins have in common. Five proteinase genes previously identified in *P. gingivalis* were also found to be partially homologous to prtP: rgp-1, prpR1, prtR, prtH, and agp. Each of these genes is thought to encode a proteinase with Arg-X specificity, but not Lys-X specificity, and none of them had homology to the N-terminal portion of PrtP. The subject proteinases from the subject strain W12 have been demonstrated to degrade fibrinogen and fibronectin and hydrolyze both N-p-tosyl-Gly-Pro-Lys-p-nitroanilide and N-p-tosyl-Gly-Pro-Arg-p-nitroanilide.

Genomic DNIA from *Porphyromonas gingivalis* W12 was isolated using standard procedures, as described herein and was purified and disrupted by shearing. EcoRI linkers were ligated to the ends of *P. gingivalis* DNA fragments of appropriate sizes, and the fragments were cloned into the λgt11 vector. The λgt11 library was screened using polyclonal antibodies raised against a 120-kD cysteine proteinase (porphypain), purified from *P. gingivalis* W12. Several clones were isolated that reacted strongly with the anti-proteinase antibody. One of the clones, λFBP1, reacted strongly with the antibody, and contained a protein which bound fibrinogen.

The gene prtP has an open reading frame extending from bases 696 to 5894 and encodes a unique protein of 1732 amino acids, including a putative signal sequence for protein secretion. The predicted molecular mass for the mature protein was 186 kD, which is close to the observed molecular mass of 180 kD. There was one copy of prtP in the genomes of seven *P. gingivalis* strains examined (ATCC 33277, 381, W50, W83, W12, HG66, and ATCC 53977). The gene is located 5' to a region with a high degree of homology to the insertion element IS1126 in *P. gingivalis* strain W12. The PrtP protein had regions of high homology to Hag A, a hemagglutinin of *P. gingivalis*, and ta several purported proteinases of *P. gingivalis* that have Arg-X specificity. A detailed comparison of genes encoding the latter and cpgR indicates that rgp-1, prpR1, prtR, agp, cpgR, and possibly prtH can be derived from identical genetic loci.

Although an rgp-1-like locus was detected in seven *P. gingivalis* strains by Southern blot analyses, agp and cpgR were not detected, not even in the strains from which they were originally isolated. In addition, at least 20 copies of a repeat region common to PrtP, the Rgp-1-like proteins, and Hag A were observed in each of the seven genomes examined. The repeat region hybridization patterns for strains W83 and W50 were very similar, and they were identical for strains 381 and ATCC 33277, providing further evidence that these strains are closely related genetically.

*P. gingivalis* organisms produce a number of proteolytic enzymes which are found both extra cellularly and associated with the bacterial cell surface. Most of these *P. gingivalis* enzymes have been referred to previously as "trypsin-like," based on their preferential hydrolysis of proteins and peptides on the carboxyl side of basic amino acid residues. However, the designation is inappropriate because all of the enzymes that have been recent characterizations of the enzymes indicate they are cysteine proteinases.

The large, cell surface-associated cysteine proteinase (porphypain; PrtP) from *P. gingivalis* W12 can hydrolyze synthetic peptide substrates with either arginine or lysine residues in the $P_1$ position. Hydrolysis of both Arg-X substrates and Lys-X substrates is activated by reducing agents (Cysteine>>β-mercaptoethanol=DTT), and derivatives of glycine stimulate both activities. Both activities are inhibited by EDTA; however, hydrolysis of Arg-X substrates is inhibited by leupeptin and preferentially by Tyr-Pro-Arg chloromethyl ketone (YPRCK) over TLCK, and hydrolysis of Lys-X substrates is unaffected by leupeptin and preferentially inhibited by TLCK over YPRCK, indicating the presence of two types of active sites. The porphypain of the subject invention can contain two separate enzymes or a single enzyme which has one active site with two different conformations—one which accepts lysine in $P_1$, and the other which accepts arginine in $P_1$.

EXAMPLE 14

Construction of DNA Probes

DNA-DNA hybridization assays (DNA probes) are based on the fact that single-stranded DNA will re-anneal only with a complementary strand of DNA whose sequence is homologous. More recently, DNA probes have been used as a means of detecting various infectious agents and some are now used routinely in clinical microbiology laboratories. The identification of DNA sequences of oral Porphyromonas sp. make it possible to create DNA probes for the identification of these species. Therefore, one application of the identification and isolation of genomic sequences which encode bacterial antigens is the use of the DNA fragments as DNA probes. In the current case, these probes may comprise the Porphyromonas clones identified herein, or fragments of these clones. Also, the DNA sequence shown in SEQ ID NOS. 1, 3, 5, 7, 9, 11, 13, 15, 17, 19, 21, 23, 25, and 28, or fragments of those sequences, can be used to construct suitable probes.

Each recombinant plasmid is isolated and digested with whichever restriction enzyme was used to generate that particular genomic library. The digested plasmid DNA is then separated electrophoretically on an agarose gel as described earlier. The Porphyromonas DNA band containing the fragment is cut out of the gel and the DNA fragment is recovered by electro-elution employing centrifugal filtration of DNA fragments through a Durapore (Millipore) membrane inside a conical tip. This rapid and simple method recovers 70% of the DNA in a highly pure state.

The conical tip is assembled as follows: the conical portion of a 1.5 ml Eppendorf tube is cut off and a hole pierced in the bottom with a thin wire. A 4.5 $cm^2$ piece of Durapore (Millipore) membrane is wetted (d. $H_2O$) on a piece of parafilm, the filter square is then formed around a blunt-ended glass rod, and the filter is placed inside the conical bottom (cone). Excess filter is cut away, the filter tip is placed inside a 1.5 ml Eppendorf tube, and the filter is prewetted with 200 μl of elution buffer (0.1% SDS+50 mM Tris-HCl, pH 7.5). The gel slice is then transferred to the prepared conical tip. After centrifugation of the DNA preparation in a microcentrifuge (Eppendorf) for 10 minutes, the filtered aqueous phase containing the DNA is precipitated by the addition of 5M NaCl (to 1M) and two volumes of ethanol. After ethanol precipitation, the DNA fragment(s) is labeled non-radioactively, using, a photo-activatable biotin tag as described by the supplier (Clontech Laboratories, Inc.).

For biotin labelling, the DNA fragment preparation is adjusted to a concentration of 1 mg/ml (TE) and is mixed with photo-activatable biotin (PAB) at a ratio of 1:3 (DNA:PAB) in a 1.5 ml Eppendorf tube. The tube is placed in an ice bath 10 cm below a 275 W (GE RSM) sunlamp and the DNA+PAB is irradiated for 15 minutes. The DNA solution is then mixed with an equal volume of 0.1M Tris-Cl (pH 9.0) and the volume adjusted to ≧100 μl with $H_2$). The unincorporated PAB is extracted from the DNA by the addition of an equal volume of 2-butanol, vortexing, centrifuging briefly, and withdrawing the lower aqueous phase with a Pipetman. The extraction can be repeated to remove any traces of unbound PAB. 3M NaOAc (pH 5.6) is added to the DNA solution to a final concentration of 0.3M and the labeled DNA is precipitated by the addition of three volumes of ethanol.

After the sample is cooled at −70° C. for 15 minutes, the precipitated DNA is recovered by centrifugation for 10 minutes. The DNA pellet is dissolved in 10 mM Tris (pH 7.9) and 0.1 mM EDTA. The labeled probe DNA remains stable for one year if stored at −20° C.

A non-radioactive method of labeling the DNA probes may be desirable because: (1) the photoactivatable reactions are simple and rapid, (2) the sensitivity is as high as $^{32}P$-labeled probes, (3) the PAB-labeled probes have a long storage life, (4) these probes are relatively inexpensive, and (5) detection of bound probes is by simple colorimetric methods. The radioactive labeling of probes requires the use of $^{32}P$, which has a very short half-life (14 days) and is thus unstable and expensive. The use of radioactive probes would be limited because of cost, the dangers of radioactivity, strict requirements for disposal, and the need for licensing. However, if for some reason the biotin-HRP method of labeling is unacceptable, the DNA fragments can be labeled with [δ P] 32 deoxy-CTP by standard nick translation methods as described by Maniatis et al. (1982, supra). Other labelling techniques which are well known or accepted by ordinary skilled artisans can also be employed for visualization of the nucleic acid probes.

EXAMPLE 15

Determining the Specificity of the DNA Probes

The prepared DNA probes are screened for specificity against a battery of oral Porphyromoncs species, other oral species, and other non-oral gram-negative bacteria.

Cultures of the test strains are grown in appropriate medium to a density of approximately $10^9$ cells per ml. The cells are centrifuged and suspended in 5.0 ml of distilled water. Sodium hydroxide is added to 0.5N and the cells are incubated at 90° C. for 20 to 30 minutes in order to lyse the cells and denature the DNA. The cell suspension is neutralized by the addition of 0.5N HCl diluted in 20×SSC and chilled on ice for 20 minutes. A volume of 0.5 ml (or less) of the suspension is diluted to 4.0 ml volume with 10×SSC and vacuum filtered in a manifold onto nitrocellulose paper (type HAWP, 0.45 μm, Millipore Corp.) which is prewetted with 10×SSC. After the filters are rinsed with 4.0 ml of 10×SSC, they are dried and heated at 85° C. for 3 hours in a vacuum oven (this fixes the chromosomal DNA onto the filter). After the filters are incubated for 2–3 hours at 42° C. with the prehybridization buffer (6×SSPE [1.08M NaCl, 0.06M $NaH_2PO_4$, 0.48M NaOH, 6.0 mM $Na_2$ EDTA, pH 7.0], 5×BFP [0.1% BSA, 0.1% Ficoll, and 0.1% polyvinyl pyrrolidine], 1% [w/v] glycine, 50% formamide, and 100 μg denatured salmon sperm DNA/ml), the prehybridization buffer is replaced with hybridization buffer containing 0.01 to 0.1 μg of labeled heat-denatured probe DNA in 5×SSPE, 1×BFP, 50% formamide, 100 μg salmon sperm/ml, 0.3% SDS, and 10% sulfate. Hybridization is accomplished by incubating the DNA mixtures for 12 hours at 42° C. The filters are then washed twice in 2×SSPE—0.2% SDA for 25 minutes at 60° C. in order to remove any unhybridized probe DNA.

The hybridized (bound) probe DNA can be detected by incubation of the filters for 30 minutes on 1M NaCl+0.1M Tris-HCl (pH 7.5)+2 mM $MgCl_2$+0.05% "TRITON" X-100+3% BSA and then for 25 minutes in 1 mg/ml streptavidin alkaline phosphate conjugate in the same buffer. Next, the filters are washed 3 times with 50–100 ml of buffer containing 1M NaCl, 0.1M Tris-HCl, pH 7.5, 2 mM $MgCl_2$, and 0.05% "TRITON" X-100. A fourth wash of buffer contains 0.1M NaCl and 0.3M sodium citrate, pH 7.0. The color is developed by the addition of 32 μl nitroblue tetrazolium, 16 μl 5-bromo-4-chloro-3-indosyl-phosphate in 5.0 ml of 0.1M NaCl+0.3M sodium citrate. After incubation in subdued light for 30 minutes, any spots which are visible indicate hybridization of probe DNA to target DNA.

If $^{32}P$-labeled probes are used the same hybridization conditions can be used (adding $10^6$ CPM of $^{32}P$ probe) but instead of adding the streptavidin conjugate, the filters are dried for 1–2 hours at 70° C., and hybridization is detected by autoradiography. Alternatively, the filters can be cut into squares, placed into scintillation vials, and counted in scintillant.

Once probes are identified which are specific for either *B. intermedius* or *P. gingivalis*, or several *Porphyromonas spp*., they can be tested with known mixtures of the test bacteria grown on plates as follows: various mixtures of the test bacteria can be prepared with a known concentration of *B. intermedius* or *P. gingivalis* and spread on agar plates and incubated anaerobically as described earlier in this proposal. After the colonies have appeared (2–4 days), they are blotted onto nitrocellulose membranes, and the membranes processed for hybridization. If the DNA probe(s) is specific and sensitive, then only the *P. gingivalis* or *B. intermedius* colony blots should be positive. It is also possible that a probe may be found that is genus or group specific.

DNA probes for chromosomally-encoded genes require $10^5$ to $10^6$ bacteria per colony or dot blot in order to give a reliable positive result. This is comparable to 1 to 10 pg of DNA. Given this level of detection, a primary culturing step is desirable prior to blotting the colonies onto membrane filters and hybridization with the probe DNA.

EXAMPLE 16

Vaccines

In view of the immunoprotectant activity exhibited by certain of the compositions of matter of the subject invention, vaccines may be produced from the polypeptides expressed by cells which have been transformed with DNA fragments from *Porphyromonas gingivalis*. By introducing these peptides, along with a pharmacologically suitable vehicle, into the human or animal host, that host can be induced to generate immunological protection against *P. gingivalis*. The preparation of such a vaccine composition is within the skill of one trained in the medical and immunological sciences. Cells which can be used to produce recombinant peptides include, but are not limited to, bacteria, yeasts, insects, and eukaryotic cells.

EXAMPLE 17

Construction of an Oral Vaccine

It has been recognized that natural infection with enteric organisms produces the highest levels of antibodies and the longest lasting immunity to reinfection. The use of Salmonella as an attenuated vaccine carrier organism has several advantages. *Salmonella spp.* are capable of colonizing the Peyer's patches and gut lamina propria where they elicit a strong local IgA response in the intestine. The IgA response is also spread to other external secretions such as saliva by the seeding of these tissues with plasma cell precursors primed in the gut via the so called common mucosal immune system. These responses are important in preventing initial adhesion and colonization of mucosal surfaces—the initial step in the etiology of periodontal disease. In addition, live Salmonella elicits a humoral (serum) response of the IgM, IgG and IgA isotypes due to its invasive nature. Finally, infection with live organisms also stimulates a cell-mediated immune response—primarily T-cell mediated stimulation of macrophages—which is important in immunity since Salmonella can survive intracellularly within phagocytic cells. Several non-virulent mutants of *Salmonella spp.* have been developed. For example, an attenuated galE mutant of *S. typhi* (strain Ty21a) which lacks the enzyme UDP-galactose-4-epimerase has been developed.

Another approach to attenuation has been to use aromatic amino acid dependent (aro—) strains of Salmonella which are nonvirulent because they require metabolites not found in mammalian tissues, i.e., p-aminobenzoate and 2,3-dihydroxybenzoate. The strains are constructed using the aro:A554::Tn10 transposon, and, because it can cause deletion or deletion-inversion mutations, one can generate non-reverting mutants. These mutants synthesize a complete smooth LPS, are able to effectively colonize the Peyer's patches and gut, and are highly immunogenic. In mice of the Salmonlella-susceptible line BALB/c, intraperitoneal injection of as few as $2\times10^5$ $aro^-$S. typhimurium protected against an i.p. challenge of $5\times10^5$ virulent parent cells 30 days later (>25,000 i.p.$LD_{50}$). Oral immunization with $2\times10^8$ $aro^-$ cells protected mice against an oral challenge of $3\times10^7$ virulent organisms (ca. 100 oral $LD_{50}$).

Because live Salmonella is such an efficient stimulator of mucosal immunity it can be used as a carrier to deliver recombinant gene products cloned from other pathogens directly to the tissues (i.e., Peyer's patches) which most efficiently generate an immune response in the gut, and through the common mucosal immune system, to other distant secretory sites. At the same time a humoral immune response is stimulated which may further help prevent or abort invasion. Using cloned antigens in a Salmonella carrier system gives one the ability to target the immune response to important virulence antigens leading to a protective immune response.

Chromosomal DNA was isolated from *P. gingivalis* strain 381 by the following method: One to three liters of cells were pelleted by centrifugation and washed (on ice) in 1/50 volume of 1×SSC buffer (0.87% NaCl, 0.04% Na citrate) containing 27% sucrose and 10 mM EDTA. The cells were again pelleted and resuspended to $10^{10}$ cells/ml in the same buffer. Lysozyme (5 mg/ml in 1×SSC buffer) was added to 0.5 mg/ml, the cells were mixed thoroughly and incubated at 37° C. for 10 minutes. Nine volumes of 1×SSC containing 27% sucrose, 10 mM EDTA and 1.11% SDS (prewarmed to 39° C.) were added to the cells and incubated at 37° C. until cell lysis was complete (10–30 minutes). The lysed cells were mixed gently and incubated at 37° C. for 30 minutes. Proteinase K (Sigma, St. Louis, Mo.) was added to a final concentration of 1 mg/ml and the lysate was incubated at 37° C. for 4 hours. An equal volume of phenol-Tris (9:1 freshly distilled phenol:1M Tris-HCl, pH 7.5) was added to the Proteinase K-treated mixture and the mixture was agitated gently at room temperature for 30 minutes. The DNA mixture was then centrifuged in 150 ml Corex tubes at 3000 rpm. The top (phenol) layer was removed and discarded. The phenol extraction was repeated and the DNA (aqueous) layer was dialyzed extensively against 10 mM Tris-HCl, pH 8.0, 1 mM EDTA. Finally, the DNA was incubated with RNase at 37° C. for 1 hour.

Expression vectors which contain a promoter upstream from the cloning site were used to help insure that cloned DNA was expressed whether or not a structural gene was cloned with its own promoter. The expression plasmid pUC9 (2.7 kb) contains the origin of replication, ampicillin resistance gene, and lac gene of pBR 322. The lac HaeII fragment (lac gene) contains a polylinker region from M12mp9 which has multiple unique cloning sites in the gene that encodes for the peptide of β-galactosidase. Thus, recombinant vectors that contain an insert in any of the cloning sites generate white colonies on X-GAL plates since they are not able to degrade the lactose analog, X-GAL. Vectors without an insert degrade X-GAL and result in blue colonies on X-GAL plates since the gene is not interrupted by an insert. Other plasmid vectors are available and could be used. One such plasmid is pAD 230.

The chromosomal DNA and vector DNA were ligated with T4 DNA ligase at ratios of 2:1 and 5:1. The ligated DNA was phenol-chloroform (24:1 isoamyl alcohol) extracted, ethanol precipitated, washed, dried, and redissolved in TE. Early log-phase cells (OD=0.2 to 0.5) were washed with transformation buffer 1 (TFM 1, 10 mM Tris-Cl, pH 7.5, 0.15M NaCl). The cells were pelleted, resuspended, and incubated on ice for 45 minuates in TFM 2 (50 mM $CaCl_2$). After the cells are again pelleted, they are gently resuspended once more in TFM 2. A 0.2 ml volume of cells were added to 0.1 ml TFM 3 (10 mM Tris-HCl, pH 7.5, 50 mM $CaCl_2$, 10 mM $MgSO_4$. $7H_2O$) on ice. Varying amounts of DNA were added to the cells. The tubes were incubated on ice for 45 minutes, at which time the cells were heat shocked at 37° C. for 2 minutes. A 0.5 ml volume of LB broth was added per tube and the cells were incubated at 37° C. for 30 to 60 minutes to allow expression of antibiotic resistance. Finally, the cells were spread on plates of LB+antibiotic (50 μg/ml ampicillin) and X-GAL and incubated 24 to 48 hours at 37° C.

Any colonies which appeared on the LB+ampicillin+X-GAL plates after 24–36 hours of incubation were transformants which contained and expressed pUC9. A large number (80–90%) of these were white colonies which contain a plasmid with inserted *P. gingivalis* DNA. Once a transformant was identified which expressed *P. gingivalis* SHA adhesin, the protein was identified by Western blotting cell lysates of the transformant.

Because the initial cloning was done in *E. coli*, the recombinant plasmids may be modified by the *E. coli* modification system. These modified recombinant plasmids were used to transform strains of Salmonella. Initially, recombinant plasmids were passed into *Salmonella typhimurium* strain LB 5000, which is restriction (is not able to restrict foreign DNA) but modification$^+$. This modifies the plasmid DNA according to the Salmonella system.

Recombinant *P. gingivalis* plasmids encoding for the Porphyromonas (SHA) adhesin can be isolated and purified as described above. The identity and purity of the preparation can be monitored by restriction analysis and agarose gel electrophoresis. Cells of Salmonella strain LB 5000 can be made competent and transformed with the recombinant plasmid as described above. Transformants can be selected by growth in the presence of ampicillin and are tested for the expression of the Porphyromonas antigen also by procedures described above.

The recombinant plasmid can be isolated from strain LB 5000 and the identity of the plasmid verified. The purified plasmid can be used to transform non-reverting nonvirulent mutants of various *Salmonella spp*. These strains include (but are not limited to) *S. enieriditis* (typhimurium) SL 3261 (WRAY his G46 aro A), SL 1479 (UCD his C527 aro A), SL 3237 (FIRN rps L120 aro A), and *S. dublin* SL 3261 (his 646 aro A). Transformants can be screened for resistance to ampicillin and assayed for expression of the Porphyromonas antigen by enzyme-linked immunosorbent assay as described above. In addition, SDS-PAGE and Western blotting can be done to confirm the presence of the antigen in the Salmonella transformants.

The *P. gingivalis* hemagglutinin protein was expressed in nonvirulent *Salmonella typhimurium* strain SL3261/CL7 and tested for activity as a competitive inhibitor of hemagglutination. The *S. typhimurium* cells were broken by sonic disruption, whole cells and debris removed by centrifugation and the supernatant adjusted to 40% saturation with $NH_4SO_3$. The supernatant was collected, dialyzed, and fractionated on a CM-Sephadex column using a 50–450 mM NaCl gradient. Fractions were evaluated via Western blot analysis for reactivity with absorbed sera directed against *P. gingivalis*. The peak fraction was found to inhibit hemagglutination of erythrocytes by whole *P. gingivalis* cells. This same material was analyzed for the N-terminal amino acid sequence and found to match the sequence predicted from the cloned gene.

The gene for the Porphyromonas antigen can also be transduced into the Salmonella carrier strains by P22 transduction. Transductants can be selected by growth in the presence of ampicillin and by the expression of the Porphyromonas antigen, as detected by immunoblotting using the monospecific or monoclonal antibody.

Additional carrier strains can be generated from other Salmonella serotypes. These strains can be derived from virulent strains by the introduction of mutations such as (auxotrophic) aro A or gal E. In addition, the "O" antigen may be altered or mutated to a rough LPS in strains already a virulent by $P_1$ transduction.

EXAMPLE 18

Monoclonal Antibodies

Appropriate mice can be immunized with antigens of, or cells expressing antigens of, *Porphyromonas gingivalis*. The antigens used for this immunization can be those which are identified and described in the previous examples in view of their exhibited immunogenic activity. The techniques employed to accomplish this immunization procedure are familiar to those skilled in this art. The spleens can then be removed from the immunized mice and the cells therefrom fused to SP-2 myeloma cells using polyethylene glycol. The desired hybrid cells can then be selected by adding hypozanthine-aminopterin-thymidine to the medium. The surviving cells can then be tested for antibody production. The testing for antibody production can be accomplished using ELISA, immunoblot, and/or Western blot procedures as described in the previous examples.

The monoclonal antibodies produced by the procedure just described can be used to test for the presence of *P. gingivalis* antigens in a sample of biological fluid. The testing procedure involves contacting the biological fluid with a composition containing one or more of the monoclonal antibodies. If *P. gingivalis* antigens are present in the biological fluid, then a reaction will occur and this reaction can be detected and quantified by fluorescence or other means.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A purified and isolated *Porphyromonas gingivalis* gene encoding a polypeptide, said polypeptide having an amino acid sequence selected from the group consisting of SEQ ID NO.2, SEQ ID NO.4, SEQ ID NO.6, SEQ ID NO.8, SEQ ID NO.10, SEQ ID NO.14, SEQ ID NO.16, SEQ ID NO.18, SEQ ID NO.20, SEQ ID NO.22, SEQ ID NO.26, SEQ ID NO.27, SEQ ID NO.29.

2. A gene, comprising a purified and isolated nucleotide sequence selected from the group consisting of SEQ ID NO.1, SEQ ID NO.3, SEQ ID NO.5, SEQ ID NO.7, SEQ ID NO.9, SEQ ID NO.13, SEQ ID NO.15, SEQ ID NO.17, SEQ ID NO.19, SEQ ID NO.21, SEQ ID NO.25, and SEQ ID NO.28.

3. A host cell transformed with a *Porphyromonas gingivalis* gene which encodes a *Porphyromonas gingivalis* polypeptide, said gene being selected from the group consisting of SEQ ID NO.1, SEQ ID NO.3, SEQ ID NO.5, SEQ ID NO.7, SEQ ID NO.9, SEQ ID NO.13, SEQ ID NO.15, SEQ ID NO.17, SEQ ID NO.19, SEQ ID NO.21, SEQ ID NO.25, and SEQ ID NO.28.

4. The host cell transformed according to claim 3, wherein said cell is derived from, or is identical to ATCC 67733.

5. The host cell transformed according to claim 3, wherein said cell is derived from, or is identical to ATCC 67734.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 4510 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 27..1518

( x i ) SEQUENCE DESCRIPTION: SEQ ID NO:1:

```
ATTAATCTTT AATACTTTCA AAAGGT ATG AGA AAA TTG AAT TCT TTA TTT TCG   53
                             Met Arg Lys Leu Asn Ser Leu Phe Ser
                               1                 5

CTC GCC GTC CTA TTA TCC CTA TTG TGT TGG GGA CAG ACG GCT GCC GCA   101
Leu Ala Val Leu Leu Ser Leu Leu Cys Trp Gly Gln Thr Ala Ala Ala
 10                  15                  20                  25

CAG GGA GGG CCG AAG ACT GCT CCT TCT GTG ACG CAC CAA GCG GTG CAG   149
Gln Gly Gly Pro Lys Thr Ala Pro Ser Val Thr His Gln Ala Val Gln
                 30                  35                  40

AAA GGT ATT CGA ACA TCC AAG GTT AAG GAT CTC CGA GAT CCG ATT CCT   197
Lys Gly Ile Arg Thr Ser Lys Val Lys Asp Leu Arg Asp Pro Ile Pro
             45                  50                  55

GCC GGT ATG GCA CGA ATT ATC TTG GAG GCT CAC GAT GTA TGG GAA GAC   245
Ala Gly Met Ala Arg Ile Ile Leu Glu Ala His Asp Val Trp Glu Asp
         60                  65                  70

GGC ACA GGC TAT CAA ATG CTT TGG GAT GCA GAT CAC AAT CAG TAC GGC   293
Gly Thr Gly Tyr Gln Met Leu Trp Asp Ala Asp His Asn Gln Tyr Gly
     75                  80                  85

GCA TCC ATT CCC GAA GAA TCT TTT TGG TTT GCC AAC GGA ACG ATC CCG   341
Ala Ser Ile Pro Glu Glu Ser Phe Trp Phe Ala Asn Gly Thr Ile Pro
 90                  95                 100                 105

GCC GGT CTT TAC GAT CCT TTC GAG TAT AAA GTT CCG GTC AAT GCC GAT   389
Ala Gly Leu Tyr Asp Pro Phe Glu Tyr Lys Val Pro Val Asn Ala Asp
                110                 115                 120

GCA TCT TTT TCT CCC ACG AAT TTC GTG CTT GAT GGA ACA GCA TCA GCC   437
Ala Ser Phe Ser Pro Thr Asn Phe Val Leu Asp Gly Thr Ala Ser Ala
            125                 130                 135

GAT ATT CCT GCC GGC ACT TAT GAC TAT GTA ATC ATT AAC CCC AAT CCT   485
Asp Ile Pro Ala Gly Thr Tyr Asp Tyr Val Ile Ile Asn Pro Asn Pro
        140                 145                 150
```

-continued

GGC ATA ATA TAT ATA GTA GGA GAG GGT GTC TCC AAA GGT AAC GAT TAT 533
Gly Ile Ile Tyr Ile Val Gly Glu Gly Val Ser Lys Gly Asn Asp Tyr
155 160 165

GTG GTA GAG GCC GGT AAG ACT TAT CAT TTC ACT GTC CAA CGA CAA GGC 581
Val Val Glu Ala Gly Lys Thr Tyr His Phe Thr Val Gln Arg Gln Gly
170 175 180 185

CCC GGC GAT GCT GCG TCC GTT GTA GTG ACC GGA GAA GGT GGC AAT GAA 629
Pro Gly Asp Ala Ala Ser Val Val Val Thr Gly Glu Gly Gly Asn Glu
190 195 200

TTC GCT CCC GTA CAG AAT CTC CAA TGG TCT GTA TCT GGG CAG ACA GTG 677
Phe Ala Pro Val Gln Asn Leu Gln Trp Ser Val Ser Gly Gln Thr Val
205 210 215

ACC CTC ACT TGG CAA GCC CCC GCA TCC GAC AAA CGG ACT TAT GTG TTG 725
Thr Leu Thr Trp Gln Ala Pro Ala Ser Asp Lys Arg Thr Tyr Val Leu
220 225 230

AAC GAA AGC TTC GAT ACG CAA ACG CTT CCT AAC GGC TGG ACA ATG ATC 773
Asn Glu Ser Phe Asp Thr Gln Thr Leu Pro Asn Gly Trp Thr Met Ile
235 240 245

GAT GCT GAT GGT GAT GGT CAC AAT TGG CTA TCT ACA ATA AAC GTT TAC 821
Asp Ala Asp Gly Asp Gly His Asn Trp Leu Ser Thr Ile Asn Val Tyr
250 255 260 265

AAC ACT GCT ACT CAT ACA GGT GAC GGT GCT ATG TTT AGC AAA TCA TGG 869
Asn Thr Ala Thr His Thr Gly Asp Gly Ala Met Phe Ser Lys Ser Trp
270 275 280

ACT GCT AGC GGT GGT GCA AAA ATT GAT TTG AGT CCT GAC AAC TAT TTG 917
Thr Ala Ser Gly Gly Ala Lys Ile Asp Leu Ser Pro Asp Asn Tyr Leu
285 290 295

GTA ACT CCA AAG GTT ACG GTT CCT GAG AAT GGT AAA CTT TCT TAT TGG 965
Val Thr Pro Lys Val Thr Val Pro Glu Asn Gly Lys Leu Ser Tyr Trp
300 305 310

GTT TCA TCT CAA GTG CCT TGG ACT AAT GAG CAT TAT GGA GTG TTC TTG 1013
Val Ser Ser Gln Val Pro Trp Thr Asn Glu His Tyr Gly Val Phe Leu
315 320 325

TCC ACA ACC GGA AAC GAG GCT GCA AAC TTT ACG ATA AAG CTA CTG GAA 1061
Ser Thr Thr Gly Asn Glu Ala Ala Asn Phe Thr Ile Lys Leu Leu Glu
330 335 340 345

GAA ACC CTC GGA TCC GAC AAA CCT GCT CCG ATG AAC TTG GTG AAG AGT 1109
Glu Thr Leu Gly Ser Asp Lys Pro Ala Pro Met Asn Leu Val Lys Ser
350 355 360

GAA GGA GTA AAG CTT CCT GCA CCT TAT CAG GAA AGA ACC ATC GAT CTC 1157
Glu Gly Val Lys Leu Pro Ala Pro Tyr Gln Glu Arg Thr Ile Asp Leu
365 370 375

TCT GCC TAT GCC GGA CAA CAG GTG TAC TTG GCA TTC CGT CAT TTC AAC 1205
Ser Ala Tyr Ala Gly Gln Gln Val Tyr Leu Ala Phe Arg His Phe Asn
380 385 390

TCT ACA GGT ATA TTC CGT CTT TAT CTT GAT GAT GTG GCT GTT TCT GGT 1253
Ser Thr Gly Ile Phe Arg Leu Tyr Leu Asp Asp Val Ala Val Ser Gly
395 400 405

GAA GGT TCT TCC AAC GAC TAC ACG TAC ACG GTA TAT CGT GAC AAT GTT 1301
Glu Gly Ser Ser Asn Asp Tyr Thr Tyr Thr Val Tyr Arg Asp Asn Val
410 415 420 425

GTT ATT GCC CAG AAT CTC GCG GCA ACG ACA TTC AAT CAG GAA AAT GTA 1349
Val Ile Ala Gln Asn Leu Ala Ala Thr Thr Phe Asn Gln Glu Asn Val
430 435 440

GCT CCC GGC CAG TAT AAC TAC TGT GTT GAA GTT AAG TAC ACA GCC GGC 1397
Ala Pro Gly Gln Tyr Asn Tyr Cys Val Glu Val Lys Tyr Thr Ala Gly
445 450 455

GTA TCT CCG AAG GTA TGT AAA GAC GTT ACG GTA GAA GGA TCC AAC GAA 1445
Val Ser Pro Lys Val Cys Lys Asp Val Thr Val Glu Gly Ser Asn Glu
460 465 470

-continued

```
TTT GCT CAT GTA CAG AAC CTG ACC GGT AGT GCA GTA GGT CAG AAA GTA     1493
Phe Ala His Val Gln Asn Leu Thr Gly Ser Ala Val Gly Gln Lys Val
    475                 480                 485

ACG CTT AAG TGG GAT GCA CCT AAT G GTACCCCGAA TCCGAATCCC             1538
Thr Leu Lys Trp Asp Ala Pro Asn
490                 495

GGAACAACAA CACTTTCCGA ATCATTCGAA AATGGTATTC CTGCCTCATG GAAGACGATC   1598

GATGCAGACG GTGACGGCAA CAATTGGACG ACGACCCCTC CTCCCGGAGG CACCTCTTTT   1658

GCAGGTCACA ACAGTGCAAT CTGTGCCTCT TCGGCTTCTT ATATCAACTT TGAAGGTCCT   1718

CAGAACCCTG ATAACTATCT GGTTACACCG GAGCTATCTC TTCCTAACGG AGGAACGCTT   1778

ACTTTCTGGG TATGTGCACA AGATGCCAAT TATGCATCAG AGCACTATGC CGTGTACGCA   1838

TCTTCTACGG GTAACGACGC TTCCAACTTC GCCAACGCTT TGTTGGAAGA AGTGCTGACG   1898

GCCAAGACAG TTGTTACGGC ACCTGAAGCC ATTCGTGGCA CTCGTGTTCA GGGCACCTGG   1958

TATCAAAAGA CGGTACAGTT GCCTGCGGGT ACTAAGTATG TTGCTTTCCG TCACTTCGGC   2018

TGTACGGACT TCTTCTGGAT TAACCTTGAT GATGTTGAGA TCAAGGCCAA CGGCAAGCGC   2078

GCAGACTTCA CGGAAACGTT CGAGTCTTCT ACTCATGGAG AGGCACCGGC GGAATGGACT   2138

ACTATCGATG CCGATGGCGA TGGTCAGGGT TGGCTCTGTC TGTCTTCCGG ACAATTGGAC   2198

TGGCTGACAG CTCATGGCGG CACCAACGTA GTAGCCTCTT TCTCATGGAA TGGAATGGCT   2258

TTGAATCCTG ATAACTATCT CATCTCAAAG GATGTTACAG GCGCAACTAA GGTAAAGTAC   2318

TACTATGCAG TCAACGACGG TTTTCCCGGG GATCACTATG CGGTGATGAT CTCCAAGACG   2378

GGCACGAACG CCGGAGACTT CACGGTTGTT TTCGAAGAAA CGCCTAACGG AATAAATAAG   2438

GGCGGAGCAA GATTCGGTCT TTCCACGGAA GCCGATGGCG CCAAACCTCA AAGTGTATGG   2498

ATCGAGCGTA CGGTAGATTT GCCTGCGGGT ACTAAGTATG TTGCTTTCCG TCACTACAAT   2558

TGCTCGGATT TGAACTACAT TCTTTTGGAT GATATTCAGT TCACCATGGG TGGCAGCCCC   2618

ACCCCGACCG ATTATACCTA CACGGTGTAT CGTGACGGTA CGAAGATCAA GGAAGGTCTG   2678

ACCGAAACGA CCTTCGAAGA AGACGGTGTA GCTACGGGCA ACCATGAGTA TTGCGTGGAA   2738

GTGAAGTACA CAGCCGGCGT ATCTCCGAAA GAGTGTGTAA ACGTAACTGT TGATCCTGTG   2798

CAGTTCAATC CTGTACAGAA CCTGACCGGT AGTGCAGTCG GCCAGAAAGT AACGCTTAAG   2858

TGGGATGCAC CTAATGGTAC CCCGAATCCA AATCCAAATC CGAATCCGGG AACAACAACA   2918

CTTTCCGAAT CATTCGAAAA TGGTATTCCT GCCTCATGGA AGACGATCGA TGCAGACGGT   2978

GACGGCAACA ATTGGACGAC GACCCCTCCT CCCGGAGGCA CCTCTTTTGC AGGTCACAAC   3038

AGTGCGATCT GTGCCTCTTC GGCTTCTTAT ATCAACTTTG AAGGCCCTCA GAACCCTGAT   3098

AACTATCTGG TTACACCGGA GCTATCTCTT CCTAACGGAG GAACGCTTAC TTTCTGGGTA   3158

TGTGCACAAG ATGCCAATTA TGCATCAGAG CACTATGCCG TGTATGCATC TTCTACGGGT   3218

AACGACGCTT CCAACTTCGC CAACGCTTTG TTGGAAGAAG TGCTGACGGC CAAGACAGTT   3278

GTTACGGCAC CTGAAGCCAT TCGTGGCACT CGTGTTCAGG GCACCTGGTA TCAAAAGACG   3338

GTACAGTTGC CTGCGGGTAC TAAGTATGTT GCTTTCCGTC ACTTCGGCTG TACGGACTTC   3398

TTCTGGATCA ACCTTGATGA TGTTGAGATC AAGGCCAACG GCAAGCGCGC AGACTTCACG   3458

GAAACGTTCG AGTCTTCTAC TCATGGAGAG GCACCGGCGG AATGGACTAC TATCGATGCC   3518

GATGGCGATG GTCAGGGTTG GCTCTGTCTG TCTTCCGGAC AATTGGGCTG GCTGACAGCT   3578

CATGGCGGCA CCAACGTAGT AGCCTCTTTC TCATGGAATG GAATGGCTTT GAATCCTGAT   3638

AACTATCTCA TCTCAAAGGA TGTTACAGGC GCAACTAAGG TAAAGTACTA CTATGCAGTC   3698
```

AACGACGGTT TTCCCGGGGA TCACTATGCG GTGATGTTCT CCAAGACGGG CACGAACGCC 3758

GGAGACTTCA CGGTTGTTTT CGAAGAAACG CCTAACGGAA TAAATAAGGG CGGAGCAAGA 3818

TTCGGTCTTT CCACGGAAGC CGATGGCGCC AAACCTCAAA GTGTATGGTT CGAGCGTACG 3878

GTAGATTTGC CTGCGGGTAC TAAGTATGTT GCTTTCCGTC ACTACAATTG CTCGGATTTG 3938

AACTACATTC TTTTGGATGA TATTCAGTTC ACCATGGGTG GCAGCCCCAC CCCGACCGAT 3998

TATACCTACA CGGTGTATCG TGACGGTACG AAGATCAAGG AAGGTCTGAC CGAAACGACC 4058

TTCGAAGAAG ACGGTGTAGC TACGGGCAAC CATGAGTATT GCGTGGAAGT GAAGTACACA 4118

GCCGGCGTAT CTCCGAAAGA GTGTGTAAAC GTAACTGTTG ATCCTGTGCA GTTCAATCCT 4178

GTACAGAACC TGACCGGTAG TGCAGTCGGC CAGAAAGTAA CGCTTAAGTG GGATGCACCT 4238

AATGGTACCC CGAATCCAAA TCCAAATCCG AATCCGGGAA CAACAACACT TTCCGAATCA 4298

TTCGAAAATG GTATTCCTGC CTCATGGAAG ACGATCGATG CAGACGGTGA CGGCAACAAT 4358

TGGACGACGA CCCCTCCTCC CGGAGGCACC TCTTTTGCAG GTCACAACAG TGCGATCTGT 4418

GTCTCTTCGG CTTCTTATAT CAACTTTGAA GGCCCTCAGA ACCCTGATAA CTATCTGGTT 4478

ACACCGGAGC TATCTCTTCC TGGCGGATTA AT 4510

( 2 ) INFORMATION FOR SEQ ID NO:2:

( i ) SEQUENCE CHARACTERISTICS:
( A ) LENGTH: 497 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Arg Lys Leu Asn Ser Leu Phe Ser Leu Ala Val Leu Leu Ser Leu
1 5 10 15

Leu Cys Trp Gly Gln Thr Ala Ala Ala Gln Gly Gly Pro Lys Thr Ala
20 25 30

Pro Ser Val Thr His Gln Ala Val Gln Lys Gly Ile Arg Thr Ser Lys
35 40 45

Val Lys Asp Leu Arg Asp Pro Ile Pro Ala Gly Met Ala Arg Ile Ile
50 55 60

Leu Glu Ala His Asp Val Trp Glu Asp Gly Thr Gly Tyr Gln Met Leu
65 70 75 80

Trp Asp Ala Asp His Asn Gln Tyr Gly Ala Ser Ile Pro Glu Glu Ser
85 90 95

Phe Trp Phe Ala Asn Gly Thr Ile Pro Ala Gly Leu Tyr Asp Pro Phe
100 105 110

Glu Tyr Lys Val Pro Val Asn Ala Asp Ala Ser Phe Ser Pro Thr Asn
115 120 125

Phe Val Leu Asp Gly Thr Ala Ser Ala Asp Ile Pro Ala Gly Thr Tyr
130 135 140

Asp Tyr Val Ile Ile Asn Pro Asn Pro Gly Ile Ile Tyr Ile Val Gly
145 150 155 160

Glu Gly Val Ser Lys Gly Asn Asp Tyr Val Val Glu Ala Gly Lys Thr
165 170 175

Tyr His Phe Thr Val Gln Arg Gln Gly Pro Gly Asp Ala Ala Ser Val
180 185 190

Val Val Thr Gly Glu Gly Gly Asn Glu Phe Ala Pro Val Gln Asn Leu
195 200 205

-continued

```
Gln Trp Ser Val Ser Gly Gln Thr Val Thr Leu Thr Trp Gln Ala Pro
    210                 215                 220

Ala Ser Asp Lys Arg Thr Tyr Val Leu Asn Glu Ser Phe Asp Thr Gln
225                 230                 235                 240

Thr Leu Pro Asn Gly Trp Thr Met Ile Asp Ala Asp Gly Asp Gly His
                245                 250                 255

Asn Trp Leu Ser Thr Ile Asn Val Tyr Asn Thr Ala Thr His Thr Gly
            260                 265                 270

Asp Gly Ala Met Phe Ser Lys Ser Trp Thr Ala Ser Gly Gly Ala Lys
        275                 280                 285

Ile Asp Leu Ser Pro Asp Asn Tyr Leu Val Thr Pro Lys Val Thr Val
    290                 295                 300

Pro Glu Asn Gly Lys Leu Ser Tyr Trp Val Ser Ser Gln Val Pro Trp
305                 310                 315                 320

Thr Asn Glu His Tyr Gly Val Phe Leu Ser Thr Thr Gly Asn Glu Ala
                325                 330                 335

Ala Asn Phe Thr Ile Lys Leu Leu Glu Glu Thr Leu Gly Ser Asp Lys
            340                 345                 350

Pro Ala Pro Met Asn Leu Val Lys Ser Glu Gly Val Lys Leu Pro Ala
        355                 360                 365

Pro Tyr Gln Glu Arg Thr Ile Asp Leu Ser Ala Tyr Ala Gly Gln Gln
    370                 375                 380

Val Tyr Leu Ala Phe Arg His Phe Asn Ser Thr Gly Ile Phe Arg Leu
385                 390                 395                 400

Tyr Leu Asp Asp Val Ala Val Ser Gly Glu Gly Ser Ser Asn Asp Tyr
                405                 410                 415

Thr Tyr Thr Val Tyr Arg Asp Asn Val Val Ile Ala Gln Asn Leu Ala
            420                 425                 430

Ala Thr Thr Phe Asn Gln Glu Asn Val Ala Pro Gly Gln Tyr Asn Tyr
        435                 440                 445

Cys Val Glu Val Lys Tyr Thr Ala Gly Val Ser Pro Lys Val Cys Lys
    450                 455                 460

Asp Val Thr Val Glu Gly Ser Asn Glu Phe Ala His Val Gln Asn Leu
465                 470                 475                 480

Thr Gly Ser Ala Val Gly Gln Lys Val Thr Leu Lys Trp Asp Ala Pro
                485                 490                 495

Asn
```

( 2 ) INFORMATION FOR SEQ ID NO:3:

( i ) SEQUENCE CHARACTERISTICS:
( A ) LENGTH: 1470 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Porphyromonas gingivalis
( B ) STRAIN: FDC381

( v i i ) IMMEDIATE SOURCE:
( A ) LIBRARY: genomic
( B ) CLONE: ST7

( i x ) FEATURE:

-continued ( A ) NAME/KEY: CDS
( B ) LOCATION: 310..1359

( x i ) SEQUENCE DESCRIPTION: SEQ ID NO:3:

```
GTTTCTTGCT CCCTGCACGA TGTAGGAAGC CGTTGTCACG TGACAATCAC TCCGTGCATG     60

ATGCAGGAAG CCGTTGTCAC GTGACAATCA CTCCGTGCAC GATGCAGGAA GCTGTCGTCA    120

CGTGACAATC ACGTCCTGCA CGATGCAGGA AACGATTGTC AGCCGACAAT CGTTTCGCGC    180

ACGGCTGTTT TGACCTTTCG TCGCCTGACA ATGCTTATAT AAAAGCTGTT TCAGGGGGCA    240

GTGTCACTTG ACACTGCTAC CAATAACAGA TTAATAATCA ATCAAATACA ACAAAAAAAG    300

GAAAAACAA ATG ACT GTA GAA AAT TTG CGT CTG CAG CGG CTC CAA AAT       348
          Met Thr Val Glu Asn Leu Arg Leu Gln Arg Leu Gln Asn
           1               5                  10

TTG GAG CAC TAC CGT TTT GCC AAG AAT GTG CTG ACG CTC TGT CGC ACG      396
Leu Glu His Tyr Arg Phe Ala Lys Asn Val Leu Thr Leu Cys Arg Thr
    15                  20                  25

GCA AAT ATC GCT AAA CTG AAT CCC AAA CTG CCC GAG CTG GAA AAG GCT      444
Ala Asn Ile Ala Lys Leu Asn Pro Lys Leu Pro Glu Leu Glu Lys Ala
30                  35                  40                  45

ATC GAA ATG GAG GAT TTG GCT CTG AAT CCG CCC GTC GCG AAC GAG CTG      492
Ile Glu Met Glu Asp Leu Ala Leu Asn Pro Pro Val Ala Asn Glu Leu
                50                  55                  60

ACG CCT CAG GTC ATA GCC CTC GAC GAG GAA CGC GAC AGA GCC TAT CAG      540
Thr Pro Gln Val Ile Ala Leu Asp Glu Glu Arg Asp Arg Ala Tyr Gln
            65                  70                  75

GCG CTG ATG TCG CGC GTG CGT TCG TAT GCT TTC GAC GAG GAC AGC CAG      588
Ala Leu Met Ser Arg Val Arg Ser Tyr Ala Phe Asp Glu Asp Ser Gln
        80                  85                  90

CTG CGC AAC GCG GCA GCC AGA ATC GAA GAC GTG GCC GCT CGC TAC GGC      636
Leu Arg Asn Ala Ala Ala Arg Ile Glu Asp Val Ala Ala Arg Tyr Gly
    95                 100                 105

AAC GTG ATC CGA ATG AAC TAT GAC AAG GAG ACG GCC GCG ATA GAG AAT      684
Asn Val Ile Arg Met Asn Tyr Asp Lys Glu Thr Ala Ala Ile Glu Asn
110                 115                 120                 125

TTC CTC ACC GAT CTC AAG GGC GAG AAC ATT CGC CCC CTC GTA ACG AAA      732
Phe Leu Thr Asp Leu Lys Gly Glu Asn Ile Arg Pro Leu Val Thr Lys
                130                 135                 140

CTC GGC GTG ACG GCA CTC GTT GAC AGA CTG GAA AAG AAC AAT AAG GCC      780
Leu Gly Val Thr Ala Leu Val Asp Arg Leu Glu Lys Asn Asn Lys Ala
            145                 150                 155

TTC GCC GAC TTC TTC CTC CGC CGT CTG AGC ACC GAC CAA CGA GGC AAA      828
Phe Ala Asp Phe Phe Leu Arg Arg Leu Ser Thr Asp Gln Arg Gly Lys
        160                 165                 170

TAT GAC GTG AAG GCA CTC CGT GCC GAG ACC GAC CGC ACA TTG GTA GCC      876
Tyr Asp Val Lys Ala Leu Arg Ala Glu Thr Asp Arg Thr Leu Val Ala
    175                 180                 185

GTG GTG CGC CGC ATG GAC TCC ATC GAC GAC ATG GAG CCG AGC CCG GAG      924
Val Val Arg Arg Met Asp Ser Ile Asp Asp Met Glu Pro Ser Pro Glu
190                 195                 200                 205

ATC CGT GCG CTC ATC GAG CTC TAC AAC CGA CTC GTG GCC AAT CGC CGC      972
Ile Arg Ala Leu Ile Glu Leu Tyr Asn Arg Leu Val Ala Asn Arg Arg
                210                 215                 220

GCT CTC TTG GCT CGT CGC GCC AGC TAC GGA GAA GCA GCC GTG GAG AAG     1020
Ala Leu Leu Ala Arg Arg Ala Ser Tyr Gly Glu Ala Ala Val Glu Lys
            225                 230                 235

CGT CGT GCC GAG ATC GCC GAG ATG CTC CGC CCC CTG CTC GCC CGG ATC     1068
Arg Arg Ala Glu Ile Ala Glu Met Leu Arg Pro Leu Leu Ala Arg Ile
        240                 245                 250

GTG GAG GAG AAG AAG ACG GCC GTC TTT GCC GGT CGC ACC CTC GGC ACG     1116
```

-continued

```
Val Glu Glu Lys Lys Thr Ala Val Phe Ala Gly Arg Thr Leu Gly Thr
    255                 260                 265

GGC AAG AAC CGC CAC TAT CTC ATC ACA TTC GTA GCC GAG AAC GGC GAC     1164
Gly Lys Asn Arg His Tyr Leu Ile Thr Phe Val Ala Glu Asn Gly Asp
270                 275                 280                 285

GAG GAG GAT CGC TGG TAC CGC ATC AAC GGG GAG CAA CTC GTC TAT GTG     1212
Glu Glu Asp Arg Trp Tyr Arg Ile Asn Gly Glu Gln Leu Val Tyr Val
                290                 295                 300

CCC GAA GAC GAA CTC CCC AAG CCG AAG AAA AAG AAG AAA CCC GCA AGC     1260
Pro Glu Asp Glu Leu Pro Lys Pro Lys Lys Lys Lys Lys Pro Ala Ser
            305                 310                 315

AGC ACG GAC ACT CCA TCC GAG CCG CCC GTC CTG CCG GAT CCA TCG CAA     1308
Ser Thr Asp Thr Pro Ser Glu Pro Pro Val Leu Pro Asp Pro Ser Gln
        320                 325                 330

GGA GGC AGC AGT AGC GGC GGT GGC GAG CAA GGC TCT ACC GGC GGC GGA     1356
Gly Gly Ser Ser Ser Gly Gly Gly Glu Gln Gly Ser Thr Gly Gly Gly
    335                 340                 345

CTC TGATCCCCCC GTGCCGTCCT GCCGGCCGCA GCAGCACAGG CAACCGAGTA          1409
Leu
350

TAAAAGACAA AGGGGCTGTG ACCAAATTCA TTTTTGGCAC AGCCCCTTGT ATATTCGAAA   1469

A                                                                   1470
```

( 2 ) INFORMATION FOR SEQ ID NO:4:

( i ) SEQUENCE CHARACTERISTICS:
( A ) LENGTH: 350 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Thr Val Glu Asn Leu Arg Leu Gln Arg Leu Gln Asn Leu Glu His
  1               5                  10                  15

Tyr Arg Phe Ala Lys Asn Val Leu Thr Leu Cys Arg Thr Ala Asn Ile
            20                  25                  30

Ala Lys Leu Asn Pro Lys Leu Pro Glu Leu Glu Lys Ala Ile Glu Met
        35                  40                  45

Glu Asp Leu Ala Leu Asn Pro Pro Val Ala Asn Glu Leu Thr Pro Gln
    50                  55                  60

Val Ile Ala Leu Asp Glu Glu Arg Asp Arg Ala Tyr Gln Ala Leu Met
 65                  70                  75                  80

Ser Arg Val Arg Ser Tyr Ala Phe Asp Glu Asp Ser Gln Leu Arg Asn
                 85                  90                  95

Ala Ala Ala Arg Ile Glu Asp Val Ala Ala Arg Tyr Gly Asn Val Ile
            100                 105                 110

Arg Met Asn Tyr Asp Lys Glu Thr Ala Ala Ile Glu Asn Phe Leu Thr
        115                 120                 125

Asp Leu Lys Gly Glu Asn Ile Arg Pro Leu Val Thr Lys Leu Gly Val
    130                 135                 140

Thr Ala Leu Val Asp Arg Leu Glu Lys Asn Asn Lys Ala Phe Ala Asp
145                 150                 155                 160

Phe Phe Leu Arg Arg Leu Ser Thr Asp Gln Arg Gly Lys Tyr Asp Val
                165                 170                 175

Lys Ala Leu Arg Ala Glu Thr Asp Arg Thr Leu Val Ala Val Val Arg
            180                 185                 190

Arg Met Asp Ser Ile Asp Asp Met Glu Pro Ser Pro Glu Ile Arg Ala
```

-continued

```
          195                           200                           205

Leu  Ile  Glu  Leu  Tyr  Asn  Arg  Leu  Val  Ala  Asn  Arg  Arg  Ala  Leu  Leu
     210                      215                      220

Ala  Arg  Arg  Ala  Ser  Tyr  Gly  Glu  Ala  Ala  Val  Glu  Lys  Arg  Arg  Ala
225                      230                      235                      240

Glu  Ile  Ala  Glu  Met  Leu  Arg  Pro  Leu  Leu  Ala  Arg  Ile  Val  Glu  Glu
                    245                      250                      255

Lys  Lys  Thr  Ala  Val  Phe  Ala  Gly  Arg  Thr  Leu  Gly  Thr  Gly  Lys  Asn
               260                      265                      270

Arg  His  Tyr  Leu  Ile  Thr  Phe  Val  Ala  Glu  Asn  Gly  Asp  Glu  Glu  Asp
          275                      280                      285

Arg  Trp  Tyr  Arg  Ile  Asn  Gly  Glu  Gln  Leu  Val  Tyr  Val  Pro  Glu  Asp
     290                      295                      300

Glu  Leu  Pro  Lys  Pro  Lys  Lys  Lys  Lys  Lys  Pro  Ala  Ser  Ser  Thr  Asp
305                      310                      315                      320

Thr  Pro  Ser  Glu  Pro  Pro  Val  Leu  Pro  Asp  Pro  Ser  Gln  Gly  Gly  Ser
                    325                      330                      335

Ser  Ser  Gly  Gly  Gly  Glu  Gln  Gly  Ser  Thr  Gly  Gly  Gly  Leu
               340                      345                      350
```

( 2 ) INFORMATION FOR SEQ ID NO:5:

( i ) SEQUENCE CHARACTERISTICS:
( A ) LENGTH: 1841 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 374..1424

( x i ) SEQUENCE DESCRIPTION: SEQ ID NO:5:

```
AAGCTTGCAC CTACGACAAA AGATTTTTTC ATCTTACTAT ATTTTGGGAT TATATTTCTA      60

CACCTCCTTA TCCGGAATTT GGAAATGCGG GGCAAAAGTA GAAAAATTTT ATTTCCATCA     120

AAAAAAATCT TCAAATTTTT TTCACTTTGC GCATTCTGCA TATAAATGCT GCTACGTCGG     180

CAGATTATTC TGGTTAAAAA GTTATAGATG CAGCTCTTGG TTATAGTGTC CTAAGATCGC     240

TATGCAACCT GTAAGAAACG ATTGTAGGGT GTTTCTTGCT TCCTGCACGA ATGCAGGAGA     300

GCAGAAACGC CCGTTGCTGC TCCCGTCAAT ACACTAATTA TTATCGACTT AACCCCTTAA     360

TTCAAAAACT AAA ATG ACT GCA GAA ATT TTC TCG TTT TCC CGG CTC CAA        409
               Met Thr Ala Glu Ile Phe Ser Phe Ser Arg Leu Gln
                 1               5                  10

AAT TTG GAG CAC TAC CGT TTT GCC AAG AAT GTG CTG ACG CTC TGT CGC       457
Asn Leu Glu His Tyr Arg Phe Ala Lys Asn Val Leu Thr Leu Cys Arg
         15                  20                  25

ACG GCA AAT ATC GCT AAA CTG AAT CCC AAA CTG CCC GAG CTG GAA AAG       505
Thr Ala Asn Ile Ala Lys Leu Asn Pro Lys Leu Pro Glu Leu Glu Lys
     30                  35                  40

GCT ATC GAA ATG GAG GAT TTG GCT CTG AAT CCG CCC GTC GCG AAC GAG       553
Ala Ile Glu Met Glu Asp Leu Ala Leu Asn Pro Pro Val Ala Asn Glu
 45                  50                  55                  60

CTG ACG CCT CAG GTC ATA GCC CTC GAC GAG GAA CGC GAC AGA GCC TAT       601
Leu Thr Pro Gln Val Ile Ala Leu Asp Glu Glu Arg Asp Arg Ala Tyr
                 65                  70                  75

CAG GCG CTG ATG TCG CGC GTG CGT TCG TAT GCT TTC GAC GAG GAC AGC       649
Gln Ala Leu Met Ser Arg Val Arg Ser Tyr Ala Phe Asp Glu Asp Ser
```

-continued

```
                        80                      85                      90

CAG CTG CGC AAC GCG GCA GCC AGA ATC GAA GAC GTG GCC GCT CGC TAC      697
Gln Leu Arg Asn Ala Ala Ala Arg Ile Glu Asp Val Ala Ala Arg Tyr
             95                     100                     105

GGC AAC GTG ATC CGA ATG AAC TAT GAC AAG GAG ACG GCC GCG ATA GAG      745
Gly Asn Val Ile Arg Met Asn Tyr Asp Lys Glu Thr Ala Ala Ile Glu
    110                     115                     120

AAT TTC CTC ACC GAT CTC AAG GGC GAG AAC ATT CGC CCC CTC GTA ACG      793
Asn Phe Leu Thr Asp Leu Lys Gly Glu Asn Ile Arg Pro Leu Val Thr
125                     130                     135                     140

AAA CTC GGC GTG ACG GCA CTC GTT GAC AGA CTG GAA AAG AAC AAT AAG      841
Lys Leu Gly Val Thr Ala Leu Val Asp Arg Leu Glu Lys Asn Asn Lys
                145                     150                     155

GCC TTC GCC GAC TTC TTC CTC CGC CGT CTG AGC ACC GAC CAA CGA GGC      889
Ala Phe Ala Asp Phe Phe Leu Arg Arg Leu Ser Thr Asp Gln Arg Gly
            160                     165                     170

AAA TAT GAC GTG AAG GCA CTC CGT GCC GAG ACC GAC CGC ACA TTG GTA      937
Lys Tyr Asp Val Lys Ala Leu Arg Ala Glu Thr Asp Arg Thr Leu Val
        175                     180                     185

GCC GTG GTG CGC CGC ATG GAC TCC ATC GAC GAC ATG GAG CCG AGC CCG      985
Ala Val Val Arg Arg Met Asp Ser Ile Asp Asp Met Glu Pro Ser Pro
    190                     195                     200

GAG ATC CGT GCG CTC ATC GAG CTC TAC AAC CGA CTC GTG GCC AAT CGC     1033
Glu Ile Arg Ala Leu Ile Glu Leu Tyr Asn Arg Leu Val Ala Asn Arg
205                     210                     215                     220

CGC GCT CTC TTG GCT CGT CGC GCC AGC TAC GGA GAA GCA GCC GTG GAG     1081
Arg Ala Leu Leu Ala Arg Arg Ala Ser Tyr Gly Glu Ala Ala Val Glu
                225                     230                     235

AAG CGT CGT GCC GAG ATC GCC GAG ATG CTC CGC CCC CTG CTC GCC CGG     1129
Lys Arg Arg Ala Glu Ile Ala Glu Met Leu Arg Pro Leu Leu Ala Arg
            240                     245                     250

ATC GTG GAG GAG AAG AAG ACG GCC GTC TTT GCC GGT CGC ACC CTC GGC     1177
Ile Val Glu Glu Lys Lys Thr Ala Val Phe Ala Gly Arg Thr Leu Gly
        255                     260                     265

ACG GGC AAG AAC CGC CAC TAT CTC ATC ACA TTC GTA GCC GAG AAC GGC     1225
Thr Gly Lys Asn Arg His Tyr Leu Ile Thr Phe Val Ala Glu Asn Gly
    270                     275                     280

GAC GAG GAG GAT CGC TGG TAC CGC ATC AAC GGG GAG CAA CTC GTC TAT     1273
Asp Glu Glu Asp Arg Trp Tyr Arg Ile Asn Gly Glu Gln Leu Val Tyr
285                     290                     295                     300

GTG CCC GAA GAC GAA CTC CCC AAG CCG AAG AAA AAG AAG AAA CCC GCA     1321
Val Pro Glu Asp Glu Leu Pro Lys Pro Lys Lys Lys Lys Lys Pro Ala
                305                     310                     315

AGC AGC ACG GAC ACT CCA TCC GAG CCG CCC GTC CTG CCG GAT CCA TCG     1369
Ser Ser Thr Asp Thr Pro Ser Glu Pro Pro Val Leu Pro Asp Pro Ser
            320                     325                     330

CAA GGA GGC AGC AGT AGC GGC GGT GGC GAG CAA GGC TCT ACC GGC GGC     1417
Gln Gly Gly Ser Ser Ser Gly Gly Gly Glu Gln Gly Ser Thr Gly Gly
        335                     340                     345

GGA CTC T GATCCGCACT CCCCCGTGCC GTCCTGTCGG CCGCAGCAGC ACAGGCAACC    1474
Gly Leu
    350

GAGTATAAAA GACAAAGGGG CTGTGACCAA ATTCATTTTT GGCACAGCCC CTTTCAGGTG   1534

CATAAGAATC TATATTACGG GAGAACAATC CCTGTAAGAG CAGTCACGAT GCCGTTTTCC   1594

TCATATACAG TAATCCGGAA GACGTCTTCC AGCAGATCGG GATGTCTCAG AACCCATGCT   1654

CCTTTTATGG GCTGGGGTTT TGGTTTGGCT CTGTAAATTT TTCCAAGGGA TCTAGTTTTT   1714

AGCTCTCAAT GGGCCAGATC CCCCCTCAAG TGCAATTCGA GAGAGGATAA AAGGGATAAT   1774
```

CCGTGAACGC TCTGCGGTCT ATCGGTAGCG TACGGTCATG AACAGGTGTG TACGTGCCTG 1834

TCCGCGG 1841

( 2 ) INFORMATION FOR SEQ ID NO:6:

( i ) SEQUENCE CHARACTERISTICS:
( A ) LENGTH: 350 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Thr Ala Glu Ile Phe Ser Phe Ser Arg Leu Gln Asn Leu Glu His
1 5 10 15

Tyr Arg Phe Ala Lys Asn Val Leu Thr Leu Cys Arg Thr Ala Asn Ile
20 25 30

Ala Lys Leu Asn Pro Lys Leu Pro Glu Leu Glu Lys Ala Ile Glu Met
35 40 45

Glu Asp Leu Ala Leu Asn Pro Pro Val Ala Asn Glu Leu Thr Pro Gln
50 55 60

Val Ile Ala Leu Asp Glu Glu Arg Asp Arg Ala Tyr Gln Ala Leu Met
65 70 75 80

Ser Arg Val Arg Ser Tyr Ala Phe Asp Glu Asp Ser Gln Leu Arg Asn
85 90 95

Ala Ala Ala Arg Ile Glu Asp Val Ala Ala Arg Tyr Gly Asn Val Ile
100 105 110

Arg Met Asn Tyr Asp Lys Glu Thr Ala Ala Ile Glu Asn Phe Leu Thr
115 120 125

Asp Leu Lys Gly Glu Asn Ile Arg Pro Leu Val Thr Lys Leu Gly Val
130 135 140

Thr Ala Leu Val Asp Arg Leu Glu Lys Asn Asn Lys Ala Phe Ala Asp
145 150 155 160

Phe Phe Leu Arg Arg Leu Ser Thr Asp Gln Arg Gly Lys Tyr Asp Val
165 170 175

Lys Ala Leu Arg Ala Glu Thr Asp Arg Thr Leu Val Ala Val Val Arg
180 185 190

Arg Met Asp Ser Ile Asp Asp Met Glu Pro Ser Pro Glu Ile Arg Ala
195 200 205

Leu Ile Glu Leu Tyr Asn Arg Leu Val Ala Asn Arg Arg Ala Leu Leu
210 215 220

Ala Arg Arg Ala Ser Tyr Gly Glu Ala Ala Val Glu Lys Arg Arg Ala
225 230 235 240

Glu Ile Ala Glu Met Leu Arg Pro Leu Leu Ala Arg Ile Val Glu Glu
245 250 255

Lys Lys Thr Ala Val Phe Ala Gly Arg Thr Leu Gly Thr Gly Lys Asn
260 265 270

Arg His Tyr Leu Ile Thr Phe Val Ala Glu Asn Gly Asp Glu Glu Asp
275 280 285

Arg Trp Tyr Arg Ile Asn Gly Glu Gln Leu Val Tyr Val Pro Glu Asp
290 295 300

Glu Leu Pro Lys Pro Lys Lys Lys Lys Lys Pro Ala Ser Ser Thr Asp
305 310 315 320

Thr Pro Ser Glu Pro Pro Val Leu Pro Asp Pro Ser Gln Gly Gly Ser
325 330 335

Ser Ser Gly Gly Gly Glu Gln Gly Ser Thr Gly Gly Gly Leu 340 345 350

( 2 ) INFORMATION FOR SEQ ID NO:7:

( i ) SEQUENCE CHARACTERISTICS:
( A ) LENGTH: 4080 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 87..3347

( x i ) SEQUENCE DESCRIPTION: SEQ ID NO:7:

```
TCAAGAATCA GGCCTTCTTA ATAACCAATT CAGGCCTTCC TCCGGGTTCT TACCGTAAAC      60

TAATTTACTA AAAGTTGGAG TTTTGT ATG GGA ACA GTT GTT GCT GAT CCC ACC      113
                             Met Gly Thr Val Val Ala Asp Pro Thr
                               1               5

GTT GCT GCG CCT GTG AAA ATG GCT AAA CAG ATA GCC GAA AAT GGT AAT      161
Val Ala Ala Pro Val Lys Met Ala Lys Gln Ile Ala Glu Asn Gly Asn
 10                  15                  20                  25

TAT GAT GTA GTG ATG ACT CGC TCT AAC TAT CTT CCT GTG ATC AAC CAA      209
Tyr Asp Val Val Met Thr Arg Ser Asn Tyr Leu Pro Val Ile Asn Gln
                 30                  35                  40

ATT CAG GCA GGA GAG CCT AGC CCC TAC CAG CCT GTT AAC AAC TTG ACT      257
Ile Gln Ala Gly Glu Pro Ser Pro Tyr Gln Pro Val Asn Asn Leu Thr
             45                  50                  55

GCT CCA CCG GAG GGT GAG GAA GTG GCG CTC AAG TGG GAT ACC CCG AGC      305
Ala Pro Pro Glu Gly Glu Glu Val Ala Leu Lys Trp Asp Thr Pro Ser
         60                  65                  70

GCA AAG AAG GCA GAA GCT TCC CGT GAA GTA AAA CGG ATC GGA GAC GGT      353
Ala Lys Lys Ala Glu Ala Ser Arg Glu Val Lys Arg Ile Gly Asp Gly
     75                  80                  85

CTT TTC GTT ACG ATC GAA CCT GCA AAC GAT GTA CGT GCC AAC GAA GCC      401
Leu Phe Val Thr Ile Glu Pro Ala Asn Asp Val Arg Ala Asn Glu Ala
 90                  95                 100                 105

AAG GTT GTG CTC GCA GCA GAC AAC GTA TGG GGA GAC AAT ACG GGT TAC      449
Lys Val Val Leu Ala Ala Asp Asn Val Trp Gly Asp Asn Thr Gly Tyr
                110                 115                 120

CAG TTC TTG TTG GAT GCC GAT CAC AAT ACA TTC GGA AGT GTC ATT CCG      497
Gln Phe Leu Leu Asp Ala Asp His Asn Thr Phe Gly Ser Val Ile Pro
            125                 130                 135

GCA ACC GGT CCT CTC TTT ACC GGA ACA GCT TCT TCC AAT CTT TAC AGT      545
Ala Thr Gly Pro Leu Phe Thr Gly Thr Ala Ser Ser Asn Leu Tyr Ser
        140                 145                 150

GCG AAC TTC GAG TAT TTG ATC CCG GCC AAT GCC GAT CCT GTT GTT ACT      593
Ala Asn Phe Glu Tyr Leu Ile Pro Ala Asn Ala Asp Pro Val Val Thr
    155                 160                 165

ACA CAG AAT ATT ATC GTT ACA GGA CAG GGT GAA GTT GTA ATC CCC GGT      641
Thr Gln Asn Ile Ile Val Thr Gly Gln Gly Glu Val Val Ile Pro Gly
170                 175                 180                 185

GGT GTT TAC GAC TAT TGC ATT ACG AAC CCG GAA CCT GCA TCC GGA AAG      689
Gly Val Tyr Asp Tyr Cys Ile Thr Asn Pro Glu Pro Ala Ser Gly Lys
                190                 195                 200

ATG TGG ATC GCA GGA GAT GGA GAC AAC CAG CCT GCA CGT TAT GAC GAT      737
Met Trp Ile Ala Gly Asp Gly Asp Asn Gln Pro Ala Arg Tyr Asp Asp
            205                 210                 215

TTC ACA TTC GAA GCA GGC AAG AAG TAC ACC TTC ACG ATG CGT CGC GCC      785
Phe Thr Phe Glu Ala Gly Lys Lys Tyr Thr Phe Thr Met Arg Arg Ala
        220                 225                 230
```

-continued

```
GGA ATG GGA GAT GGA ACT GAT ATG GAA GTC GAA GAC GAT TCA CCT GCA      833
Gly Met Gly Asp Gly Thr Asp Met Glu Val Glu Asp Asp Ser Pro Ala
    235                 240                 245

AGC TAT ACC TAT ACA GTC TAT CGT GAC GGC ACG AAG ATC AAG GAA GGT      881
Ser Tyr Thr Tyr Thr Val Tyr Arg Asp Gly Thr Lys Ile Lys Glu Gly
250                 255                 260                 265

CTG ACG GCT ACG ACA TTC GAA GAA GAC GGT GTA GCT GCA GGC AAT CAT      929
Leu Thr Ala Thr Thr Phe Glu Glu Asp Gly Val Ala Ala Gly Asn His
                270                 275                 280

GAG TAT TGC GTG GAA GTT AAG TAC ACA GCC GGC GTA TCT CCG AAG GTA      977
Glu Tyr Cys Val Glu Val Lys Tyr Thr Ala Gly Val Ser Pro Lys Val
            285                 290                 295

TGT AAA GAC GTT ACG GTA GAA GGA TCC AAT GAA TTT GCT CCT GTA CAG     1025
Cys Lys Asp Val Thr Val Glu Gly Ser Asn Glu Phe Ala Pro Val Gln
        300                 305                 310

AAC CTG ACC GGT AGT GCA GTC GGC CAG AAA GTA ACG CTT AAG TGG GAT     1073
Asn Leu Thr Gly Ser Ala Val Gly Gln Lys Val Thr Leu Lys Trp Asp
    315                 320                 325

GCA CCT AAT GGT ACC CCA AAT CCG AAT CCG AAT CCG AAT CCG GGA ACA     1121
Ala Pro Asn Gly Thr Pro Asn Pro Asn Pro Asn Pro Asn Pro Gly Thr
330                 335                 340                 345

ACA ACA CTT TCC GAA TCA TTC GAA AAT GGT ATT CCT GCC TCA TGG AAG     1169
Thr Thr Leu Ser Glu Ser Phe Glu Asn Gly Ile Pro Ala Ser Trp Lys
                350                 355                 360

ACG ATC GAT GCA GAC GGT GAC GGG CAT GGC TGG AAA CCT GGA AAT GCT     1217
Thr Ile Asp Ala Asp Gly Asp Gly His Gly Trp Lys Pro Gly Asn Ala
            365                 370                 375

CCC GGA ATC GCT GGC TAC AAT AGC AAT GGT TGT GTA TAT TCA GAG TCA     1265
Pro Gly Ile Ala Gly Tyr Asn Ser Asn Gly Cys Val Tyr Ser Glu Ser
        380                 385                 390

TTC GGT CTT GGT GGT ATA GGA GTT CTT ACC CCT GAC AAC TAT CTG ATA     1313
Phe Gly Leu Gly Gly Ile Gly Val Leu Thr Pro Asp Asn Tyr Leu Ile
    395                 400                 405

ACA CCG GCA TTG GAT TTG GCT AAC GGA GGT AAG TTG ACT TTC TGG GTA     1361
Thr Pro Ala Leu Asp Leu Ala Asn Gly Gly Lys Leu Thr Phe Trp Val
410                 415                 420                 425

TGC GCA CAG GAT GCT AAT TAT GCA TCC GAG CAC TAT GCG GTG TAT GCA     1409
Cys Ala Gln Asp Ala Asn Tyr Ala Ser Glu His Tyr Ala Val Tyr Ala
                430                 435                 440

TCT TCG ACC GGT AAC GAT GCA TCC AAC TTC ACG AAT GCT TTG TTG GAA     1457
Ser Ser Thr Gly Asn Asp Ala Ser Asn Phe Thr Asn Ala Leu Leu Glu
            445                 450                 455

GAG ACG ATT ACG GCA AAA GGT GTT CGC TCG CCG GAA GCT ATT CGT GGT     1505
Glu Thr Ile Thr Ala Lys Gly Val Arg Ser Pro Glu Ala Ile Arg Gly
        460                 465                 470

CGT ATA CAG GGT ACT TGG CGC CAG AAG ACG GTA GAC CTT CCC GCA GGT     1553
Arg Ile Gln Gly Thr Trp Arg Gln Lys Thr Val Asp Leu Pro Ala Gly
    475                 480                 485

ACG AAA TAT GTT GCT TTC CGT CAC TTC CAA AGC ACG GAT ATG TTC TAC     1601
Thr Lys Tyr Val Ala Phe Arg His Phe Gln Ser Thr Asp Met Phe Tyr
490                 495                 500                 505

ATC GAC CTT GAT GAG GTT GAG ATC AAG GCC AAT GGC AAG CGC GCA GAC     1649
Ile Asp Leu Asp Glu Val Glu Ile Lys Ala Asn Gly Lys Arg Ala Asp
                510                 515                 520

TTC ACG GAA ACG TTC GAG TCT TCT ACT CAT GGA GAG GCA CCA GCG GAA     1697
Phe Thr Glu Thr Phe Glu Ser Ser Thr His Gly Glu Ala Pro Ala Glu
            525                 530                 535

TGG ACT ACT ATC GAT GCC GAT GGC GAT GGT CAG GAT TGG CTC TGT CTG     1745
Trp Thr Thr Ile Asp Ala Asp Gly Asp Gly Gln Asp Trp Leu Cys Leu
        540                 545                 550
```

```
TCT TCC GGA CAA TTG GAC TGG CTG ACA GCT CAT GGC GGC ACC AAC GTA      1793
Ser Ser Gly Gln Leu Asp Trp Leu Thr Ala His Gly Gly Thr Asn Val
    555                 560                 565

GTA GCC TCT TTC TCA TGG AAT GGA ATG GCT TTG AAT CCT GAT AAC TAT      1841
Val Ala Ser Phe Ser Trp Asn Gly Met Ala Leu Asn Pro Asp Asn Tyr
570                 575                 580                 585

CTC ATC TCA AAG GAT GTT ACA GGC GCA ACG AAG GTA AAG TAC TAC TAT      1889
Leu Ile Ser Lys Asp Val Thr Gly Ala Thr Lys Val Lys Tyr Tyr Tyr
                590                 595                 600

GCA GTC AAC GAC GGT TTT CCC GGG GAT CAC TAT GCG GTG ATG ATC TCC      1937
Ala Val Asn Asp Gly Phe Pro Gly Asp His Tyr Ala Val Met Ile Ser
            605                 610                 615

AAG ACG GGC ACG AAC GCC GGA GAC TTC ACG GTT GTT TTC GAA GAA ACG      1985
Lys Thr Gly Thr Asn Ala Gly Asp Phe Thr Val Val Phe Glu Glu Thr
        620                 625                 630

CCT AAC GGA ATA AAT AAG GGC GGA GCA AGA TTC GGT CTT TCC ACG GAA      2033
Pro Asn Gly Ile Asn Lys Gly Gly Ala Arg Phe Gly Leu Ser Thr Glu
    635                 640                 645

GCC AAT GGC GCC AAA CCT CAA AGT GTA TGG ATC GAG CGT ACG GTA GAT      2081
Ala Asn Gly Ala Lys Pro Gln Ser Val Trp Ile Glu Arg Thr Val Asp
650                 655                 660                 665

TTG CCT GCG GGC ACG AAG TAT GTT GCT TTC CGT CAC TAC AAT TGC TCG      2129
Leu Pro Ala Gly Thr Lys Tyr Val Ala Phe Arg His Tyr Asn Cys Ser
                670                 675                 680

GAT TTG GAC TAC ATT CTT TTG GAT GAT ATT CAG TTC ACC ATG GGT GGC      2177
Asp Leu Asp Tyr Ile Leu Leu Asp Asp Ile Gln Phe Thr Met Gly Gly
            685                 690                 695

AGC CCC ACC CCG ACC GAT TAT ACC TAC ACG GTA TAT CGT GAT GGT ACG      2225
Ser Pro Thr Pro Thr Asp Tyr Thr Tyr Thr Val Tyr Arg Asp Gly Thr
        700                 705                 710

AAG ATC AAG GAA GGT CTG ACC GAA ACG ACC TTC GAA GAA GAC GGC GTA      2273
Lys Ile Lys Glu Gly Leu Thr Glu Thr Thr Phe Glu Glu Asp Gly Val
    715                 720                 725

GCT ACG GGC AAT CAT GAG TAT TGC GTG GAA GTG AAG TAC ACA GCC GGC      2321
Ala Thr Gly Asn His Glu Tyr Cys Val Glu Val Lys Tyr Thr Ala Gly
730                 735                 740                 745

GTA TCT CCG AAG GTG TGT GTA AAC GTA ACT ATT AAT CCG ACT CAG TTC      2369
Val Ser Pro Lys Val Cys Val Asn Val Thr Ile Asn Pro Thr Gln Phe
                750                 755                 760

AAT CCT GTA AAG AAC CTG AAG GCA CAA CCG GAT GGC GGC GAC GTG GTT      2417
Asn Pro Val Lys Asn Leu Lys Ala Gln Pro Asp Gly Gly Asp Val Val
            765                 770                 775

CTC AAG TGG GAA GCC CCG AGT GGC AAA CGA GGA GAA CTG CTT AAT GAA      2465
Leu Lys Trp Glu Ala Pro Ser Gly Lys Arg Gly Glu Leu Leu Asn Glu
        780                 785                 790

GAT TTT GAA GGA GAC GCT ATT CCC ACA GGG TGG ACA GCA TTG GAT GCC      2513
Asp Phe Glu Gly Asp Ala Ile Pro Thr Gly Trp Thr Ala Leu Asp Ala
    795                 800                 805

GAT GGT GAC GGT AAT AAC TGG GAT ATC ACG CTC AAT GAA TTT ACG CGA      2561
Asp Gly Asp Gly Asn Asn Trp Asp Ile Thr Leu Asn Glu Phe Thr Arg
810                 815                 820                 825

GGA GAG CGT CAT GTT CTT TCA CCT TTA CGC GCC AGC AAC GTA GCC ATA      2609
Gly Glu Arg His Val Leu Ser Pro Leu Arg Ala Ser Asn Val Ala Ile
                830                 835                 840

TCC TAT TCT TCT TTA CTT CAG GGT CAA GAA TAT TTG CCT CTC ACG CCG      2657
Ser Tyr Ser Ser Leu Leu Gln Gly Gln Glu Tyr Leu Pro Leu Thr Pro
            845                 850                 855

AAC AAC TTT CTG ATC ACT CCG AAG GTT GAA GGA GCA AAG AAG ATT ACT      2705
Asn Asn Phe Leu Ile Thr Pro Lys Val Glu Gly Ala Lys Lys Ile Thr
        860                 865                 870
```

-continued

TAT AAG GTG GGT TCA CCG GGT CTT CCT CAA TGG AGT CAT GAT CAT TAT 2753
Tyr Lys Val Gly Ser Pro Gly Leu Pro Gln Trp Ser His Asp His Tyr
875 880 885

GCA CTC TGT ATC TCC AAG AGC GGA ACG GCT GCA GCC GAC TTC GAA GTA 2801
Ala Leu Cys Ile Ser Lys Ser Gly Thr Ala Ala Ala Asp Phe Glu Val
890 895 900 905

ATC TTT GAA GAA ACG ATG ACC TAC ACT CAA GGA GGA GCC AAC TTG ACA 2849
Ile Phe Glu Glu Thr Met Thr Tyr Thr Gln Gly Gly Ala Asn Leu Thr
910 915 920

AGA GAA AAA GAC CTC CCT GCC GGC ACG AAA TAT GTC GCT TTC CGT CAT 2897
Arg Glu Lys Asp Leu Pro Ala Gly Thr Lys Tyr Val Ala Phe Arg His
925 930 935

TAC AAT TGC ACG GAT GTT CTG GGC ATA ATG ATT GAC GAT GTA GTG ATA 2945
Tyr Asn Cys Thr Asp Val Leu Gly Ile Met Ile Asp Asp Val Val Ile
940 945 950

ACA GGT GAA GGC GAA GGT CCC AGT TAC ACC TAC ACG GTG TAT CGT GAC 2993
Thr Gly Glu Gly Glu Gly Pro Ser Tyr Thr Tyr Thr Val Tyr Arg Asp
955 960 965

GGC ACG AAG ATC CAG GAA GGT CTG ACC GAA ACG ACC TAC CGC GAT GCA 3041
Gly Thr Lys Ile Gln Glu Gly Leu Thr Glu Thr Thr Tyr Arg Asp Ala
970 975 980 985

GGA ATG AGT GCA CAA TCT CAT GAG TAT TGC GTA GAG GTT AAG TAC GCA 3089
Gly Met Ser Ala Gln Ser His Glu Tyr Cys Val Glu Val Lys Tyr Ala
990 995 1000

GCC GGC GTA TCT CCG AAG GTT TGT GTG GAT TAT ATT CCT GAT GGA GTG 3137
Ala Gly Val Ser Pro Lys Val Cys Val Asp Tyr Ile Pro Asp Gly Val
1005 1010 1015

GCA GAC GTA ACT GCT CAG AAG CCT TAC ACG CTG ACG GTT GTA GGA AAG 3185
Ala Asp Val Thr Ala Gln Lys Pro Tyr Thr Leu Thr Val Val Gly Lys
1020 1025 1030

ACT ATC ACG GTA ACT TGC CAA GGC GAA GCT ATG ATC TAC GAC ATG AAC 3233
Thr Ile Thr Val Thr Cys Gln Gly Glu Ala Met Ile Tyr Asp Met Asn
1035 1040 1045

GGT CGT CGT CTG GCA GCG GGT CGC AAC ACG GTT GTT TAC ACG GCT CAG 3281
Gly Arg Arg Leu Ala Ala Gly Arg Asn Thr Val Val Tyr Thr Ala Gln
1050 1055 1060 1065

GGC GGC TAC TAT GCA GTC ATG GTT GTC GTT GAC GGC AAG TCT TAC GTA 3329
Gly Gly Tyr Tyr Ala Val Met Val Val Val Asp Gly Lys Ser Tyr Val
1070 1075 1080

GAG AAA CTC GCT ATC AAG TAATTCTGTC TTGGACTCGG AGACTTTGTG 3377
Glu Lys Leu Ala Ile Lys
1085

CAGACACTTT TAATATAGGT CTGTAATTGT CTCAGAGTAT GAATCGGTCG CCCGACTTCC 3437

TTAAAAGGAG GTCGGGCGAC TTCGTTTTTA TTATTGCTGT CTGGTAAACT TGTCAAGAGG 3497

AGACCTTTGA AAAATGGGGC GGTCAATAAT TTTCGGTCTA TGGGTCAAAT TGCAGGCTAC 3557

TGTTTTAGGT GTATGTTGGG CTATCTTCCT ATCTTTAAGA GACCTTTGAA AAATAAGGAG 3617

ATGGAGGGAA GAGGAGTTCT TGGCATAAAA GGAGCGAGTG AAAGGGGTGG CAGTAAGGAG 3677

TGAAAGTAGT TGTAAATCCC CCCTTTGAGG AGCTACTTGT ACGAGCTCCT CAAGGGTGGT 3737

TATGCCTTAT CCTACGGATG AGGACATAAT TATCCCCGGC GTTCTGTATA AATTAAAGGC 3797

GATGCTTTCA AGAATGTTTT GAGTATGGGT CTTGGCAAGT CCCCGGTATC GACATGTCCG 3857

CCATGAAACC ACCGGCGAAT ACTGCCAAAG GTGCGTTCGA TGGTGCTCCG TATCGGACTG 3917

ATTGCTTTGT TTCGTTGCTT CTCTTCCTCG GTCAATGCCC TGTTGCGTTG TGCCTTGTGC 3977

ATAATGCCGT CTTGAAGGTG ATGGGTTTGC AGGTAGGAAC GATTTTCCCC GCAAGCATAT 4037

CCTTTGTCCG CCAAGACGGC TGTACCTTGA GGTATGTTTG CAC 4080

( 2 ) INFORMATION FOR SEQ ID NO:8:

( i ) SEQUENCE CHARACTERISTICS:
( A ) LENGTH: 1087 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met Gly Thr Val Val Ala Asp Pro Thr Val Ala Ala Pro Val Lys Met
  1               5                  10                  15

Ala Lys Gln Ile Ala Glu Asn Gly Asn Tyr Asp Val Val Met Thr Arg
             20                  25                  30

Ser Asn Tyr Leu Pro Val Ile Asn Gln Ile Gln Ala Gly Glu Pro Ser
         35                  40                  45

Pro Tyr Gln Pro Val Asn Asn Leu Thr Ala Pro Pro Glu Gly Glu Glu
     50                  55                  60

Val Ala Leu Lys Trp Asp Thr Pro Ser Ala Lys Lys Ala Glu Ala Ser
 65                  70                  75                      80

Arg Glu Val Lys Arg Ile Gly Asp Gly Leu Phe Val Thr Ile Glu Pro
                 85                  90                  95

Ala Asn Asp Val Arg Ala Asn Glu Ala Lys Val Val Leu Ala Ala Asp
            100                 105                 110

Asn Val Trp Gly Asp Asn Thr Gly Tyr Gln Phe Leu Leu Asp Ala Asp
        115                 120                 125

His Asn Thr Phe Gly Ser Val Ile Pro Ala Thr Gly Pro Leu Phe Thr
    130                 135                 140

Gly Thr Ala Ser Ser Asn Leu Tyr Ser Ala Asn Phe Glu Tyr Leu Ile
145                 150                 155                     160

Pro Ala Asn Ala Asp Pro Val Val Thr Thr Gln Asn Ile Ile Val Thr
                165                 170                 175

Gly Gln Gly Glu Val Val Ile Pro Gly Gly Val Tyr Asp Tyr Cys Ile
            180                 185                 190

Thr Asn Pro Glu Pro Ala Ser Gly Lys Met Trp Ile Ala Gly Asp Gly
        195                 200                 205

Asp Asn Gln Pro Ala Arg Tyr Asp Asp Phe Thr Phe Glu Ala Gly Lys
    210                 215                 220

Lys Tyr Thr Phe Thr Met Arg Arg Ala Gly Met Gly Asp Gly Thr Asp
225                 230                 235                     240

Met Glu Val Glu Asp Asp Ser Pro Ala Ser Tyr Thr Tyr Thr Val Tyr
                245                 250                 255

Arg Asp Gly Thr Lys Ile Lys Glu Gly Leu Thr Ala Thr Thr Phe Glu
            260                 265                 270

Glu Asp Gly Val Ala Ala Gly Asn His Glu Tyr Cys Val Glu Val Lys
        275                 280                 285

Tyr Thr Ala Gly Val Ser Pro Lys Val Cys Lys Asp Val Thr Val Glu
    290                 295                 300

Gly Ser Asn Glu Phe Ala Pro Val Gln Asn Leu Thr Gly Ser Ala Val
305                 310                 315                     320

Gly Gln Lys Val Thr Leu Lys Trp Asp Ala Pro Asn Gly Thr Pro Asn
                325                 330                 335

Pro Asn Pro Asn Pro Asn Pro Gly Thr Thr Thr Leu Ser Glu Ser Phe
            340                 345                 350

Glu Asn Gly Ile Pro Ala Ser Trp Lys Thr Ile Asp Ala Asp Gly Asp
```

-continued

```
        355                     360                     365

Gly His Gly Trp Lys Pro Gly Asn Ala Pro Gly Ile Ala Gly Tyr Asn
    370                     375                     380

Ser Asn Gly Cys Val Tyr Ser Glu Ser Phe Gly Leu Gly Gly Ile Gly
385                     390                     395                     400

Val Leu Thr Pro Asp Asn Tyr Leu Ile Thr Pro Ala Leu Asp Leu Ala
                405                     410                     415

Asn Gly Gly Lys Leu Thr Phe Trp Val Cys Ala Gln Asp Ala Asn Tyr
            420                     425                     430

Ala Ser Glu His Tyr Ala Val Tyr Ala Ser Ser Thr Gly Asn Asp Ala
        435                     440                     445

Ser Asn Phe Thr Asn Ala Leu Leu Glu Glu Thr Ile Thr Ala Lys Gly
    450                     455                     460

Val Arg Ser Pro Glu Ala Ile Arg Gly Arg Ile Gln Gly Thr Trp Arg
465                     470                     475                     480

Gln Lys Thr Val Asp Leu Pro Ala Gly Thr Lys Tyr Val Ala Phe Arg
                485                     490                     495

His Phe Gln Ser Thr Asp Met Phe Tyr Ile Asp Leu Asp Glu Val Glu
            500                     505                     510

Ile Lys Ala Asn Gly Lys Arg Ala Asp Phe Thr Glu Thr Phe Glu Ser
        515                     520                     525

Ser Thr His Gly Glu Ala Pro Ala Glu Trp Thr Thr Ile Asp Ala Asp
    530                     535                     540

Gly Asp Gly Gln Asp Trp Leu Cys Leu Ser Ser Gly Gln Leu Asp Trp
545                     550                     555                     560

Leu Thr Ala His Gly Gly Thr Asn Val Val Ala Ser Phe Ser Trp Asn
                565                     570                     575

Gly Met Ala Leu Asn Pro Asp Asn Tyr Leu Ile Ser Lys Asp Val Thr
            580                     585                     590

Gly Ala Thr Lys Val Lys Tyr Tyr Tyr Ala Val Asn Asp Gly Phe Pro
        595                     600                     605

Gly Asp His Tyr Ala Val Met Ile Ser Lys Thr Gly Thr Asn Ala Gly
    610                     615                     620

Asp Phe Thr Val Val Phe Glu Glu Thr Pro Asn Gly Ile Asn Lys Gly
625                     630                     635                     640

Gly Ala Arg Phe Gly Leu Ser Thr Glu Ala Asn Gly Ala Lys Pro Gln
                645                     650                     655

Ser Val Trp Ile Glu Arg Thr Val Asp Leu Pro Ala Gly Thr Lys Tyr
            660                     665                     670

Val Ala Phe Arg His Tyr Asn Cys Ser Asp Leu Asp Tyr Ile Leu Leu
        675                     680                     685

Asp Asp Ile Gln Phe Thr Met Gly Gly Ser Pro Thr Pro Thr Asp Tyr
    690                     695                     700

Thr Tyr Thr Val Tyr Arg Asp Gly Thr Lys Ile Lys Glu Gly Leu Thr
705                     710                     715                     720

Glu Thr Thr Phe Glu Glu Asp Gly Val Ala Thr Gly Asn His Glu Tyr
                725                     730                     735

Cys Val Glu Val Lys Tyr Thr Ala Gly Val Ser Pro Lys Val Cys Val
            740                     745                     750

Asn Val Thr Ile Asn Pro Thr Gln Phe Asn Pro Val Lys Asn Leu Lys
        755                     760                     765

Ala Gln Pro Asp Gly Gly Asp Val Val Leu Lys Trp Glu Ala Pro Ser
    770                     775                     780
```

-continued

Gly Lys Arg Gly Glu Leu Leu Asn Glu Asp Phe Glu Gly Asp Ala Ile
785 790 795 800

Pro Thr Gly Trp Thr Ala Leu Asp Ala Asp Gly Asp Gly Asn Asn Trp
805 810 815

Asp Ile Thr Leu Asn Glu Phe Thr Arg Gly Glu Arg His Val Leu Ser
820 825 830

Pro Leu Arg Ala Ser Asn Val Ala Ile Ser Tyr Ser Ser Leu Leu Gln
835 840 845

Gly Gln Glu Tyr Leu Pro Leu Thr Pro Asn Asn Phe Leu Ile Thr Pro
850 855 860

Lys Val Glu Gly Ala Lys Lys Ile Thr Tyr Lys Val Gly Ser Pro Gly
865 870 875 880

Leu Pro Gln Trp Ser His Asp His Tyr Ala Leu Cys Ile Ser Lys Ser
885 890 895

Gly Thr Ala Ala Ala Asp Phe Glu Val Ile Phe Glu Glu Thr Met Thr
900 905 910

Tyr Thr Gln Gly Gly Ala Asn Leu Thr Arg Glu Lys Asp Leu Pro Ala
915 920 925

Gly Thr Lys Tyr Val Ala Phe Arg His Tyr Asn Cys Thr Asp Val Leu
930 935 940

Gly Ile Met Ile Asp Asp Val Val Ile Thr Gly Glu Gly Glu Gly Pro
945 950 955 960

Ser Tyr Thr Tyr Thr Val Tyr Arg Asp Gly Thr Lys Ile Gln Glu Gly
965 970 975

Leu Thr Glu Thr Thr Tyr Arg Asp Ala Gly Met Ser Ala Gln Ser His
980 985 990

Glu Tyr Cys Val Glu Val Lys Tyr Ala Ala Gly Val Ser Pro Lys Val
995 1000 1005

Cys Val Asp Tyr Ile Pro Asp Gly Val Ala Asp Val Thr Ala Gln Lys
1010 1015 1020

Pro Tyr Thr Leu Thr Val Val Gly Lys Thr Ile Thr Val Thr Cys Gln
1025 1030 1035 1040

Gly Glu Ala Met Ile Tyr Asp Met Asn Gly Arg Arg Leu Ala Ala Gly
1045 1050 1055

Arg Asn Thr Val Val Tyr Thr Ala Gln Gly Gly Tyr Tyr Ala Val Met
1060 1065 1070

Val Val Val Asp Gly Lys Ser Tyr Val Glu Lys Leu Ala Ile Lys
1075 1080 1085

( 2 ) INFORMATION FOR SEQ ID NO:9:

( i ) SEQUENCE CHARACTERISTICS:
( A ) LENGTH: 6895 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 696..5894

( x i ) SEQUENCE DESCRIPTION: SEQ ID NO:9:

GGATCCTACG CCCGATACCC ATACTCGAAG CCTTTGCTCA GTACCATCCT GCAGAAGGTT 60

ACTCTTTCGC ATATAGTGAC CCTCTTTTCT CTCAGCATAA TGGTACCTAT CATATCAGTA 120

AGGGGCGTAT TGTCTTTTCG AACAATGTAC AGCCCGAGAA CTCTTTACTT CCACATCACA 180

-continued

```
CCCCCGACTC CTTAGTCAAG GATCTTTTTT CCCCTTTCCC CTCCGCTCTC TTCCTCATGC   240

TGGACTGACT TAACCTTGGT CTGCTCTACT TTTCGGTTGT AAATACATGC AACACAATAA   300

CTTTAAGTGT TGTTAGACAA CACTTTTACA AGACTCTGAC TTTTAATGAG GTGGAGCATG   360

AACCTTTTCC TCTTTCATCT TCTCCTTCAG ATTACAGTCA ATATTTTGGC AAAAGGCTAA   420

TTGACAGCCT TTTATAAGGG TTAATCCCTT GTGGCTTATA TTGAAAACAT GTTCTTTATA   480

ATCCGATACT CTTCTTAAAT CGAATTTTTT CTCTAAATTG CGCCGCAACA AAACTCCTTG   540

AGAAAAGTAC CAATAGAAAT AGAAGGTAGC ATTTTGCCTT TAAATTCCTT TTCTTTTCTT   600

GGATTGTTCT TGAAATGAAT CTTATTTGTG GATTTTTTTT GTTTTTTTAA CCCGGCCGTG   660

GTTCTCTGAA TCACGACCAT AAATTGTTTT AAAGT ATG AGG AAA TTA TTA TTG   713
                                       Met Arg Lys Leu Leu Leu
                                         1               5

CTG ATC GCG GCG TCC CTT TTG GGA GTT GGT CTT TAC GCC CAA AGC GCC   761
Leu Ile Ala Ala Ser Leu Leu Gly Val Gly Leu Tyr Ala Gln Ser Ala
             10                  15                  20

AAG ATT AAG CTT GAT GCT CCG ACT ACT CGA ACG ACA TGT ACG AAC AAT   809
Lys Ile Lys Leu Asp Ala Pro Thr Thr Arg Thr Thr Cys Thr Asn Asn
         25                  30                  35

AGC TTC AAG CAG TTC GAT GCA AGC TTT TCG TTC AAT GAA GTC GAG CTG   857
Ser Phe Lys Gln Phe Asp Ala Ser Phe Ser Phe Asn Glu Val Glu Leu
     40                  45                  50

ACA AAG GTG GAG ACC AAA GGT GGT ACT TTC GCC TCA GTG TCA ATT CCG   905
Thr Lys Val Glu Thr Lys Gly Gly Thr Phe Ala Ser Val Ser Ile Pro
 55                  60                  65                  70

GGT GCA TTC CCG ACC GGT GAG GTT GGT TCT CCC GAA GTG CCA GCA GTT   953
Gly Ala Phe Pro Thr Gly Glu Val Gly Ser Pro Glu Val Pro Ala Val
                 75                  80                  85

AGG AAG TTG ATT GCT GTG CCT GTC GGA GCC ACA CCT GTT GTT CGC GTG   1001
Arg Lys Leu Ile Ala Val Pro Val Gly Ala Thr Pro Val Val Arg Val
             90                  95                 100

AAA AGT TTT ACC GAG CAA GTT TAC TCT CTG AAC CAA TAC GGT TCC GAA   1049
Lys Ser Phe Thr Glu Gln Val Tyr Ser Leu Asn Gln Tyr Gly Ser Glu
        105                 110                 115

AAA CTC ATG CCA CAT CAA CCC TCT ATG AGC AAG AGT GAT GAT CCC GAA   1097
Lys Leu Met Pro His Gln Pro Ser Met Ser Lys Ser Asp Asp Pro Glu
    120                 125                 130

AAG GTT CCC TTC GTT TAC AAT GCT GCT GCT TAT GCA CGC AAA GGT TTT   1145
Lys Val Pro Phe Val Tyr Asn Ala Ala Ala Tyr Ala Arg Lys Gly Phe
135                 140                 145                 150

GTC GGA CAA GAA CTG ACC CAA GTA GAA ATG TTG GGG ACA ATG CGT GGT   1193
Val Gly Gln Glu Leu Thr Gln Val Glu Met Leu Gly Thr Met Arg Gly
                155                 160                 165

GTT CGC ATT GCA GCT CTT ACC ATT AAT CCT GTT CAG TAT GAT GTG GTT   1241
Val Arg Ile Ala Ala Leu Thr Ile Asn Pro Val Gln Tyr Asp Val Val
            170                 175                 180

GCA AAC CAA TTG AAG GTT AGA AAC AAC ATC GAA ATT GAA GTA AGC TTT   1289
Ala Asn Gln Leu Lys Val Arg Asn Asn Ile Glu Ile Glu Val Ser Phe
        185                 190                 195

CAA GGA GCT GAT GAA GTA GCT ACA CAA CGT TTG TAT GAT GCT TCT TTT   1337
Gln Gly Ala Asp Glu Val Ala Thr Gln Arg Leu Tyr Asp Ala Ser Phe
    200                 205                 210

AGC CCT TAT TTC GAA ACA GCT TAT AAA CAG CTC TTC AAT AGA GAT GTT   1385
Ser Pro Tyr Phe Glu Thr Ala Tyr Lys Gln Leu Phe Asn Arg Asp Val
215                 220                 225                 230

TAT ACA GAT CAT GGC GAC TTG TAT AAT ACG CCG GTT CGT ATG CTT GTT   1433
Tyr Thr Asp His Gly Asp Leu Tyr Asn Thr Pro Val Arg Met Leu Val
                235                 240                 245
```

-continued

GTT GCA GGT GCA AAA TTC AAA GAA GCT CTC AAG CCT TGG CTC ACT TGG 1481
Val Ala Gly Ala Lys Phe Lys Glu Ala Leu Lys Pro Trp Leu Thr Trp
250 255 260

AAG GCT CAA AAG GGC TTC TAT CTG GAT GTG CAT TAC ACA GAC GAA GCT 1529
Lys Ala Gln Lys Gly Phe Tyr Leu Asp Val His Tyr Thr Asp Glu Ala
265 270 275

GAA GTA GGA ACG ACA AAC GCC TCT ATC AAG GCA TTT ATT CAC AAG AAA 1577
Glu Val Gly Thr Thr Asn Ala Ser Ile Lys Ala Phe Ile His Lys Lys
280 285 290

TAC AAT GAT GGA TTG GCA GCT AGT GCT GCT CCG GTC TTC TTG GCT TTG 1625
Tyr Asn Asp Gly Leu Ala Ala Ser Ala Ala Pro Val Phe Leu Ala Leu
295 300 305 310

GTT GGT GAC ACT GAC GTT ATT AGC GGA GAA AAA GGA AAG AAA ACA AAA 1673
Val Gly Asp Thr Asp Val Ile Ser Gly Glu Lys Gly Lys Lys Thr Lys
315 320 325

AAA GTT ACC GAC TTG TAT TAC AGT GCA GTC GAT GGC GAC TAT TTC CCT 1721
Lys Val Thr Asp Leu Tyr Tyr Ser Ala Val Asp Gly Asp Tyr Phe Pro
330 335 340

GAA ATG TAT ACT TTC CGT ATG TCT GCT TCT TCC CCA GAA GAA CTG ACG 1769
Glu Met Tyr Thr Phe Arg Met Ser Ala Ser Ser Pro Glu Glu Leu Thr
345 350 355

AAC ATC ATT GAT AAG GTA TTG ATG TAT GAA AAG GCT ACT ATG CCA GAT 1817
Asn Ile Ile Asp Lys Val Leu Met Tyr Glu Lys Ala Thr Met Pro Asp
360 365 370

AAG AGT TAT TTG GAG AAA GTT CTC TTG ATT GCA GGT GCA GAT TAT AGC 1865
Lys Ser Tyr Leu Glu Lys Val Leu Leu Ile Ala Gly Ala Asp Tyr Ser
375 380 385 390

TGG AAT TCC CAG GTA GGT CAG CCA ACC ATT AAA TAC GGT ATG CAG TAC 1913
Trp Asn Ser Gln Val Gly Gln Pro Thr Ile Lys Tyr Gly Met Gln Tyr
395 400 405

TAC TAC AAC CAA GAG CAT GGT TAT ACC GAC GTG TAC AAC TAT CTC AAA 1961
Tyr Tyr Asn Gln Glu His Gly Tyr Thr Asp Val Tyr Asn Tyr Leu Lys
410 415 420

GCC CCT TAT ACA GGT TGC TAC AGT CAT TTG AAT ACC GGA GTC AGC TTT 2009
Ala Pro Tyr Thr Gly Cys Tyr Ser His Leu Asn Thr Gly Val Ser Phe
425 430 435

GCA AAC TAT ACA GCG CAT GGA TCT GAG ACC GCA TGG GCT GAT CCA CTT 2057
Ala Asn Tyr Thr Ala His Gly Ser Glu Thr Ala Trp Ala Asp Pro Leu
440 445 450

CTG ACT ACT TCT CAA CTG AAA GCA CTC ACT AAT AAG GAC AAA TAC TTC 2105
Leu Thr Thr Ser Gln Leu Lys Ala Leu Thr Asn Lys Asp Lys Tyr Phe
455 460 465 470

TTA GCT ATT GGC AAC TGC TGT ATT ACA GCT CAA TTC GAT TAT GTA CAG 2153
Leu Ala Ile Gly Asn Cys Cys Ile Thr Ala Gln Phe Asp Tyr Val Gln
475 480 485

CCT TGC TTC GGA GAG GTA ATA ACT CGC GTT AAG GAG AAA GGG GCT TAT 2201
Pro Cys Phe Gly Glu Val Ile Thr Arg Val Lys Glu Lys Gly Ala Tyr
490 495 500

GCC TAT ATC GGT TCA TCT CCA AAT TCT TAT TGG GGC GAG GAC TAC TAT 2249
Ala Tyr Ile Gly Ser Ser Pro Asn Ser Tyr Trp Gly Glu Asp Tyr Tyr
505 510 515

TGG AGT GTG GGT GCT AAT GCC GTA TTT GGT GTT CAG CCT ACT TTT GAA 2297
Trp Ser Val Gly Ala Asn Ala Val Phe Gly Val Gln Pro Thr Phe Glu
520 525 530

GGT ACG TCT ATG GGT TCT TAT GAT GCT ACA TTC TTG GAG GAT TCG TAC 2345
Gly Thr Ser Met Gly Ser Tyr Asp Ala Thr Phe Leu Glu Asp Ser Tyr
535 540 545 550

AAC ACA GTG AAT TCT ATT ATG TGG GCA GGT AAT CTT GCC GCT ACT CAT 2393
Asn Thr Val Asn Ser Ile Met Trp Ala Gly Asn Leu Ala Ala Thr His
555 560 565

-continued

```
GCT GGA AAT ATC GGC AAT ATT ACC CAT ATT GGT GCT CAT TAC TAT TGG     2441
Ala Gly Asn Ile Gly Asn Ile Thr His Ile Gly Ala His Tyr Tyr Trp
            570                 575                 580

GAA GCT TAT CAT GTC CTT GGC GAT GGT TCG GTT ATG CCT TAT CGT GCA     2489
Glu Ala Tyr His Val Leu Gly Asp Gly Ser Val Met Pro Tyr Arg Ala
        585                 590                 595

ATG CCT AAG ACC AAT ACT TAT ACG CTT CCT GCC TCT TTG CCT CAG AAT     2537
Met Pro Lys Thr Asn Thr Tyr Thr Leu Pro Ala Ser Leu Pro Gln Asn
    600                 605                 610

CAG GCT TCT TAT AGC ATT CAG GCT TCT GCC GGT TCT TAC GTA GCT ATT     2585
Gln Ala Ser Tyr Ser Ile Gln Ala Ser Ala Gly Ser Tyr Val Ala Ile
615                 620                 625                 630

TCT AAA GAT GGA GTT TTG TAT GGA ACA GGT GTT GCT AAT GCC AGC GGT     2633
Ser Lys Asp Gly Val Leu Tyr Gly Thr Gly Val Ala Asn Ala Ser Gly
                635                 640                 645

GTT GCG ACT GTG AGT ATG ACT AAG CAG ATT ACG GAA AAT GGT AAT TAT     2681
Val Ala Thr Val Ser Met Thr Lys Gln Ile Thr Glu Asn Gly Asn Tyr
            650                 655                 660

GAT GTA GTT ATC ACT CGC TCT AAT TAT CTT CCT GTG ATC AAG CAA ATT     2729
Asp Val Val Ile Thr Arg Ser Asn Tyr Leu Pro Val Ile Lys Gln Ile
        665                 670                 675

CAG GTA GGT GAG CCT AGC CCC TAC CAG CCC GTT TCC AAC TTG ACA GCT     2777
Gln Val Gly Glu Pro Ser Pro Tyr Gln Pro Val Ser Asn Leu Thr Ala
    680                 685                 690

ACA ACG CAG GGT CAG AAA GTA ACG CTC AAG TGG GAA GCA CCG AGC GCA     2825
Thr Thr Gln Gly Gln Lys Val Thr Leu Lys Trp Glu Ala Pro Ser Ala
695                 700                 705                 710

AAG AAG GCA GAA GGT TCC CGT GAA GTA AAA CGG ATC GGA GAC GGT CTT     2873
Lys Lys Ala Glu Gly Ser Arg Glu Val Lys Arg Ile Gly Asp Gly Leu
                715                 720                 725

TTC GTT ACG ATC GAA CCT GCA AAC GAT GTA CGT GCC AAC GAA GCC AAG     2921
Phe Val Thr Ile Glu Pro Ala Asn Asp Val Arg Ala Asn Glu Ala Lys
            730                 735                 740

GTT GTG CTT GCG GCA GAC AAC GTA TGG GGA GAC AAT ACG GGT TAC CAG     2969
Val Val Leu Ala Ala Asp Asn Val Trp Gly Asp Asn Thr Gly Tyr Gln
        745                 750                 755

TTC TTG TTG GAT GCC GAT CAC AAT ACA TTC GGA AGT GTC ATT CCG GCA     3017
Phe Leu Leu Asp Ala Asp His Asn Thr Phe Gly Ser Val Ile Pro Ala
    760                 765                 770

ACC GGT CCT CTC TTT ACC GGA ACA GCT TCT TCC AAT CTT TAC AGT GCG     3065
Thr Gly Pro Leu Phe Thr Gly Thr Ala Ser Ser Asn Leu Tyr Ser Ala
775                 780                 785                 790

AAC TTC GAG TAT TTG GTC CCG GCC AAT GCC GAT CCT GTT GTT ACT ACA     3113
Asn Phe Glu Tyr Leu Val Pro Ala Asn Ala Asp Pro Val Val Thr Thr
                795                 800                 805

CAG AAT ATT ATC GTT ACA GGA CAG GGT GAA GTT GTA ATC CCC GGT GGT     3161
Gln Asn Ile Ile Val Thr Gly Gln Gly Glu Val Val Ile Pro Gly Gly
            810                 815                 820

GTT TAC GAC TAT TGC ATT ACG AAC CCG GAA CCT GCA TCC GGA AAG ATG     3209
Val Tyr Asp Tyr Cys Ile Thr Asn Pro Glu Pro Ala Ser Gly Lys Met
        825                 830                 835

TGG ATC GCA GGA GAT GGA GGC AAC CAG CCT GCA CGT TAT GAC GAT TTC     3257
Trp Ile Ala Gly Asp Gly Gly Asn Gln Pro Ala Arg Tyr Asp Asp Phe
    840                 845                 850

ACA TTC GAA GCA GGC AAG AAG TAC ACC TTC ACG ATG CGT CGC GCC GGA     3305
Thr Phe Glu Ala Gly Lys Lys Tyr Thr Phe Thr Met Arg Arg Ala Gly
855                 860                 865                 870

ATG GGA GAT GGA ACT GAT ATG GAA GTC GAA GAC GAT TCA CCT GCA AGC     3353
Met Gly Asp Gly Thr Asp Met Glu Val Glu Asp Asp Ser Pro Ala Ser
                875                 880                 885
```

-continued

```
TAT ACC TAC ACG GTG TAT CGT GAC GGC ACG AAG ATC AAG GAA GGT CTG     3401
Tyr Thr Tyr Thr Val Tyr Arg Asp Gly Thr Lys Ile Lys Glu Gly Leu
            890                 895                 900

ACA GCT ACG ACA TTC GAA GAA GAC GGT GTA GCT GCA GGC AAT CAT GAG     3449
Thr Ala Thr Thr Phe Glu Glu Asp Gly Val Ala Ala Gly Asn His Glu
        905                 910                 915

TAT TGC GTG GAA GTT AAG TAC ACA GCC GGC GTA TCT CCG AAG GTA TGT     3497
Tyr Cys Val Glu Val Lys Tyr Thr Ala Gly Val Ser Pro Lys Val Cys
    920                 925                 930

AAA GAC GTT ACG GTA GAA GGA TCC AAT GAA TTT GCT CCT GTA CAG AAC     3545
Lys Asp Val Thr Val Glu Gly Ser Asn Glu Phe Ala Pro Val Gln Asn
935                 940                 945                 950

CTG ACC GGT AGT TCA GTA GGT CAG AAA GTA ACG CTT AAG TGG GAT GCA     3593
Leu Thr Gly Ser Ser Val Gly Gln Lys Val Thr Leu Lys Trp Asp Ala
                955                 960                 965

CCT AAT GGT ACC CCG AAT CCG AAT CCA AAT CCG AAT CCG AAT CCG GGA     3641
Pro Asn Gly Thr Pro Asn Pro Asn Pro Asn Pro Asn Pro Asn Pro Gly
            970                 975                 980

ACA ACA CTT TCC GAA TCA TTC GAA AAT GGT ATT CCG GCA TCT TGG AAG     3689
Thr Thr Leu Ser Glu Ser Phe Glu Asn Gly Ile Pro Ala Ser Trp Lys
        985                 990                 995

ACG ATC GAT GCA GAC GGT GAC GGG CAT GGC TGG AAA CCT GGA AAT GCT     3737
Thr Ile Asp Ala Asp Gly Asp Gly His Gly Trp Lys Pro Gly Asn Ala
    1000                1005                1010

CCC GGA ATC GCT GGC TAC AAT AGC AAT GGT TGT GTA TAT TCA GAG TCA     3785
Pro Gly Ile Ala Gly Tyr Asn Ser Asn Gly Cys Val Tyr Ser Glu Ser
1015                1020                1025                1030

TTC GGT CTT GGT GGT ATA GGA GTT CTT ACC CCT GAC AAC TAT CTG ATA     3833
Phe Gly Leu Gly Gly Ile Gly Val Leu Thr Pro Asp Asn Tyr Leu Ile
                1035                1040                1045

ACA CCG GCA TTG GAT TTG CCT AAC GGA GGT AAG TTG ACT TTC TGG GTA     3881
Thr Pro Ala Leu Asp Leu Pro Asn Gly Gly Lys Leu Thr Phe Trp Val
            1050                1055                1060

TGC GCA CAG GAT GCT AAT TAT GCA TCC GAG CAC TAT GCG GTG TAT GCA     3929
Cys Ala Gln Asp Ala Asn Tyr Ala Ser Glu His Tyr Ala Val Tyr Ala
        1065                1070                1075

TCT TCG ACC GGT AAC GAT GCA TCC AAC TTC ACG AAT GCT TTG TTG GAA     3977
Ser Ser Thr Gly Asn Asp Ala Ser Asn Phe Thr Asn Ala Leu Leu Glu
    1080                1085                1090

GAG ACG ATT ACG GCA AAA GGT GTT CGC TCG CCG AAA GCT ATT CGT GGT     4025
Glu Thr Ile Thr Ala Lys Gly Val Arg Ser Pro Lys Ala Ile Arg Gly
1095                1100                1105                1110

CGT ATA CAG GGT ACT TGG CGC CAG AAG ACG GTA GAC CTT CCC GCA GGT     4073
Arg Ile Gln Gly Thr Trp Arg Gln Lys Thr Val Asp Leu Pro Ala Gly
                1115                1120                1125

ACG AAA TAT GTT GCT TTC CGT CAC TTC CAA AGC ACG GAT ATG TTC TAC     4121
Thr Lys Tyr Val Ala Phe Arg His Phe Gln Ser Thr Asp Met Phe Tyr
            1130                1135                1140

ATC GAC CTT GAT GAG GTT GAG ATC AAG GCC AAT GGC AAG CGC GCA GAC     4169
Ile Asp Leu Asp Glu Val Glu Ile Lys Ala Asn Gly Lys Arg Ala Asp
        1145                1150                1155

TTC ACG GAA ACG TTC GAG TCT TCT ACT CAT GGA GAG GCA CCA GCG GAA     4217
Phe Thr Glu Thr Phe Glu Ser Ser Thr His Gly Glu Ala Pro Ala Glu
    1160                1165                1170

TGG ACT ACT ATC GAT GCC GAT GGC GAT GGT CAG GGT TGG CTC TGT CTG     4265
Trp Thr Thr Ile Asp Ala Asp Gly Asp Gly Gln Gly Trp Leu Cys Leu
1175                1180                1185                1190

TCT TCC GGA CAA TTG GAC TGG CTG ACA GCT CAT GGC GGC AGC AAC GTA     4313
Ser Ser Gly Gln Leu Asp Trp Leu Thr Ala His Gly Gly Ser Asn Val
                1195                1200                1205
```

-continued

GTA AGC TCT TTC TCA TGG AAT GGA ATG GCT TTG AAT CCT GAT AAC TAT 4361
Val Ser Ser Phe Ser Trp Asn Gly Met Ala Leu Asn Pro Asp Asn Tyr
1210 1215 1220

CTC ATC TCA AAG GAT GTT ACA GGC GCA ACG AAG GTA AAG TAC TAC TAT 4409
Leu Ile Ser Lys Asp Val Thr Gly Ala Thr Lys Val Lys Tyr Tyr Tyr
1225 1230 1235

GCA GTC AAC GAC GGT TTT CCC GGG GAT CAC TAT GCG GTG ATG ATC TCC 4457
Ala Val Asn Asp Gly Phe Pro Gly Asp His Tyr Ala Val Met Ile Ser
1240 1245 1250

AAG ACG GGC ACG AAC GCC GGA GAC TTC ACG GTT GTT TTC GAA GAA ACG 4505
Lys Thr Gly Thr Asn Ala Gly Asp Phe Thr Val Val Phe Glu Glu Thr
1255 1260 1265 1270

CCT AAC GGA ATA AAT AAG GGC GGA GCA AGA TTC GGT CTT TCC ACG GAA 4553
Pro Asn Gly Ile Asn Lys Gly Gly Ala Arg Phe Gly Leu Ser Thr Glu
1275 1280 1285

GCC AAT GGC GCC AAA CCT CAA AGT GTA TGG ATC GAG CGT ACG GTA GAT 4601
Ala Asn Gly Ala Lys Pro Gln Ser Val Trp Ile Glu Arg Thr Val Asp
1290 1295 1300

TTG CCT GCA GGC ACG AAG TAT GTT GCT TTC CGT CAC TAC AAT TGC TCG 4649
Leu Pro Ala Gly Thr Lys Tyr Val Ala Phe Arg His Tyr Asn Cys Ser
1305 1310 1315

GAT TTG AAC TAC ATT CTT TTG GAT GAT ATT CAG TTC ACC ATG GGT GGC 4697
Asp Leu Asn Tyr Ile Leu Leu Asp Asp Ile Gln Phe Thr Met Gly Gly
1320 1325 1330

AGC CCC ACC CCG ACC GAT TAT ACC TAC ACG GTG TAT CGT GAT GGT ACG 4745
Ser Pro Thr Pro Thr Asp Tyr Thr Tyr Thr Val Tyr Arg Asp Gly Thr
1335 1340 1345 1350

AAG ATC AAG GAA GGT TTG ACC GAA ACG ACC TTC GAA GAA GAC GGC GTA 4793
Lys Ile Lys Glu Gly Leu Thr Glu Thr Thr Phe Glu Glu Asp Gly Val
1355 1360 1365

GCT ACG GGC AAT CAT GAG TAT TGC GTG GAA GTG AAG TAC ACA GCC GGC 4841
Ala Thr Gly Asn His Glu Tyr Cys Val Glu Val Lys Tyr Thr Ala Gly
1370 1375 1380

GTA TCT CCG AAG AAA TGT GTA GAC GTA ACT GTT AAT TCG ACA CAG TTC 4889
Val Ser Pro Lys Lys Cys Val Asp Val Thr Val Asn Ser Thr Gln Phe
1385 1390 1395

AAT CCT GTA CAG AAC CTG ACG GCA GAA CAA GCT CCT AAC AGC ATG GAT 4937
Asn Pro Val Gln Asn Leu Thr Ala Glu Gln Ala Pro Asn Ser Met Asp
1400 1405 1410

GCA ATC CTT AAA TGG AAT GCA CCG GCA TCT AAG CGT GCG GAA GTT CTG 4985
Ala Ile Leu Lys Trp Asn Ala Pro Ala Ser Lys Arg Ala Glu Val Leu
1415 1420 1425 1430

AAC GAA GAC TTC GAA AAT GGT ATT CCT GCC TCA TGG AAG ACG ATC GAT 5033
Asn Glu Asp Phe Glu Asn Gly Ile Pro Ala Ser Trp Lys Thr Ile Asp
1435 1440 1445

GCA GAC GGT GAC GGC AAC AAT TGG ACG ACG ACC CCT CCT CCC GGA GGC 5081
Ala Asp Gly Asp Gly Asn Asn Trp Thr Thr Thr Pro Pro Pro Gly Gly
1450 1455 1460

TCC TCT TTT GCA GGT CAC AAC AGT GCG ATC TGT GTC TCT TCA GCT TCT 5129
Ser Ser Phe Ala Gly His Asn Ser Ala Ile Cys Val Ser Ser Ala Ser
1465 1470 1475

CAT ATC AAC TTT GAA GGT CCT CAG AAC CCT GAT AAC TAT CTG GTT ACA 5177
His Ile Asn Phe Glu Gly Pro Gln Asn Pro Asp Asn Tyr Leu Val Thr
1480 1485 1490

CCG GAG CTT TCT CTT CCT GGC GGA GGA ACG CTT ACT TTC TGG GTA TGT 5225
Pro Glu Leu Ser Leu Pro Gly Gly Gly Thr Leu Thr Phe Trp Val Cys
1495 1500 1505 1510

GCA CAA GAT GCC AAT TAT GCA TCA GAG CAC TAT GCC GTG TAC GCA TCT 5273
Ala Gln Asp Ala Asn Tyr Ala Ser Glu His Tyr Ala Val Tyr Ala Ser
1515 1520 1525

-continued

```
TCT ACG GGT AAC GAC GCT TCC AAC TTC GCC AAC GCT TTG TTG GAA GAA      5321
Ser Thr Gly Asn Asp Ala Ser Asn Phe Ala Asn Ala Leu Leu Glu Glu
            1530                1535                1540

GTG CTG ACG GCC AAG ACA GTT GTT ACG GCA CCT GAA GCC ATT CGT GGT      5369
Val Leu Thr Ala Lys Thr Val Val Thr Ala Pro Glu Ala Ile Arg Gly
        1545                1550                1555

ACT CGT GCT CAG GGC ACC TGG TAT CAA AAG ACG GTA CAG TTG CCT GCG      5417
Thr Arg Ala Gln Gly Thr Trp Tyr Gln Lys Thr Val Gln Leu Pro Ala
    1560                1565                1570

GGT ACT AAG TAT GTT GCC TTC CGT CAC TTC GGC TGT ACG GAC TTC TTC      5465
Gly Thr Lys Tyr Val Ala Phe Arg His Phe Gly Cys Thr Asp Phe Phe
1575                1580                1585                1590

TGG ATC AAC CTT GAT GAT GTT GTA ATC ACT TCA GGG AAC GCT CCG TCT      5513
Trp Ile Asn Leu Asp Asp Val Val Ile Thr Ser Gly Asn Ala Pro Ser
                1595                1600                1605

TAC ACC TAT ACG ATC TAT CGT AAT AAT ACA CAG ATA GCA TCA GGC GTA      5561
Tyr Thr Tyr Thr Ile Tyr Arg Asn Asn Thr Gln Ile Ala Ser Gly Val
            1610                1615                1620

ACG GAG ACT ACT TAC CGA GAT CCG GAC TTG GCT ACC GGT TTT TAC ACG      5609
Thr Glu Thr Thr Tyr Arg Asp Pro Asp Leu Ala Thr Gly Phe Tyr Thr
        1625                1630                1635

TAC GGT GTA AAG GTT GTT TAC CCG AAC GGA GAA TCA GCT ATC GAA ACT      5657
Tyr Gly Val Lys Val Val Tyr Pro Asn Gly Glu Ser Ala Ile Glu Thr
    1640                1645                1650

GCT ACG TTG AAT ATC ACT TCG TTG GCA GAC GTA ACG GCT CAG AAG CCT      5705
Ala Thr Leu Asn Ile Thr Ser Leu Ala Asp Val Thr Ala Gln Lys Pro
1655                1660                1665                1670

TAC ACG CTG ACA GTT GTA GGA AAG ACG ATC ACG GTA ACT TGC CAA GGC      5753
Tyr Thr Leu Thr Val Val Gly Lys Thr Ile Thr Val Thr Cys Gln Gly
                1675                1680                1685

GAA GCT ATG ATC TAC GAC ATG AAC GGT CGT CGT CTG GCA GCG GGT CGC      5801
Glu Ala Met Ile Tyr Asp Met Asn Gly Arg Arg Leu Ala Ala Gly Arg
            1690                1695                1700

AAC ACG GTT GTT TAC ACG GCT CAG GGC GGC CAC TAT GCA GTC ATG GTT      5849
Asn Thr Val Val Tyr Thr Ala Gln Gly Gly His Tyr Ala Val Met Val
        1705                1710                1715

GTC GTT GAC GGC AAG TCT TAC GTA GAG AAA CTC GCT GTA AAG TAAATCTGTC   5901
Val Val Asp Gly Lys Ser Tyr Val Glu Lys Leu Ala Val Lys
    1720                1725                1730

TTGGACTCGG AGACTTTGTG CAGACACTTT TAAGATAGGT CTGTAATTGT CTCAGAGTAT    5961

GAATCGGTCG CCCGACTTCC TTAAAAGGAG GTCGGGCGAC TTCGTTTTTA TTATTGCTGT    6021

CCGGTAAACT TGTCAAGAGG AGACCTTTGA AAAATGAGAC CTTTGCACGG CGATTGGTGT    6081

GTATTTTGTT TGTTAATTCA TTGTATAATA GGGAGTTATT TTGTATATTT GAGTATTAAA    6141

AACAGCATAA TATTCCTCCC ATGGCATACC AATCCAAGAA TACCGATGAG CATGTAACAT    6201

TTGCAGACGC ACTCCTTTCA AAGCGTTATC GCAAAGCACA AAACGACTTC CTCAATCAGG    6261

TTGACAGGCT TATCGATTGG CGTCCGATCA GGACGCTGAT CAACAAGAAA TACACGAAGC    6321

GACAAAATGC CATCGGCGCC CCGGCTTATG ACGTGATTCT CTTATTCAAG ATGTTGCTTC    6381

CGAAGACATG GTACAACCTC AGTGATTGTG CTTTGGAGGA GCGCATCAAT GATTCAATCA    6441

CCTTTTCCCG ATTCTTGGGG CTATGGAAGA GGTATCTCCC GACCACAGCA CCATCAGTCG    6501

ATTTCGTTCG GCACTGACAG AGTTGGGGCT CATGGACAAA CTATTGGCGC AGTTTAACAA    6561

ACAACTTTTC CGCCATCACA TTTCGGTCAG GGAAAGGGTG CTTGTCGATG CAAGCCTTGT    6621

GGAGATACGG AGCACCATCG AACGCACCTT TGGCAGTATT CGCCGGTGGT TTCATGGCGG    6681

ACGATGTCGA TACCGGGGAC TTGCCAAGAC CCATACTCAA AACATTCTTG AAAGCATCGC    6741
```

-continued

CTTTAATTTA TACAGAACCC CGGGGATAAT TATGTCCTCA TCTCTAGGAT AAGGTATAAC 6801

CACCCTTGAG GAGCTCGTGC AAGCAGCTCC TCAAGGGGGA TTTACAACTA CTTTCACTCC 6861

TTACCGCCAC CCTTTTCCCT CCCTCCCGGA ATTC 6895

( 2 ) INFORMATION FOR SEQ ID NO:10:

( i ) SEQUENCE CHARACTERISTICS:
( A ) LENGTH: 1732 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Arg Lys Leu Leu Leu Leu Ile Ala Ala Ser Leu Leu Gly Val Gly
  1               5                  10                  15

Leu Tyr Ala Gln Ser Ala Lys Ile Lys Leu Asp Ala Pro Thr Thr Arg
             20                  25                  30

Thr Thr Cys Thr Asn Asn Ser Phe Lys Gln Phe Asp Ala Ser Phe Ser
         35                  40                  45

Phe Asn Glu Val Glu Leu Thr Lys Val Glu Thr Lys Gly Gly Thr Phe
     50                  55                  60

Ala Ser Val Ser Ile Pro Gly Ala Phe Pro Thr Gly Glu Val Gly Ser
 65                  70                  75                      80

Pro Glu Val Pro Ala Val Arg Lys Leu Ile Ala Val Pro Val Gly Ala
                 85                  90                  95

Thr Pro Val Val Arg Val Lys Ser Phe Thr Glu Gln Val Tyr Ser Leu
            100                 105                 110

Asn Gln Tyr Gly Ser Glu Lys Leu Met Pro His Gln Pro Ser Met Ser
        115                 120                 125

Lys Ser Asp Asp Pro Glu Lys Val Pro Phe Val Tyr Asn Ala Ala Ala
    130                 135                 140

Tyr Ala Arg Lys Gly Phe Val Gly Gln Glu Leu Thr Gln Val Glu Met
145                 150                 155                     160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Glu Val Ala Thr Gln Arg
        195                 200                 205

Leu Tyr Asp Ala Ser Phe Ser Pro Tyr Phe Glu Thr Ala Tyr Lys Gln
    210                 215                 220

Leu Phe Asn Arg Asp Val Tyr Thr Asp His Gly Asp Leu Tyr Asn Thr
225                 230                 235                     240

Pro Val Arg Met Leu Val Val Ala Gly Ala Lys Phe Lys Glu Ala Leu
                245                 250                 255

Lys Pro Trp Leu Thr Trp Lys Ala Gln Lys Gly Phe Tyr Leu Asp Val
            260                 265                 270

His Tyr Thr Asp Glu Ala Glu Val Gly Thr Thr Asn Ala Ser Ile Lys
        275                 280                 285

Ala Phe Ile His Lys Lys Tyr Asn Asp Gly Leu Ala Ala Ser Ala Ala
    290                 295                 300

Pro Val Phe Leu Ala Leu Val Gly Asp Thr Asp Val Ile Ser Gly Glu
305                 310                 315                     320

Lys Gly Lys Lys Thr Lys Lys Val Thr Asp Leu Tyr Tyr Ser Ala Val
                325                 330                 335
```

-continued

```
Asp Gly Asp Tyr Phe Pro Glu Met Tyr Thr Phe Arg Met Ser Ala Ser
            340                 345                 350

Ser Pro Glu Glu Leu Thr Asn Ile Ile Asp Lys Val Leu Met Tyr Glu
        355                 360                 365

Lys Ala Thr Met Pro Asp Lys Ser Tyr Leu Glu Lys Val Leu Leu Ile
    370                 375                 380

Ala Gly Ala Asp Tyr Ser Trp Asn Ser Gln Val Gly Gln Pro Thr Ile
385                 390                 395                 400

Lys Tyr Gly Met Gln Tyr Tyr Tyr Asn Gln Glu His Gly Tyr Thr Asp
                405                 410                 415

Val Tyr Asn Tyr Leu Lys Ala Pro Tyr Thr Gly Cys Tyr Ser His Leu
            420                 425                 430

Asn Thr Gly Val Ser Phe Ala Asn Tyr Thr Ala His Gly Ser Glu Thr
        435                 440                 445

Ala Trp Ala Asp Pro Leu Leu Thr Thr Ser Gln Leu Lys Ala Leu Thr
    450                 455                 460

Asn Lys Asp Lys Tyr Phe Leu Ala Ile Gly Asn Cys Cys Ile Thr Ala
465                 470                 475                 480

Gln Phe Asp Tyr Val Gln Pro Cys Phe Gly Glu Val Ile Thr Arg Val
                485                 490                 495

Lys Glu Lys Gly Ala Tyr Ala Tyr Ile Gly Ser Ser Pro Asn Ser Tyr
            500                 505                 510

Trp Gly Glu Asp Tyr Tyr Trp Ser Val Gly Ala Asn Ala Val Phe Gly
        515                 520                 525

Val Gln Pro Thr Phe Glu Gly Thr Ser Met Gly Ser Tyr Asp Ala Thr
    530                 535                 540

Phe Leu Glu Asp Ser Tyr Asn Thr Val Asn Ser Ile Met Trp Ala Gly
545                 550                 555                 560

Asn Leu Ala Ala Thr His Ala Gly Asn Ile Gly Asn Ile Thr His Ile
                565                 570                 575

Gly Ala His Tyr Tyr Trp Glu Ala Tyr His Val Leu Gly Asp Gly Ser
            580                 585                 590

Val Met Pro Tyr Arg Ala Met Pro Lys Thr Asn Thr Tyr Thr Leu Pro
        595                 600                 605

Ala Ser Leu Pro Gln Asn Gln Ala Ser Tyr Ser Ile Gln Ala Ser Ala
    610                 615                 620

Gly Ser Tyr Val Ala Ile Ser Lys Asp Gly Val Leu Tyr Gly Thr Gly
625                 630                 635                 640

Val Ala Asn Ala Ser Gly Val Ala Thr Val Ser Met Thr Lys Gln Ile
                645                 650                 655

Thr Glu Asn Gly Asn Tyr Asp Val Val Ile Thr Arg Ser Asn Tyr Leu
            660                 665                 670

Pro Val Ile Lys Gln Ile Gln Val Gly Glu Pro Ser Pro Tyr Gln Pro
        675                 680                 685

Val Ser Asn Leu Thr Ala Thr Thr Gln Gly Gln Lys Val Thr Leu Lys
    690                 695                 700

Trp Glu Ala Pro Ser Ala Lys Lys Ala Glu Gly Ser Arg Glu Val Lys
705                 710                 715                 720

Arg Ile Gly Asp Gly Leu Phe Val Thr Ile Glu Pro Ala Asn Asp Val
                725                 730                 735

Arg Ala Asn Glu Ala Lys Val Val Leu Ala Ala Asp Asn Val Trp Gly
            740                 745                 750

Asp Asn Thr Gly Tyr Gln Phe Leu Leu Asp Ala Asp His Asn Thr Phe
```

755 760 765

Gly Ser Val Ile Pro Ala Thr Gly Pro Leu Phe Thr Gly Thr Ala Ser
770 775 780

Ser Asn Leu Tyr Ser Ala Asn Phe Glu Tyr Leu Val Pro Ala Asn Ala
785 790 795 800

Asp Pro Val Val Thr Thr Gln Asn Ile Ile Val Thr Gly Gln Gly Glu
805 810 815

Val Val Ile Pro Gly Gly Val Tyr Asp Tyr Cys Ile Thr Asn Pro Glu
820 825 830

Pro Ala Ser Gly Lys Met Trp Ile Ala Gly Asp Gly Gly Asn Gln Pro
835 840 845

Ala Arg Tyr Asp Asp Phe Thr Phe Glu Ala Gly Lys Lys Tyr Thr Phe
850 855 860

Thr Met Arg Arg Ala Gly Met Gly Asp Gly Thr Asp Met Glu Val Glu
865 870 875 880

Asp Asp Ser Pro Ala Ser Tyr Thr Tyr Thr Val Tyr Arg Asp Gly Thr
885 890 895

Lys Ile Lys Glu Gly Leu Thr Ala Thr Thr Phe Glu Glu Asp Gly Val
900 905 910

Ala Ala Gly Asn His Glu Tyr Cys Val Glu Val Lys Tyr Thr Ala Gly
915 920 925

Val Ser Pro Lys Val Cys Lys Asp Val Thr Val Glu Gly Ser Asn Glu
930 935 940

Phe Ala Pro Val Gln Asn Leu Thr Gly Ser Ser Val Gly Gln Lys Val
945 950 955 960

Thr Leu Lys Trp Asp Ala Pro Asn Gly Thr Pro Asn Pro Asn Pro Asn
965 970 975

Pro Asn Pro Asn Pro Gly Thr Thr Leu Ser Glu Ser Phe Glu Asn Gly
980 985 990

Ile Pro Ala Ser Trp Lys Thr Ile Asp Ala Asp Gly Asp Gly His Gly
995 1000 1005

Trp Lys Pro Gly Asn Ala Pro Gly Ile Ala Gly Tyr Asn Ser Asn Gly
1010 1015 1020

Cys Val Tyr Ser Glu Ser Phe Gly Leu Gly Gly Ile Gly Val Leu Thr
1025 1030 1035 1040

Pro Asp Asn Tyr Leu Ile Thr Pro Ala Leu Asp Leu Pro Asn Gly Gly
1045 1050 1055

Lys Leu Thr Phe Trp Val Cys Ala Gln Asp Ala Asn Tyr Ala Ser Glu
1060 1065 1070

His Tyr Ala Val Tyr Ala Ser Ser Thr Gly Asn Asp Ala Ser Asn Phe
1075 1080 1085

Thr Asn Ala Leu Leu Glu Glu Thr Ile Thr Ala Lys Gly Val Arg Ser
1090 1095 1100

Pro Lys Ala Ile Arg Gly Arg Ile Gln Gly Thr Trp Arg Gln Lys Thr
1105 1110 1115 1120

Val Asp Leu Pro Ala Gly Thr Lys Tyr Val Ala Phe Arg His Phe Gln
1125 1130 1135

Ser Thr Asp Met Phe Tyr Ile Asp Leu Asp Glu Val Glu Ile Lys Ala
1140 1145 1150

Asn Gly Lys Arg Ala Asp Phe Thr Glu Thr Phe Glu Ser Ser Thr His
1155 1160 1165

Gly Glu Ala Pro Ala Glu Trp Thr Thr Ile Asp Ala Asp Gly Asp Gly
1170 1175 1180

-continued

Gln Gly Trp Leu Cys Leu Ser Ser Gly Gln Leu Asp Trp Leu Thr Ala
1185 1190 1195 1200

His Gly Gly Ser Asn Val Val Ser Ser Phe Ser Trp Asn Gly Met Ala
1205 1210 1215

Leu Asn Pro Asp Asn Tyr Leu Ile Ser Lys Asp Val Thr Gly Ala Thr
1220 1225 1230

Lys Val Lys Tyr Tyr Tyr Ala Val Asn Asp Gly Phe Pro Gly Asp His
1235 1240 1245

Tyr Ala Val Met Ile Ser Lys Thr Gly Thr Asn Ala Gly Asp Phe Thr
1250 1255 1260

Val Val Phe Glu Glu Thr Pro Asn Gly Ile Asn Lys Gly Gly Ala Arg
1265 1270 1275 1280

Phe Gly Leu Ser Thr Glu Ala Asn Gly Ala Lys Pro Gln Ser Val Trp
1285 1290 1295

Ile Glu Arg Thr Val Asp Leu Pro Ala Gly Thr Lys Tyr Val Ala Phe
1300 1305 1310

Arg His Tyr Asn Cys Ser Asp Leu Asn Tyr Ile Leu Leu Asp Asp Ile
1315 1320 1325

Gln Phe Thr Met Gly Gly Ser Pro Thr Pro Thr Asp Tyr Thr Tyr Thr
1330 1335 1340

Val Tyr Arg Asp Gly Thr Lys Ile Lys Glu Gly Leu Thr Glu Thr Thr
1345 1350 1355 1360

Phe Glu Glu Asp Gly Val Ala Thr Gly Asn His Glu Tyr Cys Val Glu
1365 1370 1375

Val Lys Tyr Thr Ala Gly Val Ser Pro Lys Lys Cys Val Asp Val Thr
1380 1385 1390

Val Asn Ser Thr Gln Phe Asn Pro Val Gln Asn Leu Thr Ala Glu Gln
1395 1400 1405

Ala Pro Asn Ser Met Asp Ala Ile Leu Lys Trp Asn Ala Pro Ala Ser
1410 1415 1420

Lys Arg Ala Glu Val Leu Asn Glu Asp Phe Glu Asn Gly Ile Pro Ala
1425 1430 1435 1440

Ser Trp Lys Thr Ile Asp Ala Asp Gly Asp Gly Asn Asn Trp Thr Thr
1445 1450 1455

Thr Pro Pro Pro Gly Gly Ser Ser Phe Ala Gly His Asn Ser Ala Ile
1460 1465 1470

Cys Val Ser Ser Ala Ser His Ile Asn Phe Glu Gly Pro Gln Asn Pro
1475 1480 1485

Asp Asn Tyr Leu Val Thr Pro Glu Leu Ser Leu Pro Gly Gly Gly Thr
1490 1495 1500

Leu Thr Phe Trp Val Cys Ala Gln Asp Ala Asn Tyr Ala Ser Glu His
1505 1510 1515 1520

Tyr Ala Val Tyr Ala Ser Ser Thr Gly Asn Asp Ala Ser Asn Phe Ala
1525 1530 1535

Asn Ala Leu Leu Glu Glu Val Leu Thr Ala Lys Thr Val Val Thr Ala
1540 1545 1550

Pro Glu Ala Ile Arg Gly Thr Arg Ala Gln Gly Thr Trp Tyr Gln Lys
1555 1560 1565

Thr Val Gln Leu Pro Ala Gly Thr Lys Tyr Val Ala Phe Arg His Phe
1570 1575 1580

Gly Cys Thr Asp Phe Phe Trp Ile Asn Leu Asp Asp Val Val Ile Thr
1585 1590 1595 1600

Ser Gly Asn Ala Pro Ser Tyr Thr Tyr Thr Ile Tyr Arg Asn Asn Thr
1605 1610 1615

Gln Ile Ala Ser Gly Val Thr Glu Thr Thr Tyr Arg Asp Pro Asp Leu
1620 1625 1630

Ala Thr Gly Phe Tyr Thr Tyr Gly Val Lys Val Val Tyr Pro Asn Gly
1635 1640 1645

Glu Ser Ala Ile Glu Thr Ala Thr Leu Asn Ile Thr Ser Leu Ala Asp
1650 1655 1660

Val Thr Ala Gln Lys Pro Tyr Thr Leu Thr Val Val Gly Lys Thr Ile
1665 1670 1675 1680

Thr Val Thr Cys Gln Gly Glu Ala Met Ile Tyr Asp Met Asn Gly Arg
1685 1690 1695

Arg Leu Ala Ala Gly Arg Asn Thr Val Val Tyr Thr Ala Gln Gly Gly
1700 1705 1710

His Tyr Ala Val Met Val Val Val Asp Gly Lys Ser Tyr Val Glu Lys
1715 1720 1725

Leu Ala Val Lys
1730

( 2 ) INFORMATION FOR SEQ ID NO:11:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GGAATGGGAG ATGGAACT 18

( 2 ) INFORMATION FOR SEQ ID NO:12:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

GTAACCCGTA TTGTCTCC 18

( 2 ) INFORMATION FOR SEQ ID NO:13:

( i ) SEQUENCE CHARACTERISTICS:
( A ) LENGTH: 8588 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 365..8248

( x i ) SEQUENCE DESCRIPTION: SEQ ID NO:13:

GATATCCGGC TCTTCGGCAG AGAATGCGAG AGATTCAGGA TATATCGCAA CGGCCTTGTC 60

AAGATCGAGG CCTCTTTAGG TCATGGATAT AACGTGAGTT CGATGTAAGC TTTTCGGCCT 120

TTCCATCATA CAATCGATTC GATTCTCTTT GGACTCAATA AAAAATATAA AATACTCAAA 180

GAGTTGGCAT ATAACTTTGC CTCAGTGGCG AGTGGGTTTT TCGGCCAATT CCTAAAGAAG 240

-continued

```
AAAATAGCTG TTTGTATCTT TTTGCGAAAA AAGTTTGGCG GATTAAGATT AAAAACATAT     300

CTTTCGGGCG ATAGTGGTAG AGCACTATCT TGCGAAACAT TAATCTTTAA TACTTTCAAA     360

AGGT ATG AGA AAA TTG AAT TCT TTA TTT TCG CTC GCC GTC CTA TTA TCC     409
     Met Arg Lys Leu Asn Ser Leu Phe Ser Leu Ala Val Leu Leu Ser
      1               5                  10                  15

CTA TTG TGT TGG GGA CAG ACG GCT GCC GCA CAG GGA GGG CCG AAG ACT     457
Leu Leu Cys Trp Gly Gln Thr Ala Ala Ala Gln Gly Gly Pro Lys Thr
                 20                  25                  30

GCT CCT TCT GTG ACG CAC CAA GCG GTG CAG AAA GGT ATT CGA ACA TCC     505
Ala Pro Ser Val Thr His Gln Ala Val Gln Lys Gly Ile Arg Thr Ser
             35                  40                  45

AAG GTT AAG GAT CTC CGA GAT CCG ATT CCT GCC GGT ATG GCA CGA ATT     553
Lys Val Lys Asp Leu Arg Asp Pro Ile Pro Ala Gly Met Ala Arg Ile
         50                  55                  60

ATC TTG GAG GCT CAC GAT GTA TGG GAA GAC GGC ACA GGC TAT CAA ATG     601
Ile Leu Glu Ala His Asp Val Trp Glu Asp Gly Thr Gly Tyr Gln Met
     65                  70                  75

CTT TGG GAT GCA GAT CAC AAT CAG TAC GGC GCA TCC ATT CCC GAA GAA     649
Leu Trp Asp Ala Asp His Asn Gln Tyr Gly Ala Ser Ile Pro Glu Glu
 80                  85                  90                  95

TCT TTT TGG TTT GCC AAC GGA ACG ATC CCG GCC GGT CTT TAC GAT CCT     697
Ser Phe Trp Phe Ala Asn Gly Thr Ile Pro Ala Gly Leu Tyr Asp Pro
                100                 105                 110

TTC GAG TAT AAA GTT CCG GTC AAT GCC GAT GCA TCT TTT TCT CCC ACG     745
Phe Glu Tyr Lys Val Pro Val Asn Ala Asp Ala Ser Phe Ser Pro Thr
            115                 120                 125

AAT TTC GTG CTT GAT GGA ACA GCA TCA GCC GAT ATT CCT GCC GGC ACT     793
Asn Phe Val Leu Asp Gly Thr Ala Ser Ala Asp Ile Pro Ala Gly Thr
        130                 135                 140

TAT GAC TAT GTA ATC ATT AAC CCC AAT CCT GGC ATA ATA TAT ATA GTA     841
Tyr Asp Tyr Val Ile Ile Asn Pro Asn Pro Gly Ile Ile Tyr Ile Val
    145                 150                 155

GGA GAG GGT GTC TCC AAA GGT AAC GAT TAT GTG GTA GAG GCC GGT AAG     889
Gly Glu Gly Val Ser Lys Gly Asn Asp Tyr Val Val Glu Ala Gly Lys
160                 165                 170                 175

ACT TAT CAT TTC ACT GTC CAA CGA CAA GGC CCC GGC GAT GCT GCG TCC     937
Thr Tyr His Phe Thr Val Gln Arg Gln Gly Pro Gly Asp Ala Ala Ser
                180                 185                 190

GTT GTA GTG ACC GGA GAA GGT GGC AAT GAA TTC GCT CCC GTA CAG AAT     985
Val Val Val Thr Gly Glu Gly Gly Asn Glu Phe Ala Pro Val Gln Asn
            195                 200                 205

CTC CAA TGG TCT GTA TCT GGG CAG ACA GTG ACC CTC ACT TGG CAA GCC    1033
Leu Gln Trp Ser Val Ser Gly Gln Thr Val Thr Leu Thr Trp Gln Ala
        210                 215                 220

CCC GCA TCC GAC AAA CGG ACT TAT GTG TTG AAC GAA AGC TTC GAT ACG    1081
Pro Ala Ser Asp Lys Arg Thr Tyr Val Leu Asn Glu Ser Phe Asp Thr
    225                 230                 235

CAA ACG CTT CCT AAC GGC TGG ACA ATG ATC GAT GCT GAT GGT GAT GGT    1129
Gln Thr Leu Pro Asn Gly Trp Thr Met Ile Asp Ala Asp Gly Asp Gly
240                 245                 250                 255

CAC AAT TGG CTA TCT ACA ATA AAC GTT TAC AAC ACT GCT ACT CAT ACA    1177
His Asn Trp Leu Ser Thr Ile Asn Val Tyr Asn Thr Ala Thr His Thr
                260                 265                 270

GGT GAC GGT GCT ATG TTT AGC AAA TCA TGG ACT GCT AGC GGT GGT GCA    1225
Gly Asp Gly Ala Met Phe Ser Lys Ser Trp Thr Ala Ser Gly Gly Ala
            275                 280                 285

AAA ATT GAT TTG AGT CCT GAC AAC TAT TTG GTA ACT CCA AAG GTT ACG    1273
Lys Ile Asp Leu Ser Pro Asp Asn Tyr Leu Val Thr Pro Lys Val Thr
        290                 295                 300
```

-continued

```
GTT CCT GAG AAT GGT AAA CTT TCT TAT TGG GTT TCA TCT CAA GTG CCT     1321
Val Pro Glu Asn Gly Lys Leu Ser Tyr Trp Val Ser Ser Gln Val Pro
    305                 310                 315

TGG ACT AAT GAG CAT TAT GGA GTG TTC TTG TCC ACA ACC GGA AAC GAG     1369
Trp Thr Asn Glu His Tyr Gly Val Phe Leu Ser Thr Thr Gly Asn Glu
320                 325                 330                 335

GCT GCA AAC TTT ACG ATA AAG CTA CTG GAA GAA ACC CTC GGA TCC GAC     1417
Ala Ala Asn Phe Thr Ile Lys Leu Leu Glu Glu Thr Leu Gly Ser Asp
                340                 345                 350

AAA CCT GCT CCG ATG AAC TTG GTG AAG AGT GAA GGA GTA AAG CTT CCT     1465
Lys Pro Ala Pro Met Asn Leu Val Lys Ser Glu Gly Val Lys Leu Pro
            355                 360                 365

GCA CCT TAT CAG GAA AGA ACC ATC GAT CTC TCT GCC TAT GCC GGA CAA     1513
Ala Pro Tyr Gln Glu Arg Thr Ile Asp Leu Ser Ala Tyr Ala Gly Gln
        370                 375                 380

CAG GTG TAC TTG GCA TTC CGT CAT TTC AAC TCT ACA GGT ATA TTC CGT     1561
Gln Val Tyr Leu Ala Phe Arg His Phe Asn Ser Thr Gly Ile Phe Arg
    385                 390                 395

CTT TAT CTT GAT GAT GTG GCT GTT TCT GGT GAA GGT TCT TCC AAC GAC     1609
Leu Tyr Leu Asp Asp Val Ala Val Ser Gly Glu Gly Ser Ser Asn Asp
400                 405                 410                 415

TAC ACG TAC ACG GTA TAT CGT GAC AAT GTT GTT ATT GCC CAG AAT CTC     1657
Tyr Thr Tyr Thr Val Tyr Arg Asp Asn Val Val Ile Ala Gln Asn Leu
                420                 425                 430

GCG GCA ACG ACA TTC AAT CAG GAA AAT GTA GCT CCC GGC CAG TAT AAC     1705
Ala Ala Thr Thr Phe Asn Gln Glu Asn Val Ala Pro Gly Gln Tyr Asn
            435                 440                 445

TAC TGT GTT GAA GTT AAG TAC ACA GCC GGC GTA TCT CCG AAG GTA TGT     1753
Tyr Cys Val Glu Val Lys Tyr Thr Ala Gly Val Ser Pro Lys Val Cys
        450                 455                 460

AAA GAC GTT ACG GTA GAA GGA TCC AAC GAA TTT GCT CAT GTA CAG AAC     1801
Lys Asp Val Thr Val Glu Gly Ser Asn Glu Phe Ala His Val Gln Asn
    465                 470                 475

CTG ACC GGT AGT GCA GTA GGT CAG AAA GTA ACG CTT AAG TGG GAT GCA     1849
Leu Thr Gly Ser Ala Val Gly Gln Lys Val Thr Leu Lys Trp Asp Ala
480                 485                 490                 495

CCT AAT GGT ACC CCG AAT CCG AAT CCC GGA ACA ACA ACA CTT TCC GAA     1897
Pro Asn Gly Thr Pro Asn Pro Asn Pro Gly Thr Thr Thr Leu Ser Glu
                500                 505                 510

TCA TTC GAA AAT GGT ATT CCT GCC TCA TGG AAG ACG ATC GAT GCA GAC     1945
Ser Phe Glu Asn Gly Ile Pro Ala Ser Trp Lys Thr Ile Asp Ala Asp
            515                 520                 525

GGT GAC GGC AAC AAT TGG ACG ACG ACC CCT CCT CCC GGA GGC ACC TCT     1993
Gly Asp Gly Asn Asn Trp Thr Thr Thr Pro Pro Pro Gly Gly Thr Ser
        530                 535                 540

TTT GCA GGT CAC AAC AGT GCA ATC TGT GCC TCT TCG GCT TCT TAT ATC     2041
Phe Ala Gly His Asn Ser Ala Ile Cys Ala Ser Ser Ala Ser Tyr Ile
    545                 550                 555

AAC TTT GAA GGT CCT CAG AAC CCT GAT AAC TAT CTG GTT ACA CCG GAG     2089
Asn Phe Glu Gly Pro Gln Asn Pro Asp Asn Tyr Leu Val Thr Pro Glu
560                 565                 570                 575

CTA TCT CTT CCT AAC GGA GGA ACG CTT ACT TTC TGG GTA TGT GCA CAA     2137
Leu Ser Leu Pro Asn Gly Gly Thr Leu Thr Phe Trp Val Cys Ala Gln
                580                 585                 590

GAT GCC AAT TAT GCA TCA GAG CAC TAT GCC GTG TAC GCA TCT TCT ACG     2185
Asp Ala Asn Tyr Ala Ser Glu His Tyr Ala Val Tyr Ala Ser Ser Thr
            595                 600                 605

GGT AAC GAC GCT TCC AAC TTC GCC AAC GCT TTG TTG GAA GAA GTG CTG     2233
Gly Asn Asp Ala Ser Asn Phe Ala Asn Ala Leu Leu Glu Glu Val Leu
        610                 615                 620
```

-continued

```
ACG GCC AAG ACA GTT GTT ACG GCA CCT GAA GCC ATT CGT GGC ACT CGT      2281
Thr Ala Lys Thr Val Val Thr Ala Pro Glu Ala Ile Arg Gly Thr Arg
    625                 630                 635

GTT CAG GGC ACC TGG TAT CAA AAG ACG GTA CAG TTG CCT GCG GGT ACT      2329
Val Gln Gly Thr Trp Tyr Gln Lys Thr Val Gln Leu Pro Ala Gly Thr
640                 645                 650                 655

AAG TAT GTT GCT TTC CGT CAC TTC GGC TGT ACG GAC TTC TTC TGG ATT      2377
Lys Tyr Val Ala Phe Arg His Phe Gly Cys Thr Asp Phe Phe Trp Ile
                660                 665                 670

AAC CTT GAT GAT GTT GAG ATC AAG GCC AAC GGC AAG CGC GCA GAC TTC      2425
Asn Leu Asp Asp Val Glu Ile Lys Ala Asn Gly Lys Arg Ala Asp Phe
            675                 680                 685

ACG GAA ACG TTC GAG TCT TCT ACT CAT GGA GAG GCA CCG GCG GAA TGG      2473
Thr Glu Thr Phe Glu Ser Ser Thr His Gly Glu Ala Pro Ala Glu Trp
        690                 695                 700

ACT ACT ATC GAT GCC GAT GGC GAT GGT CAG GGT TGG CTC TGT CTG TCT      2521
Thr Thr Ile Asp Ala Asp Gly Asp Gly Gln Gly Trp Leu Cys Leu Ser
    705                 710                 715

TCC GGA CAA TTG GAC TGG CTG ACA GCT CAT GGC GGC ACC AAC GTA GTA      2569
Ser Gly Gln Leu Asp Trp Leu Thr Ala His Gly Gly Thr Asn Val Val
720                 725                 730                 735

GCC TCT TTC TCA TGG AAT GGA ATG GCT TTG AAT CCT GAT AAC TAT CTC      2617
Ala Ser Phe Ser Trp Asn Gly Met Ala Leu Asn Pro Asp Asn Tyr Leu
                740                 745                 750

ATC TCA AAG GAT GTT ACA GGC GCA ACT AAG GTA AAG TAC TAC TAT GCA      2665
Ile Ser Lys Asp Val Thr Gly Ala Thr Lys Val Lys Tyr Tyr Tyr Ala
            755                 760                 765

GTC AAC GAC GGT TTT CCC GGG GAT CAC TAT GCG GTG ATG ATC TCC AAG      2713
Val Asn Asp Gly Phe Pro Gly Asp His Tyr Ala Val Met Ile Ser Lys
        770                 775                 780

ACG GGC ACG AAC GCC GGA GAC TTC ACG GTT GTT TTC GAA GAA ACG CCT      2761
Thr Gly Thr Asn Ala Gly Asp Phe Thr Val Val Phe Glu Glu Thr Pro
    785                 790                 795

AAC GGA ATA AAT AAG GGC GGA GCA AGA TTC GGT CTT TCC ACG GAA GCC      2809
Asn Gly Ile Asn Lys Gly Gly Ala Arg Phe Gly Leu Ser Thr Glu Ala
800                 805                 810                 815

GAT GGC GCC AAA CCT CAA AGT GTA TGG ATC GAG CGT ACG GTA GAT TTG      2857
Asp Gly Ala Lys Pro Gln Ser Val Trp Ile Glu Arg Thr Val Asp Leu
                820                 825                 830

CCT GCG GGT ACT AAG TAT GTT GCT TTC CGT CAC TAC AAT TGC TCG GAT      2905
Pro Ala Gly Thr Lys Tyr Val Ala Phe Arg His Tyr Asn Cys Ser Asp
            835                 840                 845

TTG AAC TAC ATT CTT TTG GAT GAT ATT CAG TTC ACC ATG GGT GGC AGC      2953
Leu Asn Tyr Ile Leu Leu Asp Asp Ile Gln Phe Thr Met Gly Gly Ser
        850                 855                 860

CCC ACC CCG ACC GAT TAT ACC TAC ACG GTG TAT CGT GAC GGT ACG AAG      3001
Pro Thr Pro Thr Asp Tyr Thr Tyr Thr Val Tyr Arg Asp Gly Thr Lys
    865                 870                 875

ATC AAG GAA GGT CTG ACC GAA ACG ACC TTC GAA GAA GAC GGT GTA GCT      3049
Ile Lys Glu Gly Leu Thr Glu Thr Thr Phe Glu Glu Asp Gly Val Ala
880                 885                 890                 895

ACG GGC AAC CAT GAG TAT TGC GTG GAA GTG AAG TAC ACA GCC GGC GTA      3097
Thr Gly Asn His Glu Tyr Cys Val Glu Val Lys Tyr Thr Ala Gly Val
                900                 905                 910

TCT CCG AAA GAG TGT GTA AAC GTA ACT GTT GAT CCT GTG CAG TTC AAT      3145
Ser Pro Lys Glu Cys Val Asn Val Thr Val Asp Pro Val Gln Phe Asn
            915                 920                 925

CCT GTA CAG AAC CTG ACC GGT AGT GCA GTC GGC CAG AAA GTA ACG CTT      3193
Pro Val Gln Asn Leu Thr Gly Ser Ala Val Gly Gln Lys Val Thr Leu
        930                 935                 940
```

-continued

```
AAG TGG GAT GCA CCT AAT GGT ACC CCG AAT CCA AAT CCA AAT CCG AAT     3241
Lys Trp Asp Ala Pro Asn Gly Thr Pro Asn Pro Asn Pro Asn Pro Asn
    945                 950                 955

CCG GGA ACA ACA ACA CTT TCC GAA TCA TTC GAA AAT GGT ATT CCT GCC     3289
Pro Gly Thr Thr Thr Leu Ser Glu Ser Phe Glu Asn Gly Ile Pro Ala
960                 965                 970                 975

TCA TGG AAG ACG ATC GAT GCA GAC GGT GAC GGC AAC AAT TGG ACG ACG     3337
Ser Trp Lys Thr Ile Asp Ala Asp Gly Asp Gly Asn Asn Trp Thr Thr
                980                 985                 990

ACC CCT CCT CCC GGA GGC ACC TCT TTT GCA GGT CAC AAC AGT GCG ATC     3385
Thr Pro Pro Pro Gly Gly Thr Ser Phe Ala Gly His Asn Ser Ala Ile
            995                 1000                1005

TGT GCC TCT TCG GCT TCT TAT ATC AAC TTT GAA GGC CCT CAG AAC CCT     3433
Cys Ala Ser Ser Ala Ser Tyr Ile Asn Phe Glu Gly Pro Gln Asn Pro
        1010                1015                1020

GAT AAC TAT CTG GTT ACA CCG GAG CTA TCT CTT CCT AAC GGA GGA ACG     3481
Asp Asn Tyr Leu Val Thr Pro Glu Leu Ser Leu Pro Asn Gly Gly Thr
    1025                1030                1035

CTT ACT TTC TGG GTA TGT GCA CAA GAT GCC AAT TAT GCA TCA GAG CAC     3529
Leu Thr Phe Trp Val Cys Ala Gln Asp Ala Asn Tyr Ala Ser Glu His
1040                1045                1050                1055

TAT GCC GTG TAT GCA TCT TCT ACG GGT AAC GAC GCT TCC AAC TTC GCC     3577
Tyr Ala Val Tyr Ala Ser Ser Thr Gly Asn Asp Ala Ser Asn Phe Ala
                1060                1065                1070

AAC GCT TTG TTG GAA GAA GTG CTG ACG GCC AAG ACA GTT GTT ACG GCA     3625
Asn Ala Leu Leu Glu Glu Val Leu Thr Ala Lys Thr Val Val Thr Ala
            1075                1080                1085

CCT GAA GCC ATT CGT GGC ACT CGT GTT CAG GGC ACC TGG TAT CAA AAG     3673
Pro Glu Ala Ile Arg Gly Thr Arg Val Gln Gly Thr Trp Tyr Gln Lys
        1090                1095                1100

ACG GTA CAG TTG CCT GCG GGT ACT AAG TAT GTT GCT TTC CGT CAC TTC     3721
Thr Val Gln Leu Pro Ala Gly Thr Lys Tyr Val Ala Phe Arg His Phe
    1105                1110                1115

GGC TGT ACG GAC TTC TTC TGG ATC AAC CTT GAT GAT GTT GAG ATC AAG     3769
Gly Cys Thr Asp Phe Phe Trp Ile Asn Leu Asp Asp Val Glu Ile Lys
1120                1125                1130                1135

GCC AAC GGC AAG CGC GCA GAC TTC ACG GAA ACG TTC GAG TCT TCT ACT     3817
Ala Asn Gly Lys Arg Ala Asp Phe Thr Glu Thr Phe Glu Ser Ser Thr
                1140                1145                1150

CAT GGA GAG GCA CCG GCG GAA TGG ACT ACT ATC GAT GCC GAT GGC GAT     3865
His Gly Glu Ala Pro Ala Glu Trp Thr Thr Ile Asp Ala Asp Gly Asp
            1155                1160                1165

GGT CAG GGT TGG CTC TGT CTG TCT TCC GGA CAA TTG GGC TGG CTG ACA     3913
Gly Gln Gly Trp Leu Cys Leu Ser Ser Gly Gln Leu Gly Trp Leu Thr
        1170                1175                1180

GCT CAT GGC GGC ACC AAC GTA GTA GCC TCT TTC TCA TGG AAT GGA ATG     3961
Ala His Gly Gly Thr Asn Val Val Ala Ser Phe Ser Trp Asn Gly Met
    1185                1190                1195

GCT TTG AAT CCT GAT AAC TAT CTC ATC TCA AAG GAT GTT ACA GGC GCA     4009
Ala Leu Asn Pro Asp Asn Tyr Leu Ile Ser Lys Asp Val Thr Gly Ala
1200                1205                1210                1215

ACT AAG GTA AAG TAC TAC TAT GCA GTC AAC GAC GGT TTT CCC GGG GAT     4057
Thr Lys Val Lys Tyr Tyr Tyr Ala Val Asn Asp Gly Phe Pro Gly Asp
                1220                1225                1230

CAC TAT GCG GTG ATG ATC TCC AAG ACG GGC ACG AAC GCC GGA GAC TTC     4105
His Tyr Ala Val Met Ile Ser Lys Thr Gly Thr Asn Ala Gly Asp Phe
            1235                1240                1245

ACG GTT GTT TTC GAA GAA ACG CCT AAC GGA ATA AAT AAG GGC GGA GCA     4153
Thr Val Val Phe Glu Glu Thr Pro Asn Gly Ile Asn Lys Gly Gly Ala
        1250                1255                1260
```

-continued

AGA TTC GGT CTT TCC ACG GAA GCC GAT GGC GCC AAA CCT CAA AGT GTA 4201
Arg Phe Gly Leu Ser Thr Glu Ala Asp Gly Ala Lys Pro Gln Ser Val
1265 1270 1275

TGG ATC GAG CGT ACG GTA GAT TTG CCT GCG GGT ACT AAG TAT GTT GCT 4249
Trp Ile Glu Arg Thr Val Asp Leu Pro Ala Gly Thr Lys Tyr Val Ala
1280 1285 1290 1295

TTC CGT CAC TAC AAT TGC TCG GAT TTG AAC TAC ATT CTT TTG GAT GAT 4297
Phe Arg His Tyr Asn Cys Ser Asp Leu Asn Tyr Ile Leu Leu Asp Asp
1300 1305 1310

ATT CAG TTC ACC ATG GGT GGC AGC CCC ACC CCG ACC GAT TAT ACC TAC 4345
Ile Gln Phe Thr Met Gly Gly Ser Pro Thr Pro Thr Asp Tyr Thr Tyr
1315 1320 1325

ACG GTG TAT CGT GAC GGT ACG AAG ATC AAG GAA GGT CTG ACC GAA ACG 4393
Thr Val Tyr Arg Asp Gly Thr Lys Ile Lys Glu Gly Leu Thr Glu Thr
1330 1335 1340

ACC TTC GAA GAA GAC GGT GTA GCT ACG GGC AAC CAT GAG TAT TGC GTG 4441
Thr Phe Glu Glu Asp Gly Val Ala Thr Gly Asn His Glu Tyr Cys Val
1345 1350 1355

GAA GTG AAG TAC ACA GCC GGC GTA TCT CCG AAA GAG TGT GTA AAC GTA 4489
Glu Val Lys Tyr Thr Ala Gly Val Ser Pro Lys Glu Cys Val Asn Val
1360 1365 1370 1375

ACT GTT GAT CCT GTG CAG TTC AAT CCT GTA CAG AAC CTG ACC GGT AGT 4537
Thr Val Asp Pro Val Gln Phe Asn Pro Val Gln Asn Leu Thr Gly Ser
1380 1385 1390

GCA GTC GGC CAG AAA GTA ACG CTT AAG TGG GAT GCA CCT AAT GGT ACC 4585
Ala Val Gly Gln Lys Val Thr Leu Lys Trp Asp Ala Pro Asn Gly Thr
1395 1400 1405

CCG AAT CCA AAT CCA AAT CCG AAT CCG GGA ACA ACA ACA CTT TCC GAA 4633
Pro Asn Pro Asn Pro Asn Pro Asn Pro Gly Thr Thr Thr Leu Ser Glu
1410 1415 1420

TCA TTC GAA AAT GGT ATT CCT GCC TCA TGG AAG ACG ATC GAT GCA GAC 4681
Ser Phe Glu Asn Gly Ile Pro Ala Ser Trp Lys Thr Ile Asp Ala Asp
1425 1430 1435

GGT GAC GGC AAC AAT TGG ACG ACG ACC CCT CCT CCC GGA GGC ACC TCT 4729
Gly Asp Gly Asn Asn Trp Thr Thr Thr Pro Pro Pro Gly Gly Thr Ser
1440 1445 1450 1455

TTT GCA GGT CAC AAC AGT GCG ATC TGT GCC TCT TCG GCT TCT TAT ATC 4777
Phe Ala Gly His Asn Ser Ala Ile Cys Ala Ser Ser Ala Ser Tyr Ile
1460 1465 1470

AAC TTT GAA GGC CCT CAG AAC CCT GAT AAC TAT CTG GTT ACA CCG GAG 4825
Asn Phe Glu Gly Pro Gln Asn Pro Asp Asn Tyr Leu Val Thr Pro Glu
1475 1480 1485

CTA TCT CTT CCT AAC GGA GGA ACG CTT ACT TTC TGG GTA TGT GCA CAA 4873
Leu Ser Leu Pro Asn Gly Gly Thr Leu Thr Phe Trp Val Cys Ala Gln
1490 1495 1500

GAT GCC AAT TAT GCA TCA GAG CAC TAT GCC GTG TAT GCA TCT TCT ACG 4921
Asp Ala Asn Tyr Ala Ser Glu His Tyr Ala Val Tyr Ala Ser Ser Thr
1505 1510 1515

GGT AAC GAC GCT TCC AAC TTC GCC AAC GCT TTG TTG GAA GAA GTG CTG 4969
Gly Asn Asp Ala Ser Asn Phe Ala Asn Ala Leu Leu Glu Glu Val Leu
1520 1525 1530 1535

ACG GCC AAG ACA GTT GTT ACG GCA CCT GAA GCC ATT CGT GGC ACT CGT 5017
Thr Ala Lys Thr Val Val Thr Ala Pro Glu Ala Ile Arg Gly Thr Arg
1540 1545 1550

GTT CAG GGC ACC TGG TAT CAA AAG ACG GTA CAG TTG CCT GCG GGT ACT 5065
Val Gln Gly Thr Trp Tyr Gln Lys Thr Val Gln Leu Pro Ala Gly Thr
1555 1560 1565

AAG TAT GTT GCT TTC CGT CAC TTC GGC TGT ACG GAC TTC TTC TGG ATC 5113
Lys Tyr Val Ala Phe Arg His Phe Gly Cys Thr Asp Phe Phe Trp Ile
1570 1575 1580

-continued

AAC CTT GAT GAT GTT GAG ATC AAG GCC AAC GGC AAG CGC GCA GAC TTC 5161
Asn Leu Asp Asp Val Glu Ile Lys Ala Asn Gly Lys Arg Ala Asp Phe
1585 1590 1595

ACG GAA ACG TTC GAG TCT TCT ACT CAT GGA GAG GCA CCG GCG GAA TGG 5209
Thr Glu Thr Phe Glu Ser Ser Thr His Gly Glu Ala Pro Ala Glu Trp
1600 1605 1610 1615

ACT ACT ATC GAT GCC GAT GGC GAT GGT CAG GGT TGG CTC TGT CTG TCT 5257
Thr Thr Ile Asp Ala Asp Gly Asp Gly Gln Gly Trp Leu Cys Leu Ser
1620 1625 1630

TCC GGA CAA TTG GGC TGG CTG ACA GCT CAT GGC GGC ACC AAC GTA GTA 5305
Ser Gly Gln Leu Gly Trp Leu Thr Ala His Gly Gly Thr Asn Val Val
1635 1640 1645

GCC TCT TTC TCA TGG AAT GGA ATG GCT TTG AAT CCT GAT AAC TAT CTC 5353
Ala Ser Phe Ser Trp Asn Gly Met Ala Leu Asn Pro Asp Asn Tyr Leu
1650 1655 1660

ATC TCA AAG GAT GTT ACA GGC GCA ACT AAG GTA AAG TAC TAC TAT GCA 5401
Ile Ser Lys Asp Val Thr Gly Ala Thr Lys Val Lys Tyr Tyr Tyr Ala
1665 1670 1675

GTC AAC GAC GGT TTT CCC GGG GAT CAC TAT GCG GTG ATG ATC TCC AAG 5449
Val Asn Asp Gly Phe Pro Gly Asp His Tyr Ala Val Met Ile Ser Lys
1680 1685 1690 1695

ACG GGC ACG AAC GCC GGA GAC TTC ACG GTT GTT TTC GAA GAA ACG CCT 5497
Thr Gly Thr Asn Ala Gly Asp Phe Thr Val Val Phe Glu Glu Thr Pro
1700 1705 1710

AAC GGA ATA AAT AAG GGC GGA GCA AGA TTC GGT CTT TCC ACG GAA GCC 5545
Asn Gly Ile Asn Lys Gly Gly Ala Arg Phe Gly Leu Ser Thr Glu Ala
1715 1720 1725

GAT GGC GCC AAA CCT CAA AGT GTA TGG ATC GAG CGT ACG GTA GAT TTG 5593
Asp Gly Ala Lys Pro Gln Ser Val Trp Ile Glu Arg Thr Val Asp Leu
1730 1735 1740

CCT GCG GGT ACT AAG TAT GTT GCT TTC CGA CAC TAC AAT TGC TCG GAT 5641
Pro Ala Gly Thr Lys Tyr Val Ala Phe Arg His Tyr Asn Cys Ser Asp
1745 1750 1755

TTG AAC TAC ATT CTT TTG GAT GAT ATT CAG TTC ACC ATG GGT GGC AGC 5689
Leu Asn Tyr Ile Leu Leu Asp Asp Ile Gln Phe Thr Met Gly Gly Ser
1760 1765 1770 1775

CCC ACC CCG ACC GAT TAT ACC TAC ACG GTG TAT CGT GAC GGT ACG AAG 5737
Pro Thr Pro Thr Asp Tyr Thr Tyr Thr Val Tyr Arg Asp Gly Thr Lys
1780 1785 1790

ATC AAG GAA GGT CTG ACC GAA ACG ACC TTC GAA GAA GAC GGT GTA GCT 5785
Ile Lys Glu Gly Leu Thr Glu Thr Thr Phe Glu Glu Asp Gly Val Ala
1795 1800 1805

ACG GGC AAC CAT GAG TAT TGC GTG GAA GTG AAG TAC ACA GCC GGC GTA 5833
Thr Gly Asn His Glu Tyr Cys Val Glu Val Lys Tyr Thr Ala Gly Val
1810 1815 1820

TCT CCG AAA GAG TGT GTA AAC GTA ACT GTT GAT CCT GTG CAG TTC AAT 5881
Ser Pro Lys Glu Cys Val Asn Val Thr Val Asp Pro Val Gln Phe Asn
1825 1830 1835

CCT GTA CAG AAC CTG ACC GGT AGT GCA GTC GGC CAG AAA GTA ACG CTT 5929
Pro Val Gln Asn Leu Thr Gly Ser Ala Val Gly Gln Lys Val Thr Leu
1840 1845 1850 1855

AAG TGG GAT GCA CCT AAT GGT ACC CCG AAT CCA AAT CCA AAT CCG AAT 5977
Lys Trp Asp Ala Pro Asn Gly Thr Pro Asn Pro Asn Pro Asn Pro Asn
1860 1865 1870

CCG GGA ACA ACA ACA CTT TCC GAA TCA TTC GAA AAT GGT ATT CCT GCC 6025
Pro Gly Thr Thr Thr Leu Ser Glu Ser Phe Glu Asn Gly Ile Pro Ala
1875 1880 1885

TCA TGG AAG ACG ATC GAT GCA GAC GGT GAC GGC AAC AAT TGG ACG ACG 6073
Ser Trp Lys Thr Ile Asp Ala Asp Gly Asp Gly Asn Asn Trp Thr Thr
1890 1895 1900

-continued

ACC CCT CCT CCC GGA GGC ACC TCT TTT GCA GGT CAC AAC AGT GCG ATC 6121
Thr Pro Pro Pro Gly Gly Thr Ser Phe Ala Gly His Asn Ser Ala Ile
1905 1910 1915

TGT GTC TCT TCG GCT TCT TAT ATC AAC TTT GAA GGC CCT CAG AAC CCT 6169
Cys Val Ser Ser Ala Ser Tyr Ile Asn Phe Glu Gly Pro Gln Asn Pro
1920 1925 1930 1935

GAT AAC TAT CTG GTT ACA CCG GAG CTA TCT CTT CCT GGC GGA GGA ACG 6217
Asp Asn Tyr Leu Val Thr Pro Glu Leu Ser Leu Pro Gly Gly Gly Thr
1940 1945 1950

CTT ACT TTC TGG GTA TGT GCA CAA GAT GCC AAT TAT GCA TCA GAG CAC 6265
Leu Thr Phe Trp Val Cys Ala Gln Asp Ala Asn Tyr Ala Ser Glu His
1955 1960 1965

TAT GCC GTG TAT GCA TCT TCT ACG GGT AAC GAC GCT TCC AAC TTC GCC 6313
Tyr Ala Val Tyr Ala Ser Ser Thr Gly Asn Asp Ala Ser Asn Phe Ala
1970 1975 1980

AAC GCT TTG TTG GAA GAA GTG CTG ACG GCC AAG ACA GTT GTT ACG GCA 6361
Asn Ala Leu Leu Glu Glu Val Leu Thr Ala Lys Thr Val Val Thr Ala
1985 1990 1995

CCT GAA GCC ATT CGT GGC ACT CGT GTT CAG GGC ACC TGG TAT CAA AAG 6409
Pro Glu Ala Ile Arg Gly Thr Arg Val Gln Gly Thr Trp Tyr Gln Lys
2000 2005 2010 2015

ACG GTA CAG TTG CCT GCG GGT ACT AAG TAT GTT GCC TTC CGT CAC TTC 6457
Thr Val Gln Leu Pro Ala Gly Thr Lys Tyr Val Ala Phe Arg His Phe
2020 2025 2030

GGC TGT ACG GAC TTC TTC TGG ATC AAC CTT GAT GAA GTT GAG ATC AAG 6505
Gly Cys Thr Asp Phe Phe Trp Ile Asn Leu Asp Glu Val Glu Ile Lys
2035 2040 2045

GCC AAC GGC AAG CGC GCA GAC TTC ACG GAA ACG TTC GAG TCT TCT ACT 6553
Ala Asn Gly Lys Arg Ala Asp Phe Thr Glu Thr Phe Glu Ser Ser Thr
2050 2055 2060

CAT GGA GAG GCA CCG GCG GAA TGG ACT ACT ATC GAT GCC GAT GGC GAT 6601
His Gly Glu Ala Pro Ala Glu Trp Thr Thr Ile Asp Ala Asp Gly Asp
2065 2070 2075

GGT CAG GGT TGG CTC TGT CTG TCT TCC GGA CAA TTG GAC TGG CTG ACA 6649
Gly Gln Gly Trp Leu Cys Leu Ser Ser Gly Gln Leu Asp Trp Leu Thr
2080 2085 2090 2095

GCT CAT GGC GGC ACC AAC GTA GTA GCC TCT TTC TCA TGG AAT GGA ATG 6697
Ala His Gly Gly Thr Asn Val Val Ala Ser Phe Ser Trp Asn Gly Met
2100 2105 2110

GCT TTG AAT CCT GAT AAC TAT CTC ATC TCA AAG GAT GTT ACA GGC GCA 6745
Ala Leu Asn Pro Asp Asn Tyr Leu Ile Ser Lys Asp Val Thr Gly Ala
2115 2120 2125

ACT AAG GTA AAG TAC TAC TAT GCA GTC AAC GAC GGT TTT CCC GGG GAT 6793
Thr Lys Val Lys Tyr Tyr Tyr Ala Val Asn Asp Gly Phe Pro Gly Asp
2130 2135 2140

CAC TAT GCG GTG ATG ATC TCC AAG ACG GGC ACG AAC GCC GGA GAC TTC 6841
His Tyr Ala Val Met Ile Ser Lys Thr Gly Thr Asn Ala Gly Asp Phe
2145 2150 2155

ACG GTT GTT TTC GAA GAA ACG CCT AAC GGA ATA AAT AAG GGC GGA GCA 6889
Thr Val Val Phe Glu Glu Thr Pro Asn Gly Ile Asn Lys Gly Gly Ala
2160 2165 2170 2175

AGA TTC GGT CTT TCC ACG GAA GCC GAT GGC GCC AAA CCT CAA AGT GTA 6937
Arg Phe Gly Leu Ser Thr Glu Ala Asp Gly Ala Lys Pro Gln Ser Val
2180 2185 2190

TGG ATC GAG CGT ACG GTA GAT TTG CCT GCG GGC ACG AAG TAT GTT GCT 6985
Trp Ile Glu Arg Thr Val Asp Leu Pro Ala Gly Thr Lys Tyr Val Ala
2195 2200 2205

TTC CGT CAC TAC AAT TGC TCG GAT TTG AAC TAC ATT CTT TTG GAT GAT 7033
Phe Arg His Tyr Asn Cys Ser Asp Leu Asn Tyr Ile Leu Leu Asp Asp
2210 2215 2220

-continued

```
ATT CAG TTC ACC ATG GGT GGC AGC CCC ACC CCG ACC GAT TAT ACC TAC      7081
Ile Gln Phe Thr Met Gly Gly Ser Pro Thr Pro Thr Asp Tyr Thr Tyr
    2225                2230                2235

ACG GTG TAT CGT GAC GGT ACG AAG ATC AAG GAA GGT CTG ACC GAA ACG      7129
Thr Val Tyr Arg Asp Gly Thr Lys Ile Lys Glu Gly Leu Thr Glu Thr
2240                2245                2250                2255

ACC TTC GAA GAA GAT GGT GTA GCT ACG GGC AAT CAT GAG TAT TGC GTG      7177
Thr Phe Glu Glu Asp Gly Val Ala Thr Gly Asn His Glu Tyr Cys Val
                2260                2265                2270

GAA GTG AAG TAC ACA GCC GGC GTA TCT CCG AAG GTG TGT GTA AAC GTA      7225
Glu Val Lys Tyr Thr Ala Gly Val Ser Pro Lys Val Cys Val Asn Val
            2275                2280                2285

ACT ATT AAT CCG ACT CAG TTC AAT CCT GTA CAG AAC CTG ACG GCA GAA      7273
Thr Ile Asn Pro Thr Gln Phe Asn Pro Val Gln Asn Leu Thr Ala Glu
        2290                2295                2300

CAA GCT CCT AAC AGC ATG GAT GCA ATC CTT AAA TGG AAT GCA CCG GCA      7321
Gln Ala Pro Asn Ser Met Asp Ala Ile Leu Lys Trp Asn Ala Pro Ala
    2305                2310                2315

TCT AAG CGT GCG GAA GTT CTG AAC GAA GAC TTC GAA AAT GGT ATT CCT      7369
Ser Lys Arg Ala Glu Val Leu Asn Glu Asp Phe Glu Asn Gly Ile Pro
2320                2325                2330                2335

TCC TCA TGG AAG ACG ATC GAT GCA GAC GGG GAC GGC AAC AAT TGG ACG      7417
Ser Ser Trp Lys Thr Ile Asp Ala Asp Gly Asp Gly Asn Asn Trp Thr
                2340                2345                2350

ACG ACC CCT CCT CCC GGA GGC TCC TCT TTT GCA GGT CAC AAC AGT GCG      7465
Thr Thr Pro Pro Pro Gly Gly Ser Ser Phe Ala Gly His Asn Ser Ala
            2355                2360                2365

ATC TGT GTC TCT TCG GCT TCT TAT ATC AAC TTT GAA GGT CCT CAG AAC      7513
Ile Cys Val Ser Ser Ala Ser Tyr Ile Asn Phe Glu Gly Pro Gln Asn
        2370                2375                2380

CCT GAT AAC TAT CTG GTT ACA CCG GAG CTT TCT CTT CCT GGC GGA GGA      7561
Pro Asp Asn Tyr Leu Val Thr Pro Glu Leu Ser Leu Pro Gly Gly Gly
    2385                2390                2395

ACG CTT ACT TTC TGG GTA TGT GCA CAA GAT GCC AAT TAT GCA TCA GAG      7609
Thr Leu Thr Phe Trp Val Cys Ala Gln Asp Ala Asn Tyr Ala Ser Glu
2400                2405                2410                2415

CAC TAT GCC GTG TAT GCA TCT TCT ACG GGT AAC GAC GCT TCC AAC TTC      7657
His Tyr Ala Val Tyr Ala Ser Ser Thr Gly Asn Asp Ala Ser Asn Phe
                2420                2425                2430

GCC AAC GCT TTG TTG GAA GAA GTG CTG ACG GCC AAG ACA GTT GTT ACG      7705
Ala Asn Ala Leu Leu Glu Glu Val Leu Thr Ala Lys Thr Val Val Thr
            2435                2440                2445

GCG CCT GAA GCC ATT CGT GGC ACT CGT GTT CAG GGC ACC TGG TAT CAA      7753
Ala Pro Glu Ala Ile Arg Gly Thr Arg Val Gln Gly Thr Trp Tyr Gln
        2450                2455                2460

AAG ACG GTA CAG TTG CCT GCG GGT ACT AAG TAT GTT GCC TTC CGT CAC      7801
Lys Thr Val Gln Leu Pro Ala Gly Thr Lys Tyr Val Ala Phe Arg His
    2465                2470                2475

TTC GGC TGT ACG GAC TTC TTC TGG ATC AAC CTT GAT GAT GTT GTA ATC      7849
Phe Gly Cys Thr Asp Phe Phe Trp Ile Asn Leu Asp Asp Val Val Ile
2480                2485                2490                2495

ACT TCA GGG AAC GCT CCG TCT TAC ACC TAT ACG ATC TAT CGT AAT AAT      7897
Thr Ser Gly Asn Ala Pro Ser Tyr Thr Tyr Thr Ile Tyr Arg Asn Asn
                2500                2505                2510

ACA CAG ATA GCA TCA GGC GTA ACG GAG ACT ACT TAC CGA GAT CCG GAC      7945
Thr Gln Ile Ala Ser Gly Val Thr Glu Thr Thr Tyr Arg Asp Pro Asp
            2515                2520                2525

TTG GCT ACC GGT TTT TAC ACG TAC GGT GTT AAG GTT GTT TAC CCG AAC      7993
Leu Ala Thr Gly Phe Tyr Thr Tyr Gly Val Lys Val Val Tyr Pro Asn
        2530                2535                2540
```

GGA GAA TCA GCT ATC GAA ACT GCT ACG TTG AAT ATC ACT TCG TTG GCA 8041
Gly Glu Ser Ala Ile Glu Thr Ala Thr Leu Asn Ile Thr Ser Leu Ala
2545 2550 2555

GAC GTA ACG GCT CAG AAG CCT TAC ACG CTG ACA GTT GTA GGA AAG ACG 8089
Asp Val Thr Ala Gln Lys Pro Tyr Thr Leu Thr Val Val Gly Lys Thr
2560 2565 2570 2575

ATC ACG GTA ACT TGC CAA GGC GAA GCT ATG ATC TAC GAC ATG AAC GGT 8137
Ile Thr Val Thr Cys Gln Gly Glu Ala Met Ile Tyr Asp Met Asn Gly
2580 2585 2590

CGT CGT CTG GCA GCC GGT CGC AAC ACG GTT GTT TAC ACG GCT CAG GGC 8185
Arg Arg Leu Ala Ala Gly Arg Asn Thr Val Val Tyr Thr Ala Gln Gly
2595 2600 2605

GGC CAC TAT GCA GTC ATG GTT GTC GTT GAC GGC AAG TCC TAC GTA GAG 8233
Gly His Tyr Ala Val Met Val Val Val Asp Gly Lys Ser Tyr Val Glu
2610 2615 2620

AAA CTC GCT GTA AAG TAACGAGATG ATTATTTTCG ATCGGTATGC TCTACCAACC 8288
Lys Leu Ala Val Lys
2625

GATCGCTTTA ATCGGTCGCC CGGCTTCCAT AAAAAGGAGT CGGGCGACTC TTTTACTCCA 8348

ACCAAATAAG CATTGTTTTA TAGCCTTTCG GAATATACTC CGGAAGGGGG TCGAGCTACG 8408

CCCTACAGCG ACTCGGGCTA CGCCGTAGAG CGTACCGAGC TGCGCTCTAC GGCTCTTCGA 8468

GCTACGCTGT AGGGCTCACT GCGCCAAGCT CTACGGCTCA GCTCGGCCAC CTCTACGGCT 8528

CCCGGAGCGG AACTCTACGG CTCGGCTCGC TACGCTGTAG AGCGTACCTA CGCCGAGCTC 8588

( 2 ) INFORMATION FOR SEQ ID NO:14:

( i ) SEQUENCE CHARACTERISTICS:
( A ) LENGTH: 2628 amino acids
( B ) TYPE: amino acid
( D ) TOPOLOGY: linear ( i i ) MOLECULE TYPE: protein ( x i ) SEQUENCE DESCRIPTION: SEQ ID NO:14:

Met Arg Lys Leu Asn Ser Leu Phe Ser Leu Ala Val Leu Leu Ser Leu
1 5 10 15

Leu Cys Trp Gly Gln Thr Ala Ala Ala Gln Gly Gly Pro Lys Thr Ala
20 25 30

Pro Ser Val Thr His Gln Ala Val Gln Lys Gly Ile Arg Thr Ser Lys
35 40 45

Val Lys Asp Leu Arg Asp Pro Ile Pro Ala Gly Met Ala Arg Ile Ile
50 55 60

Leu Glu Ala His Asp Val Trp Glu Asp Gly Thr Gly Tyr Gln Met Leu
65 70 75 80

Trp Asp Ala Asp His Asn Gln Tyr Gly Ala Ser Ile Pro Glu Glu Ser
85 90 95

Phe Trp Phe Ala Asn Gly Thr Ile Pro Ala Gly Leu Tyr Asp Pro Phe
100 105 110

Glu Tyr Lys Val Pro Val Asn Ala Asp Ala Ser Phe Ser Pro Thr Asn
115 120 125

Phe Val Leu Asp Gly Thr Ala Ser Ala Asp Ile Pro Ala Gly Thr Tyr
130 135 140

Asp Tyr Val Ile Ile Asn Pro Asn Pro Gly Ile Ile Tyr Ile Val Gly
145 150 155 160

Glu Gly Val Ser Lys Gly Asn Asp Tyr Val Val Glu Ala Gly Lys Thr
165 170 175

Tyr His Phe Thr Val Gln Arg Gln Gly Pro Gly Asp Ala Ala Ser Val

-continued

```
            180                 185                 190

Val Val Thr Gly Glu Gly Gly Asn Glu Phe Ala Pro Val Gln Asn Leu
        195                 200                 205

Gln Trp Ser Val Ser Gly Gln Thr Val Thr Leu Thr Trp Gln Ala Pro
    210                 215                 220

Ala Ser Asp Lys Arg Thr Tyr Val Leu Asn Glu Ser Phe Asp Thr Gln
225                 230                 235                 240

Thr Leu Pro Asn Gly Trp Thr Met Ile Asp Ala Asp Gly Asp Gly His
                245                 250                 255

Asn Trp Leu Ser Thr Ile Asn Val Tyr Asn Thr Ala Thr His Thr Gly
            260                 265                 270

Asp Gly Ala Met Phe Ser Lys Ser Trp Thr Ala Ser Gly Gly Ala Lys
        275                 280                 285

Ile Asp Leu Ser Pro Asp Asn Tyr Leu Val Thr Pro Lys Val Thr Val
    290                 295                 300

Pro Glu Asn Gly Lys Leu Ser Tyr Trp Val Ser Ser Gln Val Pro Trp
305                 310                 315                 320

Thr Asn Glu His Tyr Gly Val Phe Leu Ser Thr Thr Gly Asn Glu Ala
                325                 330                 335

Ala Asn Phe Thr Ile Lys Leu Leu Glu Glu Thr Leu Gly Ser Asp Lys
            340                 345                 350

Pro Ala Pro Met Asn Leu Val Lys Ser Glu Gly Val Lys Leu Pro Ala
        355                 360                 365

Pro Tyr Gln Glu Arg Thr Ile Asp Leu Ser Ala Tyr Ala Gly Gln Gln
    370                 375                 380

Val Tyr Leu Ala Phe Arg His Phe Asn Ser Thr Gly Ile Phe Arg Leu
385                 390                 395                 400

Tyr Leu Asp Asp Val Ala Val Ser Gly Glu Gly Ser Ser Asn Asp Tyr
                405                 410                 415

Thr Tyr Thr Val Tyr Arg Asp Asn Val Val Ile Ala Gln Asn Leu Ala
            420                 425                 430

Ala Thr Thr Phe Asn Gln Glu Asn Val Ala Pro Gly Gln Tyr Asn Tyr
        435                 440                 445

Cys Val Glu Val Lys Tyr Thr Ala Gly Val Ser Pro Lys Val Cys Lys
    450                 455                 460

Asp Val Thr Val Glu Gly Ser Asn Glu Phe Ala His Val Gln Asn Leu
465                 470                 475                 480

Thr Gly Ser Ala Val Gly Gln Lys Val Thr Leu Lys Trp Asp Ala Pro
                485                 490                 495

Asn Gly Thr Pro Asn Pro Asn Pro Gly Thr Thr Thr Leu Ser Glu Ser
            500                 505                 510

Phe Glu Asn Gly Ile Pro Ala Ser Trp Lys Thr Ile Asp Ala Asp Gly
        515                 520                 525

Asp Gly Asn Asn Trp Thr Thr Thr Pro Pro Pro Gly Gly Thr Ser Phe
    530                 535                 540

Ala Gly His Asn Ser Ala Ile Cys Ala Ser Ser Ala Ser Tyr Ile Asn
545                 550                 555                 560

Phe Glu Gly Pro Gln Asn Pro Asp Asn Tyr Leu Val Thr Pro Glu Leu
                565                 570                 575

Ser Leu Pro Asn Gly Gly Thr Leu Thr Phe Trp Val Cys Ala Gln Asp
            580                 585                 590

Ala Asn Tyr Ala Ser Glu His Tyr Ala Val Tyr Ala Ser Ser Thr Gly
        595                 600                 605
```

-continued

Asn Asp Ala Ser Asn Phe Ala Asn Ala Leu Leu Glu Glu Val Leu Thr
610 615 620

Ala Lys Thr Val Val Thr Ala Pro Glu Ala Ile Arg Gly Thr Arg Val
625 630 635 640

Gln Gly Thr Trp Tyr Gln Lys Thr Val Gln Leu Pro Ala Gly Thr Lys
645 650 655

Tyr Val Ala Phe Arg His Phe Gly Cys Thr Asp Phe Phe Trp Ile Asn
660 665 670

Leu Asp Asp Val Glu Ile Lys Ala Asn Gly Lys Arg Ala Asp Phe Thr
675 680 685

Glu Thr Phe Glu Ser Ser Thr His Gly Glu Ala Pro Ala Glu Trp Thr
690 695 700

Thr Ile Asp Ala Asp Gly Asp Gly Gln Gly Trp Leu Cys Leu Ser Ser
705 710 715 720

Gly Gln Leu Asp Trp Leu Thr Ala His Gly Gly Thr Asn Val Val Ala
725 730 735

Ser Phe Ser Trp Asn Gly Met Ala Leu Asn Pro Asp Asn Tyr Leu Ile
740 745 750

Ser Lys Asp Val Thr Gly Ala Thr Lys Val Lys Tyr Tyr Tyr Ala Val
755 760 765

Asn Asp Gly Phe Pro Gly Asp His Tyr Ala Val Met Ile Ser Lys Thr
770 775 780

Gly Thr Asn Ala Gly Asp Phe Thr Val Val Phe Glu Glu Thr Pro Asn
785 790 795 800

Gly Ile Asn Lys Gly Gly Ala Arg Phe Gly Leu Ser Thr Glu Ala Asp
805 810 815

Gly Ala Lys Pro Gln Ser Val Trp Ile Glu Arg Thr Val Asp Leu Pro
820 825 830

Ala Gly Thr Lys Tyr Val Ala Phe Arg His Tyr Asn Cys Ser Asp Leu
835 840 845

Asn Tyr Ile Leu Leu Asp Asp Ile Gln Phe Thr Met Gly Gly Ser Pro
850 855 860

Thr Pro Thr Asp Tyr Thr Tyr Thr Val Tyr Arg Asp Gly Thr Lys Ile
865 870 875 880

Lys Glu Gly Leu Thr Glu Thr Thr Phe Glu Glu Asp Gly Val Ala Thr
885 890 895

Gly Asn His Glu Tyr Cys Val Glu Val Lys Tyr Thr Ala Gly Val Ser
900 905 910

Pro Lys Glu Cys Val Asn Val Thr Val Asp Pro Val Gln Phe Asn Pro
915 920 925

Val Gln Asn Leu Thr Gly Ser Ala Val Gly Gln Lys Val Thr Leu Lys
930 935 940

Trp Asp Ala Pro Asn Gly Thr Pro Asn Pro Asn Pro Asn Pro Asn Pro
945 950 955 960

Gly Thr Thr Thr Leu Ser Glu Ser Phe Glu Asn Gly Ile Pro Ala Ser
965 970 975

Trp Lys Thr Ile Asp Ala Asp Gly Asp Gly Asn Asn Trp Thr Thr Thr
980 985 990

Pro Pro Pro Gly Gly Thr Ser Phe Ala Gly His Asn Ser Ala Ile Cys
995 1000 1005

Ala Ser Ser Ala Ser Tyr Ile Asn Phe Glu Gly Pro Gln Asn Pro Asp
1010 1015 1020

Asn Tyr Leu Val Thr Pro Glu Leu Ser Leu Pro Asn Gly Gly Thr Leu
1025 1030 1035 1040

-continued

Thr Phe Trp Val Cys Ala Gln Asp Ala Asn Tyr Ala Ser Glu His Tyr
1045 1050 1055

Ala Val Tyr Ala Ser Ser Thr Gly Asn Asp Ala Ser Asn Phe Ala Asn
1060 1065 1070

Ala Leu Leu Glu Glu Val Leu Thr Ala Lys Thr Val Val Thr Ala Pro
1075 1080 1085

Glu Ala Ile Arg Gly Thr Arg Val Gln Gly Thr Trp Tyr Gln Lys Thr
1090 1095 1100

Val Gln Leu Pro Ala Gly Thr Lys Tyr Val Ala Phe Arg His Phe Gly
1105 1110 1115 1120

Cys Thr Asp Phe Phe Trp Ile Asn Leu Asp Asp Val Glu Ile Lys Ala
1125 1130 1135

Asn Gly Lys Arg Ala Asp Phe Thr Glu Thr Phe Glu Ser Ser Thr His
1140 1145 1150

Gly Glu Ala Pro Ala Glu Trp Thr Thr Ile Asp Ala Asp Gly Asp Gly
1155 1160 1165

Gln Gly Trp Leu Cys Leu Ser Ser Gly Gln Leu Gly Trp Leu Thr Ala
1170 1175 1180

His Gly Gly Thr Asn Val Val Ala Ser Phe Ser Trp Asn Gly Met Ala
1185 1190 1195 1200

Leu Asn Pro Asp Asn Tyr Leu Ile Ser Lys Asp Val Thr Gly Ala Thr
1205 1210 1215

Lys Val Lys Tyr Tyr Tyr Ala Val Asn Asp Gly Phe Pro Gly Asp His
1220 1225 1230

Tyr Ala Val Met Ile Ser Lys Thr Gly Thr Asn Ala Gly Asp Phe Thr
1235 1240 1245

Val Val Phe Glu Glu Thr Pro Asn Gly Ile Asn Lys Gly Gly Ala Arg
1250 1255 1260

Phe Gly Leu Ser Thr Glu Ala Asp Gly Ala Lys Pro Gln Ser Val Trp
1265 1270 1275 1280

Ile Glu Arg Thr Val Asp Leu Pro Ala Gly Thr Lys Tyr Val Ala Phe
1285 1290 1295

Arg His Tyr Asn Cys Ser Asp Leu Asn Tyr Ile Leu Leu Asp Asp Ile
1300 1305 1310

Gln Phe Thr Met Gly Gly Ser Pro Thr Pro Thr Asp Tyr Thr Tyr Thr
1315 1320 1325

Val Tyr Arg Asp Gly Thr Lys Ile Lys Glu Gly Leu Thr Glu Thr Thr
1330 1335 1340

Phe Glu Glu Asp Gly Val Ala Thr Gly Asn His Glu Tyr Cys Val Glu
1345 1350 1355 1360

Val Lys Tyr Thr Ala Gly Val Ser Pro Lys Glu Cys Val Asn Val Thr
1365 1370 1375

Val Asp Pro Val Gln Phe Asn Pro Val Gln Asn Leu Thr Gly Ser Ala
1380 1385 1390

Val Gly Gln Lys Val Thr Leu Lys Trp Asp Ala Pro Asn Gly Thr Pro
1395 1400 1405

Asn Pro Asn Pro Asn Pro Asn Pro Gly Thr Thr Thr Leu Ser Glu Ser
1410 1415 1420

Phe Glu Asn Gly Ile Pro Ala Ser Trp Lys Thr Ile Asp Ala Asp Gly
1425 1430 1435 1440

Asp Gly Asn Asn Trp Thr Thr Thr Pro Pro Pro Gly Gly Thr Ser Phe
1445 1450 1455

Ala Gly His Asn Ser Ala Ile Cys Ala Ser Ser Ala Ser Tyr Ile Asn

-continued 1460 1465 1470

Phe Glu Gly Pro Gln Asn Pro Asp Asn Tyr Leu Val Thr Pro Glu Leu
1475 1480 1485

Ser Leu Pro Asn Gly Gly Thr Leu Thr Phe Trp Val Cys Ala Gln Asp
1490 1495 1500

Ala Asn Tyr Ala Ser Glu His Tyr Ala Val Tyr Ala Ser Ser Thr Gly
1505 1510 1515 1520

Asn Asp Ala Ser Asn Phe Ala Asn Ala Leu Leu Glu Glu Val Leu Thr
1525 1530 1535

Ala Lys Thr Val Val Thr Ala Pro Glu Ala Ile Arg Gly Thr Arg Val
1540 1545 1550

Gln Gly Thr Trp Tyr Gln Lys Thr Val Gln Leu Pro Ala Gly Thr Lys
1555 1560 1565

Tyr Val Ala Phe Arg His Phe Gly Cys Thr Asp Phe Phe Trp Ile Asn
1570 1575 1580

Leu Asp Asp Val Glu Ile Lys Ala Asn Gly Lys Arg Ala Asp Phe Thr
1585 1590 1595 1600

Glu Thr Phe Glu Ser Ser Thr His Gly Glu Ala Pro Ala Glu Trp Thr
1605 1610 1615

Thr Ile Asp Ala Asp Gly Asp Gly Gln Gly Trp Leu Cys Leu Ser Ser
1620 1625 1630

Gly Gln Leu Gly Trp Leu Thr Ala His Gly Gly Thr Asn Val Val Ala
1635 1640 1645

Ser Phe Ser Trp Asn Gly Met Ala Leu Asn Pro Asp Asn Tyr Leu Ile
1650 1655 1660

Ser Lys Asp Val Thr Gly Ala Thr Lys Val Lys Tyr Tyr Tyr Ala Val
1665 1670 1675 1680

Asn Asp Gly Phe Pro Gly Asp His Tyr Ala Val Met Ile Ser Lys Thr
1685 1690 1695

Gly Thr Asn Ala Gly Asp Phe Thr Val Val Phe Glu Glu Thr Pro Asn
1700 1705 1710

Gly Ile Asn Lys Gly Gly Ala Arg Phe Gly Leu Ser Thr Glu Ala Asp
1715 1720 1725

Gly Ala Lys Pro Gln Ser Val Trp Ile Glu Arg Thr Val Asp Leu Pro
1730 1735 1740

Ala Gly Thr Lys Tyr Val Ala Phe Arg His Tyr Asn Cys Ser Asp Leu
1745 1750 1755 1760

Asn Tyr Ile Leu Leu Asp Asp Ile Gln Phe Thr Met Gly Gly Ser Pro
1765 1770 1775

Thr Pro Thr Asp Tyr Thr Tyr Thr Val Tyr Arg Asp Gly Thr Lys Ile
1780 1785 1790

Lys Glu Gly Leu Thr Glu Thr Thr Phe Glu Glu Asp Gly Val Ala Thr
1795 1800 1805

Gly Asn His Glu Tyr Cys Val Glu Val Lys Tyr Thr Ala Gly Val Ser
1810 1815 1820

Pro Lys Glu Cys Val Asn Val Thr Val Asp Pro Val Gln Phe Asn Pro
1825 1830 1835 1840

Val Gln Asn Leu Thr Gly Ser Ala Val Gly Gln Lys Val Thr Leu Lys
1845 1850 1855

Trp Asp Ala Pro Asn Gly Thr Pro Asn Pro Asn Pro Asn Pro Asn Pro
1860 1865 1870

Gly Thr Thr Thr Leu Ser Glu Ser Phe Glu Asn Gly Ile Pro Ala Ser
1875 1880 1885

-continued

Trp Lys Thr Ile Asp Ala Asp Gly Asp Gly Asn Asn Trp Thr Thr Thr
1890 1895 1900

Pro Pro Pro Gly Gly Thr Ser Phe Ala Gly His Asn Ser Ala Ile Cys
1905 1910 1915 1920

Val Ser Ser Ala Ser Tyr Ile Asn Phe Glu Gly Pro Gln Asn Pro Asp
1925 1930 1935

Asn Tyr Leu Val Thr Pro Glu Leu Ser Leu Pro Gly Gly Gly Thr Leu
1940 1945 1950

Thr Phe Trp Val Cys Ala Gln Asp Ala Asn Tyr Ala Ser Glu His Tyr
1955 1960 1965

Ala Val Tyr Ala Ser Ser Thr Gly Asn Asp Ala Ser Asn Phe Ala Asn
1970 1975 1980

Ala Leu Leu Glu Glu Val Leu Thr Ala Lys Thr Val Val Thr Ala Pro
1985 1990 1995 2000

Glu Ala Ile Arg Gly Thr Arg Val Gln Gly Thr Trp Tyr Gln Lys Thr
2005 2010 2015

Val Gln Leu Pro Ala Gly Thr Lys Tyr Val Ala Phe Arg His Phe Gly
2020 2025 2030

Cys Thr Asp Phe Phe Trp Ile Asn Leu Asp Glu Val Glu Ile Lys Ala
2035 2040 2045

Asn Gly Lys Arg Ala Asp Phe Thr Glu Thr Phe Glu Ser Ser Thr His
2050 2055 2060

Gly Glu Ala Pro Ala Glu Trp Thr Thr Ile Asp Ala Asp Gly Asp Gly
2065 2070 2075 2080

Gln Gly Trp Leu Cys Leu Ser Ser Gly Gln Leu Asp Trp Leu Thr Ala
2085 2090 2095

His Gly Gly Thr Asn Val Val Ala Ser Phe Ser Trp Asn Gly Met Ala
2100 2105 2110

Leu Asn Pro Asp Asn Tyr Leu Ile Ser Lys Asp Val Thr Gly Ala Thr
2115 2120 2125

Lys Val Lys Tyr Tyr Tyr Ala Val Asn Asp Gly Phe Pro Gly Asp His
2130 2135 2140

Tyr Ala Val Met Ile Ser Lys Thr Gly Thr Asn Ala Gly Asp Phe Thr
2145 2150 2155 2160

Val Val Phe Glu Glu Thr Pro Asn Gly Ile Asn Lys Gly Gly Ala Arg
2165 2170 2175

Phe Gly Leu Ser Thr Glu Ala Asp Gly Ala Lys Pro Gln Ser Val Trp
2180 2185 2190

Ile Glu Arg Thr Val Asp Leu Pro Ala Gly Thr Lys Tyr Val Ala Phe
2195 2200 2205

Arg His Tyr Asn Cys Ser Asp Leu Asn Tyr Ile Leu Leu Asp Asp Ile
2210 2215 2220

Gln Phe Thr Met Gly Gly Ser Pro Thr Pro Thr Asp Tyr Thr Tyr Thr
2225 2230 2235 2240

Val Tyr Arg Asp Gly Thr Lys Ile Lys Glu Gly Leu Thr Glu Thr Thr
2245 2250 2255

Phe Glu Glu Asp Gly Val Ala Thr Gly Asn His Glu Tyr Cys Val Glu
2260 2265 2270

Val Lys Tyr Thr Ala Gly Val Ser Pro Lys Val Cys Val Asn Val Thr
2275 2280 2285

Ile Asn Pro Thr Gln Phe Asn Pro Val Gln Asn Leu Thr Ala Glu Gln
2290 2295 2300

Ala Pro Asn Ser Met Asp Ala Ile Leu Lys Trp Asn Ala Pro Ala Ser
2305 2310 2315 2320

```
Lys Arg Ala Glu Val Leu Asn Glu Asp Phe Glu Asn Gly Ile Pro Ser
                2325                2330                2335

Ser Trp Lys Thr Ile Asp Ala Asp Gly Asp Gly Asn Asn Trp Thr Thr
            2340                2345                2350

Thr Pro Pro Pro Gly Gly Ser Ser Phe Ala Gly His Asn Ser Ala Ile
        2355                2360                2365

Cys Val Ser Ser Ala Ser Tyr Ile Asn Phe Glu Gly Pro Gln Asn Pro
    2370                2375                2380

Asp Asn Tyr Leu Val Thr Pro Glu Leu Ser Leu Pro Gly Gly Gly Thr
2385                2390                2395                2400

Leu Thr Phe Trp Val Cys Ala Gln Asp Ala Asn Tyr Ala Ser Glu His
                2405                2410                2415

Tyr Ala Val Tyr Ala Ser Ser Thr Gly Asn Asp Ala Ser Asn Phe Ala
            2420                2425                2430

Asn Ala Leu Leu Glu Glu Val Leu Thr Ala Lys Thr Val Val Thr Ala
        2435                2440                2445

Pro Glu Ala Ile Arg Gly Thr Arg Val Gln Gly Thr Trp Tyr Gln Lys
    2450                2455                2460

Thr Val Gln Leu Pro Ala Gly Thr Lys Tyr Val Ala Phe Arg His Phe
2465                2470                2475                2480

Gly Cys Thr Asp Phe Phe Trp Ile Asn Leu Asp Asp Val Val Ile Thr
                2485                2490                2495

Ser Gly Asn Ala Pro Ser Tyr Thr Tyr Thr Ile Tyr Arg Asn Asn Thr
            2500                2505                2510

Gln Ile Ala Ser Gly Val Thr Glu Thr Thr Tyr Arg Asp Pro Asp Leu
        2515                2520                2525

Ala Thr Gly Phe Tyr Thr Tyr Gly Val Lys Val Val Tyr Pro Asn Gly
    2530                2535                2540

Glu Ser Ala Ile Glu Thr Ala Thr Leu Asn Ile Thr Ser Leu Ala Asp
2545                2550                2555                2560

Val Thr Ala Gln Lys Pro Tyr Thr Leu Thr Val Val Gly Lys Thr Ile
                2565                2570                2575

Thr Val Thr Cys Gln Gly Glu Ala Met Ile Tyr Asp Met Asn Gly Arg
            2580                2585                2590

Arg Leu Ala Ala Gly Arg Asn Thr Val Val Tyr Thr Ala Gln Gly Gly
        2595                2600                2605

His Tyr Ala Val Met Val Val Val Asp Gly Lys Ser Tyr Val Glu Lys
    2610                2615                2620

Leu Ala Val Lys
2625
```

( 2 ) INFORMATION FOR SEQ ID NO:15:

( i ) SEQUENCE CHARACTERISTICS:
( A ) LENGTH: 1350 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1350

( x i ) SEQUENCE DESCRIPTION: SEQ ID NO:15:

```
CCG AAT CCG AAT CCC GGA ACA ACA ACA CTT TCC GAA TCA TTC GAA AAT      48
Pro Asn Pro Asn Pro Gly Thr Thr Thr Leu Ser Glu Ser Phe Glu Asn
```

-continued

```
    2630                    2635                    2640

GGT ATT CCT GCC TCA TGG AAG ACG ATC GAT GCA GAC GGT GAC GGC AAC      96
Gly Ile Pro Ala Ser Trp Lys Thr Ile Asp Ala Asp Gly Asp Gly Asn
2645                    2650                    2655                2660

AAT TGG ACG ACG ACC CCT CCT CCC GGA GGC ACC TCT TTT GCA GGT CAC     144
Asn Trp Thr Thr Thr Pro Pro Pro Gly Gly Thr Ser Phe Ala Gly His
                2665                    2670                    2675

AAC AGT GCA ATC TGT GCC TCT TCG GCT TCT TAT ATC AAC TTT GAA GGT     192
Asn Ser Ala Ile Cys Ala Ser Ser Ala Ser Tyr Ile Asn Phe Glu Gly
            2680                    2685                    2690

CCT CAG AAC CCT GAT AAC TAT CTG GTT ACA CCG GAG CTA TCT CTT CCT     240
Pro Gln Asn Pro Asp Asn Tyr Leu Val Thr Pro Glu Leu Ser Leu Pro
        2695                    2700                    2705

AAC GGA GGA ACG CTT ACT TTC TGG GTA TGT GCA CAA GAT GCC AAT TAT     288
Asn Gly Gly Thr Leu Thr Phe Trp Val Cys Ala Gln Asp Ala Asn Tyr
    2710                    2715                    2720

GCA TCA GAG CAC TAT GCC GTG TAC GCA TCT TCT ACG GGT AAC GAC GCT     336
Ala Ser Glu His Tyr Ala Val Tyr Ala Ser Ser Thr Gly Asn Asp Ala
2725                    2730                    2735                2740

TCC AAC TTC GCC AAC GCT TTG TTG GAA GAA GTG CTG ACG GCC AAG ACA     384
Ser Asn Phe Ala Asn Ala Leu Leu Glu Glu Val Leu Thr Ala Lys Thr
                2745                    2750                    2755

GTT GTT ACG GCA CCT GAA GCC ATT CGT GGC ACT CGT GTT CAG GGC ACC     432
Val Val Thr Ala Pro Glu Ala Ile Arg Gly Thr Arg Val Gln Gly Thr
            2760                    2765                    2770

TGG TAT CAA AAG ACG GTA CAG TTG CCT GCG GGT ACT AAG TAT GTT GCT     480
Trp Tyr Gln Lys Thr Val Gln Leu Pro Ala Gly Thr Lys Tyr Val Ala
        2775                    2780                    2785

TTC CGT CAC TTC GGC TGT ACG GAC TTC TTC TGG ATT AAC CTT GAT GAT     528
Phe Arg His Phe Gly Cys Thr Asp Phe Phe Trp Ile Asn Leu Asp Asp
    2790                    2795                    2800

GTT GAG ATC AAG GCC AAC GGC AAG CGC GCA GAC TTC ACG GAA ACG TTC     576
Val Glu Ile Lys Ala Asn Gly Lys Arg Ala Asp Phe Thr Glu Thr Phe
2805                    2810                    2815                2820

GAG TCT TCT ACT CAT GGA GAG GCA CCG GCG GAA TGG ACT ACT ATC GAT     624
Glu Ser Ser Thr His Gly Glu Ala Pro Ala Glu Trp Thr Thr Ile Asp
                2825                    2830                    2835

GCC GAT GGC GAT GGT CAG GGT TGG CTC TGT CTG TCT TCC GGA CAA TTG     672
Ala Asp Gly Asp Gly Gln Gly Trp Leu Cys Leu Ser Ser Gly Gln Leu
            2840                    2845                    2850

GAC TGG CTG ACA GCT CAT GGC GGC ACC AAC GTA GTA GCC TCT TTC TCA     720
Asp Trp Leu Thr Ala His Gly Gly Thr Asn Val Val Ala Ser Phe Ser
        2855                    2860                    2865

TGG AAT GGA ATG GCT TTG AAT CCT GAT AAC TAT CTC ATC TCA AAG GAT     768
Trp Asn Gly Met Ala Leu Asn Pro Asp Asn Tyr Leu Ile Ser Lys Asp
    2870                    2875                    2880

GTT ACA GGC GCA ACT AAG GTA AAG TAC TAC TAT GCA GTC AAC GAC GGT     816
Val Thr Gly Ala Thr Lys Val Lys Tyr Tyr Tyr Ala Val Asn Asp Gly
2885                    2890                    2895                2900

TTT CCC GGG GAT CAC TAT GCG GTG ATG ATC TCC AAG ACG GGC ACG AAC     864
Phe Pro Gly Asp His Tyr Ala Val Met Ile Ser Lys Thr Gly Thr Asn
                2905                    2910                    2915

GCC GGA GAC TTC ACG GTT GTT TTC GAA GAA ACG CCT AAC GGA ATA AAT     912
Ala Gly Asp Phe Thr Val Val Phe Glu Glu Thr Pro Asn Gly Ile Asn
            2920                    2925                    2930

AAG GGC GGA GCA AGA TTC GGT CTT TCC ACG GAA GCC GAT GGC GCC AAA     960
Lys Gly Gly Ala Arg Phe Gly Leu Ser Thr Glu Ala Asp Gly Ala Lys
        2935                    2940                    2945

CCT CAA AGT GTA TGG ATC GAG CGT ACG GTA GAT TTG CCT GCG GGT ACT    1008
Pro Gln Ser Val Trp Ile Glu Arg Thr Val Asp Leu Pro Ala Gly Thr
```

2950 2955 2960

AAG TAT GTT GCT TTC CGT CAC TAC AAT TGC TCG GAT TTG AAC TAC ATT 1056
Lys Tyr Val Ala Phe Arg His Tyr Asn Cys Ser Asp Leu Asn Tyr Ile
2965 2970 2975 2980

CTT TTG GAT GAT ATT CAG TTC ACC ATG GGT GGC AGC CCC ACC CCG ACC 1104
Leu Leu Asp Asp Ile Gln Phe Thr Met Gly Gly Ser Pro Thr Pro Thr
2985 2990 2995

GAT TAT ACC TAC ACG GTG TAT CGT GAC GGT ACG AAG ATC AAG GAA GGT 1152
Asp Tyr Thr Tyr Thr Val Tyr Arg Asp Gly Thr Lys Ile Lys Glu Gly
3000 3005 3010

CTG ACC GAA ACG ACC TTC GAA GAA GAC GGT GTA GCT ACG GGC AAC CAT 1200
Leu Thr Glu Thr Thr Phe Glu Glu Asp Gly Val Ala Thr Gly Asn His
3015 3020 3025

GAG TAT TGC GTG GAA GTG AAG TAC ACA GCC GGC GTA TCT CCG AAA GAG 1248
Glu Tyr Cys Val Glu Val Lys Tyr Thr Ala Gly Val Ser Pro Lys Glu
3030 3035 3040

TGT GTA AAC GTA ACT GTT GAT CCT GTG CAG TTC AAT CCT GTA CAG AAC 1296
Cys Val Asn Val Thr Val Asp Pro Val Gln Phe Asn Pro Val Gln Asn
3045 3050 3055 3060

CTG ACC GGT AGT GCA GTC GGC CAG AAA GTA ACG CTT AAG TGG GAT GCA 1344
Leu Thr Gly Ser Ala Val Gly Gln Lys Val Thr Leu Lys Trp Asp Ala
3065 3070 3075

CCT AAT 1350
Pro Asn ( 2 ) INFORMATION FOR SEQ ID NO:16:

( i ) SEQUENCE CHARACTERISTICS:
( A ) LENGTH: 450 amino acids
( B ) TYPE: amino acid
( D ) TOPOLOGY: linear ( i i ) MOLECULE TYPE: protein ( x i ) SEQUENCE DESCRIPTION: SEQ ID NO:16:

Pro Asn Pro Asn Pro Gly Thr Thr Thr Leu Ser Glu Ser Phe Glu Asn
1 5 10 15

Gly Ile Pro Ala Ser Trp Lys Thr Ile Asp Ala Asp Gly Asp Gly Asn
20 25 30

Asn Trp Thr Thr Thr Pro Pro Pro Gly Gly Thr Ser Phe Ala Gly His
35 40 45

Asn Ser Ala Ile Cys Ala Ser Ser Ala Ser Tyr Ile Asn Phe Glu Gly
50 55 60

Pro Gln Asn Pro Asp Asn Tyr Leu Val Thr Pro Glu Leu Ser Leu Pro
65 70 75 80

Asn Gly Gly Thr Leu Thr Phe Trp Val Cys Ala Gln Asp Ala Asn Tyr
85 90 95

Ala Ser Glu His Tyr Ala Val Tyr Ala Ser Ser Thr Gly Asn Asp Ala
100 105 110

Ser Asn Phe Ala Asn Ala Leu Leu Glu Glu Val Leu Thr Ala Lys Thr
115 120 125

Val Val Thr Ala Pro Glu Ala Ile Arg Gly Thr Arg Val Gln Gly Thr
130 135 140

Trp Tyr Gln Lys Thr Val Gln Leu Pro Ala Gly Thr Lys Tyr Val Ala
145 150 155 160

Phe Arg His Phe Gly Cys Thr Asp Phe Phe Trp Ile Asn Leu Asp Asp
165 170 175

Val Glu Ile Lys Ala Asn Gly Lys Arg Ala Asp Phe Thr Glu Thr Phe
180 185 190

-continued

Glu Ser Ser Thr His Gly Glu Ala Pro Ala Glu Trp Thr Thr Ile Asp
        195                 200                 205

Ala Asp Gly Asp Gly Gln Gly Trp Leu Cys Leu Ser Ser Gly Gln Leu
    210                 215                 220

Asp Trp Leu Thr Ala His Gly Gly Thr Asn Val Val Ala Ser Phe Ser
225                 230                 235                 240

Trp Asn Gly Met Ala Leu Asn Pro Asp Asn Tyr Leu Ile Ser Lys Asp
                245                 250                 255

Val Thr Gly Ala Thr Lys Val Lys Tyr Tyr Tyr Ala Val Asn Asp Gly
            260                 265                 270

Phe Pro Gly Asp His Tyr Ala Val Met Ile Ser Lys Thr Gly Thr Asn
        275                 280                 285

Ala Gly Asp Phe Thr Val Val Phe Glu Glu Thr Pro Asn Gly Ile Asn
    290                 295                 300

Lys Gly Gly Ala Arg Phe Gly Leu Ser Thr Glu Ala Asp Gly Ala Lys
305                 310                 315                 320

Pro Gln Ser Val Trp Ile Glu Arg Thr Val Asp Leu Pro Ala Gly Thr
                325                 330                 335

Lys Tyr Val Ala Phe Arg His Tyr Asn Cys Ser Asp Leu Asn Tyr Ile
            340                 345                 350

Leu Leu Asp Asp Ile Gln Phe Thr Met Gly Gly Ser Pro Thr Pro Thr
        355                 360                 365

Asp Tyr Thr Tyr Thr Val Tyr Arg Asp Gly Thr Lys Ile Lys Glu Gly
    370                 375                 380

Leu Thr Glu Thr Thr Phe Glu Glu Asp Gly Val Ala Thr Gly Asn His
385                 390                 395                 400

Glu Tyr Cys Val Glu Val Lys Tyr Thr Ala Gly Val Ser Pro Lys Glu
                405                 410                 415

Cys Val Asn Val Thr Val Asp Pro Val Gln Phe Asn Pro Val Gln Asn
            420                 425                 430

Leu Thr Gly Ser Ala Val Gly Gln Lys Val Thr Leu Lys Trp Asp Ala
        435                 440                 445

Pro Asn
    450

( 2 ) INFORMATION FOR SEQ ID NO:17:

( i ) SEQUENCE CHARACTERISTICS:
( A ) LENGTH: 1368 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1368

( x i ) SEQUENCE DESCRIPTION: SEQ ID NO:17:

GGT ACC CCG AAT CCA AAT CCA AAT CCG AAT CCG GGA ACA ACA ACA CTT 48
Gly Thr Pro Asn Pro Asn Pro Asn Pro Asn Pro Gly Thr Thr Thr Leu
                455                 460                 465

TCC GAA TCA TTC GAA AAT GGT ATT CCT GCC TCA TGG AAG ACG ATC GAT 96
Ser Glu Ser Phe Glu Asn Gly Ile Pro Ala Ser Trp Lys Thr Ile Asp
            470                 475                 480

GCA GAC GGT GAC GGC AAC AAT TGG ACG ACG ACC CCT CCT CCC GGA GGC 144
Ala Asp Gly Asp Gly Asn Asn Trp Thr Thr Thr Pro Pro Pro Gly Gly
        485                 490                 495

-continued

```
ACC TCT TTT GCA GGT CAC AAC AGT GCG ATC TGT GCC TCT TCG GCT TCT      192
Thr Ser Phe Ala Gly His Asn Ser Ala Ile Cys Ala Ser Ser Ala Ser
    500                 505                 510

TAT ATC AAC TTT GAA GGC CCT CAG AAC CCT GAT AAC TAT CTG GTT ACA      240
Tyr Ile Asn Phe Glu Gly Pro Gln Asn Pro Asp Asn Tyr Leu Val Thr
515                 520                 525                 530

CCG GAG CTA TCT CTT CCT AAC GGA GGA ACG CTT ACT TTC TGG GTA TGT      288
Pro Glu Leu Ser Leu Pro Asn Gly Gly Thr Leu Thr Phe Trp Val Cys
                535                 540                 545

GCA CAA GAT GCC AAT TAT GCA TCA GAG CAC TAT GCC GTG TAT GCA TCT      336
Ala Gln Asp Ala Asn Tyr Ala Ser Glu His Tyr Ala Val Tyr Ala Ser
            550                 555                 560

TCT ACG GGT AAC GAC GCT TCC AAC TTC GCC AAC GCT TTG TTG GAA GAA      384
Ser Thr Gly Asn Asp Ala Ser Asn Phe Ala Asn Ala Leu Leu Glu Glu
        565                 570                 575

GTG CTG ACG GCC AAG ACA GTT GTT ACG GCA CCT GAA GCC ATT CGT GGC      432
Val Leu Thr Ala Lys Thr Val Val Thr Ala Pro Glu Ala Ile Arg Gly
    580                 585                 590

ACT CGT GTT CAG GGC ACC TGG TAT CAA AAG ACG GTA CAG TTG CCT GCG      480
Thr Arg Val Gln Gly Thr Trp Tyr Gln Lys Thr Val Gln Leu Pro Ala
595                 600                 605                 610

GGT ACT AAG TAT GTT GCT TTC CGT CAC TTC GGC TGT ACG GAC TTC TTC      528
Gly Thr Lys Tyr Val Ala Phe Arg His Phe Gly Cys Thr Asp Phe Phe
                615                 620                 625

TGG ATC AAC CTT GAT GAT GTT GAG ATC AAG GCC AAC GGC AAG CGC GCA      576
Trp Ile Asn Leu Asp Asp Val Glu Ile Lys Ala Asn Gly Lys Arg Ala
            630                 635                 640

GAC TTC ACG GAA ACG TTC GAG TCT TCT ACT CAT GGA GAG GCA CCG GCG      624
Asp Phe Thr Glu Thr Phe Glu Ser Ser Thr His Gly Glu Ala Pro Ala
        645                 650                 655

GAA TGG ACT ACT ATC GAT GCC GAT GGC GAT GGT CAG GGT TGG CTC TGT      672
Glu Trp Thr Thr Ile Asp Ala Asp Gly Asp Gly Gln Gly Trp Leu Cys
    660                 665                 670

CTG TCT TCC GGA CAA TTG GGC TGG CTG ACA GCT CAT GGC GGC ACC AAC      720
Leu Ser Ser Gly Gln Leu Gly Trp Leu Thr Ala His Gly Gly Thr Asn
675                 680                 685                 690

GTA GTA GCC TCT TTC TCA TGG AAT GGA ATG GCT TTG AAT CCT GAT AAC      768
Val Val Ala Ser Phe Ser Trp Asn Gly Met Ala Leu Asn Pro Asp Asn
                695                 700                 705

TAT CTC ATC TCA AAG GAT GTT ACA GGC GCA ACT AAG GTA AAG TAC TAC      816
Tyr Leu Ile Ser Lys Asp Val Thr Gly Ala Thr Lys Val Lys Tyr Tyr
            710                 715                 720

TAT GCA GTC AAC GAC GGT TTT CCC GGG GAT CAC TAT GCG GTG ATG ATC      864
Tyr Ala Val Asn Asp Gly Phe Pro Gly Asp His Tyr Ala Val Met Ile
        725                 730                 735

TCC AAG ACG GGC ACG AAC GCC GGA GAC TTC ACG GTT GTT TTC GAA GAA      912
Ser Lys Thr Gly Thr Asn Ala Gly Asp Phe Thr Val Val Phe Glu Glu
    740                 745                 750

ACG CCT AAC GGA ATA AAT AAG GGC GGA GCA AGA TTC GGT CTT TCC ACG      960
Thr Pro Asn Gly Ile Asn Lys Gly Gly Ala Arg Phe Gly Leu Ser Thr
755                 760                 765                 770

GAA GCC GAT GGC GCC AAA CCT CAA AGT GTA TGG ATC GAG CGT ACG GTA     1008
Glu Ala Asp Gly Ala Lys Pro Gln Ser Val Trp Ile Glu Arg Thr Val
                775                 780                 785

GAT TTG CCT GCG GGT ACT AAG TAT GTT GCT TTC CGT CAC TAC AAT TGC     1056
Asp Leu Pro Ala Gly Thr Lys Tyr Val Ala Phe Arg His Tyr Asn Cys
            790                 795                 800

TCG GAT TTG AAC TAC ATT CTT TTG GAT GAT ATT CAG TTC ACC ATG GGT     1104
Ser Asp Leu Asn Tyr Ile Leu Leu Asp Asp Ile Gln Phe Thr Met Gly
        805                 810                 815
```

-continued

GGC AGC CCC ACC CCG ACC GAT TAT ACC TAC ACG GTG TAT CGT GAC GGT 1152
Gly Ser Pro Thr Pro Thr Asp Tyr Thr Tyr Thr Val Tyr Arg Asp Gly
820 825 830

ACG AAG ATC AAG GAA GGT CTG ACC GAA ACG ACC TTC GAA GAA GAC GGT 1200
Thr Lys Ile Lys Glu Gly Leu Thr Glu Thr Thr Phe Glu Glu Asp Gly
835 840 845 850

GTA GCT ACG GGC AAC CAT GAG TAT TGC GTG GAA GTG AAG TAC ACA GCC 1248
Val Ala Thr Gly Asn His Glu Tyr Cys Val Glu Val Lys Tyr Thr Ala
855 860 865

GGC GTA TCT CCG AAA GAG TGT GTA AAC GTA ACT GTT GAT CCT GTG CAG 1296
Gly Val Ser Pro Lys Glu Cys Val Asn Val Thr Val Asp Pro Val Gln
870 875 880

TTC AAT CCT GTA CAG AAC CTG ACC GGT AGT GCA GTC GGC CAG AAA GTA 1344
Phe Asn Pro Val Gln Asn Leu Thr Gly Ser Ala Val Gly Gln Lys Val
885 890 895

ACG CTT AAG TGG GAT GCA CCT AAT 1368
Thr Leu Lys Trp Asp Ala Pro Asn
900 905

( 2 ) INFORMATION FOR SEQ ID NO:18:

( i ) SEQUENCE CHARACTERISTICS:
( A ) LENGTH: 456 amino acids
( B ) TYPE: amino acid
( D ) TOPOLOGY: linear ( i i ) MOLECULE TYPE: protein ( x i ) SEQUENCE DESCRIPTION: SEQ ID NO:18:

Gly Thr Pro Asn Pro Asn Pro Asn Pro Asn Pro Gly Thr Thr Thr Leu
1 5 10 15

Ser Glu Ser Phe Glu Asn Gly Ile Pro Ala Ser Trp Lys Thr Ile Asp
20 25 30

Ala Asp Gly Asp Gly Asn Asn Trp Thr Thr Thr Pro Pro Pro Gly Gly
35 40 45

Thr Ser Phe Ala Gly His Asn Ser Ala Ile Cys Ala Ser Ser Ala Ser
50 55 60

Tyr Ile Asn Phe Glu Gly Pro Gln Asn Pro Asp Asn Tyr Leu Val Thr
65 70 75 80

Pro Glu Leu Ser Leu Pro Asn Gly Gly Thr Leu Thr Phe Trp Val Cys
85 90 95

Ala Gln Asp Ala Asn Tyr Ala Ser Glu His Tyr Ala Val Tyr Ala Ser
100 105 110

Ser Thr Gly Asn Asp Ala Ser Asn Phe Ala Asn Ala Leu Leu Glu Glu
115 120 125

Val Leu Thr Ala Lys Thr Val Val Thr Ala Pro Glu Ala Ile Arg Gly
130 135 140

Thr Arg Val Gln Gly Thr Trp Tyr Gln Lys Thr Val Gln Leu Pro Ala
145 150 155 160

Gly Thr Lys Tyr Val Ala Phe Arg His Phe Gly Cys Thr Asp Phe Phe
165 170 175

Trp Ile Asn Leu Asp Asp Val Glu Ile Lys Ala Asn Gly Lys Arg Ala
180 185 190

Asp Phe Thr Glu Thr Phe Glu Ser Ser Thr His Gly Glu Ala Pro Ala
195 200 205

Glu Trp Thr Thr Ile Asp Ala Asp Gly Asp Gly Gln Gly Trp Leu Cys
210 215 220

Leu Ser Ser Gly Gln Leu Gly Trp Leu Thr Ala His Gly Gly Thr Asn

-continued

```
225                      230                      235                      240

Val Val Ala Ser Phe Ser Trp Asn Gly Met Ala Leu Asn Pro Asp Asn
                245                     250                     255

Tyr Leu Ile Ser Lys Asp Val Thr Gly Ala Thr Lys Val Lys Tyr Tyr
            260                     265                     270

Tyr Ala Val Asn Asp Gly Phe Pro Gly Asp His Tyr Ala Val Met Ile
        275                     280                     285

Ser Lys Thr Gly Thr Asn Ala Gly Asp Phe Thr Val Val Phe Glu Glu
    290                     295                     300

Thr Pro Asn Gly Ile Asn Lys Gly Gly Ala Arg Phe Gly Leu Ser Thr
305                     310                     315                     320

Glu Ala Asp Gly Ala Lys Pro Gln Ser Val Trp Ile Glu Arg Thr Val
                325                     330                     335

Asp Leu Pro Ala Gly Thr Lys Tyr Val Ala Phe Arg His Tyr Asn Cys
            340                     345                     350

Ser Asp Leu Asn Tyr Ile Leu Leu Asp Asp Ile Gln Phe Thr Met Gly
        355                     360                     365

Gly Ser Pro Thr Pro Thr Asp Tyr Thr Tyr Thr Val Tyr Arg Asp Gly
    370                     375                     380

Thr Lys Ile Lys Glu Gly Leu Thr Glu Thr Thr Phe Glu Glu Asp Gly
385                     390                     395                     400

Val Ala Thr Gly Asn His Glu Tyr Cys Val Glu Val Lys Tyr Thr Ala
                405                     410                     415

Gly Val Ser Pro Lys Glu Cys Val Asn Val Thr Val Asp Pro Val Gln
            420                     425                     430

Phe Asn Pro Val Gln Asn Leu Thr Gly Ser Ala Val Gly Gln Lys Val
        435                     440                     445

Thr Leu Lys Trp Asp Ala Pro Asn
    450                     455
```

( 2 ) INFORMATION FOR SEQ ID NO:19:

( i ) SEQUENCE CHARACTERISTICS:
( A ) LENGTH: 1368 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1368

( x i ) SEQUENCE DESCRIPTION: SEQ ID NO:19:

```
GGT ACC CCG AAT CCA AAT CCA AAT CCG AAT CCG GGA ACA ACA ACA CTT       48
Gly Thr Pro Asn Pro Asn Pro Asn Pro Asn Pro Gly Thr Thr Thr Leu
            460                     465                     470

TCC GAA TCA TTC GAA AAT GGT ATT CCT GCC TCA TGG AAG ACG ATC GAT       96
Ser Glu Ser Phe Glu Asn Gly Ile Pro Ala Ser Trp Lys Thr Ile Asp
        475                     480                     485

GCA GAC GGT GAC GGC AAC AAT TGG ACG ACG ACC CCT CCT CCC GGA GGC      144
Ala Asp Gly Asp Gly Asn Asn Trp Thr Thr Thr Pro Pro Pro Gly Gly
    490                     495                     500

ACC TCT TTT GCA GGT CAC AAC AGT GCG ATC TGT GCC TCT TCG GCT TCT      192
Thr Ser Phe Ala Gly His Asn Ser Ala Ile Cys Ala Ser Ser Ala Ser
505                     510                     515                     520

TAT ATC AAC TTT GAA GGC CCT CAG AAC CCT GAT AAC TAT CTG GTT ACA      240
Tyr Ile Asn Phe Glu Gly Pro Gln Asn Pro Asp Asn Tyr Leu Val Thr
                525                     530                     535
```

-continued

```
CCG GAG CTA TCT CTT CCT AAC GGA GGA ACG CTT ACT TTC TGG GTA TGT      288
Pro Glu Leu Ser Leu Pro Asn Gly Gly Thr Leu Thr Phe Trp Val Cys
            540                 545                 550

GCA CAA GAT GCC AAT TAT GCA TCA GAG CAC TAT GCC GTG TAT GCA TCT      336
Ala Gln Asp Ala Asn Tyr Ala Ser Glu His Tyr Ala Val Tyr Ala Ser
        555                 560                 565

TCT ACG GGT AAC GAC GCT TCC AAC TTC GCC AAC GCT TTG TTG GAA GAA      384
Ser Thr Gly Asn Asp Ala Ser Asn Phe Ala Asn Ala Leu Leu Glu Glu
    570                 575                 580

GTG CTG ACG GCC AAG ACA GTT GTT ACG GCA CCT GAA GCC ATT CGT GGC      432
Val Leu Thr Ala Lys Thr Val Val Thr Ala Pro Glu Ala Ile Arg Gly
585                 590                 595                 600

ACT CGT GTT CAG GGC ACC TGG TAT CAA AAG ACG GTA CAG TTG CCT GCG      480
Thr Arg Val Gln Gly Thr Trp Tyr Gln Lys Thr Val Gln Leu Pro Ala
                605                 610                 615

GGT ACT AAG TAT GTT GCT TTC CGT CAC TTC GGC TGT ACG GAC TTC TTC      528
Gly Thr Lys Tyr Val Ala Phe Arg His Phe Gly Cys Thr Asp Phe Phe
            620                 625                 630

TGG ATC AAC CTT GAT GAT GTT GAG ATC AAG GCC AAC GGC AAG CGC GCA      576
Trp Ile Asn Leu Asp Asp Val Glu Ile Lys Ala Asn Gly Lys Arg Ala
        635                 640                 645

GAC TTC ACG GAA ACG TTC GAG TCT TCT ACT CAT GGA GAG GCA CCG GCG      624
Asp Phe Thr Glu Thr Phe Glu Ser Ser Thr His Gly Glu Ala Pro Ala
    650                 655                 660

GAA TGG ACT ACT ATC GAT GCC GAT GGC GAT GGT CAG GGT TGG CTC TGT      672
Glu Trp Thr Thr Ile Asp Ala Asp Gly Asp Gly Gln Gly Trp Leu Cys
665                 670                 675                 680

CTG TCT TCC GGA CAA TTG GGC TGG CTG ACA GCT CAT GGC GGC ACC AAC      720
Leu Ser Ser Gly Gln Leu Gly Trp Leu Thr Ala His Gly Gly Thr Asn
                685                 690                 695

GTA GTA GCC TCT TTC TCA TGG AAT GGA ATG GCT TTG AAT CCT GAT AAC      768
Val Val Ala Ser Phe Ser Trp Asn Gly Met Ala Leu Asn Pro Asp Asn
            700                 705                 710

TAT CTC ATC TCA AAG GAT GTT ACA GGC GCA ACT AAG GTA AAG TAC TAC      816
Tyr Leu Ile Ser Lys Asp Val Thr Gly Ala Thr Lys Val Lys Tyr Tyr
        715                 720                 725

TAT GCA GTC AAC GAC GGT TTT CCC GGG GAT CAC TAT GCG GTG ATG ATC      864
Tyr Ala Val Asn Asp Gly Phe Pro Gly Asp His Tyr Ala Val Met Ile
    730                 735                 740

TCC AAG ACG GGC ACG AAC GCC GGA GAC TTC ACG GTT GTT TTC GAA GAA      912
Ser Lys Thr Gly Thr Asn Ala Gly Asp Phe Thr Val Val Phe Glu Glu
745                 750                 755                 760

ACG CCT AAC GGA ATA AAT AAG GGC GGA GCA AGA TTC GGT CTT TCC ACG      960
Thr Pro Asn Gly Ile Asn Lys Gly Gly Ala Arg Phe Gly Leu Ser Thr
                765                 770                 775

GAA GCC GAT GGC GCC AAA CCT CAA AGT GTA TGG ATC GAG CGT ACG GTA     1008
Glu Ala Asp Gly Ala Lys Pro Gln Ser Val Trp Ile Glu Arg Thr Val
            780                 785                 790

GAT TTG CCT GCG GGT ACT AAG TAT GTT GCT TTC CGA CAC TAC AAT TGC     1056
Asp Leu Pro Ala Gly Thr Lys Tyr Val Ala Phe Arg His Tyr Asn Cys
        795                 800                 805

TCG GAT TTG AAC TAC ATT CTT TTG GAT GAT ATT CAG TTC ACC ATG GGT     1104
Ser Asp Leu Asn Tyr Ile Leu Leu Asp Asp Ile Gln Phe Thr Met Gly
    810                 815                 820

GGC AGC CCC ACC CCG ACC GAT TAT ACC TAC ACG GTG TAT CGT GAC GGT     1152
Gly Ser Pro Thr Pro Thr Asp Tyr Thr Tyr Thr Val Tyr Arg Asp Gly
825                 830                 835                 840

ACG AAG ATC AAG GAA GGT CTG ACC GAA ACG ACC TTC GAA GAA GAC GGT     1200
Thr Lys Ile Lys Glu Gly Leu Thr Glu Thr Thr Phe Glu Glu Asp Gly
                845                 850                 855
```

-continued

GTA GCT ACG GGC AAC CAT GAG TAT TGC GTG GAA GTG AAG TAC ACA GCC 1248
Val Ala Thr Gly Asn His Glu Tyr Cys Val Glu Val Lys Tyr Thr Ala
860 865 870

GGC GTA TCT CCG AAA GAG TGT GTA AAC GTA ACT GTT GAT CCT GTG CAG 1296
Gly Val Ser Pro Lys Glu Cys Val Asn Val Thr Val Asp Pro Val Gln
875 880 885

TTC AAT CCT GTA CAG AAC CTG ACC GGT AGT GCA GTC GGC CAG AAA GTA 1344
Phe Asn Pro Val Gln Asn Leu Thr Gly Ser Ala Val Gly Gln Lys Val
890 895 900

ACG CTT AAG TGG GAT GCA CCT AAT 1368
Thr Leu Lys Trp Asp Ala Pro Asn
905 910

( 2 ) INFORMATION FOR SEQ ID NO:20:

( i ) SEQUENCE CHARACTERISTICS:
( A ) LENGTH: 456 amino acids
( B ) TYPE: amino acid
( D ) TOPOLOGY: linear ( i i ) MOLECULE TYPE: protein ( x i ) SEQUENCE DESCRIPTION: SEQ ID NO:20:

Gly Thr Pro Asn Pro Asn Pro Asn Pro Asn Pro Gly Thr Thr Thr Leu
1 5 10 15

Ser Glu Ser Phe Glu Asn Gly Ile Pro Ala Ser Trp Lys Thr Ile Asp
20 25 30

Ala Asp Gly Asp Gly Asn Asn Trp Thr Thr Thr Pro Pro Pro Gly Gly
35 40 45

Thr Ser Phe Ala Gly His Asn Ser Ala Ile Cys Ala Ser Ser Ala Ser
50 55 60

Tyr Ile Asn Phe Glu Gly Pro Gln Asn Pro Asp Asn Tyr Leu Val Thr
65 70 75 80

Pro Glu Leu Ser Leu Pro Asn Gly Gly Thr Leu Thr Phe Trp Val Cys
85 90 95

Ala Gln Asp Ala Asn Tyr Ala Ser Glu His Tyr Ala Val Tyr Ala Ser
100 105 110

Ser Thr Gly Asn Asp Ala Ser Asn Phe Ala Asn Ala Leu Leu Glu Glu
115 120 125

Val Leu Thr Ala Lys Thr Val Val Thr Ala Pro Glu Ala Ile Arg Gly
130 135 140

Thr Arg Val Gln Gly Thr Trp Tyr Gln Lys Thr Val Gln Leu Pro Ala
145 150 155 160

Gly Thr Lys Tyr Val Ala Phe Arg His Phe Gly Cys Thr Asp Phe Phe
165 170 175

Trp Ile Asn Leu Asp Asp Val Glu Ile Lys Ala Asn Gly Lys Arg Ala
180 185 190

Asp Phe Thr Glu Thr Phe Glu Ser Ser Thr His Gly Glu Ala Pro Ala
195 200 205

Glu Trp Thr Thr Ile Asp Ala Asp Gly Asp Gly Gln Gly Trp Leu Cys
210 215 220

Leu Ser Ser Gly Gln Leu Gly Trp Leu Thr Ala His Gly Gly Thr Asn
225 230 235 240

Val Val Ala Ser Phe Ser Trp Asn Gly Met Ala Leu Asn Pro Asp Asn
245 250 255

Tyr Leu Ile Ser Lys Asp Val Thr Gly Ala Thr Lys Val Lys Tyr Tyr
260 265 270

-continued

```
Tyr Ala Val Asn Asp Gly Phe Pro Gly Asp His Tyr Ala Val Met Ile
        275                 280                 285

Ser Lys Thr Gly Thr Asn Ala Gly Asp Phe Thr Val Val Phe Glu Glu
    290                 295                 300

Thr Pro Asn Gly Ile Asn Lys Gly Gly Ala Arg Phe Gly Leu Ser Thr
305                 310                 315                 320

Glu Ala Asp Gly Ala Lys Pro Gln Ser Val Trp Ile Glu Arg Thr Val
                325                 330                 335

Asp Leu Pro Ala Gly Thr Lys Tyr Val Ala Phe Arg His Tyr Asn Cys
            340                 345                 350

Ser Asp Leu Asn Tyr Ile Leu Leu Asp Asp Ile Gln Phe Thr Met Gly
        355                 360                 365

Gly Ser Pro Thr Pro Thr Asp Tyr Thr Tyr Thr Val Tyr Arg Asp Gly
    370                 375                 380

Thr Lys Ile Lys Glu Gly Leu Thr Glu Thr Thr Phe Glu Glu Asp Gly
385                 390                 395                 400

Val Ala Thr Gly Asn His Glu Tyr Cys Val Glu Val Lys Tyr Thr Ala
                405                 410                 415

Gly Val Ser Pro Lys Glu Cys Val Asn Val Thr Val Asp Pro Val Gln
            420                 425                 430

Phe Asn Pro Val Gln Asn Leu Thr Gly Ser Ala Val Gly Gln Lys Val
        435                 440                 445

Thr Leu Lys Trp Asp Ala Pro Asn
    450                 455
```

( 2 ) INFORMATION FOR SEQ ID NO:21:

( i ) SEQUENCE CHARACTERISTICS:
( A ) LENGTH: 1318 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1318

( x i ) SEQUENCE DESCRIPTION: SEQ ID NO:21:

```
GGT ACC CCG AAT CCA AAT CCA AAT CCG AAT CCG GGA ACA ACA ACA CTT      48
Gly Thr Pro Asn Pro Asn Pro Asn Pro Asn Pro Gly Thr Thr Thr Leu
            460                 465                 470

TCC GAA TCA TTC GAA AAT GGT ATT CCT GCC TCA TGG AAG ACG ATC GAT      96
Ser Glu Ser Phe Glu Asn Gly Ile Pro Ala Ser Trp Lys Thr Ile Asp
        475                 480                 485

GCA GAC GGT GAC GGC AAC AAT TGG ACG ACG ACC CCT CCT CCC GGA GGC     144
Ala Asp Gly Asp Gly Asn Asn Trp Thr Thr Thr Pro Pro Pro Gly Gly
    490                 495                 500

ACC TCT TTT GCA GGT CAC AAC AGT GCG ATC TGT GTC TCT TCG GCT TCT     192
Thr Ser Phe Ala Gly His Asn Ser Ala Ile Cys Val Ser Ser Ala Ser
505                 510                 515                 520

TAT ATC AAC TTT GAA GGC CCT CAG AAC CCT GAT AAC TAT CTG GTT ACA     240
Tyr Ile Asn Phe Glu Gly Pro Gln Asn Pro Asp Asn Tyr Leu Val Thr
                525                 530                 535

CCG GAG CTA TCT CTT CCT GGC GGA GGA ACG CTT ACT TTC TGG GTA TGT     288
Pro Glu Leu Ser Leu Pro Gly Gly Gly Thr Leu Thr Phe Trp Val Cys
            540                 545                 550

GCA CAA GAT GCC AAT TAT GCA TCA GAG CAC TAT GCC GTG TAT GCA TCT     336
Ala Gln Asp Ala Asn Tyr Ala Ser Glu His Tyr Ala Val Tyr Ala Ser
        555                 560                 565
```

-continued

TCT ACG GGT AAC GAC GCT TCC AAC TTC GCC AAC GCT TTG TTG GAA GAA 384
Ser Thr Gly Asn Asp Ala Ser Asn Phe Ala Asn Ala Leu Leu Glu Glu
570 575 580

GTG CTG ACG GCC AAG ACA GTT GTT ACG GCA CCT GAA GCC ATT CGT GGC 432
Val Leu Thr Ala Lys Thr Val Val Thr Ala Pro Glu Ala Ile Arg Gly
585 590 595 600

ACT CGT GTT CAG GGC ACC TGG TAT CAA AAG ACG GTA CAG TTG CCT GCG 480
Thr Arg Val Gln Gly Thr Trp Tyr Gln Lys Thr Val Gln Leu Pro Ala
605 610 615

GGT ACT AAG TAT GTT GCC TTC CGT CAC TTC GGC TGT ACG GAC TTC TTC 528
Gly Thr Lys Tyr Val Ala Phe Arg His Phe Gly Cys Thr Asp Phe Phe
620 625 630

TGG ATC AAC CTT GAT GAA GTT GAG ATC AAG GCC AAC GGC AAG CGC GCA 576
Trp Ile Asn Leu Asp Glu Val Glu Ile Lys Ala Asn Gly Lys Arg Ala
635 640 645

GAC TTC ACG GAA ACG TTC GAG TCT TCT ACT CAT GGA GAG GCA CCG GCG 624
Asp Phe Thr Glu Thr Phe Glu Ser Ser Thr His Gly Glu Ala Pro Ala
650 655 660

GAA TGG ACT ACT ATC GAT GCC GAT GGC GAT GGT CAG GGT TGG CTC TGT 672
Glu Trp Thr Thr Ile Asp Ala Asp Gly Asp Gly Gln Gly Trp Leu Cys
665 670 675 680

CTG TCT TCC GGA CAA TTG GAC TGG CTG ACA GCT CAT GGC GGC ACC AAC 720
Leu Ser Ser Gly Gln Leu Asp Trp Leu Thr Ala His Gly Gly Thr Asn
685 690 695

GTA GTA GCC TCT TTC TCA TGG AAT GGA ATG GCT TTG AAT CCT GAT AAC 768
Val Val Ala Ser Phe Ser Trp Asn Gly Met Ala Leu Asn Pro Asp Asn
700 705 710

TAT CTC ATC TCA AAG GAT GTT ACA GGC GCA ACT AAG GTA AAG TAC TAC 816
Tyr Leu Ile Ser Lys Asp Val Thr Gly Ala Thr Lys Val Lys Tyr Tyr
715 720 725

TAT GCA GTC AAC GAC GGT TTT CCC GGG GAT CAC TAT GCG GTG ATG ATC 864
Tyr Ala Val Asn Asp Gly Phe Pro Gly Asp His Tyr Ala Val Met Ile
730 735 740

TCC AAG ACG GGC ACG AAC GCC GGA GAC TTC ACG GTT GTT TTC GAA GAA 912
Ser Lys Thr Gly Thr Asn Ala Gly Asp Phe Thr Val Val Phe Glu Glu
745 750 755 760

ACG CCT AAC GGA ATA AAT AAG GGC GGA GCA AGA TTC GGT CTT TCC ACG 960
Thr Pro Asn Gly Ile Asn Lys Gly Gly Ala Arg Phe Gly Leu Ser Thr
765 770 775

GAA GCC GAT GGC GCC AAA CCT CAA AGT GTA TGG ATC GAG CGT ACG GTA 1008
Glu Ala Asp Gly Ala Lys Pro Gln Ser Val Trp Ile Glu Arg Thr Val
780 785 790

GAT TTG CCT GCG GGC ACG AAG TAT GTT GCT TTC CGT CAC TAC AAT TGC 1056
Asp Leu Pro Ala Gly Thr Lys Tyr Val Ala Phe Arg His Tyr Asn Cys
795 800 805

TCG GAT TTG AAC TAC ATT CTT TTG GAT GAT ATT CAG TTC ACC ATG GGT 1104
Ser Asp Leu Asn Tyr Ile Leu Leu Asp Asp Ile Gln Phe Thr Met Gly
810 815 820

GGC AGC CCC ACC CCG ACC GAT TAT ACC TAC ACG GTG TAT CGT GAC GGT 1152
Gly Ser Pro Thr Pro Thr Asp Tyr Thr Tyr Thr Val Tyr Arg Asp Gly
825 830 835 840

ACG AAG ATC AAG GAA GGT CTG ACC GAA ACG ACC TTC GAA GAA GAT GGT 1200
Thr Lys Ile Lys Glu Gly Leu Thr Glu Thr Thr Phe Glu Glu Asp Gly
845 850 855

GTA GCT ACG GGC AAT CAT GAG TAT TGC GTG GAA GTG AAG TAC ACA GCC 1248
Val Ala Thr Gly Asn His Glu Tyr Cys Val Glu Val Lys Tyr Thr Ala
860 865 870

GGC GTA TCT CCG AAG GTG TGT GTA AAC GTA ACT ATT AAT CCG ACT CAG 1296
Gly Val Ser Pro Lys Val Cys Val Asn Val Thr Ile Asn Pro Thr Gln
875 880 885

```
TTC AAT CCT GTA CAG AAC CTG A                              1318
Phe Asn Pro Val Gln Asn Leu
    890                 895
```

( 2 ) INFORMATION FOR SEQ ID NO:22:

( i ) SEQUENCE CHARACTERISTICS:
( A ) LENGTH: 439 amino acids
( B ) TYPE: amino acid
( D ) TOPOLOGY: linear ( i i ) MOLECULE TYPE: protein ( x i ) SEQUENCE DESCRIPTION: SEQ ID NO:22:

```
Gly Thr Pro Asn Pro Asn Pro Asn Pro Asn Pro Gly Thr Thr Thr Leu
 1               5                  10                  15

Ser Glu Ser Phe Glu Asn Gly Ile Pro Ala Ser Trp Lys Thr Ile Asp
            20                  25                  30

Ala Asp Gly Asp Gly Asn Asn Trp Thr Thr Thr Pro Pro Pro Gly Gly
        35                  40                  45

Thr Ser Phe Ala Gly His Asn Ser Ala Ile Cys Val Ser Ser Ala Ser
    50                  55                  60

Tyr Ile Asn Phe Glu Gly Pro Gln Asn Pro Asp Asn Tyr Leu Val Thr
65                  70                  75                  80

Pro Glu Leu Ser Leu Pro Gly Gly Gly Thr Leu Thr Phe Trp Val Cys
                85                  90                  95

Ala Gln Asp Ala Asn Tyr Ala Ser Glu His Tyr Ala Val Tyr Ala Ser
            100                 105                 110

Ser Thr Gly Asn Asp Ala Ser Asn Phe Ala Asn Ala Leu Leu Glu Glu
        115                 120                 125

Val Leu Thr Ala Lys Thr Val Val Thr Ala Pro Glu Ala Ile Arg Gly
    130                 135                 140

Thr Arg Val Gln Gly Thr Trp Tyr Gln Lys Thr Val Gln Leu Pro Ala
145                 150                 155                 160

Gly Thr Lys Tyr Val Ala Phe Arg His Phe Gly Cys Thr Asp Phe Phe
                165                 170                 175

Trp Ile Asn Leu Asp Glu Val Glu Ile Lys Ala Asn Gly Lys Arg Ala
            180                 185                 190

Asp Phe Thr Glu Thr Phe Glu Ser Ser Thr His Gly Glu Ala Pro Ala
        195                 200                 205

Glu Trp Thr Thr Ile Asp Ala Asp Gly Asp Gly Gln Gly Trp Leu Cys
    210                 215                 220

Leu Ser Ser Gly Gln Leu Asp Trp Leu Thr Ala His Gly Gly Thr Asn
225                 230                 235                 240

Val Val Ala Ser Phe Ser Trp Asn Gly Met Ala Leu Asn Pro Asp Asn
                245                 250                 255

Tyr Leu Ile Ser Lys Asp Val Thr Gly Ala Thr Lys Val Lys Tyr Tyr
            260                 265                 270

Tyr Ala Val Asn Asp Gly Phe Pro Gly Asp His Tyr Ala Val Met Ile
        275                 280                 285

Ser Lys Thr Gly Thr Asn Ala Gly Asp Phe Thr Val Val Phe Glu Glu
    290                 295                 300

Thr Pro Asn Gly Ile Asn Lys Gly Gly Ala Arg Phe Gly Leu Ser Thr
305                 310                 315                 320

Glu Ala Asp Gly Ala Lys Pro Gln Ser Val Trp Ile Glu Arg Thr Val
                325                 330                 335
```

-continued

| | | | | | | | | | | | | | | | |
|---|---|---|---|---|---|---|---|---|---|---|---|---|---|---|---|
| Asp | Leu | Pro | Ala 340 | Gly | Thr | Lys | Tyr | Val 345 | Ala | Phe | Arg | His | Tyr 350 | Asn | Cys |
| Ser | Asp | Leu 355 | Asn | Tyr | Ile | Leu | Leu 360 | Asp | Asp | Ile | Gln | Phe 365 | Thr | Met | Gly |
| Gly | Ser 370 | Pro | Thr | Pro | Thr | Asp 375 | Tyr | Thr | Tyr | Thr | Val 380 | Tyr | Arg | Asp | Gly |
| Thr 385 | Lys | Ile | Lys | Glu | Gly 390 | Leu | Thr | Glu | Thr | Thr 395 | Phe | Glu | Glu | Asp | Gly 400 |
| Val | Ala | Thr | Gly | Asn 405 | His | Glu | Tyr | Cys | Val 410 | Glu | Val | Lys | Tyr | Thr 415 | Ala |
| Gly | Val | Ser | Pro 420 | Lys | Val | Cys | Val | Asn 425 | Val | Thr | Ile | Asn | Pro 430 | Thr | Gln |
| Phe | Asn | Pro 435 | Val | Gln | Asn | Leu | | | | | | | | | |

( 2 ) INFORMATION FOR SEQ ID NO:23:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

GGCAAACCAA AAAGATTC 18

( 2 ) INFORMATION FOR SEQ ID NO:24:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

TTCTTCCAAC GACTACAC 18

( 2 ) INFORMATION FOR SEQ ID NO:25:

( i ) SEQUENCE CHARACTERISTICS:
( A ) LENGTH: 6241 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 696..1787
( D ) OTHER INFORMATION: /product="hagD protease"

( i x ) FEATURE:
( A ) NAME/KEY: CDS
( B ) LOCATION: 1790..5866
( D ) OTHER INFORMATION: /product="hagD hemagglutinin"

( x i ) SEQUENCE DESCRIPTION: SEQ ID NO:25:

GGATCCTACG CCCGATACCC ATACTCGAAG CCTTTGCTCA GTACCATCCT GCAGAAGTTC 60

ACTCTTTCGC ATATAGTGAC CCTCTTTTCT CTCAGCATAA TGGTACCTAT CATATCAGTA 120

AGGGGCATAT TGTCTTTTCG AACAATGTAC AGCCCGAGAA CTCTTTACTT CCACATCACA 180

-continued

```
CCCCCGACTC CTTAGTCAAG GATCTTTTTT CCCCTTTCCC CTCCGCTCTC TTCCTCATGC    240

TGGACTGACT TAACCTTGGT CTGCTCTACT TTTCGGTTGT AAATACATGC AATACAATAA    300

CTTTAAGTGT TGTTAGACAA CACTTTTACA AGACTCTGAC TTTTAATGAG GTGGAGCATG    360

AACCTTTTCC TCTTTCATCT TCTCATTCAG ATTATAGTCA ATATTTTAGT AAAAGGCTAA    420

TTGACAGCCT TTTATAAGGG TTAATCCCTT GTCGCTTATA TTGAAAACAT GTTCTTTATA    480

ATCCGATACT CTTCTTAAAT CGAATTTTTT CTCTAAATTG CGCCGCAACA AAACTCCTTG    540

AGAAAAGTAC CAATAGAAAT AGAAGGTAGC ATTTTGCCTT TAAATTCCTT TTCTTTTCTT    600

GGATTGTTCT TGAAATGAAT CTTATTTGTG GATCTTTTTT GTTTTTTTAA CCCGGCCGTG    660

GTTCTCTGAA TCACGACCAT AAATTGTTTT AAAGT ATG AGG AAA TTA TTA TTG       713
                                       Met Arg Lys Leu Leu Leu
                                       440                 445

CTG ATC GCG GCG TCC CTT TTG GGA GTT GGT CTT TAC GCC CAA AGC GCC      761
Leu Ile Ala Ala Ser Leu Leu Gly Val Gly Leu Tyr Ala Gln Ser Ala
                450                 455                 460

AAG ATT AAG CTT GAT GCT CCG ACT ACT CGA ACG ACA TGT ACG AAC AAT      809
Lys Ile Lys Leu Asp Ala Pro Thr Thr Arg Thr Thr Cys Thr Asn Asn
            465                 470                 475

AGC TTC AAG CAG TTC GAT GCA AGC TTT TCG TTC AAT GAA GTC GAG CTG      857
Ser Phe Lys Gln Phe Asp Ala Ser Phe Ser Phe Asn Glu Val Glu Leu
        480                 485                 490

ACA AAG GTG GAG ACC AAA GGT GGT ACT TTC GCC TCA GTG TCA ATT CCG      905
Thr Lys Val Glu Thr Lys Gly Gly Thr Phe Ala Ser Val Ser Ile Pro
    495                 500                 505

GGT GCA TTC CCG ACC GGT GAG GTT GGT TCT CCC GAA GTG CCA GCA GTT      953
Gly Ala Phe Pro Thr Gly Glu Val Gly Ser Pro Glu Val Pro Ala Val
510                 515                 520                 525

AGG AAG TTG ATT GCT GTG CCT GTC GGA GCC ACA CCT GTT GTT CGC GTG     1001
Arg Lys Leu Ile Ala Val Pro Val Gly Ala Thr Pro Val Val Arg Val
                530                 535                 540

AAA AGT TTT ACC GAG CAA GTT TAC TCT CTG AAC CAA TAC GGT TCC GAA     1049
Lys Ser Phe Thr Glu Gln Val Tyr Ser Leu Asn Gln Tyr Gly Ser Glu
            545                 550                 555

AAA CTC ATG CCA CAT CAA CCC TCT ATG AGC AAG AGT GAT GAT CCC GAA     1097
Lys Leu Met Pro His Gln Pro Ser Met Ser Lys Ser Asp Asp Pro Glu
        560                 565                 570

AAG GTT CCC TTC GTT TAC AAT GCT GCT GCT TAT GCA CGC AAA GGT TTT     1145
Lys Val Pro Phe Val Tyr Asn Ala Ala Ala Tyr Ala Arg Lys Gly Phe
    575                 580                 585

GTC GGA CAA GAA CTG ACC CAA GTA GAA ATG TTG GGG ACA ATG CGT GGT     1193
Val Gly Gln Glu Leu Thr Gln Val Glu Met Leu Gly Thr Met Arg Gly
590                 595                 600                 605

GTT CGC ATT GCA GCT CTT ACC ATT AAT CCT GTT CAG TAT GAT GTG GTT     1241
Val Arg Ile Ala Ala Leu Thr Ile Asn Pro Val Gln Tyr Asp Val Val
                610                 615                 620

GCA AAC CAA TTG AAG GTT AGA AAC AAC ATC GAA ATT GAA GTA AGC TTT     1289
Ala Asn Gln Leu Lys Val Arg Asn Asn Ile Glu Ile Glu Val Ser Phe
            625                 630                 635

CAA GGA GCT GAT GAA GTA GCT ACA CAA CGT TTG TAT GAT GCT TCT TTT     1337
Gln Gly Ala Asp Glu Val Ala Thr Gln Arg Leu Tyr Asp Ala Ser Phe
        640                 645                 650

AGC CCT TAT TTC GAA ACA GCT TAT AAA CAG CTC TTC AAT AGA GAT GTT     1385
Ser Pro Tyr Phe Glu Thr Ala Tyr Lys Gln Leu Phe Asn Arg Asp Val
    655                 660                 665

TAT ACA GAT CAT GGC GAC TTG TAT AAT ACG CCG GTT CGT ATG CTT GTT     1433
Tyr Thr Asp His Gly Asp Leu Tyr Asn Thr Pro Val Arg Met Leu Val
670                 675                 680                 685
```

-continued

```
GTT GCA GGT GCA AAA TTC AAA GAA GCT CTC AAG CCT TGG CTC ACT TGG      1481
Val Ala Gly Ala Lys Phe Lys Glu Ala Leu Lys Pro Trp Leu Thr Trp
                690                 695                 700

AAG GCT CAA AAG GGC TTC TAT CTG GAT GTG CAT TAC ACA GAC GAA GCT      1529
Lys Ala Gln Lys Gly Phe Tyr Leu Asp Val His Tyr Thr Asp Glu Ala
            705                 710                 715

GAA GTA GGA ACG ACA AAC GCC TCT ATC AAG GCA TTT ATT CAC AAG AAA      1577
Glu Val Gly Thr Thr Asn Ala Ser Ile Lys Ala Phe Ile His Lys Lys
        720                 725                 730

TAC AAT GAT GGA TTG GCA GCT AGT GCT GCT CCG GTC TTC TTG GCT TTG      1625
Tyr Asn Asp Gly Leu Ala Ala Ser Ala Ala Pro Val Phe Leu Ala Leu
    735                 740                 745

GTT GGT GAC ACT GAC GTT ATT AGC GGA GAA AAA GGA AAG AAA ACA AAA      1673
Val Gly Asp Thr Asp Val Ile Ser Gly Glu Lys Gly Lys Lys Thr Lys
750                 755                 760                 765

AAA GTT ACC GAC TTG TAT TAC AGT GCA GTC GAT GGC GAC TAT TTC CCT      1721
Lys Val Thr Asp Leu Tyr Tyr Ser Ala Val Asp Gly Asp Tyr Phe Pro
                770                 775                 780

GAA ATG TAT ACT TTC CGT ATG TCT GCT TCT TCC CCA GAA GAA CTG ACG      1769
Glu Met Tyr Thr Phe Arg Met Ser Ala Ser Ser Pro Glu Glu Leu Thr
            785                 790                 795

AAC ATC ATT GAT AAG TAT TG ATG TAT GAA AAG GCT ACC ATG CCG GAT       1816
Asn Ile Ile Asp Lys Tyr    Met Tyr Glu Lys Ala Thr Met Pro Asp
        800                 1               5

AAG AGC TAT TTG GAA AAG GCC CTC TTG ATT GCC GGT GCT GAC TCC TAC      1864
Lys Ser Tyr Leu Glu Lys Ala Leu Leu Ile Ala Gly Ala Asp Ser Tyr
 10                  15                  20                  25

TGG AAT CCT AAG ATA GGC CAG CAA ACC ATC AAA TAT GCT GTA CAG TAT      1912
Trp Asn Pro Lys Ile Gly Gln Gln Thr Ile Lys Tyr Ala Val Gln Tyr
                 30                  35                  40

TAC TAC AAT CAA GAT CAT GGC TAT ACA GAT GTG TAC AGT TAC CCT AAA      1960
Tyr Tyr Asn Gln Asp His Gly Tyr Thr Asp Val Tyr Ser Tyr Pro Lys
             45                  50                  55

GCT CCT TAT ACA GGC TGC TAT AGT CAC TTG AAT ACC GGT GTC GGC TTT      2008
Ala Pro Tyr Thr Gly Cys Tyr Ser His Leu Asn Thr Gly Val Gly Phe
         60                  65                  70

GCC AAC TAT ACA GCG CAT GGA TCT GAG ACA TCA TGG GCA GAT CCG TCG      2056
Ala Asn Tyr Thr Ala His Gly Ser Glu Thr Ser Trp Ala Asp Pro Ser
     75                  80                  85

CTG ACC GCC ACT CAA GTG AAA GCA CTC ACA AAT AAG GAC AAA TAC TTC      2104
Leu Thr Ala Thr Gln Val Lys Ala Leu Thr Asn Lys Asp Lys Tyr Phe
 90                  95                 100                 105

TTA GCT ATT GGG AAC TGC TGT GTT ACA GCT CAA TTC GAT TAT CCA CAG      2152
Leu Ala Ile Gly Asn Cys Cys Val Thr Ala Gln Phe Asp Tyr Pro Gln
                110                 115                 120

CCT TGC TTT GGA GAG GTA ATG ACT CGT GTC AAG GAG AAA GGT GCT TAT      2200
Pro Cys Phe Gly Glu Val Met Thr Arg Val Lys Glu Lys Gly Ala Tyr
            125                 130                 135

GCC TAT ATC GGT TCA TCT CCG AAT TCT TAT TGG GGC GAG GAC TAC TAT      2248
Ala Tyr Ile Gly Ser Ser Pro Asn Ser Tyr Trp Gly Glu Asp Tyr Tyr
        140                 145                 150

TGG AGT GTC GGT GCT AAT GCC GTA TTT GGT GTT CAG CCT ACT TTT GAA      2296
Trp Ser Val Gly Ala Asn Ala Val Phe Gly Val Gln Pro Thr Phe Glu
    155                 160                 165

GGT ACG TCT ATG GGT TCT TAT GAT GCT ACA TTC TTG GAA GAT TCG TAC      2344
Gly Thr Ser Met Gly Ser Tyr Asp Ala Thr Phe Leu Glu Asp Ser Tyr
170                 175                 180                 185

AAC ACA GTG AAT TCT ATT ATG TGG GCA GGT AAT CTT GCC GCT ACT CAT      2392
Asn Thr Val Asn Ser Ile Met Trp Ala Gly Asn Leu Ala Ala Thr His
                190                 195                 200
```

-continued

GCT GGA AAT ATC GGC AAT ATT ACC CAT ATC GGT GCT CAT TAC TAT TGG 2440
Ala Gly Asn Ile Gly Asn Ile Thr His Ile Gly Ala His Tyr Tyr Trp
205 210 215

GAA GCT TAT CAT GTC CTT GGC GAT GGT TCG GTT ATG CCT TAT CGT GCA 2488
Glu Ala Tyr His Val Leu Gly Asp Gly Ser Val Met Pro Tyr Arg Ala
220 225 230

ATG CCT AAG ACC AAT ACT TAT ACG CTT CCT GCT TCT CTG CCT CAG AAT 2536
Met Pro Lys Thr Asn Thr Tyr Thr Leu Pro Ala Ser Leu Pro Gln Asn
235 240 245

CAG GCT TCT TAT AGC ATT CAG GCT TCT GCC GGT TCT TAC GTA GCT ATT 2584
Gln Ala Ser Tyr Ser Ile Gln Ala Ser Ala Gly Ser Tyr Val Ala Ile
250 255 260 265

TCT AAA GAT GGA GTT TTG TAT GGA ACA GGT GTT GCT AAT GCC AGC GGT 2632
Ser Lys Asp Gly Val Leu Tyr Gly Thr Gly Val Ala Asn Ala Ser Gly
270 275 280

GTT GCG ACT GTG AAT ATG ACT AAG CAG ATT ACG GAA AAT GGT AAT TAT 2680
Val Ala Thr Val Asn Met Thr Lys Gln Ile Thr Glu Asn Gly Asn Tyr
285 290 295

GAT GTA GTT ATC ACT CGC TCT AAT TAT CTT CCT GTG ATC AAG CAA ATT 2728
Asp Val Val Ile Thr Arg Ser Asn Tyr Leu Pro Val Ile Lys Gln Ile
300 305 310

CAG GCA GGA GAG CCT AGC CCC TAC CAG CCT GTT TCC AAC TTG ACT GCT 2776
Gln Ala Gly Glu Pro Ser Pro Tyr Gln Pro Val Ser Asn Leu Thr Ala
315 320 325

ACA ACG CAG GGT CAG AAA GTA ACG CTC AAG TGG GAT GCC CCG AGC GCA 2824
Thr Thr Gln Gly Gln Lys Val Thr Leu Lys Trp Asp Ala Pro Ser Ala
330 335 340 345

AAG AAG GCA GAA GCT TCC CGT GAA GTA AAA CGG ATC GGA GAC GGT CTT 2872
Lys Lys Ala Glu Ala Ser Arg Glu Val Lys Arg Ile Gly Asp Gly Leu
350 355 360

TTC GTT ACG ATC GAA CCT GCA AAC GAT GTA CGT GCC AAC GAA GCC AAG 2920
Phe Val Thr Ile Glu Pro Ala Asn Asp Val Arg Ala Asn Glu Ala Lys
365 370 375

GTT GTG CTC GCA GCA GAC AAC GTA TGG GGA GAC AAT ACG GGT TAC CAG 2968
Val Val Leu Ala Ala Asp Asn Val Trp Gly Asp Asn Thr Gly Tyr Gln
380 385 390

TTC TTG TTG GAT GCC GAT CAC AAT ACA TTC GGA AGT GTC ATT CCG GCA 3016
Phe Leu Leu Asp Ala Asp His Asn Thr Phe Gly Ser Val Ile Pro Ala
395 400 405

ACC GGT CCT CTC TTT ACC GGA ACA GCT TCT TCC AAT CTT TAC AGT GCG 3064
Thr Gly Pro Leu Phe Thr Gly Thr Ala Ser Ser Asn Leu Tyr Ser Ala
410 415 420 425

AAC TTC GAG TAT TTG ATC CCG GCC AAT GCC GAT CCT GTT GTT ACT ACA 3112
Asn Phe Glu Tyr Leu Ile Pro Ala Asn Ala Asp Pro Val Val Thr Thr
430 435 440

CAG AAT ATT ATC GTT ACA GGA CAG GGT GAA GTT GTA ATC CCC GGT GGT 3160
Gln Asn Ile Ile Val Thr Gly Gln Gly Glu Val Val Ile Pro Gly Gly
445 450 455

GTT TAC GAC TAT TGC ATT ACG AAC CCG GAA CCT GCA TCC GGA AAG ATG 3208
Val Tyr Asp Tyr Cys Ile Thr Asn Pro Glu Pro Ala Ser Gly Lys Met
460 465 470

TGG ATC GCA GGA GAT GGA GAC AAC CAG CCT GCA CGT TAT GAC GAT TTC 3256
Trp Ile Ala Gly Asp Gly Asp Asn Gln Pro Ala Arg Tyr Asp Asp Phe
475 480 485

ACA TTC GAA GCA GGC AAG AAG TAC ACC TTC ACG ATG CGT CGC GCC GGA 3304
Thr Phe Glu Ala Gly Lys Lys Tyr Thr Phe Thr Met Arg Arg Ala Gly
490 495 500 505

ATG GGA GAT GGA ACT GAT ATG GAA GTC GAA GAC GAT TCA CCT GCA AGC 3352
Met Gly Asp Gly Thr Asp Met Glu Val Glu Asp Asp Ser Pro Ala Ser
510 515 520

-continued

```
TAT ACC TAT ACA GTC TAT CGT GAC GGC ACG AAG ATC AAG GAA GGT CTG    3400
Tyr Thr Tyr Thr Val Tyr Arg Asp Gly Thr Lys Ile Lys Glu Gly Leu
            525                 530                 535

ACG GCT ACG ACA TTC GAA GAA GAC GGT GTA GCT GCA GGC AAT CAT GAG    3448
Thr Ala Thr Thr Phe Glu Glu Asp Gly Val Ala Ala Gly Asn His Glu
        540                 545                 550

TAT TGC GTG GAA GTT AAG TAC ACA GCC GGC GTA TCT CCG AAG GTA TGT    3496
Tyr Cys Val Glu Val Lys Tyr Thr Ala Gly Val Ser Pro Lys Val Cys
    555                 560                 565

AAA GAC GTT ACG GTA GAA GGA TCC AAT GAA TTT GCT CCT GTA CAG AAC    3544
Lys Asp Val Thr Val Glu Gly Ser Asn Glu Phe Ala Pro Val Gln Asn
570                 575                 580                 585

CTG ACC GGT AGT GCA GTC GGC CAG AAA GTA ACG CTT AAG TGG GAT GCA    3592
Leu Thr Gly Ser Ala Val Gly Gln Lys Val Thr Leu Lys Trp Asp Ala
                590                 595                 600

CCT AAT GGT ACC CCA AAT CCG AAT CCG AAT CCG AAT CCG GGA ACA ACA    3640
Pro Asn Gly Thr Pro Asn Pro Asn Pro Asn Pro Asn Pro Gly Thr Thr
            605                 610                 615

ACA CTT TCC GAA TCA TTC GAA AAT GGT ATT CCT GCC TCA TGG AAG ACG    3688
Thr Leu Ser Glu Ser Phe Glu Asn Gly Ile Pro Ala Ser Trp Lys Thr
        620                 625                 630

ATC GAT GCA GAC GGT GAC GGG CAT GGC TGG AAA CCT GGA AAT GCT CCC    3736
Ile Asp Ala Asp Gly Asp Gly His Gly Trp Lys Pro Gly Asn Ala Pro
    635                 640                 645

GGA ATC GCT GGC TAC AAT AGC AAT GGT TGT GTA TAT TCA GAG TCA TTC    3784
Gly Ile Ala Gly Tyr Asn Ser Asn Gly Cys Val Tyr Ser Glu Ser Phe
650                 655                 660                 665

GGT CTT GGT GGT ATA GGA GTT CTT ACC CCT GAC AAC TAT CTG ATA ACA    3832
Gly Leu Gly Gly Ile Gly Val Leu Thr Pro Asp Asn Tyr Leu Ile Thr
                670                 675                 680

CCG GCA TTG GAT TTG GCT AAC GGA GGT AAG TTG ACT TTC TGG GTA TGC    3880
Pro Ala Leu Asp Leu Ala Asn Gly Gly Lys Leu Thr Phe Trp Val Cys
            685                 690                 695

GCA CAG GAT GCT AAT TAT GCA TCC GAG CAC TAT GCG GTG TAT GCA TCT    3928
Ala Gln Asp Ala Asn Tyr Ala Ser Glu His Tyr Ala Val Tyr Ala Ser
        700                 705                 710

TCG ACC GGT AAC GAT GCA TCC AAC TTC ACG AAT GCT TTG TTG GAA GAG    3976
Ser Thr Gly Asn Asp Ala Ser Asn Phe Thr Asn Ala Leu Leu Glu Glu
    715                 720                 725

ACG ATT ACG GCA AAA GGT GTT CGC TCG CCG GAA GCT ATT CGT GGT CGT    4024
Thr Ile Thr Ala Lys Gly Val Arg Ser Pro Glu Ala Ile Arg Gly Arg
730                 735                 740                 745

ATA CAG GGT ACT TGG CGC CAG AAG ACG GTA GAC CTT CCC GCA GGT ACG    4072
Ile Gln Gly Thr Trp Arg Gln Lys Thr Val Asp Leu Pro Ala Gly Thr
                750                 755                 760

AAA TAT GTT GCT TTC CGT CAC TTC CAA AGC ACG GAT ATG TTC TAC ATC    4120
Lys Tyr Val Ala Phe Arg His Phe Gln Ser Thr Asp Met Phe Tyr Ile
            765                 770                 775

GAC CTT GAT GAG GTT GAG ATC AAG GCC AAT GGC AAG CGC GCA GAC TTC    4168
Asp Leu Asp Glu Val Glu Ile Lys Ala Asn Gly Lys Arg Ala Asp Phe
        780                 785                 790

ACG GAA ACG TTC GAG TCT TCT ACT CAT GGA GAG GCA CCA GCG GAA TGG    4216
Thr Glu Thr Phe Glu Ser Ser Thr His Gly Glu Ala Pro Ala Glu Trp
    795                 800                 805

ACT ACT ATC GAT GCC GAT GGC GAT GGT CAG GAT TGG CTC TGT CTG TCT    4264
Thr Thr Ile Asp Ala Asp Gly Asp Gly Gln Asp Trp Leu Cys Leu Ser
810                 815                 820                 825

TCC GGA CAA TTG GAC TGG CTG ACA GCT CAT GGC GGC ACC AAC GTA GTA    4312
Ser Gly Gln Leu Asp Trp Leu Thr Ala His Gly Gly Thr Asn Val Val
                830                 835                 840
```

-continued

GCC TCT TTC TCA TGG AAT GGA ATG GCT TTG AAT CCT GAT AAC TAT CTC 4360
Ala Ser Phe Ser Trp Asn Gly Met Ala Leu Asn Pro Asp Asn Tyr Leu
845 850 855

ATC TCA AAG GAT GTT ACA GGC GCA ACG AAG GTA AAG TAC TAC TAT GCA 4408
Ile Ser Lys Asp Val Thr Gly Ala Thr Lys Val Lys Tyr Tyr Tyr Ala
860 865 870

GTC AAC GAC GGT TTT CCC GGG GAT CAC TAT GCG GTG ATG ATC TCC AAG 4456
Val Asn Asp Gly Phe Pro Gly Asp His Tyr Ala Val Met Ile Ser Lys
875 880 885

ACG GGC ACG AAC GCC GGA GAC TTC ACG GTT GTT TTC GAA GAA ACG CCT 4504
Thr Gly Thr Asn Ala Gly Asp Phe Thr Val Val Phe Glu Glu Thr Pro
890 895 900 905

AAC GGA ATA AAT AAG GGC GGA GCA AGA TTC GGT CTT TCC ACG GAA GCC 4552
Asn Gly Ile Asn Lys Gly Gly Ala Arg Phe Gly Leu Ser Thr Glu Ala
910 915 920

AAT GGC GCC AAA CCT CAA AGT GTA TGG ATC GAG CGT ACG GTA GAT TTG 4600
Asn Gly Ala Lys Pro Gln Ser Val Trp Ile Glu Arg Thr Val Asp Leu
925 930 935

CCT GCG GGC ACG AAG TAT GTT GCT TTC CGT CAC TAC AAT TGC TCG GAT 4648
Pro Ala Gly Thr Lys Tyr Val Ala Phe Arg His Tyr Asn Cys Ser Asp
940 945 950

TTG GAC TAC ATT CTT TTG GAT GAT ATT CAG TTC ACC ATG GGT GGC AGC 4696
Leu Asp Tyr Ile Leu Leu Asp Asp Ile Gln Phe Thr Met Gly Gly Ser
955 960 965

CCC ACC CCG ACC GAT TAT ACC TAC ACG GTA TAT CGT GAT GGT ACG AAG 4744
Pro Thr Pro Thr Asp Tyr Thr Tyr Thr Val Tyr Arg Asp Gly Thr Lys
970 975 980 985

ATC AAG GAA GGT CTG ACC GAA ACG ACC TTC GAA GAA GAC GGC GTA GCT 4792
Ile Lys Glu Gly Leu Thr Glu Thr Thr Phe Glu Glu Asp Gly Val Ala
990 995 1000

ACG GGC AAT CAT GAG TAT TGC GTG GAA GTG AAG TAC ACA GCC GGC GTA 4840
Thr Gly Asn His Glu Tyr Cys Val Glu Val Lys Tyr Thr Ala Gly Val
1005 1010 1015

TCT CCG AAG GTG TGT GTA AAC GTA ACT ATT AAT CCG ACT CAG TTC AAT 4888
Ser Pro Lys Val Cys Val Asn Val Thr Ile Asn Pro Thr Gln Phe Asn
1020 1025 1030

CCT GTA AAG AAC CTG AAG GCA CAA CCG GAT GGC GGC GAC GTG GTT CTC 4936
Pro Val Lys Asn Leu Lys Ala Gln Pro Asp Gly Gly Asp Val Val Leu
1035 1040 1045

AAG TGG GAA GCC CCG AGT GGC AAA CGA GGA GAA CTG CTT AAT GAA GAT 4984
Lys Trp Glu Ala Pro Ser Gly Lys Arg Gly Glu Leu Leu Asn Glu Asp
1050 1055 1060 1065

TTT GAA GGA GAC GCT ATT CCC ACA GGG TGG ACA GCA TTG GAT GCC GAT 5032
Phe Glu Gly Asp Ala Ile Pro Thr Gly Trp Thr Ala Leu Asp Ala Asp
1070 1075 1080

GGT GAC GGT AAT AAC TGG GAT ATC ACG CTC AAT GAA TTT ACG CGA GGA 5080
Gly Asp Gly Asn Asn Trp Asp Ile Thr Leu Asn Glu Phe Thr Arg Gly
1085 1090 1095

GAG CGT CAT GTT CTT TCA CCT TTA CGC GCC AGC AAC GTA GCC ATA TCC 5128
Glu Arg His Val Leu Ser Pro Leu Arg Ala Ser Asn Val Ala Ile Ser
1100 1105 1110

TAT TCT TCT TTA CTT CAG GGT CAA GAA TAT TTG CCT CTC ACG CCG AAC 5176
Tyr Ser Ser Leu Leu Gln Gly Gln Glu Tyr Leu Pro Leu Thr Pro Asn
1115 1120 1125

AAC TTT CTG ATC ACT CCG AAG GTT GAA GGA GCA AAG AAG ATT ACT TAT 5224
Asn Phe Leu Ile Thr Pro Lys Val Glu Gly Ala Lys Lys Ile Thr Tyr
1130 1135 1140 1145

AAG GTG GGT TCA CCG GGT CTT CCT CAA TGG AGT CAT GAT CAT TAT GCA 5272
Lys Val Gly Ser Pro Gly Leu Pro Gln Trp Ser His Asp His Tyr Ala
1150 1155 1160

CTC TGT ATC TCC AAG AGC GGA ACG GCT GCA GCC GAC TTC GAA GTA ATC 5320
Leu Cys Ile Ser Lys Ser Gly Thr Ala Ala Ala Asp Phe Glu Val Ile
1165 1170 1175

TTT GAA GAA ACG ATG ACC TAC ACT CAA GGA GGA GCC AAC TTG ACA AGA 5368
Phe Glu Glu Thr Met Thr Tyr Thr Gln Gly Gly Ala Asn Leu Thr Arg
1180 1185 1190

GAA AAA GAC CTC CCT GCC GGC ACG AAA TAT GTC GCT TTC CGT CAT TAC 5416
Glu Lys Asp Leu Pro Ala Gly Thr Lys Tyr Val Ala Phe Arg His Tyr
1195 1200 1205

AAT TGC ACG GAT GTT CTG GGC ATA ATG ATT GAC GAT GTA GTG ATA ACA 5464
Asn Cys Thr Asp Val Leu Gly Ile Met Ile Asp Asp Val Val Ile Thr
1210 1215 1220 1225

GGT GAA GGC GAA GGT CCC AGT TAC ACC TAC ACG GTG TAT CGT GAC GGC 5512
Gly Glu Gly Glu Gly Pro Ser Tyr Thr Tyr Thr Val Tyr Arg Asp Gly
1230 1235 1240

ACG AAG ATC CAG GAA GGT CTG ACC GAA ACG ACC TAC CGC GAT GCA GGA 5560
Thr Lys Ile Gln Glu Gly Leu Thr Glu Thr Thr Tyr Arg Asp Ala Gly
1245 1250 1255

ATG AGT GCA CAA TCT CAT GAG TAT TGC GTA GAG GTT AAG TAC GCA GCC 5608
Met Ser Ala Gln Ser His Glu Tyr Cys Val Glu Val Lys Tyr Ala Ala
1260 1265 1270

GGC GTA TCT CCG AAG GTT TGT GTG GAT TAT ATT CCT GAT GGA GTG GCA 5656
Gly Val Ser Pro Lys Val Cys Val Asp Tyr Ile Pro Asp Gly Val Ala
1275 1280 1285

GAC GTA ACT GCT CAG AAG CCT TAC ACG CTG ACG GTT GTA GGA AAG ACT 5704
Asp Val Thr Ala Gln Lys Pro Tyr Thr Leu Thr Val Val Gly Lys Thr
1290 1295 1300 1305

ATC ACG GTA ACT TGC CAA GGC GAA GCT ATG ATC TAC GAC ATG AAC GGT 5752
Ile Thr Val Thr Cys Gln Gly Glu Ala Met Ile Tyr Asp Met Asn Gly
1310 1315 1320

CGT CGT CTG GCA GCG GGT CGC AAC ACG GTT GTT TAC ACG GCT CAG GGC 5800
Arg Arg Leu Ala Ala Gly Arg Asn Thr Val Val Tyr Thr Ala Gln Gly
1325 1330 1335

GGC TAC TAT GCA GTC ATG GTT GTC GTT GAC GGC AAG TCT TAC GTA GAG 5848
Gly Tyr Tyr Ala Val Met Val Val Val Asp Gly Lys Ser Tyr Val Glu
1340 1345 1350

AAA CTC GCT ATC AAG TAA TTCTGTCTTG GACTCGGAGA CTTTGTGCAG 5896
Lys Leu Ala Ile Lys
1355

ACACTTTTAA TATAGGTCTG TAATTGTCTC AGAGTATGAA TCGGTCGCCC GACTTCCTTA 5956

AAAGGAGGTC GGGCGACTTC GTTTTTATTA TTGCTGTCTG GTAAACTTGT CAAGAGGAGA 6016

CCTTTGAAAA ATGGGGCGGT CAATAATTTT CGGTCTATGG GTCAAATTGC AGGCTACTGT 6076

TTTAGGTGTA TGTTGGGCTA TCTTCCTATC TTTAAGAGAC CTTTGAAAAA TAAGGAGATG 6136

GAGGGAAGAG GAGTTCTTGG CATAAAAGGA GCGAGTGAAA GGGGTGGCAG TAAGGAGTGA 6196

AAGTAGTTGT AAATCCCCCC TTTGAGGAGC TACTTGTACG AGCTC 6241

( 2 ) INFORMATION FOR SEQ ID NO:26:

( i ) SEQUENCE CHARACTERISTICS:
( A ) LENGTH: 364 amino acids
( B ) TYPE: amino acid
( D ) TOPOLOGY: linear ( i i ) MOLECULE TYPE: protein ( x i ) SEQUENCE DESCRIPTION: SEQ ID NO:26:

Met Arg Lys Leu Leu Leu Leu Ile Ala Ala Ser Leu Leu Gly Val Gly
1 5 10 15

Leu Tyr Ala Gln Ser Ala Lys Ile Lys Leu Asp Ala Pro Thr Thr Arg 20 25 30

Thr Thr Cys Thr Asn Asn Ser Phe Lys Gln Phe Asp Ala Ser Phe Ser
35 40 45

Phe Asn Glu Val Glu Leu Thr Lys Val Glu Thr Lys Gly Gly Thr Phe
50 55 60

Ala Ser Val Ser Ile Pro Gly Ala Phe Pro Thr Gly Glu Val Gly Ser
65 70 75 80

Pro Glu Val Pro Ala Val Arg Lys Leu Ile Ala Val Pro Val Gly Ala
85 90 95

Thr Pro Val Val Arg Val Lys Ser Phe Thr Glu Gln Val Tyr Ser Leu
100 105 110

Asn Gln Tyr Gly Ser Glu Lys Leu Met Pro His Gln Pro Ser Met Ser
115 120 125

Lys Ser Asp Asp Pro Glu Lys Val Pro Phe Val Tyr Asn Ala Ala Ala
130 135 140

Tyr Ala Arg Lys Gly Phe Val Gly Gln Glu Leu Thr Gln Val Glu Met
145 150 155 160

Leu Gly Thr Met Arg Gly Val Arg Ile Ala Ala Leu Thr Ile Asn Pro
165 170 175

Val Gln Tyr Asp Val Val Ala Asn Gln Leu Lys Val Arg Asn Asn Ile
180 185 190

Glu Ile Glu Val Ser Phe Gln Gly Ala Asp Glu Val Ala Thr Gln Arg
195 200 205

Leu Tyr Asp Ala Ser Phe Ser Pro Tyr Phe Glu Thr Ala Tyr Lys Gln
210 215 220

Leu Phe Asn Arg Asp Val Tyr Thr Asp His Gly Asp Leu Tyr Asn Thr
225 230 235 240

Pro Val Arg Met Leu Val Val Ala Gly Ala Lys Phe Lys Glu Ala Leu
245 250 255

Lys Pro Trp Leu Thr Trp Lys Ala Gln Lys Gly Phe Tyr Leu Asp Val
260 265 270

His Tyr Thr Asp Glu Ala Glu Val Gly Thr Thr Asn Ala Ser Ile Lys
275 280 285

Ala Phe Ile His Lys Lys Tyr Asn Asp Gly Leu Ala Ala Ser Ala Ala
290 295 300

Pro Val Phe Leu Ala Leu Val Gly Asp Thr Asp Val Ile Ser Gly Glu
305 310 315 320

Lys Gly Lys Lys Thr Lys Lys Val Thr Asp Leu Tyr Tyr Ser Ala Val
325 330 335

Asp Gly Asp Tyr Phe Pro Glu Met Tyr Thr Phe Arg Met Ser Ala Ser
340 345 350

Ser Pro Glu Glu Leu Thr Asn Ile Ile Asp Lys Tyr
355 360

( 2 ) INFORMATION FOR SEQ ID NO:27:

( i ) SEQUENCE CHARACTERISTICS:
( A ) LENGTH: 1358 amino acids
( B ) TYPE: amino acid
( D ) TOPOLOGY: linear ( i i ) MOLECULE TYPE: protein ( x i ) SEQUENCE DESCRIPTION: SEQ ID NO:27:

Met Tyr Glu Lys Ala Thr Met Pro Asp Lys Ser Tyr Leu Glu Lys Ala
1 5 10 15

-continued

| | | | | | | | | | | | | | | | |
|---|---|---|---|---|---|---|---|---|---|---|---|---|---|---|---|
| Leu | Leu | Ile | Ala | Gly | Ala | Asp | Ser | Tyr | Trp | Asn | Pro | Lys | Ile | Gly | Gln |
| | | | 20 | | | | | 25 | | | | | 30 | | |
| Gln | Thr | Ile | Lys | Tyr | Ala | Val | Gln | Tyr | Tyr | Tyr | Asn | Gln | Asp | His | Gly |
| | | 35 | | | | | 40 | | | | | 45 | | | |
| Tyr | Thr | Asp | Val | Tyr | Ser | Tyr | Pro | Lys | Ala | Pro | Tyr | Thr | Gly | Cys | Tyr |
| | 50 | | | | | 55 | | | | | 60 | | | | |
| Ser | His | Leu | Asn | Thr | Gly | Val | Gly | Phe | Ala | Asn | Tyr | Thr | Ala | His | Gly |
| 65 | | | | | 70 | | | | | 75 | | | | | 80 |
| Ser | Glu | Thr | Ser | Trp | Ala | Asp | Pro | Ser | Leu | Thr | Ala | Thr | Gln | Val | Lys |
| | | | | 85 | | | | | 90 | | | | | 95 | |
| Ala | Leu | Thr | Asn | Lys | Asp | Lys | Tyr | Phe | Leu | Ala | Ile | Gly | Asn | Cys | Cys |
| | | | 100 | | | | | 105 | | | | | 110 | | |
| Val | Thr | Ala | Gln | Phe | Asp | Tyr | Pro | Gln | Pro | Cys | Phe | Gly | Glu | Val | Met |
| | | 115 | | | | | 120 | | | | | 125 | | | |
| Thr | Arg | Val | Lys | Glu | Lys | Gly | Ala | Tyr | Ala | Tyr | Ile | Gly | Ser | Ser | Pro |
| | 130 | | | | | 135 | | | | | 140 | | | | |
| Asn | Ser | Tyr | Trp | Gly | Glu | Asp | Tyr | Tyr | Trp | Ser | Val | Gly | Ala | Asn | Ala |
| 145 | | | | | 150 | | | | | 155 | | | | | 160 |
| Val | Phe | Gly | Val | Gln | Pro | Thr | Phe | Glu | Gly | Thr | Ser | Met | Gly | Ser | Tyr |
| | | | | 165 | | | | | 170 | | | | | 175 | |
| Asp | Ala | Thr | Phe | Leu | Glu | Asp | Ser | Tyr | Asn | Thr | Val | Asn | Ser | Ile | Met |
| | | | 180 | | | | | 185 | | | | | 190 | | |
| Trp | Ala | Gly | Asn | Leu | Ala | Ala | Thr | His | Ala | Gly | Asn | Ile | Gly | Asn | Ile |
| | | 195 | | | | | 200 | | | | | 205 | | | |
| Thr | His | Ile | Gly | Ala | His | Tyr | Tyr | Trp | Glu | Ala | Tyr | His | Val | Leu | Gly |
| | 210 | | | | | 215 | | | | | 220 | | | | |
| Asp | Gly | Ser | Val | Met | Pro | Tyr | Arg | Ala | Met | Pro | Lys | Thr | Asn | Thr | Tyr |
| 225 | | | | | 230 | | | | | 235 | | | | | 240 |
| Thr | Leu | Pro | Ala | Ser | Leu | Pro | Gln | Asn | Gln | Ala | Ser | Tyr | Ser | Ile | Gln |
| | | | | 245 | | | | | 250 | | | | | 255 | |
| Ala | Ser | Ala | Gly | Ser | Tyr | Val | Ala | Ile | Ser | Lys | Asp | Gly | Val | Leu | Tyr |
| | | | 260 | | | | | 265 | | | | | 270 | | |
| Gly | Thr | Gly | Val | Ala | Asn | Ala | Ser | Gly | Val | Ala | Thr | Val | Asn | Met | Thr |
| | | 275 | | | | | 280 | | | | | 285 | | | |
| Lys | Gln | Ile | Thr | Glu | Asn | Gly | Asn | Tyr | Asp | Val | Val | Ile | Thr | Arg | Ser |
| | 290 | | | | | 295 | | | | | 300 | | | | |
| Asn | Tyr | Leu | Pro | Val | Ile | Lys | Gln | Ile | Gln | Ala | Gly | Glu | Pro | Ser | Pro |
| 305 | | | | | 310 | | | | | 315 | | | | | 320 |
| Tyr | Gln | Pro | Val | Ser | Asn | Leu | Thr | Ala | Thr | Thr | Gln | Gly | Gln | Lys | Val |
| | | | | 325 | | | | | 330 | | | | | 335 | |
| Thr | Leu | Lys | Trp | Asp | Ala | Pro | Ser | Ala | Lys | Lys | Ala | Glu | Ala | Ser | Arg |
| | | | 340 | | | | | 345 | | | | | 350 | | |
| Glu | Val | Lys | Arg | Ile | Gly | Asp | Gly | Leu | Phe | Val | Thr | Ile | Glu | Pro | Ala |
| | | 355 | | | | | 360 | | | | | 365 | | | |
| Asn | Asp | Val | Arg | Ala | Asn | Glu | Ala | Lys | Val | Val | Leu | Ala | Ala | Asp | Asn |
| | 370 | | | | | 375 | | | | | 380 | | | | |
| Val | Trp | Gly | Asp | Asn | Thr | Gly | Tyr | Gln | Phe | Leu | Leu | Asp | Ala | Asp | His |
| 385 | | | | | 390 | | | | | 395 | | | | | 400 |
| Asn | Thr | Phe | Gly | Ser | Val | Ile | Pro | Ala | Thr | Gly | Pro | Leu | Phe | Thr | Gly |
| | | | | 405 | | | | | 410 | | | | | 415 | |
| Thr | Ala | Ser | Ser | Asn | Leu | Tyr | Ser | Ala | Asn | Phe | Glu | Tyr | Leu | Ile | Pro |
| | | | 420 | | | | | 425 | | | | | 430 | | |
| Ala | Asn | Ala | Asp | Pro | Val | Val | Thr | Thr | Gln | Asn | Ile | Ile | Val | Thr | Gly |
| | | 435 | | | | | 440 | | | | | 445 | | | |

-continued

| | | | | | | | | | | | | | | | |
|---|---|---|---|---|---|---|---|---|---|---|---|---|---|---|---|
| Gln | Gly | Glu | Val | Val | Ile | Pro | Gly | Gly | Val | Tyr | Asp | Tyr | Cys | Ile | Thr |
| | 450 | | | | | 455 | | | | | 460 | | | | |
| Asn | Pro | Glu | Pro | Ala | Ser | Gly | Lys | Met | Trp | Ile | Ala | Gly | Asp | Gly | Asp |
| 465 | | | | | 470 | | | | | 475 | | | | | 480 |
| Asn | Gln | Pro | Ala | Arg | Tyr | Asp | Asp | Phe | Thr | Phe | Glu | Ala | Gly | Lys | Lys |
| | | | | 485 | | | | | 490 | | | | | 495 | |
| Tyr | Thr | Phe | Thr | Met | Arg | Arg | Ala | Gly | Met | Gly | Asp | Gly | Thr | Asp | Met |
| | | | 500 | | | | | 505 | | | | | 510 | | |
| Glu | Val | Glu | Asp | Asp | Ser | Pro | Ala | Ser | Tyr | Thr | Tyr | Thr | Val | Tyr | Arg |
| | | 515 | | | | | 520 | | | | | 525 | | | |
| Asp | Gly | Thr | Lys | Ile | Lys | Glu | Gly | Leu | Thr | Ala | Thr | Thr | Phe | Glu | Glu |
| | 530 | | | | | 535 | | | | | 540 | | | | |
| Asp | Gly | Val | Ala | Ala | Gly | Asn | His | Glu | Tyr | Cys | Val | Glu | Val | Lys | Tyr |
| 545 | | | | | 550 | | | | | 555 | | | | | 560 |
| Thr | Ala | Gly | Val | Ser | Pro | Lys | Val | Cys | Lys | Asp | Val | Thr | Val | Glu | Gly |
| | | | | 565 | | | | | 570 | | | | | 575 | |
| Ser | Asn | Glu | Phe | Ala | Pro | Val | Gln | Asn | Leu | Thr | Gly | Ser | Ala | Val | Gly |
| | | | 580 | | | | | 585 | | | | | 590 | | |
| Gln | Lys | Val | Thr | Leu | Lys | Trp | Asp | Ala | Pro | Asn | Gly | Thr | Pro | Asn | Pro |
| | | 595 | | | | | 600 | | | | | 605 | | | |
| Asn | Pro | Asn | Pro | Asn | Pro | Gly | Thr | Thr | Thr | Leu | Ser | Glu | Ser | Phe | Glu |
| | 610 | | | | | 615 | | | | | 620 | | | | |
| Asn | Gly | Ile | Pro | Ala | Ser | Trp | Lys | Thr | Ile | Asp | Ala | Asp | Gly | Asp | Gly |
| 625 | | | | | 630 | | | | | 635 | | | | | 640 |
| His | Gly | Trp | Lys | Pro | Gly | Asn | Ala | Pro | Gly | Ile | Ala | Gly | Tyr | Asn | Ser |
| | | | | 645 | | | | | 650 | | | | | 655 | |
| Asn | Gly | Cys | Val | Tyr | Ser | Glu | Ser | Phe | Gly | Leu | Gly | Gly | Ile | Gly | Val |
| | | | 660 | | | | | 665 | | | | | 670 | | |
| Leu | Thr | Pro | Asp | Asn | Tyr | Leu | Ile | Thr | Pro | Ala | Leu | Asp | Leu | Ala | Asn |
| | | 675 | | | | | 680 | | | | | 685 | | | |
| Gly | Gly | Lys | Leu | Thr | Phe | Trp | Val | Cys | Ala | Gln | Asp | Ala | Asn | Tyr | Ala |
| | 690 | | | | | 695 | | | | | 700 | | | | |
| Ser | Glu | His | Tyr | Ala | Val | Tyr | Ala | Ser | Ser | Thr | Gly | Asn | Asp | Ala | Ser |
| 705 | | | | | 710 | | | | | 715 | | | | | 720 |
| Asn | Phe | Thr | Asn | Ala | Leu | Leu | Glu | Glu | Thr | Ile | Thr | Ala | Lys | Gly | Val |
| | | | | 725 | | | | | 730 | | | | | 735 | |
| Arg | Ser | Pro | Glu | Ala | Ile | Arg | Gly | Arg | Ile | Gln | Gly | Thr | Trp | Arg | Gln |
| | | | 740 | | | | | 745 | | | | | 750 | | |
| Lys | Thr | Val | Asp | Leu | Pro | Ala | Gly | Thr | Lys | Tyr | Val | Ala | Phe | Arg | His |
| | | 755 | | | | | 760 | | | | | 765 | | | |
| Phe | Gln | Ser | Thr | Asp | Met | Phe | Tyr | Ile | Asp | Leu | Asp | Glu | Val | Glu | Ile |
| | 770 | | | | | 775 | | | | | 780 | | | | |
| Lys | Ala | Asn | Gly | Lys | Arg | Ala | Asp | Phe | Thr | Glu | Thr | Phe | Glu | Ser | Ser |
| 785 | | | | | 790 | | | | | 795 | | | | | 800 |
| Thr | His | Gly | Glu | Ala | Pro | Ala | Glu | Trp | Thr | Thr | Ile | Asp | Ala | Asp | Gly |
| | | | | 805 | | | | | 810 | | | | | 815 | |
| Asp | Gly | Gln | Asp | Trp | Leu | Cys | Leu | Ser | Ser | Gly | Gln | Leu | Asp | Trp | Leu |
| | | | 820 | | | | | 825 | | | | | 830 | | |
| Thr | Ala | His | Gly | Gly | Thr | Asn | Val | Val | Ala | Ser | Phe | Ser | Trp | Asn | Gly |
| | | 835 | | | | | 840 | | | | | 845 | | | |
| Met | Ala | Leu | Asn | Pro | Asp | Asn | Tyr | Leu | Ile | Ser | Lys | Asp | Val | Thr | Gly |
| | 850 | | | | | 855 | | | | | 860 | | | | |
| Ala | Thr | Lys | Val | Lys | Tyr | Tyr | Tyr | Ala | Val | Asn | Asp | Gly | Phe | Pro | Gly |

-continued 865 870 875 880

Asp His Tyr Ala Val Met Ile Ser Lys Thr Gly Thr Asn Ala Gly Asp
885 890 895

Phe Thr Val Val Phe Glu Glu Thr Pro Asn Gly Ile Asn Lys Gly Gly
900 905 910

Ala Arg Phe Gly Leu Ser Thr Glu Ala Asn Gly Ala Lys Pro Gln Ser
915 920 925

Val Trp Ile Glu Arg Thr Val Asp Leu Pro Ala Gly Thr Lys Tyr Val
930 935 940

Ala Phe Arg His Tyr Asn Cys Ser Asp Leu Asp Tyr Ile Leu Leu Asp
945 950 955 960

Asp Ile Gln Phe Thr Met Gly Gly Ser Pro Thr Pro Thr Asp Tyr Thr
965 970 975

Tyr Thr Val Tyr Arg Asp Gly Thr Lys Ile Lys Glu Gly Leu Thr Glu
980 985 990

Thr Thr Phe Glu Glu Asp Gly Val Ala Thr Gly Asn His Glu Tyr Cys
995 1000 1005

Val Glu Val Lys Tyr Thr Ala Gly Val Ser Pro Lys Val Cys Val Asn
1010 1015 1020

Val Thr Ile Asn Pro Thr Gln Phe Asn Pro Val Lys Asn Leu Lys Ala
1025 1030 1035 1040

Gln Pro Asp Gly Gly Asp Val Val Leu Lys Trp Glu Ala Pro Ser Gly
1045 1050 1055

Lys Arg Gly Glu Leu Leu Asn Glu Asp Phe Glu Gly Asp Ala Ile Pro
1060 1065 1070

Thr Gly Trp Thr Ala Leu Asp Ala Asp Gly Asp Gly Asn Asn Trp Asp
1075 1080 1085

Ile Thr Leu Asn Glu Phe Thr Arg Gly Glu Arg His Val Leu Ser Pro
1090 1095 1100

Leu Arg Ala Ser Asn Val Ala Ile Ser Tyr Ser Ser Leu Leu Gln Gly
1105 1110 1115 1120

Gln Glu Tyr Leu Pro Leu Thr Pro Asn Asn Phe Leu Ile Thr Pro Lys
1125 1130 1135

Val Glu Gly Ala Lys Lys Ile Thr Tyr Lys Val Gly Ser Pro Gly Leu
1140 1145 1150

Pro Gln Trp Ser His Asp His Tyr Ala Leu Cys Ile Ser Lys Ser Gly
1155 1160 1165

Thr Ala Ala Ala Asp Phe Glu Val Ile Phe Glu Glu Thr Met Thr Tyr
1170 1175 1180

Thr Gln Gly Gly Ala Asn Leu Thr Arg Glu Lys Asp Leu Pro Ala Gly
1185 1190 1195 1200

Thr Lys Tyr Val Ala Phe Arg His Tyr Asn Cys Thr Asp Val Leu Gly
1205 1210 1215

Ile Met Ile Asp Asp Val Val Ile Thr Gly Glu Gly Glu Gly Pro Ser
1220 1225 1230

Tyr Thr Tyr Thr Val Tyr Arg Asp Gly Thr Lys Ile Gln Glu Gly Leu
1235 1240 1245

Thr Glu Thr Thr Tyr Arg Asp Ala Gly Met Ser Ala Gln Ser His Glu
1250 1255 1260

Tyr Cys Val Glu Val Lys Tyr Ala Ala Gly Val Ser Pro Lys Val Cys
1265 1270 1275 1280

Val Asp Tyr Ile Pro Asp Gly Val Ala Asp Val Thr Ala Gln Lys Pro
1285 1290 1295

```
Tyr Thr Leu Thr Val Val Gly Lys Thr Ile Thr Val Thr Cys Gln Gly
            1300                     1305                     1310

Glu Ala Met Ile Tyr Asp Met Asn Gly Arg Arg Leu Ala Ala Gly Arg
        1315                     1320                     1325

Asn Thr Val Val Tyr Thr Ala Gln Gly Gly Tyr Tyr Ala Val Met Val
    1330                     1335                     1340

Val Val Asp Gly Lys Ser Tyr Val Glu Lys Leu Ala Ile Lys
1345                     1350                     1355
```

( 2 ) INFORMATION FOR SEQ ID NO:28:

( i ) SEQUENCE CHARACTERISTICS:
( A ) LENGTH: 8640 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 971..6031

( x i ) SEQUENCE DESCRIPTION: SEQ ID NO:28:

```
AGGCCTTTGA GACGGGCACA AGCCGCCGCA GCCTCCTCTT CGAAGGTGTC TCGAACGTCC     60

ACATCGGTGA ATCCGTAGCA GTGCTCATTG CCATTGAGCA GCACCGAGGT GTGGCGCATC    120

AGATATATTT TCATCAGTGG ATTATTAGGG TATCGGTCAG AAAAAGCCTT CCGAATCCGA    180

CAAAGATAGT AGAAAGAGAG TGCATCTGAA AACAGATCAT TCGAGGATTA TCGATCAACT    240

GAAAAGGCAG GAGTTGTTTT GCGTTTTGGT TCGGAAAATT ACCTGATCAG CATTCGTAAA    300

AACGTGGCGC GAGAATTTTT TCGTTTTGGC GCGAGAATTA AAAATTTTTG GAACCACAGC    360

GAAAAAAATC TCGCGCCGTT TTCTCAGGAT TTACAGACCA CAATCCGAGC ATTTTCGGTT    420

CGTAATTCAT CGAAGAGACA GGTTTTACCG CATTGAAATC AGAGAGAGAA TATCCGTAGT    480

CCAACGGTTC ATCCTTATAT CAGAGGTTAA AAGATATGGT ACGCTCATCG AGGAGCTGAT    540

TGGCTTAGTA GGTGAGACTT TCTTAAGAGA CTATCGGCAC CTACAGGAAG TTCATGGCAC    600

ACAAGGCAAA GGAGGCAATC TTCGCAGACC GGACTCATAT CAAAAGGATG AAACGACTTT    660

TCCATACGAC AACCAAATAG CCGTCTACGG TAGACGAATG CAAACCCAAT ATGAGGCCAT    720

CAATCAATCC GAATGACAGC TTTTGGGCAA TATATTATGC ATATTTTGAT TCGCGTTTAA    780

AGGAAAAGTG CATATATTTG CGATTGTGGT ATTTCTTTCG GTTTCTATGT GAATTTTGTC    840

TCCCAAGAAG ACTTTATAAT GCATAAATAC AGAAGGGGTA CTACACAGTA AAATCATATT    900

CTAATTTCAT CAAAATGAAA AACTTGAACA AGTTTGTTTC ATTGCTCTTT GCTCTTCCTT    960

ATTAGGAGGA ATG GCA TTT GCG CAG CAG ACA GAG TTG GGA CGC AAT CCG       1009
           Met Ala Phe Ala Gln Gln Thr Glu Leu Gly Arg Asn Pro
           1360                     1365                     1370

AAT GTC AGA TTG CTC GAA TCC ACT CAG CAA TCG GTG ACA AAG GTT CAG     1057
Asn Val Arg Leu Leu Glu Ser Thr Gln Gln Ser Val Thr Lys Val Gln
        1375                     1380                     1385

TTC CGT ATG GAC AAC CTC AAG TTC ACC GAA GTT CAA ACC CCT AAG GGA     1105
Phe Arg Met Asp Asn Leu Lys Phe Thr Glu Val Gln Thr Pro Lys Gly
    1390                     1395                     1400

ATG GCA CAA GTG CCG ACC TAT ACA GAA GGG GTT AAT CTT TCC GAA AAA     1153
Met Ala Gln Val Pro Thr Tyr Thr Glu Gly Val Asn Leu Ser Glu Lys
1405                     1410                     1415                     1420

GGG ATG CCT ACG CTT CCC ATT CTA TCA CGC TCT TTG GCG GTT TCA GAC     1201
Gly Met Pro Thr Leu Pro Ile Leu Ser Arg Ser Leu Ala Val Ser Asp
                1425                     1430                     1435
```

-continued

ACT CGT GAG ATG AAG GTA GAG GTT GTT TCC TCA AAG TTC ATC GAA AAG 1249
Thr Arg Glu Met Lys Val Glu Val Val Ser Ser Lys Phe Ile Glu Lys
1440 1445 1450

AAA AAT GTC CTG ATT GCA CCC TCC AAG GGC ATG ATT ATG CGT AAC GAA 1297
Lys Asn Val Leu Ile Ala Pro Ser Lys Gly Met Ile Met Arg Asn Glu
1455 1460 1465

GAT CCG AAA AAG ATC CCT TAC GTT TAT GGA AAG AGC TAC TCG CAA AAC 1345
Asp Pro Lys Lys Ile Pro Tyr Val Tyr Gly Lys Ser Tyr Ser Gln Asn
1470 1475 1480

AAA TTC TTC CCG GGA GAG ATC GCC ACG CTT GAT GAT CCT TTT ATC CTT 1393
Lys Phe Phe Pro Gly Glu Ile Ala Thr Leu Asp Asp Pro Phe Ile Leu
1485 1490 1495 1500

CGT GAT GTG CGT GGA CAG GTT GTA AAC TTT GCG CCT TTG CAG TAT AAC 1441
Arg Asp Val Arg Gly Gln Val Val Asn Phe Ala Pro Leu Gln Tyr Asn
1505 1510 1515

CCT GTG ACA AAG ACG TTG CGC ATC TAT ACG GAA ATC ACT GTG GCA GTG 1489
Pro Val Thr Lys Thr Leu Arg Ile Tyr Thr Glu Ile Thr Val Ala Val
1520 1525 1530

AGC GAA ACT TCG GAA CAA GGC AAA AAT ATT CTG AAC AAG AAA GGT ACA 1537
Ser Glu Thr Ser Glu Gln Gly Lys Asn Ile Leu Asn Lys Lys Gly Thr
1535 1540 1545

TTT GCC GGC TTT GAA GAC ACA TAC AAG CGC ATG TTC ATG AAC TAC GAG 1585
Phe Ala Gly Phe Glu Asp Thr Tyr Lys Arg Met Phe Met Asn Tyr Glu
1550 1555 1560

CCG GGG CGT TAC ACA CCG GTA GAG GAA AAA CAA AAT GGT CGT ATG ATC 1633
Pro Gly Arg Tyr Thr Pro Val Glu Glu Lys Gln Asn Gly Arg Met Ile
1565 1570 1575 1580

GTC ATC GTA GCC AAA AAG TAT GAG GGA GAT ATT AAA GAT TTC GTT GAT 1681
Val Ile Val Ala Lys Lys Tyr Glu Gly Asp Ile Lys Asp Phe Val Asp
1585 1590 1595

TGG AAA AAC CAA CGC GGT CTC CGT ACC GAG GTG AAA GTG GCA GAA GAT 1729
Trp Lys Asn Gln Arg Gly Leu Arg Thr Glu Val Lys Val Ala Glu Asp
1600 1605 1610

ATT GCT TCT CCC GTT ACA GCT AAT GCT ATT CAG CAG TTC GTT AAG CAA 1777
Ile Ala Ser Pro Val Thr Ala Asn Ala Ile Gln Gln Phe Val Lys Gln
1615 1620 1625

GAA TAC GAG AAA GAA GGT AAT GAT TTG ACC TAT GTT CTT TTG GTT GGC 1825
Glu Tyr Glu Lys Glu Gly Asn Asp Leu Thr Tyr Val Leu Leu Val Gly
1630 1635 1640

GAT CAC AAA GAT ATT CCT GCC AAA ATT ACT CCG GGG ATC AAA TCC GAC 1873
Asp His Lys Asp Ile Pro Ala Lys Ile Thr Pro Gly Ile Lys Ser Asp
1645 1650 1655 1660

CAG GTA TAT GGA CAA ATA GTA GGT AAT GAC CAC TAC AAC GAA GTC TTC 1921
Gln Val Tyr Gly Gln Ile Val Gly Asn Asp His Tyr Asn Glu Val Phe
1665 1670 1675

ATC GGT CGT TTC TCA TGT GAG AGC AAA GAG GAT CTG AAG ACA CAA ATC 1969
Ile Gly Arg Phe Ser Cys Glu Ser Lys Glu Asp Leu Lys Thr Gln Ile
1680 1685 1690

GAT CGG ACT ATT CAC TAT GAG CGC AAT ATA ACC ACG GAA GAC AAA TGG 2017
Asp Arg Thr Ile His Tyr Glu Arg Asn Ile Thr Thr Glu Asp Lys Trp
1695 1700 1705

CTC GGT CAG GCT CTT TGT ATT GCT TCG GCT GAA GGA GGC CCA TCC GCA 2065
Leu Gly Gln Ala Leu Cys Ile Ala Ser Ala Glu Gly Gly Pro Ser Ala
1710 1715 1720

GAC AAT GGT GAA AGT GAT ATC CAG CAT GAG AAT GTA ATC GCC AAT CTG 2113
Asp Asn Gly Glu Ser Asp Ile Gln His Glu Asn Val Ile Ala Asn Leu
1725 1730 1735 1740

CTT ACC CAG TAT GGC TAT ACC AAG ATT ATC AAA TGT TAT GAT CCG GGA 2161
Leu Thr Gln Tyr Gly Tyr Thr Lys Ile Ile Lys Cys Tyr Asp Pro Gly
1745 1750 1755

-continued

```
GTA ACT CCT AAA AAC ATT ATT GAT GCT TTC AAC GGA GGA ATC TCG TTG     2209
Val Thr Pro Lys Asn Ile Ile Asp Ala Phe Asn Gly Gly Ile Ser Leu
            1760                1765                1770

GTC AAC TAT ACG GGC CAC GGT AGC GAA ACA GCT TGG GGT ACG TCT CAC     2257
Val Asn Tyr Thr Gly His Gly Ser Glu Thr Ala Trp Gly Thr Ser His
        1775                1780                1785

TTC GGC ACC ACT CAT GTG AAG CAG CTT ACC AAC AGC AAC CAG CTA CCG     2305
Phe Gly Thr Thr His Val Lys Gln Leu Thr Asn Ser Asn Gln Leu Pro
    1790                1795                1800

TTT ATT TTC GAC GTA GCT TGT GTG AAT GGC GAT TTC CTA TTC AGC ATG     2353
Phe Ile Phe Asp Val Ala Cys Val Asn Gly Asp Phe Leu Phe Ser Met
1805                1810                1815                1820

CCT TGC TTC GCA GAA GCC CTG ATG CGT GCA CAA AAA GAT GGT AAG CCG     2401
Pro Cys Phe Ala Glu Ala Leu Met Arg Ala Gln Lys Asp Gly Lys Pro
                1825                1830                1835

ACA GGT ACT GTT GCT ATC ATA GCG TCT ACG ATC AAC CAG TCT TGG GCT     2449
Thr Gly Thr Val Ala Ile Ile Ala Ser Thr Ile Asn Gln Ser Trp Ala
            1840                1845                1850

TCT CCT ATG CGC GGG CAG GAT GAG ATG AAC GAA ATT CTG TGC GAA AAA     2497
Ser Pro Met Arg Gly Gln Asp Glu Met Asn Glu Ile Leu Cys Glu Lys
        1855                1860                1865

CAC CCG AAC AAC ATC AAG CGT ACT TTC GGT GGT GTC ACC ATG AAC GGT     2545
His Pro Asn Asn Ile Lys Arg Thr Phe Gly Gly Val Thr Met Asn Gly
    1870                1875                1880

ATG TTT GCT ATG GTG GAA AAG TAT AAA AAG GAT GGT GAG AAG ATG CTC     2593
Met Phe Ala Met Val Glu Lys Tyr Lys Lys Asp Gly Glu Lys Met Leu
1885                1890                1895                1900

GAC ACA TGG ACT GTT TTC GGC GAC CCC TCG CTG CTC GTT CGT ACA CTT     2641
Asp Thr Trp Thr Val Phe Gly Asp Pro Ser Leu Leu Val Arg Thr Leu
                1905                1910                1915

GTC CCG ACC AAA ATG CAG GTT ACG GCT CCG GCT CAG ATT AAT TTG ACG     2689
Val Pro Thr Lys Met Gln Val Thr Ala Pro Ala Gln Ile Asn Leu Thr
            1920                1925                1930

GAT GCT TCA GTC AAC GTA TCT TGC GAT TAT AAT GGT GCT ATT GCT ACC     2737
Asp Ala Ser Val Asn Val Ser Cys Asp Tyr Asn Gly Ala Ile Ala Thr
        1935                1940                1945

ATT TCA GCC AAT GGA AAG ATG TTC GGT TCT GCA GTT GTC GAA AAT GGA     2785
Ile Ser Ala Asn Gly Lys Met Phe Gly Ser Ala Val Val Glu Asn Gly
    1950                1955                1960

ACA GCT ACA ATC AAT CTG ACA GGT CTG ACA AAT GAA AGC ACG CTT ACC     2833
Thr Ala Thr Ile Asn Leu Thr Gly Leu Thr Asn Glu Ser Thr Leu Thr
1965                1970                1975                1980

CTT ACA GTA GTT GGT TAC AAC AAA GAG ACG GTT ATT AAG ACC ATC AAC     2881
Leu Thr Val Val Gly Tyr Asn Lys Glu Thr Val Ile Lys Thr Ile Asn
                1985                1990                1995

ACT AAT GGT GAG CCT AAC CCC TAC CAG CCC GTT TCC AAC TTG ACA GCT     2929
Thr Asn Gly Glu Pro Asn Pro Tyr Gln Pro Val Ser Asn Leu Thr Ala
            2000                2005                2010

ACA ACG CAG GGT CAG AAA GTA ACG CTC AAG TGG GAT GCA CCG AGC ACG     2977
Thr Thr Gln Gly Gln Lys Val Thr Leu Lys Trp Asp Ala Pro Ser Thr
        2015                2020                2025

AAA ACC AAT GCA ACC ACT AAT ACC GCT CGC AGC GTG GAT GGC ATA CGA     3025
Lys Thr Asn Ala Thr Thr Asn Thr Ala Arg Ser Val Asp Gly Ile Arg
    2030                2035                2040

GAA TTG GTT CTT CTG TCA GTC AGC GAT GCC CCC GAA CTT CTT CGC AGC     3073
Glu Leu Val Leu Leu Ser Val Ser Asp Ala Pro Glu Leu Leu Arg Ser
2045                2050                2055                2060

GGT CAG GCC GAG ATT GTT CTT GAA GCT CAC GAT GTT TGG AAT GAT GGA     3121
Gly Gln Ala Glu Ile Val Leu Glu Ala His Asp Val Trp Asn Asp Gly
                2065                2070                2075
```

-continued

TCC GGT TAT CAG ATT CTT TTG GAT GCA GAC CAT GAT CAA TAT GGA CAG 3169
Ser Gly Tyr Gln Ile Leu Leu Asp Ala Asp His Asp Gln Tyr Gly Gln
2080 2085 2090

GTT ATA CCC AGT GAT ACC CAT ACT CTT TGG CCG AAC TGT AGT GTC CCG 3217
Val Ile Pro Ser Asp Thr His Thr Leu Trp Pro Asn Cys Ser Val Pro
2095 2100 2105

GCC AAT CTG TTC GCT CCG TTC GAA TAT ACT GTT CCG GAA AAT GCA GAT 3265
Ala Asn Leu Phe Ala Pro Phe Glu Tyr Thr Val Pro Glu Asn Ala Asp
2110 2115 2120

CCT TCT TGT TCC CCT ACC AAT ATG ATA ATG GAT GGT ACT GCA TCC GTT 3313
Pro Ser Cys Ser Pro Thr Asn Met Ile Met Asp Gly Thr Ala Ser Val
2125 2130 2135 2140

AAT ATA CCG GCC GGA ACT TAT GAC TTT GCA ATT GCT GCT CCT CAA GCA 3361
Asn Ile Pro Ala Gly Thr Tyr Asp Phe Ala Ile Ala Ala Pro Gln Ala
2145 2150 2155

AAT GCA AAG ATT TGG ATT GCC GGA CAA GGA CCG ACG AAA GAA GAT GAT 3409
Asn Ala Lys Ile Trp Ile Ala Gly Gln Gly Pro Thr Lys Glu Asp Asp
2160 2165 2170

TAT GTA TTT GAA GCC GGT AAA AAA TAC CAT TTC CTT ATG AAG AAG ATG 3457
Tyr Val Phe Glu Ala Gly Lys Lys Tyr His Phe Leu Met Lys Lys Met
2175 2180 2185

GGT AGC GGT GAT GGA ACT GAA TTG ACT ATA AGC GAA GGT GGT GGA AGC 3505
Gly Ser Gly Asp Gly Thr Glu Leu Thr Ile Ser Glu Gly Gly Gly Ser
2190 2195 2200

GAT TAC ACC TAT ACT GTC TAT CGT GAC GGC ACG AAG ATC AAG GAA GGT 3553
Asp Tyr Thr Tyr Thr Val Tyr Arg Asp Gly Thr Lys Ile Lys Glu Gly
2205 2210 2215 2220

CTG ACG GCT ACG ACA TTC GAA GAA GAC GGT GTA GCT ACG GGC AAT CAT 3601
Leu Thr Ala Thr Thr Phe Glu Glu Asp Gly Val Ala Thr Gly Asn His
2225 2230 2235

GAG TAT TGC GTG GAA GTT AAG TAC ACA GCC GGC GTA TCT CCG AAG GTA 3649
Glu Tyr Cys Val Glu Val Lys Tyr Thr Ala Gly Val Ser Pro Lys Val
2240 2245 2250

TGT AAA GAC GTT ACG GTA GAA GGA TCC AAT GAA TTT GCT CCT GTA CAG 3697
Cys Lys Asp Val Thr Val Glu Gly Ser Asn Glu Phe Ala Pro Val Gln
2255 2260 2265

AAC CTG ACC GGT AGT GCA GTC GGC CAG AAA GTA ACG CTC AAG TGG GAT 3745
Asn Leu Thr Gly Ser Ala Val Gly Gln Lys Val Thr Leu Lys Trp Asp
2270 2275 2280

GCA CCT AAT GGT ACC CCG AAT CCA AAT CCG AAT CCG AAT CCG AAT CCG 3793
Ala Pro Asn Gly Thr Pro Asn Pro Asn Pro Asn Pro Asn Pro Asn Pro
2285 2290 2295 2300

AAT CCC GGA ACA ACA ACA CTT TCC GAA TCA TTC GAA AAT GGT ATT CCT 3841
Asn Pro Gly Thr Thr Thr Leu Ser Glu Ser Phe Glu Asn Gly Ile Pro
2305 2310 2315

GCC TCA TGG AAG ACG ATC GAT GCA GAC GGT GAC GGG CAT GGC TGG AAG 3889
Ala Ser Trp Lys Thr Ile Asp Ala Asp Gly Asp Gly His Gly Trp Lys
2320 2325 2330

CCT GGA AAT GCT CCC GGA ATC GCT GGC TAC AAT AGC AAT GGT TGT GTA 3937
Pro Gly Asn Ala Pro Gly Ile Ala Gly Tyr Asn Ser Asn Gly Cys Val
2335 2340 2345

TAT TCA GAG TCA TTC GGT CTT GGT GGT ATA GGA GTT CTT ACC CCT GAC 3985
Tyr Ser Glu Ser Phe Gly Leu Gly Gly Ile Gly Val Leu Thr Pro Asp
2350 2355 2360

AAC TAT CTG ATA ACA CCG GCA TTG GAT TTG CCT AAC GGA GGT AAG TTG 4033
Asn Tyr Leu Ile Thr Pro Ala Leu Asp Leu Pro Asn Gly Gly Lys Leu
2365 2370 2375 2380

ACT TTC TGG GTA TGC GCA CAG GAT GCT AAT TAT GCA TCC GAG CAC TAT 4081
Thr Phe Trp Val Cys Ala Gln Asp Ala Asn Tyr Ala Ser Glu His Tyr
2385 2390 2395

-continued

```
GCG GTG TAT GCA TCT TCG ACC GGT AAC GAT GCA TCC AAC TTC ACG AAT     4129
Ala Val Tyr Ala Ser Ser Thr Gly Asn Asp Ala Ser Asn Phe Thr Asn
            2400                2405                2410

GCT TTG TTG GAA GAG ACG ATT ACG GCA AAA GGT GTT CGC TCG CCG GAA     4177
Ala Leu Leu Glu Glu Thr Ile Thr Ala Lys Gly Val Arg Ser Pro Glu
        2415                2420                2425

GCT ATT CGT GGT CGT ATA CAG GGT ACT TGG CGC CAG AAG ACG GTA GAC     4225
Ala Ile Arg Gly Arg Ile Gln Gly Thr Trp Arg Gln Lys Thr Val Asp
    2430                2435                2440

CTT CCC GCA GGT ACG AAA TAT GTT GCT TTC CGT CAC TTC CAA AGC ACG     4273
Leu Pro Ala Gly Thr Lys Tyr Val Ala Phe Arg His Phe Gln Ser Thr
2445                2450                2455                2460

GAT ATG TTC TAC ATC GAC CTT GAT GAG GTT GAG ATC AAG GCC AAC GGC     4321
Asp Met Phe Tyr Ile Asp Leu Asp Glu Val Glu Ile Lys Ala Asn Gly
                2465                2470                2475

AAG CGC GCA GAC TTC ACG GAA ACG TTC GAG TCT TCT ACT CAT GGA GAG     4369
Lys Arg Ala Asp Phe Thr Glu Thr Phe Glu Ser Ser Thr His Gly Glu
            2480                2485                2490

GCA CCG GCG GAA TGG ACT ACT ATC GAT GCC GAT GGC GAT GGT CAG GGT     4417
Ala Pro Ala Glu Trp Thr Thr Ile Asp Ala Asp Gly Asp Gly Gln Gly
        2495                2500                2505

TGG CTC TGT CTG TCT TCC GGA CAA TTG GAC TGG CTG ACA GCT CAT GGC     4465
Trp Leu Cys Leu Ser Ser Gly Gln Leu Asp Trp Leu Thr Ala His Gly
    2510                2515                2520

GGC ACC AAC GTA GTA GCC TCT TTC TCA TGG AAT GGA ATG GCT TTG AAT     4513
Gly Thr Asn Val Val Ala Ser Phe Ser Trp Asn Gly Met Ala Leu Asn
2525                2530                2535                2540

CCT GAT AAC TAT CTC ATC TCA AAG GAT GTT ACA GGC GCA ACG AAG GTA     4561
Pro Asp Asn Tyr Leu Ile Ser Lys Asp Val Thr Gly Ala Thr Lys Val
                2545                2550                2555

AAG TAC TAC TAT GCA GTC AAC GAC GGT TTT CCC GGG GAT CAC TAT GCG     4609
Lys Tyr Tyr Tyr Ala Val Asn Asp Gly Phe Pro Gly Asp His Tyr Ala
            2560                2565                2570

GTG ATG ATC TCC AAG ACG GGC ACG AAC GCC GGA GAC TTC ACG GTT GTT     4657
Val Met Ile Ser Lys Thr Gly Thr Asn Ala Gly Asp Phe Thr Val Val
        2575                2580                2585

TTC GAA GAA ACG CCT AAC GGA ATA AAT AAG GGC GGA GCA AGA TTC GGT     4705
Phe Glu Glu Thr Pro Asn Gly Ile Asn Lys Gly Gly Ala Arg Phe Gly
    2590                2595                2600

CTT TCC ACG GAA GCC AAT GGC GCC AAA CCT CAA AGT GTA TGG ATC GAG     4753
Leu Ser Thr Glu Ala Asn Gly Ala Lys Pro Gln Ser Val Trp Ile Glu
2605                2610                2615                2620

CGT ACG GTA GAT TTG CCT GCG GGC ACG AAG TAT GTT GCT TTC CGT CAC     4801
Arg Thr Val Asp Leu Pro Ala Gly Thr Lys Tyr Val Ala Phe Arg His
                2625                2630                2635

TAC AAT TGC TCG GAT TTG AAC TAC ATT CTT TTG GAT GAT ATT CAG TTC     4849
Tyr Asn Cys Ser Asp Leu Asn Tyr Ile Leu Leu Asp Asp Ile Gln Phe
            2640                2645                2650

ACC ATG GGT GGC AGC CCC ACC CCG ACC GAT TAT ACC TAC ACG GTG TAT     4897
Thr Met Gly Gly Ser Pro Thr Pro Thr Asp Tyr Thr Tyr Thr Val Tyr
        2655                2660                2665

CGT GAC GGT ACG AAG ATC AAG GAA GGT CTG ACC GAA ACG ACC TTC GAA     4945
Arg Asp Gly Thr Lys Ile Lys Glu Gly Leu Thr Glu Thr Thr Phe Glu
    2670                2675                2680

GAA GAC GGC GTA GCT ACA GGC AAT CAT GAG TAT TGC GTG GAA GTG AAG     4993
Glu Asp Gly Val Ala Thr Gly Asn His Glu Tyr Cys Val Glu Val Lys
2685                2690                2695                2700

TAC ACA GCC GGC GTA TCT CCG AAA GAG TGC GTA AAC GTA ACT ATT AAT     5041
Tyr Thr Ala Gly Val Ser Pro Lys Glu Cys Val Asn Val Thr Ile Asn
                2705                2710                2715
```

-continued

CCG ACT CAG TTC AAT CCT GTA AAG AAC CTG AAG GCA CAA CCG GAT GGC 5089
Pro Thr Gln Phe Asn Pro Val Lys Asn Leu Lys Ala Gln Pro Asp Gly
2720 2725 2730

GGC GAC GTG GTT CTC AAG TGG GAA GCC CCG AGC GCA AAA AAG ACA GAA 5137
Gly Asp Val Val Leu Lys Trp Glu Ala Pro Ser Ala Lys Lys Thr Glu
2735 2740 2745

GGT TCT CGT GAA GTA AAA CGG ATC GGA GAC GGT CTT TTC GTT ACG ATC 5185
Gly Ser Arg Glu Val Lys Arg Ile Gly Asp Gly Leu Phe Val Thr Ile
2750 2755 2760

GAA CCT GCA AAC GAT GTA CGT GCC AAC GAA GCC AAG GTT GTG CTC GCA 5233
Glu Pro Ala Asn Asp Val Arg Ala Asn Glu Ala Lys Val Val Leu Ala
2765 2770 2775 2780

GCA GAC AAC GTA TGG GGA GAC AAT ACG GGT TAC CAG TTC TTG TTG GAT 5281
Ala Asp Asn Val Trp Gly Asp Asn Thr Gly Tyr Gln Phe Leu Leu Asp
2785 2790 2795

GCC GAT CAC AAT ACA TTC GGA AGT GTC ATT CCG GCA ACC GGT CCT CTC 5329
Ala Asp His Asn Thr Phe Gly Ser Val Ile Pro Ala Thr Gly Pro Leu
2800 2805 2810

TTT ACC GGA ACA GCT TCT TCC AAT CTT TAC AGT GCG AAC TTC GAG TAT 5377
Phe Thr Gly Thr Ala Ser Ser Asn Leu Tyr Ser Ala Asn Phe Glu Tyr
2815 2820 2825

TTG ATC CCG GCC AAT GCC GAT CCT GTT GTT ACT ACA CAG AAT ATT ATC 5425
Leu Ile Pro Ala Asn Ala Asp Pro Val Val Thr Thr Gln Asn Ile Ile
2830 2835 2840

GTT ACA GGA CAG GGT GAA GTT GTA ATC CCC GGT GGT GTT TAC GAC TAT 5473
Val Thr Gly Gln Gly Glu Val Val Ile Pro Gly Gly Val Tyr Asp Tyr
2845 2850 2855 2860

TGC ATT ACG AAC CCG GAA CCT GCA TCC GGA AAG ATG TGG ATC GCA GGA 5521
Cys Ile Thr Asn Pro Glu Pro Ala Ser Gly Lys Met Trp Ile Ala Gly
2865 2870 2875

GAT GGA GGC AAC CAG CCT GCA CGT TAT GAC GAT TTC ACA TTC GAA GCA 5569
Asp Gly Gly Asn Gln Pro Ala Arg Tyr Asp Asp Phe Thr Phe Glu Ala
2880 2885 2890

GGC AAG AAG TAC ACC TTC ACG ATG CGT CGC GCC GGA ATG GGA GAT GGA 5617
Gly Lys Lys Tyr Thr Phe Thr Met Arg Arg Ala Gly Met Gly Asp Gly
2895 2900 2905

ACT GAT ATG GAA GTC GAA GAC GAT TCA CCT GCA AGC TAT ACC TAT ACA 5665
Thr Asp Met Glu Val Glu Asp Asp Ser Pro Ala Ser Tyr Thr Tyr Thr
2910 2915 2920

GTC TAT CGT GAC GGC ACG AAG ATC AAG GAA GGT CTG ACC GAA ACG ACC 5713
Val Tyr Arg Asp Gly Thr Lys Ile Lys Glu Gly Leu Thr Glu Thr Thr
2925 2930 2935 2940

TAC CGC GAT GCA GGA ATG AGT GCA CAA TCT CAT GAG TAT TGC GTA GAG 5761
Tyr Arg Asp Ala Gly Met Ser Ala Gln Ser His Glu Tyr Cys Val Glu
2945 2950 2955

GTT AAG TAC GCA GCC GGC GTA TCT CCG AAG GTT TGT GTG GAT TAT ATT 5809
Val Lys Tyr Ala Ala Gly Val Ser Pro Lys Val Cys Val Asp Tyr Ile
2960 2965 2970

CCT GAC GGA GTG GCA GAC GTA ACG GCT CAG AAG CCT TAC ACG CTG ACA 5857
Pro Asp Gly Val Ala Asp Val Thr Ala Gln Lys Pro Tyr Thr Leu Thr
2975 2980 2985

GTT GTT GGA AAG ACG ATC ACG GTA ACT TGC CAA GGC GAA GCT ATG ATC 5905
Val Val Gly Lys Thr Ile Thr Val Thr Cys Gln Gly Glu Ala Met Ile
2990 2995 3000

TAC GAC ATG AAC GGT CGT CGT CTG GCA GCC GGT CGC AAC ACA GTT GTT 5953
Tyr Asp Met Asn Gly Arg Arg Leu Ala Ala Gly Arg Asn Thr Val Val
3005 3010 3015 3020

TAC ACG GCT CAG GGC GGC TAC TAT GCA GTC ATG GTT GTC GTT GAC GGC 6001
Tyr Thr Ala Gln Gly Gly Tyr Tyr Ala Val Met Val Val Val Asp Gly
3025 3030 3035

-continued

```
AAG TCT TAC GTA GAG AAA CTC GCT GTA AAG TAATTCTGTC TTGGACTCGG    6051
Lys Ser Tyr Val Glu Lys Leu Ala Val Lys
            3040                3045

AGACTTTGTG CAGACACTTT TAATATAGGT CTGTAATTGT CTCAGAGTAT GAATCGATCG    6111

CCCGACCTCC TTTTAAGGAA GTCGGGCGAC TTCGTTTTTA TGCCTATTAT TCTAATATAC    6171

TTCTGAAACA ATTTGTTCCA AAAAGTTGCA TGAAAAGATT ATCTTACTAT CTTTGCACTG    6231

CAAAAGGGGA GTTTCCTAAG GTTTTCCCCG GAGTAGTACG GTAATAACGG TGTGGTAGTT    6291

CAGCTGGTTA GAATACCTGC CTGTCACGCA GGGGGTCGCG GGTTCGAGTC CCGTCCATAC    6351

CGCTAAAATA AGGAGTTGTG TTGAAATAGT TTTTCGGCAC AGCTCCATTT TTGTATGTTA    6411

TCGCAGCACC GGAAAGTATA ATTGCCGGAT GAGATTATTC AATATGCTCG GAAGATTTTC    6471

TTAGAACGAA GCAGAAGTGT TTGTCTTTAT TACGATCTGC TTGGGACATA GGGATTAAAT    6531

TAGTATTATT GCAGGAGGGA CGGTACATGG AGTCGCCCGG CCAATCAGAT GAAGAAAGAA    6591

GAACTACGAT TGATTTTTAT GGGAACGGCC GATTTTGCTG TTCCGGCACT CCGAGCTTTG    6651

GTCGAAAACG GATACCAAGT AAAAGCTGTG GTCACTATGC CGGACAAGCC TATGGGTCGA    6711

GGACATAAGG TAAGTCCCAG TATGGTCAAA CTATACGCAC AGGAATTGGG TCTGCCTATT    6771

CTCCAGCCGG ACAATCTGAA CGAGGAATCT TTTCTCGATG AACTACGGAC TTATCAGCCG    6831

CACTTGCAAA TCGTAGTGGC TTTCCGTATG CTTCCTCGCT CCGTATGGCA AATGCCCCCC    6891

ATGGGAACAA TCAATCTGCA TGGCTCTCTG CTGCCCATGT ATCGAGGAGC AGCCCCTATC    6951

AACCACGCGA TACGCCATGG CGATACGGAA ACGGGAGTTA CCACCTTCCG CCTCCGGCAT    7011

GAGATAGATA CGGGTGAAGT ACTGCTGCAA GAGAAGTTGC CTATAGGACA TGAAGAGACT    7071

TTCGGCGAAT TGTACGAACG TATGGCTACT CTCGGTGCAT CCGTATTGGT GCACACAGTG    7131

GACTTGTTTC TCGAAGGAGA ACCCGTCTCC ATACCACAGG AGCAACTTCC GGGCTATGTT    7191

GGTGCTCGAC CGGCTCCGAA GATTTTCAAA GACGACTGCC GTATCGATTG GGACAAACCG    7251

GCTGAAGAGG TACACAATTT CATCCGCAGC ATATCGCCTG CCCCTACAGC TTGGACCAAG    7311

CTTCATCGTC CAGGGATGGA GTCCATCGTG CTGAAAATAT ACCGTACCCA AGTGATAGAA    7371

CGAGAACCGC GACACAGAGG CCGATTCGGC TCCATCATAT GGGACAAGAA AAACCTCGAC    7431

GTGATGACCC GCAAAGGGGT CATACGTATA CTCTCGCTCC AAATGCCCGG CAAGAAACAA    7491

ATGGATGCTG CCTCTTTCCT CAATGGTTTC GCTTTGTCCT CAGATATGTA TATAGAATAG    7551

GAGAGAGCTT GTTCCAAGGT TTGAACTGCT CATTTTCTGA CCTCTTGCAT ACAATAACAA    7611

TGTGCGGAGG ATACTTCTCT GCTCAACGTT CAGAGAAGCA GTTGGTCGTA GGCCGAGCCA    7671

ATCACATGGT TTTTTAACTT TGTAACCGAA AAATAAACGA CATCATGAAA GAAAACGAAA    7731

AGCCGACAGC TGCTGCCGGA ACCGTAACCA CCACCGATAA GACAAAGCCT GATTGGCGCA    7791

AAATCCTACC TTATGCTGCG GTCGTACTCC TTTTCATAGC CCTCGCTTTG GCCTATTTCT    7851

ATCCCGCCTC ATTCGACGGG CGTGTACTGT TCCAGGGCGA CGTAGCGGGA GCCAGCGGTA    7911

CGGCGCAGGA CGTACGCGAT TGGGAGGCAC AGACAGGAGA ACACTCCTAT TGGACCAACA    7971

GTCTCTTCGG GGGGATGCCT ATGTACCAGA TTTCGCCAAG CTATCCCTCT ACCCATACGC    8031

TCCAAACCAT ACAGGATGTT CTGACCCTGC GCAAGCCTTT CTATCTATTA GGCACCTATG    8091

CCTGGATGCT TTTTGCCATG ATGGGAGGGT TCTTTCTTTT CCTTAGATCG CTTCGAATCA    8151

GGATTTTGCC GGCAGTCATA GGCTCCATCG CATGGGCCTT TTCTTCCTAC TTCCTGATTC    8211

TGATTATGGC CGGACATATA TGGAAGCTGA CAGCTATGTG TTTTATTCCT CCTACTCTTG    8271

CCGGTATGAT CTGGATCTAC AATGGGAGGT GGTTGGCAGG CGGTAGCGTG ATGGCTTTTT    8331
```

```
TCACGGCTTT GCAAGTCTTG GCTAATCATG TACAGATGAG CTATTACTTC CTGTTCGTCA    8391

TGTTTTTCAT GGTGTTGGCT TTCTTGGCAG AAGCCATTCA AACAAAACGA ATCCGACACT    8451

TCTTCCTTTC CTCGGCAGTA GTCGTCATAG CAGGTCTGGT GGGTATAGCT GTGAATAGTA    8511

CCAACCTCTT CCACACCTAC CAATACGGCA AAGAGACCAT GCGTGGAGGT AGCGAACTGA    8571

CGCTCAAGCA GAGCGGAGCA CCCACGGATC AAGTGACGCA TGAGAATAAA AGCGGACTGG    8631

ACAAGGCCT                                                            8640
```

(2) INFORMATION FOR SEQ ID NO:29:

(i) SEQUENCE CHARACTERISTICS:
(A) LENGTH: 1687 amino acids
(B) TYPE: amino acid
(D) TOPOLOGY: linear (ii) MOLECULE TYPE: protein (xi) SEQUENCE DESCRIPTION: SEQ ID NO:29:

```
Met Ala Phe Ala Gln Gln Thr Glu Leu Gly Arg Asn Pro Asn Val Arg
  1               5                  10                  15

Leu Leu Glu Ser Thr Gln Gln Ser Val Thr Lys Val Gln Phe Arg Met
             20                  25                  30

Asp Asn Leu Lys Phe Thr Glu Val Gln Thr Pro Lys Gly Met Ala Gln
         35                  40                  45

Val Pro Thr Tyr Thr Glu Gly Val Asn Leu Ser Glu Lys Gly Met Pro
     50                  55                  60

Thr Leu Pro Ile Leu Ser Arg Ser Leu Ala Val Ser Asp Thr Arg Glu
 65                  70                  75                  80

Met Lys Val Glu Val Val Ser Ser Lys Phe Ile Glu Lys Lys Asn Val
                 85                  90                  95

Leu Ile Ala Pro Ser Lys Gly Met Ile Met Arg Asn Glu Asp Pro Lys
            100                 105                 110

Lys Ile Pro Tyr Val Tyr Gly Lys Ser Tyr Ser Gln Asn Lys Phe Phe
        115                 120                 125

Pro Gly Glu Ile Ala Thr Leu Asp Asp Pro Phe Ile Leu Arg Asp Val
    130                 135                 140

Arg Gly Gln Val Val Asn Phe Ala Pro Leu Gln Tyr Asn Pro Val Thr
145                 150                 155                 160

Lys Thr Leu Arg Ile Tyr Thr Glu Ile Thr Val Ala Val Ser Glu Thr
                165                 170                 175

Ser Glu Gln Gly Lys Asn Ile Leu Asn Lys Lys Gly Thr Phe Ala Gly
            180                 185                 190

Phe Glu Asp Thr Tyr Lys Arg Met Phe Met Asn Tyr Glu Pro Gly Arg
        195                 200                 205

Tyr Thr Pro Val Glu Glu Lys Gln Asn Gly Arg Met Ile Val Ile Val
    210                 215                 220

Ala Lys Lys Tyr Glu Gly Asp Ile Lys Asp Phe Val Asp Trp Lys Asn
225                 230                 235                 240

Gln Arg Gly Leu Arg Thr Glu Val Lys Val Ala Glu Asp Ile Ala Ser
                245                 250                 255

Pro Val Thr Ala Asn Ala Ile Gln Gln Phe Val Lys Gln Glu Tyr Glu
            260                 265                 270

Lys Glu Gly Asn Asp Leu Thr Tyr Val Leu Leu Val Gly Asp His Lys
        275                 280                 285

Asp Ile Pro Ala Lys Ile Thr Pro Gly Ile Lys Ser Asp Gln Val Tyr
```

-continued 290 295 300

Gly Gln Ile Val Gly Asn Asp His Tyr Asn Glu Val Phe Ile Gly Arg
305 310 315 320

Phe Ser Cys Glu Ser Lys Glu Asp Leu Lys Thr Gln Ile Asp Arg Thr
325 330 335

Ile His Tyr Glu Arg Asn Ile Thr Thr Glu Asp Lys Trp Leu Gly Gln
340 345 350

Ala Leu Cys Ile Ala Ser Ala Glu Gly Gly Pro Ser Ala Asp Asn Gly
355 360 365

Glu Ser Asp Ile Gln His Glu Asn Val Ile Ala Asn Leu Leu Thr Gln
370 375 380

Tyr Gly Tyr Thr Lys Ile Ile Lys Cys Tyr Asp Pro Gly Val Thr Pro
385 390 395 400

Lys Asn Ile Ile Asp Ala Phe Asn Gly Gly Ile Ser Leu Val Asn Tyr
405 410 415

Thr Gly His Gly Ser Glu Thr Ala Trp Gly Thr Ser His Phe Gly Thr
420 425 430

Thr His Val Lys Gln Leu Thr Asn Ser Asn Gln Leu Pro Phe Ile Phe
435 440 445

Asp Val Ala Cys Val Asn Gly Asp Phe Leu Phe Ser Met Pro Cys Phe
450 455 460

Ala Glu Ala Leu Met Arg Ala Gln Lys Asp Gly Lys Pro Thr Gly Thr
465 470 475 480

Val Ala Ile Ile Ala Ser Thr Ile Asn Gln Ser Trp Ala Ser Pro Met
485 490 495

Arg Gly Gln Asp Glu Met Asn Glu Ile Leu Cys Glu Lys His Pro Asn
500 505 510

Asn Ile Lys Arg Thr Phe Gly Gly Val Thr Met Asn Gly Met Phe Ala
515 520 525

Met Val Glu Lys Tyr Lys Lys Asp Gly Glu Lys Met Leu Asp Thr Trp
530 535 540

Thr Val Phe Gly Asp Pro Ser Leu Leu Val Arg Thr Leu Val Pro Thr
545 550 555 560

Lys Met Gln Val Thr Ala Pro Ala Gln Ile Asn Leu Thr Asp Ala Ser
565 570 575

Val Asn Val Ser Cys Asp Tyr Asn Gly Ala Ile Ala Thr Ile Ser Ala
580 585 590

Asn Gly Lys Met Phe Gly Ser Ala Val Val Glu Asn Gly Thr Ala Thr
595 600 605

Ile Asn Leu Thr Gly Leu Thr Asn Glu Ser Thr Leu Thr Leu Thr Val
610 615 620

Val Gly Tyr Asn Lys Glu Thr Val Ile Lys Thr Ile Asn Thr Asn Gly
625 630 635 640

Glu Pro Asn Pro Tyr Gln Pro Val Ser Asn Leu Thr Ala Thr Thr Gln
645 650 655

Gly Gln Lys Val Thr Leu Lys Trp Asp Ala Pro Ser Thr Lys Thr Asn
660 665 670

Ala Thr Thr Asn Thr Ala Arg Ser Val Asp Gly Ile Arg Glu Leu Val
675 680 685

Leu Leu Ser Val Ser Asp Ala Pro Glu Leu Leu Arg Ser Gly Gln Ala
690 695 700

Glu Ile Val Leu Glu Ala His Asp Val Trp Asn Asp Gly Ser Gly Tyr
705 710 715 720

-continued

Gln Ile Leu Leu Asp Ala Asp His Asp Gln Tyr Gly Gln Val Ile Pro
725 730 735

Ser Asp Thr His Thr Leu Trp Pro Asn Cys Ser Val Pro Ala Asn Leu
740 745 750

Phe Ala Pro Phe Glu Tyr Thr Val Pro Glu Asn Ala Asp Pro Ser Cys
755 760 765

Ser Pro Thr Asn Met Ile Met Asp Gly Thr Ala Ser Val Asn Ile Pro
770 775 780

Ala Gly Thr Tyr Asp Phe Ala Ile Ala Ala Pro Gln Ala Asn Ala Lys
785 790 795 800

Ile Trp Ile Ala Gly Gln Gly Pro Thr Lys Glu Asp Asp Tyr Val Phe
805 810 815

Glu Ala Gly Lys Lys Tyr His Phe Leu Met Lys Lys Met Gly Ser Gly
820 825 830

Asp Gly Thr Glu Leu Thr Ile Ser Glu Gly Gly Gly Ser Asp Tyr Thr
835 840 845

Tyr Thr Val Tyr Arg Asp Gly Thr Lys Ile Lys Glu Gly Leu Thr Ala
850 855 860

Thr Thr Phe Glu Glu Asp Gly Val Ala Thr Gly Asn His Glu Tyr Cys
865 870 875 880

Val Glu Val Lys Tyr Thr Ala Gly Val Ser Pro Lys Val Cys Lys Asp
885 890 895

Val Thr Val Glu Gly Ser Asn Glu Phe Ala Pro Val Gln Asn Leu Thr
900 905 910

Gly Ser Ala Val Gly Gln Lys Val Thr Leu Lys Trp Asp Ala Pro Asn
915 920 925

Gly Thr Pro Asn Pro Asn Pro Asn Pro Asn Pro Asn Pro Asn Pro Gly
930 935 940

Thr Thr Thr Leu Ser Glu Ser Phe Glu Asn Gly Ile Pro Ala Ser Trp
945 950 955 960

Lys Thr Ile Asp Ala Asp Gly Asp Gly His Gly Trp Lys Pro Gly Asn
965 970 975

Ala Pro Gly Ile Ala Gly Tyr Asn Ser Asn Gly Cys Val Tyr Ser Glu
980 985 990

Ser Phe Gly Leu Gly Gly Ile Gly Val Leu Thr Pro Asp Asn Tyr Leu
995 1000 1005

Ile Thr Pro Ala Leu Asp Leu Pro Asn Gly Gly Lys Leu Thr Phe Trp
1010 1015 1020

Val Cys Ala Gln Asp Ala Asn Tyr Ala Ser Glu His Tyr Ala Val Tyr
1025 1030 1035 1040

Ala Ser Ser Thr Gly Asn Asp Ala Ser Asn Phe Thr Asn Ala Leu Leu
1045 1050 1055

Glu Glu Thr Ile Thr Ala Lys Gly Val Arg Ser Pro Glu Ala Ile Arg
1060 1065 1070

Gly Arg Ile Gln Gly Thr Trp Arg Gln Lys Thr Val Asp Leu Pro Ala
1075 1080 1085

Gly Thr Lys Tyr Val Ala Phe Arg His Phe Gln Ser Thr Asp Met Phe
1090 1095 1100

Tyr Ile Asp Leu Asp Glu Val Glu Ile Lys Ala Asn Gly Lys Arg Ala
1105 1110 1115 1120

Asp Phe Thr Glu Thr Phe Glu Ser Ser Thr His Gly Glu Ala Pro Ala
1125 1130 1135

Glu Trp Thr Thr Ile Asp Ala Asp Gly Asp Gly Gln Gly Trp Leu Cys
1140 1145 1150

```
Leu Ser Ser Gly Gln Leu Asp Trp Leu Thr Ala His Gly Gly Thr Asn
        1155                1160                1165

Val Val Ala Ser Phe Ser Trp Asn Gly Met Ala Leu Asn Pro Asp Asn
    1170                1175                1180

Tyr Leu Ile Ser Lys Asp Val Thr Gly Ala Thr Lys Val Lys Tyr Tyr
1185                1190                1195                1200

Tyr Ala Val Asn Asp Gly Phe Pro Gly Asp His Tyr Ala Val Met Ile
                1205                1210                1215

Ser Lys Thr Gly Thr Asn Ala Gly Asp Phe Thr Val Val Phe Glu Glu
            1220                1225                1230

Thr Pro Asn Gly Ile Asn Lys Gly Gly Ala Arg Phe Gly Leu Ser Thr
        1235                1240                1245

Glu Ala Asn Gly Ala Lys Pro Gln Ser Val Trp Ile Glu Arg Thr Val
    1250                1255                1260

Asp Leu Pro Ala Gly Thr Lys Tyr Val Ala Phe Arg His Tyr Asn Cys
1265                1270                1275                1280

Ser Asp Leu Asn Tyr Ile Leu Leu Asp Asp Ile Gln Phe Thr Met Gly
                1285                1290                1295

Gly Ser Pro Thr Pro Thr Asp Tyr Thr Tyr Thr Val Tyr Arg Asp Gly
            1300                1305                1310

Thr Lys Ile Lys Glu Gly Leu Thr Glu Thr Thr Phe Glu Glu Asp Gly
        1315                1320                1325

Val Ala Thr Gly Asn His Glu Tyr Cys Val Glu Val Lys Tyr Thr Ala
    1330                1335                1340

Gly Val Ser Pro Lys Glu Cys Val Asn Val Thr Ile Asn Pro Thr Gln
1345                1350                1355                1360

Phe Asn Pro Val Lys Asn Leu Lys Ala Gln Pro Asp Gly Gly Asp Val
                1365                1370                1375

Val Leu Lys Trp Glu Ala Pro Ser Ala Lys Lys Thr Glu Gly Ser Arg
            1380                1385                1390

Glu Val Lys Arg Ile Gly Asp Gly Leu Phe Val Thr Ile Glu Pro Ala
        1395                1400                1405

Asn Asp Val Arg Ala Asn Glu Ala Lys Val Val Leu Ala Ala Asp Asn
    1410                1415                1420

Val Trp Gly Asp Asn Thr Gly Tyr Gln Phe Leu Leu Asp Ala Asp His
1425                1430                1435                1440

Asn Thr Phe Gly Ser Val Ile Pro Ala Thr Gly Pro Leu Phe Thr Gly
                1445                1450                1455

Thr Ala Ser Ser Asn Leu Tyr Ser Ala Asn Phe Glu Tyr Leu Ile Pro
            1460                1465                1470

Ala Asn Ala Asp Pro Val Val Thr Thr Gln Asn Ile Ile Val Thr Gly
        1475                1480                1485

Gln Gly Glu Val Val Ile Pro Gly Gly Val Tyr Asp Tyr Cys Ile Thr
    1490                1495                1500

Asn Pro Glu Pro Ala Ser Gly Lys Met Trp Ile Ala Gly Asp Gly Gly
1505                1510                1515                1520

Asn Gln Pro Ala Arg Tyr Asp Asp Phe Thr Phe Glu Ala Gly Lys Lys
                1525                1530                1535

Tyr Thr Phe Thr Met Arg Arg Ala Gly Met Gly Asp Gly Thr Asp Met
            1540                1545                1550

Glu Val Glu Asp Asp Ser Pro Ala Ser Tyr Thr Tyr Thr Val Tyr Arg
        1555                1560                1565

Asp Gly Thr Lys Ile Lys Glu Gly Leu Thr Glu Thr Thr Tyr Arg Asp
```

-continued 1570 1575 1580

Ala Gly Met Ser Ala Gln Ser His Glu Tyr Cys Val Glu Val Lys Tyr
1585 1590 1595 1600

Ala Ala Gly Val Ser Pro Lys Val Cys Val Asp Tyr Ile Pro Asp Gly
1605 1610 1615

Val Ala Asp Val Thr Ala Gln Lys Pro Tyr Thr Leu Thr Val Val Gly
1620 1625 1630

Lys Thr Ile Thr Val Thr Cys Gln Gly Glu Ala Met Ile Tyr Asp Met
1635 1640 1645

Asn Gly Arg Arg Leu Ala Ala Gly Arg Asn Thr Val Val Tyr Thr Ala
1650 1655 1660

Gln Gly Gly Tyr Tyr Ala Val Met Val Val Val Asp Gly Lys Ser Tyr
1665 1670 1675 1680

Val Glu Lys Leu Ala Val Lys
1685